US009745368B2

(12) United States Patent
Milone et al.

(10) Patent No.: US 9,745,368 B2
(45) Date of Patent: Aug. 29, 2017

(54) TARGETING CYTOTOXIC CELLS WITH CHIMERIC RECEPTORS FOR ADOPTIVE IMMUNOTHERAPY

(71) Applicants: Novartis AG, Basel (CH); The Trustees of the University of Pennsylvania, Philadelphia, PA (US)

(72) Inventors: Michael C. Milone, Cherry Hill, NJ (US); Enxiu Wang, Upper Darby, PA (US)

(73) Assignees: The Trustees of the University of Pennsylvania, Philadelphia, PA (US); Novartis AG, Basel (CH)

(*) Notice: Subject to any disclaimer, the term of this patent is extended or adjusted under 35 U.S.C. 154(b) by 184 days.

(21) Appl. No.: 14/214,824

(22) Filed: Mar. 15, 2014

(65) Prior Publication Data

US 2014/0322183 A1 Oct. 30, 2014

Related U.S. Application Data

(60) Provisional application No. 61/793,443, filed on Mar. 15, 2013.

(51) Int. Cl.

*C07K 16/18* (2006.01)
*C07K 14/705* (2006.01)
*C07K 14/735* (2006.01)

(52) U.S. Cl.

CPC ........ *C07K 16/18* (2013.01); *C07K 14/70503* (2013.01); *C07K 14/70535* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 5,359,046 | A | 10/1994 | Capon et al. |
| 5,686,281 | A | 11/1997 | Roberts |
| 5,712,149 | A | 1/1998 | Roberts |
| 5,874,240 | A | 2/1999 | Ni et al. |
| 5,906,936 | A | 5/1999 | Eshhar et al. |
| 6,103,521 | A | 8/2000 | Capon et al. |
| 6,319,494 | B1 | 11/2001 | Capon et al. |
| 6,355,779 | B1 | 3/2002 | Goodwin et al. |
| 6,410,319 | B1 | 6/2002 | Raubitschek et al. |
| 6,569,997 | B1 | 5/2003 | Kwon |
| 7,049,136 | B2 | 5/2006 | Seed et al. |
| 7,052,906 | B1 | 5/2006 | Lawson et al. |
| 7,070,995 | B2 | 7/2006 | Jensen |
| 7,265,209 | B2 | 9/2007 | Jensen |
| 7,319,143 | B2 | 1/2008 | Gross et al. |
| 7,320,787 | B2 | 1/2008 | Seed et al. |
| 7,446,190 | B2 | 11/2008 | Sadelain et al. |
| 7,446,191 | B2 | 11/2008 | Jensen |
| 7,514,537 | B2 | 4/2009 | Jensen |
| 7,638,326 | B2 | 12/2009 | June et al. |
| 7,741,465 | B1 | 6/2010 | Eshhar et al. |
| 7,745,140 | B2 | 6/2010 | June et al. |
| 7,754,482 | B2 | 7/2010 | Riley et al. |
| 7,994,298 | B2 | 8/2011 | Zhang et al. |
| 8,211,422 | B2 | 7/2012 | Eshhar et al. |
| 8,252,914 | B2 | 8/2012 | Zhang et al. |
| 8,389,282 | B2 | 3/2013 | Sadelain et al. |
| 8,399,645 | B2 | 3/2013 | Campana et al. |
| 8,465,743 | B2 | 6/2013 | Rosenberg et al. |
| 8,637,307 | B2 | 1/2014 | June et al. |
| 8,722,400 | B2 | 5/2014 | Riley et al. |
| 8,906,682 | B2 | 12/2014 | June et al. |
| 8,911,993 | B2 | 12/2014 | June et al. |
| 8,916,381 | B1 | 12/2014 | June et al. |
| 8,975,071 | B1 | 3/2015 | June et al. |
| 9,101,584 | B2 | 8/2015 | June et al. |
| 9,102,760 | B2 | 8/2015 | June et al. |
| 9,102,761 | B2 | 8/2015 | June et al. |
| 2003/0060444 | A1 | 3/2003 | Finney et al. |
| 2003/0077249 | A1 | 4/2003 | Bebbington et al. |
| 2003/0148982 | A1 | 8/2003 | Brenner et al. |
| 2003/0224520 | A1 | 12/2003 | June et al. |
| 2004/0038886 | A1 | 2/2004 | Finney et al. |
| 2004/0043401 | A1 | 3/2004 | Sadelain et al. |
| 2005/0113564 | A1 | 5/2005 | Campana et al. |
| 2005/0129671 | A1 | 6/2005 | Cooper et al. |

(Continued)

FOREIGN PATENT DOCUMENTS

| | | | |
|---|---|---|---|
| EP | 0574512 | A1 | 12/1993 |
| EP | 0871495 | A1 | 10/1998 |

(Continued)

OTHER PUBLICATIONS

Okazaki et al. (PNAS 2001, 98: 13866-13871).*
Katz et al. (J. Immunol. 2001, 166: 7260-7267).*
Baba et al. (Human Immunology 2000, 61: 1202-1218).*
Christensen et al. (Scand. J. Immunol. 2000, 51: 557-564).*
Arnon et al., "Inhibition of the NKp30 activating receptor by pp65 of human cytomegalovirus" Nature Immunology (2005) vol. 6 No. 5 pp. 515-523.
Baeksgaard & Sorensen, "Acute tumor lysis syndrome in solid tumors—a case report and review of the literature" Cancer Chemotherapy Pharmacology (2003) vol. 51 pp. 187-192.
Barrett et al., "Chimeric Antigen Receptor Therapy for Cancer" Annu Rev Med (2014) vol. 65 pp. 333-347.

(Continued)

*Primary Examiner* — Ilia Ouspenski
(74) *Attorney, Agent, or Firm* — Lando & Anastasi, LLP

(57) ABSTRACT

The present invention provides compositions and methods for regulating the specificity and activity of T cells. In one embodiment, the invention provides a type of chimeric antigen receptor (CAR) wherein the CAR is termed a "KIR-CAR" which is a CAR design comprising a component of a receptor naturally found on natural killer (NK) cells. In one embodiment, the NK receptor includes but is not limited to a naturally occurring activating and inhibitory receptor of NK cells known as a killer cell immunoglobulin-like receptor (KIR).

23 Claims, 44 Drawing Sheets

(56) References Cited

U.S. PATENT DOCUMENTS

2007/0036773 A1 2/2007 Cooper et al.
2008/0131415 A1 6/2008 Riddell et al.
2008/0274475 A1 11/2008 Braud et al.
2009/0257994 A1 10/2009 Jensen
2011/0003385 A1 1/2011 Crabtree et al.
2011/0052554 A1 3/2011 Zakrzewski et al.
2012/0029063 A1 2/2012 Zhang et al.
2012/0148552 A1 6/2012 Jensen
2012/0213783 A1* 8/2012 Rosenberg ......... C07K 14/7051 424/134.1
2012/0321667 A1 12/2012 Sentman
2013/0071409 A1 3/2013 Riley et al.
2013/0071414 A1 3/2013 Dotti et al.
2013/0149337 A1 6/2013 Cooper et al.
2013/0155909 A1 6/2013 Jackson et al.
2013/0158098 A1 6/2013 Liang et al.
2013/0280285 A1* 10/2013 Schonfeld .......... C07K 14/7051 424/185.1
2013/0287748 A1 10/2013 June et al.
2013/0309258 A1* 11/2013 June ....................... A61K 35/17 424/184.1
2014/0050708 A1 2/2014 Powell et al.
2014/0099309 A1 4/2014 Powell, Jr. et al.
2014/0099340 A1 4/2014 June et al.
2014/0106449 A1 4/2014 June et al.
2014/0186947 A1 7/2014 June et al.
2014/0212446 A1 7/2014 Riley et al.
2014/0219975 A1 8/2014 June et al.
2014/0227237 A1 8/2014 June et al.
2014/0271635 A1 9/2014 Brogdon et al.
2014/0322169 A1 10/2014 Harper et al.
2014/0322183 A1 10/2014 Milone et al.
2014/0322212 A1 10/2014 Brogdon et al.
2014/0322275 A1 10/2014 Brogdon et al.
2014/0370045 A1 12/2014 June et al.
2015/0017141 A1 1/2015 June et al.
2015/0140019 A1 5/2015 June et al.
2015/0190428 A1 7/2015 June et al.
2015/0202286 A1 7/2015 June et al.
2015/0283178 A1* 10/2015 June ....................... A61K 35/17 424/85.2
2015/0290244 A1 10/2015 June et al.
2015/0342994 A1 12/2015 Riley et al.
2016/0046724 A1* 2/2016 Brogdon ................ A61K 35/12 424/134.1
2016/0051651 A1* 2/2016 Brogdon .......... C07K 14/70578 424/185.1
2016/0068601 A1* 3/2016 Brogdon ............ C07K 16/2866 424/134.1
2016/0096892 A1* 4/2016 Brogdon .......... A61K 39/39558 424/93.21
2016/0311907 A1 10/2016 Brogdon et al.

FOREIGN PATENT DOCUMENTS

EP 1226244 A2 7/2002
WO 9215322 A1 9/1992
WO 9418317 A1 8/1994
WO 9530014 A1 11/1995
WO 9623814 A1 8/1996
WO 9624671 A1 8/1996
WO 9640140 A1 12/1996
WO 9715669 A1 5/1997
WO 9723613 A2 7/1997
WO 9818809 A1 5/1998
WO 9900494 A2 1/1999
WO 9957268 A1 11/1999
WO 0014257 A1 3/2000
WO 0233101 A1 4/2002
WO 02077029 A2 10/2002
WO 02088334 A1 11/2002
WO 03057171 A2 7/2003
WO 2005019429 A2 3/2005
WO 2005044996 A2 5/2005
WO 2005/118788 A2 12/2005
WO 2006060878 A1 6/2006
WO 2008045437 A2 4/2008
WO 2010085660 A2 7/2010
WO 2011059836 A2 5/2011
WO 2011097477 A1 8/2011
WO 2011119773 A1 9/2011
WO 2012058460 A2 5/2012
WO 2012079000 A1 6/2012
WO 2012082841 A2 6/2012
WO 2012/099973 A2 7/2012
WO 2012127464 A2 9/2012
WO 2012129514 A1 9/2012
WO 2012135854 A2 10/2012
WO 2012138858 A1 10/2012
WO 2013019615 A2 2/2013
WO 2013033626 A2 3/2013
WO 2013040371 A2 3/2013
WO 2013040557 A2 3/2013
WO 2013059593 A1 4/2013
WO 2013/126712 A1 8/2013
WO 2013126729 A1 8/2013
WO 2013126733 A1 8/2013
WO 2013153270 A1 10/2013
WO 2014/011984 A1 1/2014
WO 2014/011987 A1 1/2014
WO 2014/011993 A2 1/2014
WO 2014/012001 A2 1/2014
WO 2014011988 A2 1/2014
WO 2014011996 A1 1/2014
WO 2014031687 A1 2/2014
WO 2014039513 A2 3/2014
WO 2014/055442 A2 4/2014
WO 2014055657 A1 4/2014
WO 2014127261 A1 8/2014
WO 2014130635 A1 8/2014
WO 2014/145252 A2 9/2014
WO 2014153270 A1 9/2014
WO 2015090229 A1 6/2015
WO 2015090230 A1 6/2015
WO 2015112626 A1 7/2015
WO 2015/142661 A1 9/2015
WO 2015142675 A2 9/2015
WO 2015157252 A1 10/2015
WO 2016014501 A1 1/2016
WO 2016014530 A1 1/2016
WO 2016014535 A1 1/2016
WO 2016014553 A1 1/2016
WO 2016014565 A2 1/2016
WO 2016014576 A1 1/2016
WO 2016019300 A1 2/2016
WO 2016025880 A1 2/2016
WO 2016028896 A1 2/2016
WO 2016044605 A1 3/2016

OTHER PUBLICATIONS

Barrow et al., "You say ITAM and I say ITIM, let's call the whole thing off: the ambiguity of immunoreceptor signalling" European Journal of Immunology (2006) vol. 36 No. 7 pp. 1646-1653.

Biassoni et al., "Chapter 4 Natural Killer Cell Receptors" Multichain Immune Recognition Receptor Signaling (2008) vol. 640 pp. 35-52.

Bondanza et al. "Suicide gene therapy of graft-versus-host disease induced by central memory human T lymphocytes" Blood (2006) vol. 107 No. 5 pp. 1828-1836.

Bottino et al., "NK Cell Activating Receptors and Tumor Recognition in Humans" CTMI (2006) No. 298 pp. 175-182.

Brentjens et al. "Genetically Targeted T Cells Eradicate Systemic Acute Lymphoblastic Leukemia Xenografts", Clinical Cancer Research(2007) vol. 13, No. 18, pp. 5426-5435.

Brentjens et al. "Treatment of Chronic Lymphocytic Leukemia With Genetically Targeted Autologous T Cells: Case Report of an Unforeseen Adverse Event in a Phase I Clinical Trial" The American Society of Gene Therapy (2010) vol. 18 No. 4 pp. 666-668.

(56) References Cited

OTHER PUBLICATIONS

Brentjens et al., "A Phase I Trial for the Treatment of chemo-Refractory Chronic Lymphocytic Leukemia with CD19-Targeted Autologous T Cells" Molecular Therapy (2008) vol. 16 Suppl 1 p. S15.
Brentjens et al., "CD19-Targeted T Cells Rapidly Induce Molecular Remissions in Adults with Chemotherapy-Refractory Acute Lymphoblastic Leukemia," Sci. Transl. Med. 5:177ra138 (2013).
Brentjens et al., "Eradication of systemic B-cell tumors by genetically targeted human T lymphocytes co-stimulated by CD80 and interleukin-15" Nature Medicine (2003) vol. 9 No. 3 pp. 279-286.
Brentjens et al., "Safety and persistence of adoptively transferred autologous CD19-targeted T cells in patients with relapsed or chemotherapy refractory B-cell leukemias" Blood (2011) vol. 118 No. 18 pp. 4817-4828.
Brocker and Karjalainen, "Signals through T Cell Receptor-Chain alone Are Insufficient to Prime Resting T Lymphocytes" J. Exp. Med. (1995) vol. 181 pp. 1653-1659.
Brocker, "Chimeric Fv-? or Fv-e receptors are not sufficient to induce activation or cytokine production in peripheral T cells" Blood (2000) vol. 96 No. 5.
Bryceson & Long, "Line of attack: NK cell specificity and integration of signals" Current Opinion Immunology (2008) vol. 20 No. 3 pp. 344-352.
Call & Wucherpfennig, "The T Cell Receptor: Critical Role of the Membrane Environment in Receptor Assembly and Function" Annu. Rev. Immunol. (2005) vol. 23 pp. 101-125.
Campbell et al., "Natural killer cell biology: an update and future directions" Journal of Allergy and Clinical Immunology (2013) vol. 132 No. 3 pp. 536-544.
Carpenito et al. "Control of large, established tumor xenografts with genetically retargeted human T cells containing CD28 and CD137 domains", Proc Natl Acad Sci USA (2009) vol. 106 pp. 3360-3365.
Choudhuri et al., "T-cell receptor triggering is critically dependent on the dimensions of its peptide-MHC ligand" Nature (2005) vol. 436 pp. 578-582.
Daeron et al., "The Same Tyrosine-Based Inhibition Motif, in the Intra-cytoplasmic Domain of FcyRIIB, Regulates Negatively BCR-, TCR-, and FcR-Dependent Cell Activation" Immunity (1995) vol. 3 pp. 635-646.
Davila et al. "B Cell Aplasia in a Patient with Relapsed B Cell Acute Lymphoblastic Leukemia Following Re-Induction and Consolidation with Autologous T Cells Genetically Targeted to the CD19 Antigen" 53rd ASH Annual Meeting and Exposition (2010) Oral and Poster Abstract.
Dohner et al., "p53 Gene Deletion Predicts for Poor Survival and Non-Response to Therapy With Purine Analogs in Chronic B-Cell Leukemias" Blood (1995) vol. 85 No. 6 pp. 1580-1589.
Dropulic and June, "Gene-Based Immunotherapy for Human Immunodeficiency Virus Infection and Acquired Immunodeficiency Syndrome" Human Gene Therapy (2006) vol. 17 pp. 577-588.
Dull et al, "A Third-Generation Lentivirus Vector with a Conditional Packaging System" Journal of Virology (1998) vol. 72 No. 11 pp. 8463-8471.
Enxiu et al., "A Chimeric Antigen Receptor (CARs) Based Upon a Killer Immunoglobulin-Like Receptor (KIR) Triggers Robust Cytotoxic Activity in Solid Tumors" Molecular Therapy (2014) vol. 22 No. Supplm. 1.
Eshhar et al., "Specific activation and targeting of cytotoxic lymphocytes through chimeric single chains consisting of antibody-binding domains and the gamma or zeta subunits of the immunoglobulin and T-cell receptors," PNAS USA 90: 720-724 (1993).
Falk et al., "Non-MHC-Restricted CD4+ T Lymphocytes are Regulated by HLA-Cw 7-mediated Inhibition" Human Immunology (2000) vol. 61 pp. 1219-1232.
Feng et al, "The assembly of diverse immune receptors is focused on polar membrane-embedded interaction site." PLoS Biol. (2006) vol. 4 No. 5 e142.
Finney et al., "Activation of resting human primary T cells with chimeric receptors: costimulation from CD28, inducible costimulator, CD134, and CD137 (4-1BB) in series with signals from the TCR zeta chain," J. Immunol. 172: 104-113 (2004).
Finney et al., "Chimeric receptors providing both primary and costimulatory signaling in T cells from a single gene product," J. Immunol. 161: 2791-2797 (1998).
Frey, N. "Genetically Engineered Lymphocyte Therapy in Treating Patients With B-Cell Leukemia or Lymphoma That is Resistant or Refractory to Chemotherapy" (2015) Clinical Trial NCT01029366.
Friedmann-Morvinski et al., "Redirected primary T cells harboring a chimeric receptor require costimulation for their antigen-specific activation," Blood 105: 3087-3093 (2005).
Garfall, et al. "Imunotherapy with chimeric antigen receptors for multiple myeloma." Discovery Medicine. 17 (91) (pp. 37-46), Jan. 2014.
Geiger & Jyothi, "Development and Application of Receptor-Modified T Lymphocytes for Adoptive Immunotherapy" Transfusion Medicine Reviews (2001) vol. 15 No. 1 pp. 21-34.
Geiger et al., "Integrated src kinase and constimulatory activity enhances signal transduction through single-chain chimeric receptors in T lymphocytes," Blood 98(8): 2364-2371 (2001).
GenBank Accession No. NP_000725.1 accessed on Jan. 7, 2016 from http://www.ncbi.nlm.nih.gov/protein/NP_000725.
GenBank Accession No. NP_932170.1 accessed Jan. 7, 2016 from http://www.ncbi.nlm.nih.gov/protein/NP_932170.
Gilham et al., "Primary Polyclonal Human T Lymphocytes Targeted to Carcino-Embryonic Antigens and Neural Cell Adhesion Molecule Tumor Antigens by CD3-Based Chimeric Immune Receptors" Journal of Immunotherapy (2002) vol. 25 No. 2 pp. 139-151.
Gong et al. "Cancer Patient T Cells Genetically Targeted to Prostate-Specific Membrane Antigen Specifically Lyse Prostate Cancer Cells and Release Cytokines in Response to Prostate-Specific Membrane Antigen" Neoplasia (1999) vol. 1 No. 2 pp. 123-127.
Gribben et al., "Stem cell transplantation for indolent lymphoma and chronic lymphocytic leukemia" Biol Blood Marrow Transplant (2011) vol. 17 (1 Suppl): S63-S70.
Griffin, "Development and applications of surface-linked single chain antibodies against T-cell antigens" Journal of Immunological Methods (2001) vol. 248 pp. 77-90.
Gross et al., "Endowing T cells with antibody specificity using chimeric T cell receptors," The FASEB Journal 6: 3370-3378 (1992).
Grupp et al. "Chimeric Antigen Receptor-Modified T Cells for Acute Lymphoid Leukemia", New England Journal of Medicine (2013) vol. 368 No. 16 pp. 1509-1518.
Hallek et al., "Guidelines for the diagnosis and treatment of chronic lymphocytic leukemia: a report from the International Workshop on Chronic Lymphocytic Leukemia updating the National Cancer Institute Working Group 1996 guidelines" Blood (2008) vol. 111 No. 12 pp. 5446-5456.
Hassan et al., "Antitumor activity of SS(dsFv)PE38 and SS1(dsFv)PE38, recombinant antimesothelin immunotoxins against human gynecologic cancers grown in organotypic culture in vitro" Clinical Cancer Research (2002) vol. 8 No. 11 pp. 3520-3526.
Hekele et al., "Growth Retardation of Tumors by Adoptive Transfer of Cytotoxic T Lymphocytes Reprogrammed by CD44V6-Specific SCFV:~Chimera" Int J. Cancer (1996) vol. 68 pp. 232-238.
Ho et al., "Adoptive immunotherapy: Engineering T cell responses as biological weapons for tumor mass destruction" Cancer Cell (2003) vol. 3 pp. 431-437.
Hollyman et al. "Manufacturing validation of biologically functional T cells targeted to CD19 antigen for autologous adoptive cell therapy" J Immunother (2009) vol. 32 No. 2 pp. 169-180.
Homback et al., "The Recombinant T Cell Receptor Strategy: Insights into Structure and Function of Recombinant Immunoreceptors on the Way Towards an Optimal Receptor Design for Cellular Immunotherapy," Current Gene Therapy 2: 211-226 (2002).
Imai et al., "Chimeric receptors with 4-1BB signaling capacity provoke potent cytotoxicity against acute lymphoblastic leukemia," Leukemia 18: 676-684 (2004).
Imai et al., "Genetic modification of primary natural killer cells overcomes inhibitory signals and induces specific killing of leukemic cells" Blood (2005) vol. 106 No. 1 pp. 376-383.

(56) References Cited

OTHER PUBLICATIONS

International Preliminary Report on Patentability and Written Opinion of the International Searching Authority for PCT/US2014/029983 mailed Sep. 15, 2015.
International Search Report for PCT/US2014/029983 mailed Oct. 28, 2014.
International Search Report from PCT/US2011/064191 dated Jan. 5, 2012.
Irving et al., "The cytoplasmic domain of the T cell receptor zeta chain is sufficient to couple to receptor-associated signal transduction pathways," Cell 64: 891-901 (1991).
Jena, Bipulendu et al. "Redirecting T-cell specificity by introducing a tumor-specific chimeric antigen receptor, Blood, May 3, 2010", vol. 116, No. 7, pp. 1035-1044.
Jensen et al., "Anti-Transgene Rejection Responses Contribute to Attenuated Persistence of Adoptively Transferred CD20/CD19-Specific Chimeric Antigen Receptor Re-directed T Cells in Humans" Biol Blood Marrow Transplant (2010) vol. 16 No. 9 pp. 1245-1256.
Johnson et al., "Gene therapy with human and mouse T-cell receptors mediates cancer regression and targets normal tissues expressing cognate antigen" Blood (2009) vol. 114 No. 3 pp. 535-545.
June et al., "Engineering lymphocyte subsets: tools, trials and tribulations" Nat Rev Immunol (2009) vol. 9 No. 10 pp. 104-116.
Kalos et al. "T Cells with Chimeric Antigen Receptors Have Potent Antitumor Effects and Can Establish Memory in Patients with Advanced Leukemia", Science Translation Medicine (2011) vol. 3 No. 95 95ra73.
Karre et al., "Selective rejection of H-2-deficient lymphoma variants suggests alternative immune defence strategy." Nature (1986) vol. 319 No. 6055 pp. 675-678.
Kershaw et al., "A Phase I Study on Adoptive Immunotherapy Using Gene-Modified T Cells for Ovarian Cancer," Clin. Cancer Res. 12(20 Pt 1): 6106-6115 (2006).
Kim et al., "Human 4-1BB regulates CD28 co-stimulation to promote Th1 cell responses" Eur. J. Immunol. (1998) vol. 28 pp. 881-890.
Klingemann, "Are natural killer cells superior CAR drivers?" Oncoimmunology (2014) vol. 3 No. 1.
Kloss et al., "Combinatorial antigen recognition with balanced signaling promotes selective tumor eradication by engineered T cells" Nature Biotechnology (2013) vol. 31 No. 1 pp. 71-75.
Kochenderfer et al, "A Phase I Clinical Trial of Treatment of B-Cell Malignancies with Autologous Anti-Cd19-CAR-Transduced T Cells" Blood (2010) vol. 116 No. 21 pp. 1179-1180 & 52nd Annual Meeting of the American-Society-of-Hematology (ASH), Orlando, FL, USA; December 4-7, 2010 abstract.
Kochenderfer et al. "Construction and Pre-clinical Evaluation of an Anti-CD19 Chimeric Antigen Receptor", J Immunother (2009) vol. 32, No. 7, pp. 389-702.
Kochenderfer et al., "Eradication of B-lineage cells and regression of lymphoma in a patient treated with autologous T cells genetically-engineered to recognize CD19," Blood 116: 4099-4102 (2010).
Kohn et al., "CARs on Track in the Clinic—Workshop of the Blood and Marrow Transplant Clinical Trials Network Subcommittee on Cell and Gene Therapy" Meeting Report—Molecular Therapy (2011) vol. 19 No. 3.
Kraus et al., "Antigen-dependent CD28 Signaling Selectively Enhances Survival and Proliferation in Genetically Modified Activated Human Primary T Lymphocytes" J. Exp. Med. (1998) vol. 188 Np 4 pp. 619-626.
Kruse et al., "Natural cytotoxicity receptors and their ligands" Immunology and Cell Biology (2013) vol. 92 No. 3 pp. 221-229.
Kwon et al., "cDNA sequences of two inducible T-cell genes". Proc. Natl. Acad. Sci. U.S.A. 86(6): 1963-1967 (1989).
Lamanna et al., "Pentostatin, Cyclophosphamide, and Rutuximab Is an Active, Well-Tolerated Regimen for Patients With Previously Treated Chronic Lymphocytic Leukemia" Journal of Clinical Oncology (2008) vol. 24 No. 10 pp. 1575-1581.
Lamers et al., "Treatment of Metastatic Renal Cell Carcinoma With Autologous T-Lymphocytes Genetically Retargeted Against Carbonic Anhydrase IX: First Clinical Experience," J. Clin. Oncol. 24(13): e20-e22 (2006).
Lanier et al., "Immunoreceptor DAP12 bearing a tyrosine-based activation motif is involved in activating NK cells" Nature (1998) vol. 391 pp. 703-707.
Lanier, "Up on the tightrope: natural killer cell activation and inhibition." Nat Immunol (2008) vol. 9 No. 5 pp. 495-502.
Laport et al., "Adoptive transfer of costimulated T cells induces lymphocytosis in patients with relapsed/refractory non-Hodgkin lymphoma following CD34 +-selected hematopoietic cell transplantation" Blood (2003) vol. 102 No. 6 pp. 2004-2013.
Lee et al., "In vivo Inhibition of Human CD19-Targeted Effector T Cells by Natural T Regulatory Cells in a Xenotransplant Murine Model of B Cell Malignancy" Cancer Research (2011) vol. 71 No. 8 pp. 2871-2881.
Lee et al., "The Future is Now: Chimeric Antigen Receptors as New Targeted Therapies for Childhood Cancer," Clin. Cancer Res. 18: 2780-2790 (2012).
Letoumeur et al., "T-cell and basophil activation through the cytoplasmic tail of T-cell-receptor zeta family proteins," Proc. Natl. Acad. Sci. U.S.A 88: 8905-8909 (1991).
Levine et al., "Gene transfer in humans using a conditionally replicating lentiviral vector" PNAS (2006) vol. 103 No. 46 pp. 17372-17377.
Lo et al., "Anti-GD3 chimeric sFv-CD28/T-cell receptor zeta designer T cells for treatment of metastatic melanoma and other neuroectodermal tumors." Clin Cancer Res (2010) vol. 16 No. 10 pp. 2769-2780.
Loskog et al. "Addition of the CD28 signaling domain to chimeric T-cell receptors enhances chimeric T-cell resistance to T regulatory cells." Leukemia (2006) vol. 20 No. 10 pp. 1819-1828.
Ma et al., "Recognition of mesothelin by the therapeutic antibody MORAb-009: structural and mechanistic insights." J Biol Chem (2012) vol. 287 No. 40 pp. 33123-33131.
MacAllan et al., "Measurement and modeling of human T cell kinetics" European Journal of Immunology (2003) vol. 33 pp. 2316-2326.
Maher et al., "Human T lymphocyte cytotoxicity and proliferation directed by a single chimeric TCRzeta/CD28 receptor," Nat. Biotechnol. 20: 70-75 (2002).
McGuinness et al., "Anti-tumor activity of human T cells expressing the CC49-zeta chimeric immune receptor," Hum. Gene Ther. 10: 165-173 (1999).
Milone et al, "Chimeric Receptors Containing CD137 Signal Transduction Domains Mediate Enhanced Survival of T Cells and Increased Antileukemic Efficacy In Vivo" Molecular Therapy (2009) vol. 17 No. 8 pp. 1453-1464.
Molina, "A Decade of Rituximab: Improving Survival Outcomes in Non-Hodgkin's Lymphoma" Annu. Rev. Med. (2008) vol. 59 pp. 237-250.
Moretta et al., "Major histocompatibility complex class I-specific receptors on human natural killer and T lymphocytes" Immunological Reviews (1997) vol. 155 pp. 105-117.
Morgan et al., "Case Report of a Serious Adverse Event Following the Administration of T Cells Transduced With a Chimeric Anitgen Receptor Recognizing ErbB2," Mol. Ther. 18(4): 843-851 (2010).
Moritz and Groner, "A spacer region between the single chain antibody- and the CD3 zeta-chain domain of chimeric T cell receptor components is required for efficient ligand binding and signaling activity," Gene Therapy 2(8): 539-546 (1995).
Moritz et al., "Cytotoxic T lymphocytes with a grafted recognition specificity for ERBB2-expressing tumor cells" Proc. Natl. Acad. Sci (1994) vol. 91 pp. 4318-4322.
Naldini et al., "In Vivo Gene Delivery and Stable Transduction of Nondividing Cells by a Lentiviral Vector" Science (1996) vol. 272 pp. 263-267.
NCBI accession HM_852952 accessed Sep. 29, 2015 from http://www.ncbi.nlm.nih.gov/nuccore/hm852952.

(56) References Cited

OTHER PUBLICATIONS

Nicholson et al., "Construction and Characterisation of a Function CD19 Specific Single Chain Fv Fragment for Immunotherapy of B Lineage Leukaemia and Lymphoma," Molecular Immunology 34(16-17): 1157-1165 (1997).
Ohlen et al., "Prevention of Allogeneic Bone Marrow Graft Rejection by H-2 Transgene in Donor Mice" Science (1989) vol. 246 pp. 666-668.
Olcese et al., "Human killer cell activatory receptors for MHC class I molecules are included in a multimeric complex expressed by natural kill cells." J Immunol (1997) vol. 158 pp. 5083-5086.
Park and Brentjens "Adoptive Immunotherapy for B-cell Malignancies with Autologous Chimeric Antigen Receptor Modified Tumor Targeted T Cells" Discovery Medicine (2010) vol. 9 No. 47 pp. 277-288.
Park et al. "Adoptive Transfer of Chimeric Antigen Receptor Re-directed Cytolytic T Lymphocyte Clones in Patients with Neuroblastoma", Molecular Therapy (2007) vol. 15 No. 4 pp. 825-833.
Pasquale, "Eph receptors and ephrins in cancer: bidirectional signalling and beyond." Nat Rev Cancer (2010) vol. 10 No. 3 pp. 165-180.
Patel et al., "Impact of chimeric immune receptor extracellular protein domains on T cell function" Gene Therapy (1999) vol. 6 pp. 412-419.
Porter et al. "Chimeric Antigen Receptor-Modified T Cells in Chronic Lymphoid Leukemia", The New England Journal of Medicine (2011) vol. 365 No. 8 pp. 725-733.
Porter et al., "A phase 1 trial of donor lumphocyte infusions expanded and activated ex vivo via CD3/CD28 costimulation" Blood (2006) vol. 107 No. 4 pp. 1325-1331.
Porter et al., "Chimeric Antigen Receptor Therapy for B-cell Malignancies" Journal of Cancer (2011) vol. 2 pp. 331-332.
Pule et al., "Virus-specific T cells engineered to coexpress tumor-specific receptors: persistence and antitumor activity in individuals with neuroblastoma" Nat. Med. (2008) vol. 14 No. 11 pp. 1264-1270.
Rapoport et al., "Restoration of immunity in lymphopenic individuals with cancer by vaccination and adoptive T-cell transfer" Nature Medicine (2005) vol. 11 No. 11 pp. 1230-1237.
Ravetch & Bolland, "IcG Fc Receptors" Annu. Rev. Immunol. (2001) vol. 19 pp. 275-290.
Remtoula et al., "Selective expression of inhibitory or activating killer cell Ig-like receptors in circulating CD4 T lymphocytes" Journal of Immunology (2008) vol. 180 No. 5 pp. 2767-2771.
Roederer, "T-cell dynamics of immunodeficiency" Nature Medicine (1995) vol. 1 No. 7 pp. 621-622.
Romeo et al., "Cellular immunity to HIV activated by CD4 fused to T cell or Fc receptor polypeptides," Cell 64:1037-1046 (1991).
Rosen et al., "A Structural basis for the association of DAP12 with mouse, but not human, NKG2D." J Immunol (2004) vol. 173 No. 4 pp. 2470-2478.
Sabbagh et al., "TNF family ligands define niches for T cell memory" Trends in Immunology (2007) vol. 28 No. 8 pp. 333-339.
Sadelain et al. "The promise and potential pitfalls of chimeric antigen receptors." Current Opinion Immunology (2009) vol. 21 No. 2 pp. 215-223.
Sadelain et al., "Targeting Tumours with Genetically Enhanced T Lymphocytes," Nature Reviews: Cancer 3: 35-45 (2003).
Sadelain et al., "The Basic Principles of Chimeric Antigen Receptor Design" Cacner Discovery (2013) vol. 3 No. 4 pp. 388-398.
Savoldo et al., "CD28 costimulation improves expansion and persistence of chimeric antigen receptor-modified T cells in lymphoma patients" The Journal of Clinical Investigation (2011) vol. 121 No. 5 pp. 1822-1826.
Sebestyen et al., "Human TCR That Incorporate CD3 Induce Highly Preferred Pairing between TCR and Chains following Gene Transfer" Journal of Immunology (2008) vol. 180 pp. 7736-7746.
Shirasu et al., "Functional Design of Chimeric T-Cell Antigen Receptors for Adoptive Immunotherapy of Cancer: Architecture and Outcomes," AntiCancer Res. 32: 2377-2384 (2012).
Shook et al., "Natural killer cell engineering for cellular therapy of cancer" Tissue Antigens (2011) vol. 78 No. 6 pp. 409-415.
Singh et al., "Claudin Family of Proteins and Cancer: An Overview" Journal of Oncology (2010) Article ID 541957.
Snyder et al., "Stimulatory killer Ig-like receptors modulate T cell activation through DAP12-dependent and DAP12-independent mechanisms." J Immunol (2004) vol. 173 No. 6 pp. 3725-3731.
Sorror et al., "Outcomes after allogeneic hematopoietic cell transplantation with nonmyeloablative or myeloablative conditioning regimens for treatment of lymphoma and chronic lymphocytic leukemia" Blood (2008) vol. 111 No. 1 pp. 446-452.
Stewart et al., "Strategies of Natural Killer Cell Recognition and Signaling" CTMI (2006) vol. 298 pp. 1-21.
Takase et al., "A new 12-kilodalton dimer associated with pre-TCR complex and clonotype-independent CD3 complex on immature thymocytes." J Immunol (1997) vol. 159 pp. 741-747.
Tal et al., "An NCR1-based chimeric receptor endows T-cells with multiple anti-tumor specificities" Oncotarget (2014) pp. 1-10.
Teng et al., "T cells gene-engineered with DAP12 mediate effector function in an NKG2D-dependent and major histocompatibility complex-independent manner." J Biol Chem (2005) vol. 280 No. 46 pp. 38235-38241.
Thielens et al., "NK cell MHC class I specific receptors (KIR): from biology to clinical intervention" Curent Opinion in Immunology (2012) vol. 24 pp. 239-245.
Thomas, "Of ITAMs and ITIMs: turning on and off the B cell antigen receptor." J Exp Med (1995) vol. 181 No. 6 pp. 1953-1956.
Till et al., "Adoptive immunotherapy for indolent non-Hodgkin lymphoma and mantle cell lymphoma using genetically modified autologous CD20-specific T cells" Blood (2008) vol. 112 No. 6 pp. 2261-2271.
Uckun et al., "Detailed studies on expression and function of CD19 surface determinant by using B43 monoclonal antibody and the clinical potential of anti-CD19 immunotoxins" Blood (1988) vol. 71 pp. 13-29.
Varela-Rohena et al., "Control of HIV-1 immune escape by CD8 T cells expressing enhanced T-cell receptor." Nat Med (2008) vol. 14 No. 12 pp. 1390-1395.
Vinay & Kwon, "Role of 4-1BB in immune responses" Immunology (1998) vol. 10 pp. 481-489.
Vivier et al, "Signaling Function of Reconstituted CD16:Zeta:Gamma Receptor Complex Isoforms" International Immunology (1992) vol. 4 No. 11 pp. 1313-1323.
Willemsen et al., "Genetic Engineering of T Cell Specificity for Immunotherapy of Cancer" Human Immunology (2003) vol. 64 pp. 56-68.
Zhang et al., "An NKp30-Based Chimeric Antigen Receptor Promotes T Cell Effector Functions and Antitumor Efficacy in Vivo" The Journal of Immunology (2012) vol. 189 No. 5 pp. 2290-2299.
Zhao et al., "A Herceptin-Based Chimeric Antigen Receptor with Modified Signaling Domains Leads to Enhanced Survival of Transduced T Lymphocytes and Antitumor Activity" The Journal of Immunology (2009) vol. 183 pp. 5563-5574.
Zufferey et al., "Multiply attenuated lentiviral vector achieves efficient gene delivery in vivo" Nature Biotechnology (1997) vol. 15 pp. 871-876.
Fegan et al. "Chemically Controlled Protein Assembly: Techniques and Applications", Chem Rev (2010) vol. 110, pp. 3315-3336.
International Preliminary Report on Patentability for International Application No. PCT/US2015/020533 dated Sep. 20, 2016.
International Search Report and Written Opinion for International Application No. PCT/CN2014/082615 dated Oct. 27, 2014.
International Search Report and Written Opinion for International Application No. PCT/CN2014/094383, mailed Mar. 20, 2015.
International Search Report and Written Opinion for International Application No. PCT/US2015/20533 dated Jun. 26, 2015.
James et al. "Biophysical mechanism of T-cell receptor triggering in a reconstituted system", Nature (2012) vol. 487 pp. 64-69.

* cited by examiner

TARGETING CYTOTOXIC CELLS WITH CHIMERIC RECEPTORS FOR ADOPTIVE IMMUNOTHERAPY

This application claims priority to U.S. Ser. No. 61/793,443 filed Mar. 15, 2013, the entire contents which is incorporated herein by reference.

STATEMENT REGARDING FEDERALLY SPONSORED RESEARCH OR DEVELOPMENT

This invention was made with government support under PN2 EY016586 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jun. 10, 2014, is named N2067-704910_SL.txt and is 246,698 bytes in size.

BACKGROUND OF THE INVENTION

With the use of gene transfer technologies, T cells can be genetically modified to stably express antibody binding domains on their surface that endow the T cells with specificities that are independent of the constraints imposed by the major histocompatibility complex (MHC). Chimeric antigen receptors (CARs) represent synthetic proteins expressed on T-cells (CART cells) that fuse an antigen recognition fragment of an antibody (e.g., an scFv, or single-chain variable region fragment) with an intracellular domain of the CD3-zeta chain. Upon interaction with a target cell expressing the scFv's cognate antigen, CARs expressed on T cell cells can trigger T-cell activation leading to target cell killing (also referred to as target cell lysis). When combined with additional costimulatory signals such as the intracellular domain of CD137 or CD28, these receptors are also capable of generating proliferation. However, some of this proliferation appears to be antigen-independent, unlike normal T cell receptor (TCR) responses (Milone et al., 2009, Mol Ther 17(8):1453-64). Artificial receptors do not fully reproduce the intracellular signal transduction produced by natural TCR binding to antigenic peptide complexed with MHC molecules (Brocker, 2000, Blood 96(5):1999-2001). The signaling defects may limit the long-term survival of CART cells upon adoptive transfer in the absence of high levels of cytokines like IL-2 (Lo et al., 2010, Clin Cancer Res 16(10):2769-80). They also have altered regulation that might be beneficial in some anti-cancer applications (Loskog et al., 2006, Leukemia 20(10):1819-28), but these regulatory defects also lead to potential challenges to controlling their "off-target" activity against normal tissues that also express antigen, even at extremely low levels. These "off-target" effects are a serious limitation to CAR-based therapeutics, and have resulted in probable deaths during early Phase I evaluation of CAR-modified T cells (Morgan et al., 2010, Mol Ther 18(4):843-51).

Thus, there is a need in the art for alternative approaches for constructing CARs that overcome the limitations to current CAR-based therapeutics. The present invention addresses this unmet need in the art.

SUMMARY

In a first aspect, the invention features a purified, or non-naturally occurring, NKR-CAR comprising one, two or all of an extra-cellular antigen binding domain, a transmembrane domain, e.g., an NKR transmembrane domain, and a cytoplasmic domain, e.g., an NKR cytoplasmic domain.

In one embodiment, said NKR-CAR comprises an extra-cellular antigen binding domain; a transmembrane domain and an NKR cytoplasmic domain. In one embodiment, said NKR-CAR comprises a KIR-CAR, e.g., an actKIR-CAR or inhKIR-CAR, a NCR-CAR, e.g., an actNCR-CAR, a SLAMF-CAR, e.g., an inhSLAMF-CAR, a FcR-CAR, e.g., CD16-CAR, e.g., an actCD16-CAR, or CD64-CAR, e.g., an actCD64-CAR, or a Ly49-CAR, e.g., an actLy49-CAR or inhLy49-CAR. In one embodiment, the NKR-CAR comprises a transmembrane domain and an extra-cellular antigen binding domain, and further comprising a hinge domain disposed between said transmembrane domain and said extra-cellular antigen binding domain.

In another aspect, the invention features a nucleic acid, e.g., a purified or non-naturally occurring, nucleic acid, e.g., a nucleic acid comprising a DNA, or RNA, sequence, e.g., a mRNA, comprising a sequence that encodes a NKR-CAR described herein. In one embodiment, the nucleic acid further comprising a sequence that encodes an adaptor molecule or intracellular signaling domain that interacts with said NKR-CAR.

In another aspect, the invention features a cytotoxic cell, e.g., a naturally or non-naturally occurring T cell, NK cell or cytotoxic T cell or NK cell line comprising a NKR-CAR described herein. In one embodiment, the cytotoxic cell further comprises an adaptor molecule or intracellular signaling domain that interacts with said NKR-CAR.

In another aspect, the invention features a method of making a cytotoxic cell, e.g., a naturally or non-naturally occurring T cell, NK cell or cytotoxic T cell or NK cell line comprising a NKR-CAR, described herein comprising introducing into a cytotoxic cell a nucleic acid, e.g., a mRNA, comprising a sequence that encodes a NKR-CAR, described herein. In one embodiment, the method further comprises making a NKR-CAR, described herein, in the cytotoxic cell.

In another aspect, the invention features a method of treating a subject, e.g., a method of providing an anti-tumor immunity in a mammal, comprising administering to the mammal an effective amount of a cytotoxic cell, e.g., a naturally or non-naturally occurring T cell, NK cell or cytotoxic T cell or NK cell line comprising a NKR-CAR described herein.

In another aspect, the invention features a purified, or non-naturally occurring, KIR-CAR comprising an extra-cellular antigen binding domain and a transmembrane domain, e.g., a KIR transmembrane domain, or cytoplasmic domain, e.g., an ITIM-containing cytoplasmic domain, or a KIR-cytoplasmic domain. In one embodiment, the KIR-CAR comprises an extra-cellular antigen binding domain, a transmembrane domain, and an ITIM-containing cytoplasmic domain, or a KIR-cytoplasmic domain.

In one embodiment, said transmembrane domain can interact with, e.g., bind, the transmembrane domain of DAP12. In one embodiment, said transmembrane domain comprises a positively charged moiety, e.g., an amino acid residue comprising a positively charged moiety, e.g., side chain. In one embodiment, said transmembrane domain comprises a KIR-transmembrane domain.

In one embodiment, said KIR-CAR is an activating KIR-CAR. In one embodiment, said KIR-CAR comprises a KIR-transmembrane domain. In one embodiment, said KIR-CAR is an inhibitory KIR-CAR. In one embodiment, said KIR-CAR comprises a KIR-cytoplasmic domain. In one embodiment, said KIR-CAR comprises an extra-cellular antigen binding domain and a transmembrane domain, e.g., a transmembrane domain comprising a positively charged moiety, e.g., an amino acid residue comprising a positively charged moiety, e.g., side chain, or a KIR-transmembrane domain.

In one embodiment, a KIR-CAR described herein comprises an antigen binding domain comprising an scFv. In one embodiment, said antigen binding domain comprises a single VH domain, e.g., a camelid, shark, or lamprey single VH domain, or a single VH domain derived from a human or mouse sequence, or a non-antibody scaffold, e.g., a fibronectin, e.g., a fibronectin type III antibody-like molecule. In one embodiment, said antigen binding domain comprises a nanobody. In one embodiment, said antigen binding domain comprises a camelid VHH domain.

In one embodiment, a KIR-CAR described herein comprises an extracellular hinge domain. In one embodiment, the extracellular hinge domain is other than a KIR hinge domain, e.g., other than a KIR2DS2 hinge domain. In one embodiment, the extracellular hinge domain is derived from a natural molecule. In one embodiment, the extracellular hinge domain is derived from a natural molecule other than a KIR. In one embodiment, the extracellular hinge domain comprises a non-naturally occurring polypeptide sequence. In one embodiment, the extracellular hinge domain comprises the extracellular hinge from human CD8-alpha. In one embodiment, the extracellular hinge domain comprises a synthetic extracellular hinge. In one embodiment, the extracellular hinge domain is less than 50, 20, or 10 amino acids in length. In one embodiment, the extracellular hinge domain has fewer amino acids than a KIR2DS2 hinge domain.

In one embodiment, the KIR-CAR described herein is an actKIR-CAR. In one embodiment, said actKIR-CAR comprises a transmembrane domain comprising a positively charged moiety, e.g., an amino acid residue comprising a positively charged moiety, e.g., a positively charged side chain or an actKIR transmembrane domain. In one embodiment, said actKIR-CAR can interact with and promote signaling from an ITAM-containing polypeptide or adaptor molecule. In one embodiment, said actKIR-CAR can interact with and promote signaling from a DAP12 polypeptide. In one embodiment, said actKIR-CAR comprises a KIR D domain. In one embodiment, said actKIR-CAR comprises a KIR D1 domain. In one embodiment, said actKIR-CAR comprises a KIR D2 domain. In one embodiment, said actKIR-CAR said act KIR-CAR does not comprise a KIR D domain. In one embodiment, said actKIR-CAR comprises a KIR2DS2 transmembrane domain. In one embodiment, said actKIR-CAR further comprises a KIR2DS2 cytoplasmic domain. In one embodiment, said actKIR-CAR does not comprise a KIR D domain.

In one embodiment, the antigen binding domain of a KIR-CAR described herein binds an antigen present on a target cell, e.g., a cancer cell. In one embodiment, said antigen binding domain binds an antigen that is more highly expressed on a target cell, e.g., a cancer cell, than a non-target cell, e.g., a non-cancerous cell, e.g., a non cancerous cell of the same type as the target cell. In one embodiment, said antigen binding domain is binds an antigen described herein.

In one embodiment, the KIR-CAR described herein is an inhKIR-CAR. In one embodiment, the inhKIR-CAR comprises an inhKIR transmembrane domain. In one embodiment, the inhKIR-CAR comprises an ITIM-containing cytoplasmic domain, e.g., an inhKIR cytoplasmic domain, e.g., a KIR2DL or KIR3DL cytoplasmic domain. In one embodiment, the inhKIR-CAR comprises a transmembrane other than a KIR transmembrane, e.g., a transmembrane domain from PD-1, CTLA4 or ITIM-containing receptors from ILT (CD85), Siglec, LMIR (CD300) and/or SLAM gene families of receptors. In one embodiment, the inhKIR-CAR comprises a cytoplasmic domain from an inhibitory receptor other than a KIR, e.g., from PD-1, CTLA4 or ITIM-containing receptors from ILT (CD85), Siglec, LMIR (CD300) and/or SLAM gene families of receptors. In one embodiment, the inhKIR-CAR comprises a transmembrane and cytoplasmic domain from an inhibitory receptor other than a KIR, e.g., transmembrane and cytoplasmic domain, independently, from e.g., PD-1, CTLA4 or ITIM-containing receptors from ILT (CD85), Siglec, LMIR (CD300) and/or SLAM gene families of receptors. In one embodiment, said cytoplasmic domain comprises an ITIM. In one embodiment, the inhKIR-CAR comprises a KIR D domain. In one embodiment, the inhKIR-CAR comprises a KIR D0 domain. In one embodiment, the inhKIR-CAR comprises a KIR D1 domain. In one embodiment, the inhKIR-CAR comprises a KIR D2 domain. In one embodiment, the inhKIR-CAR does not comprise a KIR D domain.

In one embodiment, the antigen binding domain of the inhKIR-CARs described herein binds an antigen not present on a target cell, e.g., a cancer cell. In one embodiment, said antigen binding domain binds an antigen that is more highly expressed on a non-target cell, e.g., a non-cancer cell, than a target cell, e.g., cancerous cell, e.g., a cancerous cell of the same type as the target cell. In one embodiment, said antigen binding domain binds desmoglein1/3 (DSG1/3). In an embodiment, an inhCAR, e.g., an inhTCAR or inhNKR-CAR, e.g., an inhKIR-CAR, and an actCAR, e.g., an act-TCAR or actNKR-CAR, e.g., an actKIR-CAR, are provided in which the inhCAR comprises an antigen binding domain that targets desmoglein1/3 (DSG1/3) and the actCAR comprises an antigen binding domain that targets an antigen other than DSG1/3, e.g., EGFR. In an embodiment, this pair is used to treat an EGFR expressing cancer, e.g., an adenocarcinoma of the lung or colon. In an embodiment the cancer cells express less DSG1/3 than non-cancer cells. In an embodiment this combination can minimize CAR-mediated attack of skin cells or squamous cells of the GI track (i.e. oral mucosa). In one embodiment, said antigen binding domain binds an ephrin receptor or a claudin.

In another aspect, the invention features a nucleic acid, e.g., a purified or non-naturally occurring, nucleic acid, e.g., a nucleic acid comprising a DNA, or RNA, sequence, e.g., a mRNA, comprising (a) a sequence that encodes a KIR-CAR, e.g., a first KIR-CAR described herein. In one embodiment, said KIR-CAR, e.g., said first KIR-CAR, is an actKIR-CAR, e.g., an actKIR-CAR described herein. In one embodiment, said KIR-CAR, e.g., said first KIR-CAR, is an inhKIR-CAR, e.g., an inhKIR-CAR described herein. In one embodiment, said nucleic acid comprises a DNA sequence. In one embodiment, said nucleic acid comprises a RNA sequence, e.g., a mRNA sequence.

In an embodiment, said nucleic acid comprises sequence that encodes a KIR-CAR, e.g., an actKIR-CAR, and sequence that encodes an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In an embodiment, said nucleic acid comprises sequence that encodes a KIR-CAR, e.g., an actKIR-CAR, and sequence that encodes an inhibitory molecule comprising: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring SLAM family member.

In one embodiment, said nucleic acid described herein further comprises (b) a sequence that encodes a second KIR-CAR described herein, e.g., a second KIR-CAR that is different from said first KIR-CAR. In one embodiment, (a) and (b) are disposed on the same nucleic acid molecule, e.g., the same vector, e.g., the same viral vector, e.g., a lenti-viral vector. In one embodiment, one of (a) and (b) is disposed on a first nucleic acid molecule, e.g., a first vector, e.g., a viral vector, e.g., a lenti-viral vector, and the other is disposed on a second nucleic acid molecule, e.g., a second vector, e.g., a viral vector, e.g., a lenti-viral vector. In one embodiment, said first KIR-CAR and said second KIR-CAR is an actKIR-CAR. In an embodiment, engagement of either act KIR-CAR alone is insufficient to trigger substantial levels of activation. In an embodiment, engagement of both the first and second actKIR-CAR gives an additive, or synergistic, level of activation. In one embodiment, said first KIR-CAR and said second KIR-CAR is an inhKIR-CAR. In one embodiment, one of said first KIR-CAR and said second KIR-CAR is an actKIR-CAR and the other is an inhKIR-CAR. In one embodiment, said actKIR-CAR is an actKIR-CAR described herein. In one embodiment, said inhKIR-CAR is an inhKIR-CAR described herein. In one embodiment, the nucleic acid described herein comprises an actKIR-CAR described herein and an inhKIR-CAR described herein.

In an embodiment the nucleic further comprises (c) sequence that encodes an intracellular signaling domain, e.g., an adaptor molecule, which can produce an activating signal. In one embodiment, said intracellular signaling domain comprises an ITAM motif. In one embodiment, said sequence encodes a DAP 12 polypeptide comprising a DAP 12 intracellular signaling domain. In one embodiment, said DAP 12 polypeptide further comprises a transmembrane domain. In one embodiment, said DAP 12 polypeptide further comprises an extracellular domain. In one embodiment, each of (a), (b), and (c) are present on the same nucleic acid molecule, e.g., a vector, e.g., a viral vector, e.g., a lenti-viral vector. In one embodiment, one of (a), (b), and (c) is encoded on a first nucleic acid molecule, e.g., a vector, e.g., a viral vector, e.g., a lenti-viral vector and a second and third of (a), (b), and (c) is encoded on a second nucleic acid molecule, e.g., a vector, e.g., a viral vector, e.g., a lenti-viral vector. In one embodiment (a) is present on a first nucleic acid molecule, e.g., a vector, e.g., a viral vector, e.g., a lenti-viral vector, and (b) and (c) are present on a second nucleic acid molecule, e.g., a vector, e.g., a viral vector, e.g., a lenti-viral vector. In another embodiment, (b) is present on a first nucleic acid molecule, e.g., a vector, e.g., a viral vector, e.g., a lenti-viral vector, and (a) and (c) are present on a second nucleic acid molecule, e.g., a vector, e.g., a viral vector, e.g., a lenti-viral vector. In one embodiment, (c) is present on a first nucleic acid molecule, e.g., a vector, e.g., a viral vector, e.g., a lenti-viral vector, and (b) and (a) are present on a second nucleic acid molecule, e.g., a vector, e.g., a viral vector, e.g., a lenti-viral vector. In one embodiment, each of (a), (b), and (c) are present on different nucleic acid molecules, e.g., different vectors, e.g., viral vectors, e.g., a lenti-viral vectors.

In an embodiment, (i) the antigen binding domain of one of said first KIR-CAR said second KIR-CAR does not comprise a light chain variable domain and a heavy chain variable domain, (ii) the antigen binding domain of one of said first KIR-CAR said second KIR-CAR is an scFv, and the other is other is other than an scFv, (iii) when present on the surface of a cell, the antigen binding domains of said first KIR-CAR and said second KIR-CAR, associate with one another less than if both were scFv antigen binding domains, (iv) wherein, when present on the surface of a cell, binding of the antigen binding domain of said first KIR-CAR to its cognate antigen is not substantially reduced by the presence of said second KIR-CAR, (v) the antigen binding domain of one of said first KIR-CAR said second KIR-CAR, comprises a single VH domain, e.g., a camelid, shark, or lamprey single VH domain, or a single VH domain derived from a human or mouse sequence, or a non-antibody scaffold, e.g., a fibronectin, e.g., a fibronectin type III antibody-like molecule, (vi) the antigen binding domain of one of said first KIR-CAR said second KIR-CAR, is an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vii) the antigen binding domain of one of said first KIR-CAR said second KIR-CAR, is an scFv, and the other comprises a nanobody, or (viii) the antigen binding domain of one of said first KIR-CAR said second KIR-CAR, is an scFv, and the other comprises a camelid VHH domain.

In one embodiment, the antigen binding domain of one of said first KIR-CAR said second KIR-CAR does not comprise a light chain variable domain and a heavy chain variable domain. In one embodiment, the antigen binding domain of one of said first KIR-CAR said second KIR-CAR is an scFv, and the other is other than an scFv. In one embodiment, when present on the surface of a cell, the antigen binding domains of said first KIR-CAR said second KIR-CAR, associate with one another less than if both were scFv antigen binding domains. In one embodiment, when present on the surface of a cell, binding of the antigen binding domain of said first KIR-CAR to its cognate antigen is not substantially reduced by the presence of said second KIR-CAR. In one embodiment, the antigen binding domain of one of said first KIR-CAR said second KIR-CAR, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said first KIR-CAR said second KIR-CAR, is an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said first KIR-CAR said second KIR-CAR, is an scFv, and the other comprises a nanobody. In one embodiment, the antigen binding domain of one of said first KIR-CAR said second KIR-CAR, is an scFv, and the other comprises a camelid VHH domain.

In a embodiment the nucleic acid comprises a sequence that encodes a TCAR. In one embodiment, said TCAR comprises an antigen binding domain and an activating cytoplasmic domain from the T cell receptor complex with CD3 e.g. CD3 zeta chain, CD3 epsilon chain, CD3 gamma chain, CD3 delta chain. In one embodiment, said TCAR comprises a costimulatory domain from costimulatory receptor e.g. CD28, CD137, CD27, ICOS or OX40.

In an embodiment (i) the antigen binding domain of one of said KIR-CAR said TCAR does not comprise a light chain variable domain and a heavy chain variable domain, (ii) the antigen binding domain of one of said KIR-CAR said TCAR is an scFv, and the other is other than an scFv, (iii) when present on the surface of a cell, the antigen binding domains of said KIR-CAR and said TCAR, associate with one another less than if both were scFv antigen binding domains, (iv) when present on the surface of a cell, binding of the antigen binding domain of said KIR-CAR to its cognate antigen is not substantially reduced by the presence of said second TCAR, (v) the antigen binding domain of one of said KIR-CAR said TCAR, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vi) the antigen binding domain of one of said KIR-CAR said TCAR, is an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vii) the antigen binding domain of one of said KIR-CAR said TCAR, is an scFv, and the other comprises a nanobody, or (viii) wherein, the antigen binding domain of one of said KIR-CAR said TCAR, is an scFv, and the other comprises a camelid VHH domain. In one embodiment, the antigen binding domain of one of said KIR-CAR said TCAR does not comprise a light chain variable domain and a heavy chain variable domain.

In one embodiment, the antigen-binding domain of one of said KIR-CAR said TCAR is an scFv, and the other is other than an scFv. In one embodiment, when present on the surface of a cell, the antigen binding domains of said KIR-CAR said TCAR, associate with one another less than if both were scFv antigen binding domains. In one embodiment, when present on the surface of a cell, binding of the antigen binding domain of said KIR-CAR to its cognate antigen is not substantially reduced by the presence of said second TCAR. In one embodiment, the antigen binding domain of one of said KIR-CAR said TCAR, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said KIR-CAR said TCAR, is an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said KIR-CAR said TCAR, is an scFv, and the other comprises a nanobody. In one embodiment, the antigen binding domain of one of said KIR-CAR said TCAR, is an scFv, and the other comprises a camelid VHH domain.

In another aspect, the invention features a cytotoxic cell, e.g., a naturally or non-naturally occurring T cell, NK cell or cytotoxic T cell or cell of an NK cell line, e.g., NK92, comprising (a) a first KIR-CAR described herein. In one embodiment, said cytotoxic cell is T cell. In one embodiment, said cytotoxic cell is an NK cell. In one embodiment, said cytotoxic cell is from an NK cell line, e.g., an NK92 cell. In one embodiment, In one embodiment, said first KIR-CAR is an actKIR-CAR described herein. In one embodiment, In one embodiment, said first KIR-CAR is an inhKIR-CAR described herein.

In an embodiment, said cytotoxic cell comprises a KIR-CAR, e.g., an actKIR-CAR, and an inhibitory molecule comprising: an inhKIR cytoplasmic domain; a transmembrane domain, e.g., a KIR transmembrane domain; and an inhibitor cytoplasmic domain, e.g., an ITIM domain, e.g., an inhKIR ITIM domain. In an embodiment the inhibitory molecule is a naturally occurring inhKIR, or a sequence sharing at least 50, 60, 70, 80, 85, 90, 95, or 99% homology with, or that differs by no more than 1, 2, 3, 4, 5, 6, 7, 8, 9, 10, 15, or 20 residues from, a naturally occurring inhKIR.

In an embodiment, said cytotoxic cell comprises a KIR-CAR, e.g., an actKIR-CAR, and an inhibitory molecule comprising: a SLAM family cytoplasmic domain; a transmembrane domain, e.g., a SLAM family transmembrane domain; and an inhibitor cytoplasmic domain, e.g., a SLAM family domain, e.g., an SLAM family ITIM domain. In an embodiment the inhibitory molecule is a naturally occurring SLAM family member, or a sequence sharing at least 50, 60, 70, 80, 85, 90, 95, or 99% homology with, or that differs by no more than 1, 2, 3, 4, 5, In one embodiment, the cytotoxic cell further comprises (b) a second KIR-CAR described herein, e.g., a second KIR-CAR that is different from said first KIR-CAR. In one embodiment, one of said KIR-CAR and said second KIR-CAR is an actKIR-CAR and the other is an inhKIR-CAR. In one embodiment, said actKIR-CAR is an actKIR-CAR described herein. In one embodiment, one of said inhKIR-CAR is an inhKIR-CAR described herein. In one embodiment, the cytotoxic cell described herein comprises actKIR-CAR described herein and an inhKIR-CAR described herein.

In an embodiment the cytotoxic cell further comprises an intracellular signaling domain, e.g., an adaptor molecule, which can produce an activating signal, e.g., which is exogenous to said cell, which can produce an activating signal. In one embodiment, said intracellular signaling domain comprises an ITAM motif. In one embodiment, said intracellular signaling domain comprises a DAP 12 polypeptide comprising DAP 12 intracellular signaling domain. In one embodiment, said DAP 12 polypeptide further comprises a transmembrane domain. In one embodiment, said DAP 12 polypeptide further comprises an extracellular domain.

In an embodiment a cytotoxic cell comprises a first and second KIR-CAR described herein wherein (i) the antigen binding domain of one of said first KIR-CAR said second KIR-CAR does not comprise a light chain variable domain and a heavy chain variable domain, (ii) the antigen binding domain of one of said first KIR-CAR said second KIR-CAR is an scFv, and the other is other than an scFv, (iii) when present on the surface of a cell, the antigen binding domains of said first KIR-CAR and said second KIR-CAR, associate with one another less than if both were scFv antigen binding domains, (iv) when present on the surface of a cell, binding of the antigen binding domain of said first KIR-CAR to its cognate antigen is not substantially reduced by the presence of said second KIR-CAR, (v) the antigen binding domain of one of said first KIR-CAR said second KIR-CAR, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vi) the antigen binding domain of one of said first KIR-CAR said second KIR-CAR, comprises an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vii) wherein, the antigen binding domain of one of said first KIR-CAR said second KIR-CAR, comprises an scFv, and the other comprises a nanobody, or (viii) the antigen binding domain of one of said first KIR-CAR said second KIR-CAR, comprises an scFv, and the other comprises a camelid VHH domain.

In one embodiment, the antigen binding domain of one of said first KIR-CAR said second KIR-CAR does not comprise a light chain variable domain and a heavy chain variable domain. In one embodiment, the antigen-binding domain of one of said first KIR-CAR said second KIR-CAR is an scFv, and the other is other than an scFv. In one embodiment, when present on the surface of a cell, the antigen binding domains of said first KIR-CAR said second KIR-CAR, associate with one another less than if both were scFv antigen binding domains. In one embodiment, when present on the surface of a cell, binding of the antigen binding domain of said first KIR-CAR to its cognate antigen is not substantially reduced by the presence of said second KIR-CAR. In one embodiment, the antigen binding domain of one of said first KIR-CAR said second KIR-CAR, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said first KIR-CAR said second KIR-CAR, comprises an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen-binding domain of one of said first KIR-CAR said second KIR-CAR, comprises an scFv, and the other comprises a nanobody. In one embodiment, the antigen-binding domain of one of said first KIR-CAR said second KIR-CAR, comprises an scFv, and the other comprises a camelid VHH domain.

In an embodiment a cytotoxic cell comprises KIR-CARs as described herein and further comprises a TCAR. In one embodiment, said TCAR comprises an antigen binding domain and a primary stimulation domain. In one embodiment, said TCAR comprises a costimulation domain.

In an embodiment the cytotoxic cell, e.g., a naturally or non-naturally occurring T cell, NK cell or cytotoxic T cell or NK cell line, e.g., an NK92 cell, comprises a nucleic acid as described herein; or a KIR-CAR encoded by a nucleic acid described herein. In one embodiment, said cytotoxic cell is T cell. In one embodiment, said cytotoxic cell is an NK cell. In one embodiment, said cytotoxic cell is from an NK cell line, e.g., NK92.

In another aspect, the invention features methods of making a cell described herein comprising, introducing into a cytotoxic cell, a nucleic acid described herein into said cell. In one embodiment, said method comprises forming in a cytotoxic cell, a KIR-CAR described herein.

In another aspect, the invention features methods of treating a subject, e.g., a method of providing an anti-tumor immunity in a mammal, comprising administering to the mammal an effective amount of a cell described herein. In one embodiment, said cell is autologous. In one embodiment, said cell is allogenic. In one embodiment, the cell is T cell, e.g., an autologous T cell. In one embodiment, the cell is an allogeneic T cell. In one embodiment, the cell is an NK cell, e.g., an autologous NK cell. In one embodiment, the cell is an allogeneic NK cell. In one embodiment, the cell is cell from an NK cell line, e.g., NK92. In one embodiment, said mammal is a human. In one embodiment, the method further comprises evaluating said mammal, e.g., human, for a side effect of said treatment. In one embodiment, said side effect comprises acute respiratory distress syndrome, febrile neutropenia, hypotension, encephalopathy, hepatic transaminitis, seizure, or macrophage activation syndrome. In one embodiment, the method further comprises treating said human having a side effect with anti-cytokine agent, e.g., a tumor necrosis factor antagonist, e.g., a TNF-Ig fusion, e.g., etanercept, an IL-6 antagonist, e.g., an IL-6 receptor antagonist, e.g., an anti-IL6 receptor antibody, e.g., tocilizumab, or a corticosteroid. In one embodiment, treating comprises administering an anti-IL6 receptor antibody to said human. In one embodiment, the method comprises treating a mammal, e.g., a human, having a disease associated with expression of mesothelin or CD19. In one embodiment, the method comprises treating a mammal, e.g., a human, having a disorder associated with unwanted cell proliferation, e.g., cancer. In one embodiment, said disorder is pancreatic carcinoma, mesothelioma, lung carcinoma, ovarian carcinoma, leukemia or lymphoma.

In another aspect, the invention features a purified, or non-naturally occurring, NCR-CAR, e.g., an activating NCR-CAR, comprising an extra-cellular antigen binding domain, a transmembrane domain, e.g., a transmembrane domain comprising a positively charged moiety, e.g., an amino acid residue comprising a positively charged moiety, e.g., a positively charged side chain or an NCR transmembrane domain, and a cytoplasmic domain, e.g., a NCR cytoplasmic domain. In one embodiment, said NCR-CAR comprises an a transmembrane domain comprising a positively charged moiety, e.g., an amino acid residue comprising a positively charged moiety, e.g., a positively charged side chain, e.g., NCR transmembrane domain, e.g., a NKp30, NKp44, or NKp46 cytoplasmic domain. In one embodiment, said NCR-CAR comprises a cytoplasmic domain which can interact with an adaptor molecule or intracellular signaling molecule comprising, e.g., a DAP12, FcRγ or CD3 ζ cytoplasmic domain. In one embodiment, said NCR-CAR, e.g., a NKp30-CAR, comprises a transmembrane domain which can interact with an adaptor molecule or intracellular signaling molecule, e.g., DAP12. In one embodiment, said NCR-CAR comprises a NKp46-CAR. In one embodiment, said NKp46-CAR, comprises a transmembrane domain comprising a positively charged moiety, e.g., an amino acid residue comprising a positively charged moiety, e.g., a positively charged side chain or, e.g., an NCR transmembrane domain, which can interact with an adaptor molecule or intracellular signaling molecule, e.g., one having a FcRγ or CD3 ζ cytoplasmic domain. In one embodiment, said NCR-CAR described herein further comprises a hinge domain disposed between said transmembrane domain and said an extra-cellular antigen binding domain.

In another aspect, the invention features a nucleic acid, e.g., a purified or non-naturally occurring, nucleic acid, e.g., a nucleic acid comprising a DNA, or RNA, sequence, e.g., a mRNA, comprising a sequence that encodes a NCR-CAR described herein. In one embodiment, the nucleic acid comprises a sequence that encodes a NKp30-CAR and optionally, an adaptor molecule or intracellular signaling molecule, e.g., DAP12. In one embodiment, said NCR-CAR, e.g., NKp46-CAR, comprises a transmembrane domain comprising a positively charged moiety, e.g., an amino acid residue comprising a positively charged moiety, e.g., a positively charged side chain or an NCR transmembrane domain which can interact with an adaptor molecule or intracellular signaling molecule, e.g., a FcRγ or CD3 ζ molecule. In one embodiment, the nucleic acid further comprises sequence encoding an adaptor molecule or intracellular signaling molecule, which e.g., comprises a DAP12, FcRγ or CD3 ζ.

In another aspect, the invention features a cytotoxic cell, e.g., a naturally or non-naturally occurring T cell, NK cell or cytotoxic T cell or NK cell line comprising a NCR-CAR described herein. In one embodiment, the cytotoxic cell further comprises an adaptor molecule or intracellular signaling molecule, which e.g., comprises a DAP12, FcRγ or CD3 ζ cytoplasmic domain. In one embodiment, the cytotoxic cell comprises a NKp30-CAR and optionally, an adaptor molecule or intracellular signaling molecule, e.g., DAP12. In one embodiment, said NKp46-CAR comprises a transmembrane domain which can interact with an adaptor molecule or intracellular signaling molecule, e.g., a FcRγ or CD3 ζ molecule.

In another aspect, the invention features a method of making a cell described herein comprising, introducing into a cytotoxic cell, a nucleic acid comprising a sequence that encodes a NCR-CAR described herein. In one embodiment, the method comprises forming in a cytotoxic cell, a NCR-CAR described herein.

In another aspect, the invention features a method of treating a subject, e.g., a method of providing an anti-tumor immunity in a mammal, comprising administering to the mammal an effective amount of a cell described herein, e.g., a cell of claim described herein comprising NCR-CAR described herein.

In another aspect, the invention features a purified, or non-naturally occurring, SLAMF-CAR, e.g., an inhibitory SLAMF-CAR, comprising an extra-cellular antigen binding domain, a transmembrane domain, e.g., a transmembrane domain comprising a positively charged moiety, e.g., an amino acid residue comprising a positively charged moiety, e.g., a positively charged side chain, e.g., a SLAMF transmembrane domain, and a SLAMF cytoplasmic domain. In one embodiment, said SLAMF-CAR comprises a SLAMF, CD48, CD229, 2B4, CD84, NTB-A, CRACC, BLAME, or CD2F-10 cytoplasmic domain. In one embodiment, said SLAMF-CAR further comprises a hinge domain, disposed between said transmembrane domain and said an extra-cellular antigen binding domain.

In another aspect, the invention features a nucleic acid, e.g., a purified or non-naturally occurring, nucleic acid, e.g., a nucleic acid comprising a DNA, or RNA, sequence, e.g., a mRNA, comprising a sequence that encodes a SLAMF-CAR described herein.

In another aspect, the invention features a cytotoxic cell, e.g., a naturally or non-naturally occurring T cell, NK cell or cytotoxic T cell or NK cell line comprising a SLAMF-CAR described herein.

In another aspect, the invention features a method of making a cytotoxic cell comprising a SLAMF-CAR described herein, comprising, introducing into a cytotoxic cell a nucleic acid comprising a sequence that encodes a SLAMF-CAR described herein. In one embodiment, the method comprises forming in a cytotoxic cell, a SLAMF-CAR described herein.

In another aspect, the invention features a method of treating a subject, e.g., a method of providing an anti-tumor immunity in a mammal, comprising administering to the mammal an effective amount of a cell comprising a SLAMF-CAR described herein.

In another aspect, the invention features a purified, or non-naturally occurring, FcR-CAR, e.g., CD16-CAR, e.g., an activating CD16-CAR or a CD64-CAR, e.g., an activating CD64-CAR, comprising an extra-cellular antigen binding domain, a transmembrane domain, and a CD16 or CD64 cytoplasmic domain. In one embodiment, said FcR-CAR is a CD16-CAR. In one embodiment, said FcR-CAR is a CD64-CAR. In one embodiment, said FcR-CAR can interact with an adaptor molecule or intracellular signaling molecule, e.g., a FcRγ or CD3 ζ domain, e.g., via a transmembrane domain, e.g., a transmembrane domain comprising a positively charged moiety, e.g., an amino acid residue comprising a positively charged moiety, e.g., a positively charged side chain or e.g., a CD16 or CD64 transmembrane domain. In one embodiment, said FcR-CAR further comprises a hinge domain, disposed between said transmembrane domain and said an extra-cellular antigen binding domain.

In another aspect, the invention features a purified or non-naturally occurring, nucleic acid, e.g., a nucleic acid comprising a DNA, or RNA, sequence, e.g., a mRNA comprising a sequence that encodes a FcR-CAR described herein. In one embodiment, the nucleic acid further comprises an adaptor molecule or intracellular signaling molecule comprising a cytoplasmic activation domain, e.g., FcRγ or CD3 ζ cytoplasmic domain. In one embodiment, said FcR-CAR and said cytoplasmic activation domain are disposed on separated nucleic acid molecules, e.g., separate vectors, e.g., separate viral vectors, e.g., separate lenti-viral vectors.

In another aspect, the invention features a cytotoxic cell, e.g., a naturally or non-naturally occurring T cell, NK cell or cytotoxic T cell or NK cell line comprising a FcR-CAR described herein. In one embodiment, the cytotoxic cell further comprises a cytoplasmic activation domain, e.g., FcRγ or CD3 ζ cytoplasmic domain.

In another aspect, the invention features a method of making a cell comprising a FcR-CAR described herein, comprising, introducing into a cytotoxic cell, a nucleic acid comprising a sequence that encodes a FcR-CAR described herein. In one embodiment, the method comprises forming in a cytotoxic cell, a FcR-CAR described herein.

In another aspect, the invention features a method of treating a subject, e.g., a method of providing an anti-tumor immunity in a mammal, comprising administering to the mammal an effective amount of a cell comprising a FcR-CAR described herein.

In another aspect, the invention features purified, or non-naturally occurring, Ly49-CAR comprising an extra-cellular antigen binding domain, and a transmembrane domain, e.g., a Ly49-transmembrane domain, or a cytoplasmic domain, e.g., an ITIM-containing cytoplasmic domain, e.g., a Ly49-cytoplasmic domain. In one embodiment, the Ly49-CAR comprises a transmembrane domain and a Ly49-cytoplasmic domain. In one embodiment, said Ly49-CAR is an activating Ly49-CAR, e.g., Ly49D or Ly49H. In one embodiment, said Ly49-CAR comprises a positively charged transmembrane domain, e.g., a positively charged Ly49 transmembrane domain. In one embodiment, said Ly49-CAR can interact with an ITAM-containing cytoplasmic domain, e.g., DAP 12. In one embodiment, said Ly49-CAR comprises a Ly49-transmembrane domain. In one embodiment, said KIR-CAR is an inhibitory Ly49-CAR, e.g., Ly49A or Ly49C. In one embodiment, said Ly49-CAR comprises an ITIM-containing cytoplasmic domain, e.g., a Ly49-cytoplasmic domain. In one embodiment, said Ly49-CAR comprises a Ly49-transmembrane domain or a Ly49-cytoplasmic domain selected, independently from Ly49A-Ly49W. In one embodiment, said Ly49-CAR further comprises a hinge domain, disposed between said transmembrane domain and said an extra-cellular antigen binding domain.

In another aspect, the invention features a nucleic acid, e.g., a purified or non-naturally occurring, nucleic acid, e.g., a nucleic acid comprising a DNA, or RNA, sequence, e.g., a mRNA, comprising a sequence that encodes a Ly49-CAR described herein. In one embodiment, the nucleic acid further comprises a cytoplasmic activation domain, e.g., DAP12 cytoplasmic domain. In one embodiment, said Ly49-CAR and said cytoplasmic activation domain are disposed on separate nucleic acid molecules, e.g., separate vectors, e.g., separate viral vectors, e.g., separate lenti-viral vectors.

In another aspect, the invention features a cytotoxic cell, e.g., a naturally or non-naturally occurring T cell, NK cell or cytotoxic T cell or NK cell line comprising a Ly49-CAR described herein. In one embodiment, the cytotoxic cell further comprises a cytoplasmic activation domain, e.g., DAP12 cytoplasmic domain.

In another aspect, the invention features a method of making a cell comprising a Ly49-CAR described herein, comprising, introducing into a cytotoxic cell, a nucleic acid comprising a sequence that encodes a Ly49-CAR described herein into said cell.

In another aspect, the invention features a method of making a cell comprising a Ly49-CAR described herein, comprising, forming in a cytotoxic cell, a Ly49-CAR described herein.

In another aspect, the invention features a method of treating a subject, e.g., a method of providing an anti-tumor immunity in a mammal, comprising administering to the mammal an effective amount of a cell described herein, e.g., a cell comprising a Ly49-CAR described herein.

In another aspect, the invention features a cell comprising, e.g., a cytotoxic cell, comprising a first non-naturally occurring chimeric membrane embedded receptor comprising an antigen binding domain and a second non-naturally occurring chimeric membrane embedded receptor comprising an antigen binding domain wherein, (i) the antigen binding domain of one of said first and said second non-naturally occurring chimeric membrane embedded receptor does not comprise a light chain variable domain and a heavy chain variable domain, (ii) the antigen binding domain of one of said first and said second non-naturally occurring chimeric membrane embedded receptor comprises an scFv, and the other is other than an scFv, (iii) when present on the surface of a cell, the antigen binding domains of said first and said second non-naturally occurring chimeric membrane embedded receptor, associate with one another less than if both were scFv antigen binding domains, (iv) when present on the surface of a cell, binding of the antigen binding domain of said first non-naturally occurring chimeric membrane embedded receptor to its cognate antigen is not substantially reduced by the presence of said second non-naturally occurring chimeric membrane embedded receptor, (v) the antigen binding domain of one of said first and said second non-naturally occurring chimeric membrane embedded receptor, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vi) the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule, (vii) the antigen binding domain of one of said first and said second non-naturally occurring chimeric membrane embedded receptor, comprises an scFv, and the other comprises a nanobody, and (viii) the antigen binding domain of one of said first and said second non-naturally occurring chimeric membrane embedded receptor, comprises an scFv, and the other comprises a camelid VHH domain. In one embodiment, said cell is T cell. In one embodiment, said cell is an NK cell. In one embodiment, said cell is from an NK cell line, e.g., NK92. In one embodiment, one of said first and said second non-naturally occurring chimeric membrane embedded receptors is a TCAR. In one embodiment, both of said first and said second non-naturally occurring chimeric membrane embedded receptors is a TCAR. In one embodiment, one of said first and said second non-naturally occurring chimeric membrane embedded receptors is a NKR-CAR, e.g., a KIR-CAR. In one embodiment, both of said first and said second non-naturally occurring chimeric membrane embedded receptors is a NKR-CAR, e.g., a KIR-CAR. In one embodiment, the antigen binding domain of one of said first and said second non-naturally occurring chimeric membrane embedded receptor does not comprise a light chain variable domain and a heavy chain variable domain. In one embodiment, when present on the surface of a cell, the antigen binding domains of said first and said second non-naturally occurring chimeric membrane embedded receptor, associate with one another less than if both were scFv antigen binding domains. In one embodiment, when present on the surface of a cell, binding of the antigen binding domain of said first non-naturally occurring chimeric membrane embedded receptor to its cognate antigen is not substantially reduced by the presence of said second non-naturally occurring chimeric membrane embedded receptor. In one embodiment, the antigen binding domain of one of said first and said second non-naturally occurring chimeric membrane embedded receptor, comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said first said second non-naturally occurring chimeric membrane embedded receptor, comprises an scFv, and the other comprises a single VH domain, e.g., a camelid, shark, or lamprey single VH domain, or a single VH domain derived from a human or mouse sequence or a non-antibody scaffold, e.g., a fibronectin, e.g., a fibronectin type III antibody-like molecule. In one embodiment, the antigen binding domain of one of said first and said second non-naturally occurring chimeric membrane embedded receptor, comprises an scFv, and the other comprises a nanobody. In one embodiment, the antigen binding domain of one of said first and said second non-naturally occurring chimeric membrane embedded receptor, comprises an scFv, and the other comprises a camelid VHH domain. In one embodiment, the invention comprises a nucleic acid, e.g., a purified or non-naturally occurring, nucleic acid, comprising a sequence that encodes a first and second non-naturally occurring chimeric membrane embedded receptor comprising an antigen binding domain described herein. In one embodiment, the invention comprises a method of making a cell described herein comprised introducing into a cell the nucleic acid described herein. In one embodiment, the invention comprises a method of making a cell described herein, comprising, forming in a cytotoxic cell, a first and said second non-naturally occurring chimeric membrane embedded receptor described herein. In one embodiment, the invention comprises a method of treating a subject e.g., a method of providing an anti-tumor immunity in a mammal, comprising administering to the mammal an effective amount of a cell described herein.

In another aspect, the invention features a kit comprising a cell or nucleic acid described herein.

In another aspect, the invention features an isolated nucleic acid sequence encoding a KIR-CAR (killer cell immunoglobulin receptor-like-chimeric antigen receptor), wherein the isolated nucleic acid sequence comprises the nucleic acid sequence of an antigen binding domain and a KIR or fragment thereof. In one embodiment, the antigen binding domain is selected from the group consisting of a murine antibody, a humanized antibody, a human antibody, a chimeric antibody, and a fragment thereof. In one embodiment, the fragment is a Fab or an scFv. In one embodiment, the KIR is selected from the group consisting of an activating KIR, an inhibitory KIR, and any combination thereof. In one embodiment, at least one hinge region has been removed from the activating KIR.

In another aspect, the invention features an isolated KIR-CAR (killer cell immunoglobulin-like receptor-chimeric antigen receptor) comprising an antigen binding domain and a KIR or fragment thereof. In one embodiment, the antigen binding domain is selected from the group consisting of a murine antibody, a humanized antibody, a human antibody, a chimeric antibody, and a fragment thereof. In one embodiment, the fragment is a Fab or an scFv. In one embodiment, the KIR is selected from the group consisting of an activating KIR, an inhibitory KIR, and any combination thereof. In one embodiment, at least one hinge region has been removed from the activating KIR. In another aspect, the invention features a composition comprising at least two KIR-CARs, wherein the first KIR-CAR comprises an antigen binding domain and an activating KIR or fragment thereof and the second KIR-CAR comprises an antigen binding domain and an inhibitory KIR or fragment thereof. In one embodiment, the antigen binding domain in the first KIR-CAR is specific for an antigen present on a tumor and the antigen binding domain in the second KIR-CAR is specific for an antigen present on a normal cell.

In another aspect, the invention features a genetically modified T cell comprising at least two KIR-CARs, wherein the first KIR-CAR comprises an antigen binding domain and an activating KIR or fragment thereof and the second KIR-CAR comprises an antigen binding domain and an inhibitory KIR or fragment thereof. In one embodiment, the antigen binding domain in the first KIR-CAR is specific for an antigen present on a tumor and the antigen binding domain in the second KIR-CAR is specific for an antigen present on a normal cell. In one embodiment, the cell is a T cell.

In another aspect, the invention features a method of providing an anti-tumor immunity in a mammal, the method comprising administering to the mammal an effective amount of a cell comprising at least two KIR-CARs, wherein the first KIR-CAR comprises an antigen binding domain and an activating KIR or fragment thereof and the second KIR-CAR comprises an antigen binding domain and an inhibitory KIR or fragment thereof. In one embodiment, the antigen binding domain in the first KIR-CAR is specific for an antigen present on a tumor and the antigen binding domain in the second KIR-CAR is specific for an antigen present on a normal cell, thereby controlling the off-target activity of the cell. In one embodiment, the cell is a T cell.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A and 1B, is a series of schematics showing the structure of naturally occurring inhibitory and activating KIRs (FIG. 1A) and a scFv-based activating KIR-CAR (FIG. 1B).

FIGS. 5A and 5B, is a series of schematics showing an activating KIR CAR in which the KIR2DS2 hinge was removed (KIR2S CAR). Based upon the kinetic segregation model of TCR activation diagrammed in FIG. 5A, it is believed that the mesothelin-specific SS1 KIR CAR has a hinge that is too long to permit appropriate segregation. Therefore making the mesothelin-specific KIR CAR hinge shorter is believed to improve the function. FIG. 5B is a schematic showing that the SS1 scFv was fused to the KIR transmembrane domain without the two Ig-like domains from KIR2DS2 as the hinge.

FIGS. 6A and 6B, is a series of images demonstrating that SS1 scFv based KIRS2 CAR exhibits enhanced cytolytic activity towards mesothelin-expressing target cells compared with the CAR formed by fusion of the SS1 scFv onto full length wildtype KIR2DS2. Primary human T cells were stimulated with CD3/28 microbeads followed by lentiviral transduction with either the SS1-KIR2DS2 activating KIR-CAR, SS1-KIRS2 activating KIR CAR, the SS1-zeta CAR. Mock non-transduced T cells (NTD) were used as a control. The T cells were expanded until the end of log-phase growth. The surface expression of the SS1-specific CARs was determined by flow cytometry using a biotinylated goat anti-mouse F(ab)2 specific polyclonal antibody followed by streptavidin-PE detection as shown in FIG. 6A. Shown in FIG. 6B, K562 target cells with or without mesothelin and stained with CFSE were mixed with the effector T cells characterized in FIG. 6A as indicated using varying effector T cell to target ratios ranging from 10:1 to 1:1. Target K562 cell lysis was assessed using flow cytometry to determine the % of viable CFSE+ cells as described for FIG. 4. Data shown is the calculated % target cell lysis compared against target cells without effector cells.

FIGS. 7A and 7B, is a series of images showing co-expression of the CD19 actKIR-CAR and the SS1 inhKIR-CAR. Jurkat NFAT-GFP reporter cells were transduced with the indicated KIR CAR or non-transduced (NDT) and mixed 1:1 with target cells with or without the CD19 and mesothelin antigens as indicated. Results shows GFP expression at 24 hours following mixing of Jurkat and Target cells (FIG. 7A). FIG. 7B shows surface expression of the mesothelin and CD19 idiotypes as determined by staining with a mesothelin-Fc fusion protein and a monoclonal antibody specific for the FMC63 anti-CD19 scFv idiotype.

FIGS. 8A through 8C, is a series of images demonstrating co-expression of wild-type PD-1 with both an activating KIR-based CAR or TCR-zeta based CAR targeting mesothelin. Primary human T cells were stimulated with CD3/28 microbeads followed by lentiviral transduction with either the SS1-KIRS2 activating KIR CAR or the SS1-zeta CAR. Mock non-transduced cells (NTD) were used as a negative control. The T cells were expanded over 9 days, and surface CAR expression was determined by staining with mesothelin-Fc followed by a goat-anti-human Fc specific antibody conjugated to PE (FIG. 8A). K562 cell lines (wildtype [wt], mesothelin expressing [meso] or mesothelin and PD-L1 co-expressing [meso-PDL1]) were stained using the CAK1 anti-mesothelin specific monoclonal antibody to confirm mesothelin expression on the targets (FIG. 8B). The primary human T cells transduced as shown in FIG. 8A were electroporated with 10 ug of in vitro transcribed RNA encoding wild-type PD1 using a BTX ECM830 electroporator (PD1+) or mock transfected (PD1−). The surface expression of PD-1 was expressed using an anti-PD1 monoclonal conjugated to APC (FIG. 8C).

FIGS. 12A-12B, depicts construction of a mesothelin-specific KIR-based chimeric antigen receptor (KIR-CAR) engineered T cell with robust cytotoxic activity. Primary human T cells were stimulated with CD3/28 microbeads followed by transduction with a lentiviral vector expressing either GFP and dsRed (Control) or DAP12 and dsRed (DAP12). The cells were expanded ex vivo until the end of log phase growth. $5\times10^6$ T cells from each transduced population were electroporated with 10 ug of in vitro transcribed RNA encoding SS1-KIRS2 using a BTX ECM830 electroporator. The expression of both dsRed and SS1-KIRS2 was assessed by flow cytometry with the SS1-KIRS2 detected using a biotinylated goat anti-mouse F(ab)2 specific polyclonal antibody followed by streptavidin-PE. The upper panel of FIG. 12A shows the gating strategy for identification of T cells expressing dsRed, which were then analyzed for SS1-KIRS2 expression as shown in the lower portion of the panel. FIG. 12B shows the ability of the cells characterized in FIG. 12A to mediate cytotoxicity against wild-type K562 cells (K562-wt) or K562 cells that express mesothelin (K562-mesothelin) as assessed using a 4-hr $^{51}Cr$-release assay.

FIG. 15A shows an experiment in which NOD-SCID-$\gamma_c^{-/-}$ (NSG) mice were subcutaneously implanted with a mesothelioma-derived cell expressing mesothelin (EM-meso cells). 20 days following tumor implantation, each animal was injected intravenously with 7 million T cells that were stimulated with anti-CD3/anti-CD28 stimulator beads followed lentiviral transduction with a series of CD3ζ-based CAR with or without a costimulatory domain (SS1-ζ, SS1-BBζ and SS1-28ζ) or the mesothelin-specific KIR-based CARs, SS1-KIRS2 with DAP12. Mock transduced T cells (NTD) were used as a control. Tumor volume was assessed via caliper measurement. 8 animals were analyzed for each T cell condition FIG. 15B shows that the in vivo activity of the KIR-CAR is independent of T cell engraftment in blood, spleen or tumor. The frequency of human CD45+ T cells was assessed at the end of the experiment by flow cytometry, and data are expressed as a percentage of total viable cells in the blood, spleen and tumor digest. FIG. 15C shows that DAP12-modified T cells require the mesothelin-specific KIR-based CAR for tumor eradication. The same model as that shown in FIG. 15A was used. 4 million T cells expressing DAP12 and dsRed (DAP12), SS1-28z or SS1-KIRS2 and DAP12 (SS1-KIRS2) were injected intravenously on day 20, and tumor volume was assessed over time via caliper measurement.

FIGS. 17A-17B shows CD19-KIRS2 in vivo activity. NOD-SCID-$\gamma_c^{-/-}$ (NSG) mice were engrafted intravenously by tail vein injection on day 0 of 1 million Nalm-6 CBG tumor cells, a leukemic cell line expressing CD19. T cells were stimulated with anti-CD3/anti-CD28 stimulator beads followed by lentiviral transduction on day 1 with a series of CD19-specific CD3ζ-based CAR with or without a costimulatory domain (CD19z, 19BBz) or the CD19-specific KIR-based CARs, CD19-KIRS2 with DAP12 (19KIRS2). Mock non-transduced T cells (NTD) were used as a control. The T cells were expanded until the end of log-phase growth ex vivo and injected intravenously on day 5 post leukemic cell line injection with 2 million CAR T cells per mouse. Tumor burden was assessed via bioluminescent imaging. 5 animals were analyzed for each T cell condition. FIG. 17A shows the individual bioluminescent photon flux for individual animals on day 5 (baseline prior to T cell injection) and at day 15 following leukemic cell engraftment. FIG. 17B shows the median total flux for each treatment group over time.

FIGS. 27A-27B, depict the putative mechanism for loss of scFv binding when two scFv molecules are co-expressed on the cell surface (FIG. 27A) and the putative avoidance of this interaction when a camelid single VHH domain-based CAR is expressed on a T cell surface in combination with a scFv-based CAR.

DETAILED DESCRIPTION

Figure 1:
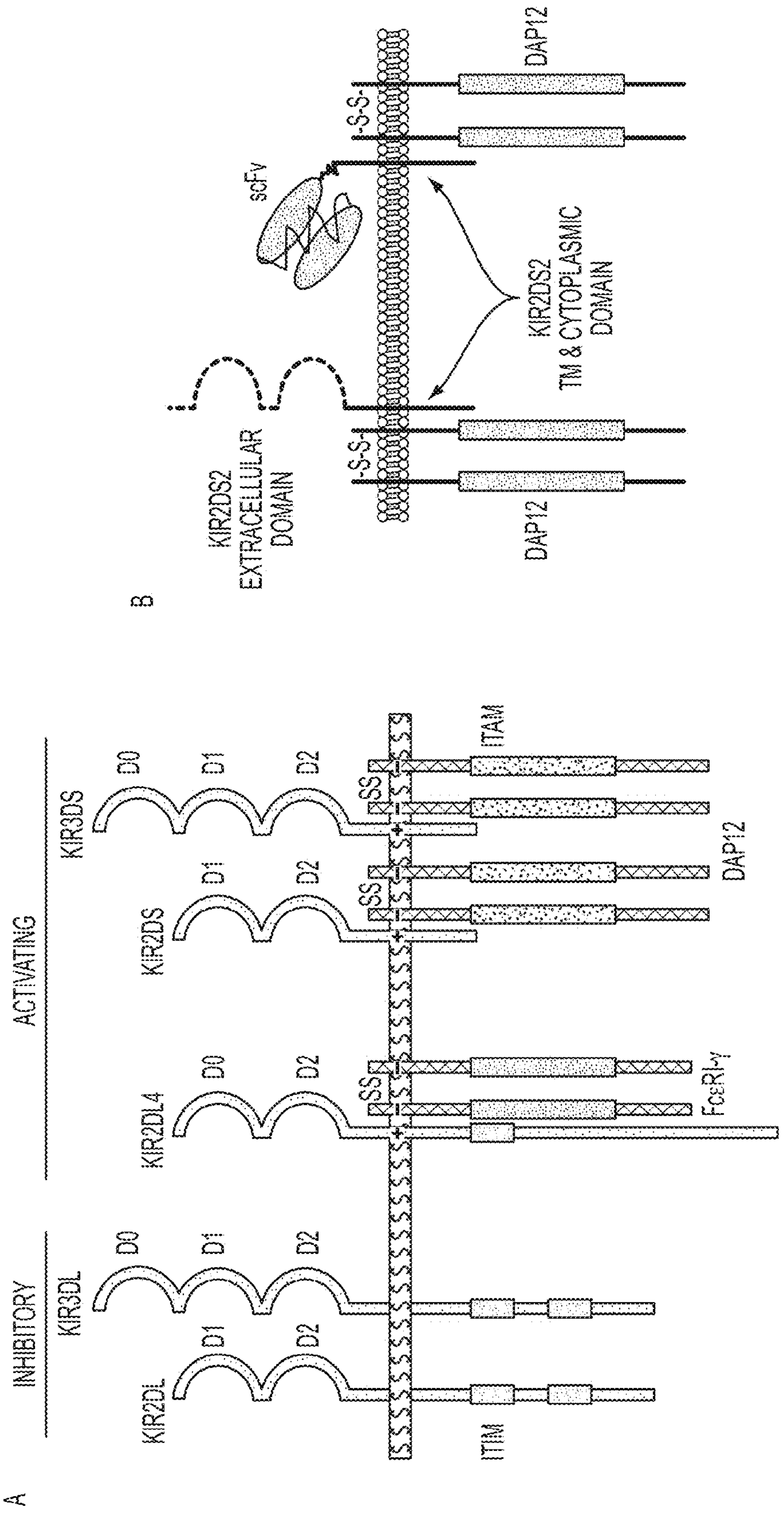
FIG. 1, comprising

In one aspect, the present invention provides compositions and methods for regulating the specificity and activity of T cells, or other cytotoxic cells, e.g., NK cells. In an embodiment a chimeric antigen receptor (a CAR), e.g., a NK cell receptor CAR (a NKR-CAR) based on an NK cell receptor (a NKR), e.g., a KIR-CAR, a NCR-CAR, a SLAMF-CAR, a FcR-CAR, or a Ly49-CAR is provided. In one embodiment, the invention provides a type of chimeric antigen receptor (CAR) wherein the CAR is termed an NKR, e.g., a "KIR-CAR," which is a CAR design comprising a component of a receptor found on natural killer (NK) cells. In one embodiment, the NK receptor includes but is not limited to a killer cell immunoglobulin-like receptor (KIR). KIRs can function as an activating KIR or an inhibiting KIR.

One advantage of the NKR-CARs, e.g., KIR-CARs, of the invention is that a NKR-CAR, e.g., a KIR-CARs provides a method for regulating cytotoxic cell, e.g., T cell, specificity to control off-target activity of the engineered T cell. In some instances, the KIR-CARs of the invention do not require a costimulation to proliferate.

NKR-CARs can deliver a signal through an adaptor protein, e.g., an ITAM containing adaptor protein. In one embodiment, the KIR-CARs of the invention comprise an activating KIR which delivers its signal through an interaction with the immunotyrosine-based activation motif (ITAM) containing membrane protein, DAP12 that is mediated by residues within the transmembrane domains of these proteins.

In an embodiment a NKR-CAR can deliver an inhibitory signal by means of an inhibitory motif. In one embodiment, the KIR-CARs of the invention comprise an inhibitory KIR which delivers its signal through an interaction with the immunotyrosine-based inhibitory motifs (ITIMs). KIRs bearing cytoplasmic domains that contain ITIMs abrogate the activating signal leading to inhibition of NK cytolytic and cytokine producing activity. However, the invention should not be limited to inhibitory KIRs. Rather, any inhibitory protein having a cytoplasmic domain that is associated with an inhibitory signal can be used in the construction of the CARs of the invention.

Accordingly, the invention provides a composition comprising a NKR-CAR, e.g., a KIR-CAR, vectors comprising the same, compositions comprising a NKR-CAR, e.g., a KIR-CAR, vectors packaged in viral particles, and recombinant T cells or other cytotoxic cells comprising a NKR-CAR, e.g., a KIR-CAR. The invention also includes methods of making a genetically modified T cell or other cytotoxic cell, e.g., a NK cell, or cultured NK cell, e.g., a NK92 cell, expressing a NKR-CAR, e.g., a KIR-CAR (KIR-CART), wherein the expressed NKR-CAR, e.g., a KIR-CAR, comprises an antigen recognition domain of a specific antibody with an intracellular signaling molecule from a NKR, e.g., a KIR. For example, in some embodiments, the intracellular signaling molecule includes, but is not limited to, a KIR ITAM, a KIR ITIM, and the like.

Accordingly, the invention provides compositions and methods to regulate the specificity and activity of T cells or other cytotoxic cells modified to express a NKR-CAR, e.g., a KIR-CAR. The present invention also provides cells comprising a plurality of types of NKR-CARs, e.g., KIR-CARs (e.g. activating NKR-CARs, e.g., KIR-CARs and inhibiting NKR-CAR, e.g., a KIR-CAR), wherein the plurality of types of NKR-CARs, e.g., KIR-CARs, participate in signaling to regulate T cell activation. In this aspect, it is beneficial to effectively control and regulate NKR-CAR cytotoxic cells, e.g., KIR-CAR T cells, such that they kill tumor cells while not affecting normal bystander cells. Thus, in one embodiment, the present invention also provides methods of killing cancerous cells while minimizing the depletion of normal non-cancerous cells, thereby improving the specificity of a NKR-CAR, e.g., a KIR-CAR, therapy.

In one embodiment, the NKR-CAR, e.g., KIR-CAR approach includes the physical separation of a plurality of types of CARs expressed on a cell, wherein binding of a plurality of types of NKR-CARs, e.g., KIR-CARs to their target antigen is required for NKR-CAR cytotoxic cell, e.g., KIR-CAR T cell, activation. For example in the KIR-CAR approach, each KIR-CAR from the plurality of type of KIR-CARs have different intracellular signaling domain. For example, when a plurality of types of KIR-CARs is used to induce KIR-CAR T cell activation, the first type of KIR-CARs can only comprise an intracellular domain from an activating KIR and the second type of CAR can only comprise an intracellular domain from an inhibiting KIR. In this manner, conditional activation of T cells is generated by engagement of the activating KIR-CAR (actKIR-CAR) to an antigen on a malignant cell of interest. An inhibitory KIR-CAR (inhKIR-CAR) bearing an antigen binding moiety directed against an antigen that is present on a normal, but not malignant cell provides dampening of the activating effects from the actKIR-CAR when the T cell encounters normal cells.

In one embodiment, the present invention provides a T cell or other cytotoxic cell engineered to express at least two NKR-CARs, e.g., at least two KIR-CARs, wherein the first NKR-CAR, e.g., a KIR-CAR, is an actNKR-CAR, e.g., an actKIR-CAR, and the second NKR-CAR, e.g., a KIR-CAR, is an inhNKR-CAR, e.g., an inhKIR-CAR. In one embodiment, the invention provides an inhNKR-CAR, e.g., an inhKIR-CAR, wherein binding of the inhNKR-CAR, e.g., an inhKIR-CAR, to a normal cell results in inhibition of the cytotoxic cell, e.g., inhibition of KIR-CAR T cell activity. In one embodiment, binding of the inhNKR-CAR, e.g., an inhKIR-CAR, to an antigen associated with a non-cancerous cell results in the death of the NKR-CAR cytotoxic cell, e.g., a KIR-CAR T cell.

In one embodiment, an inhNKR-CAR, e.g., an actKIR-CAR, of the invention can be used in combination with existing CARs in order to regulate the activity of the CARs. Exemplary CARs have been described in PCT/US11/64191, which is incorporated in its entirety by reference herein.

It has also been discovered that, in cells having a plurality of chimeric membrane embedded receptors comprising an antigen binding domain (CMERs), interactions between the antigen binding domain of the CMERs can be undesirable, e.g., because interaction inhibits the ability of one or more of the antigen binding domains to bind its cognate antigen or might generate novel binding sites with unknown cognate antigen. Accordingly, disclosed herein are cells having a first and a second non-naturally occurring CMER wherein the antigen binding domains minimizes such interactions. Also disclosed herein are nucleic acids encoding a first and a second non-naturally occurring such CMERs, as well as methods of making and using such cells and nucleic acids. In an embodiment, the antigen binding domain of one of said first said second non-naturally occurring CMER, comprises an scFv, and the other comprises a single VH domain, e.g., a camelid, shark, or lamprey single VH domain, or a single VH domain derived from a human or mouse sequence or a non-antibody scaffold.

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles “a” and “an” are used herein to refer to one or to more than one (i.e., to at least one) of the grammatical object of the article. By way of example, “an element” means one element or more than one element.

“About” as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

Adaptor molecule, as that term is used herein, refers to a polypeptide with a sequence that permits interaction with two or more molecules, and in embodiments, promotes activation or inactivation of a cytotoxic cell. E.g., in the case of DAP12, this comprises interactions with an activating KIR via charge interactions within the transmembrane domain and interactions with signaling molecules like ZAP70 or Syk via a phosphorylated ITAM sequence within the cytoplasmic domain.

The term “antigen” or “Ag” as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an “antigen” as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a “gene” at all. It is readily apparent that an antigen can be generated synthesized or can be derived from a biological sample. Such a biological sample can include, but is not limited to a tissue sample, a tumor sample, a cell or a biological fluid.

The term “anti-tumor effect” as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An “anti-tumor effect” can also be manifested by the ability of the peptides, polynucleotides, cells and antibodies of the invention in prevention of the occurrence of tumor in the first place.

The term “auto-antigen” means, in accordance with the present invention, any self-antigen which is recognized by the immune system as if it were foreign. Auto-antigens comprise, but are not limited to, cellular proteins, phosphoproteins, cellular surface proteins, cellular lipids, nucleic acids, glycoproteins, including cell surface receptors.

The term “autoimmune disease” as used herein is defined as a disorder that results from an autoimmune response. An autoimmune disease is the result of an inappropriate and excessive response to a self-antigen. Examples of autoimmune diseases include but are not limited to, Addision’s disease, alopecia areata, ankylosing spondylitis, autoimmune hepatitis, autoimmune parotitis, Crohn’s disease, diabetes (Type I), dystrophic epidermolysis bullosa, epididymitis, glomerulonephritis, Graves’ disease, Guillain-Barr syndrome, Hashimoto’s disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren’s syndrome, spondyloarthropathies, thyroiditis, vasculitis, vitiligo, myxedema, pernicious anemia, ulcerative colitis, among others.

As used herein, the term “autologous” is meant to refer to any material derived from the same individual to which it is later to be re-introduced into the individual.

“Allogeneic” refers to a graft derived from a different animal of the same species.

CAR, as that term is used herein, refers to a chimeric polypeptide that shares structural and functional properties with a cell immune-function receptor or adaptor molecule, from e.g., a T cell or a NK cell. CARs include TCARs and NKR-CARs. Upon binding to cognate antigen, a CAR can activate or inactivate the cytotoxic cell in which it is disposed, or modulate the cell’s antitumor activity or otherwise modulate the cells immune response.

The term “cancer” as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, glioma, and the like.

As used herein, the term “conservative sequence modifications” is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the CDR regions of an antibody of the invention can be replaced with other amino acid residues from the same side chain family and the altered antibody can be tested for the ability to bind FRβ using the functional assays described herein.

A “constitutive” promoter is a nucleotide sequence which, when operably linked with a polynucleotide which encodes or specifies a gene product, causes the gene product to be produced in a cell under most or all physiological conditions of the cell.

Cytoplasmic and intracellular, as applied to adaptor molecules and signaling domains are used interchangeably herein.

“Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a “nucleotide sequence encoding an amino acid sequence” includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

FcR-CAR, as that term is used herein, refers to a CAR which shares functional and structural properties with a FcR.

"Fully human" refers to an immunoglobulin, such as an antibody, where the whole molecule is of human origin or consists of an amino acid sequence identical to a human form of the antibody.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Intracellular signaling domain", as used herein, refers to a polypeptide sequence that is a component of a larger integral membrane protein. This polypeptide sequence, through regulated interactions with other cellular proteins, is capable of stimulating or inhibiting immune cell function such as lytic granule release, cytokine production or proliferation.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

KIR-CAR, as that term is used herein, refers to a CAR which shares functional and structural properties with a KIR.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

Ly49-CAR, as that term is used herein, refers to a CAR which shares functional and structural properties with a Ly49.

NCR-CAR, as that term is used herein, refers to a CAR which shares functional and structural properties with a NCR.

NK cell immune-function receptor (or NKR), as that term is used herein, refers to an endogenous naturally occurring transmembrane protein expressed in NK cells, which can engage with a ligand on an antigen presenting cell and modulate an NK cell immune-function response, e.g., it can modulate the cytolytic activity or cytokine secretion of the NK cell. The NKR can contribute to activation (an activating NKR, or actNKR), or inhibition (an inhibitory NKR, or inhNKR). Typically, an NKR comprises an extracellular ligand-binding domain (ECD), a transmembrane domain (TM) and an intracellular cytoplasmic domain (ICD). NKRs include the Killer Immunoglobulin-like Receptor (KIR) family of receptors such as KIR2DS2, the NK cell receptor (NCR) receptor family of receptors such as NKp46 (NCR1), the signaling lymphocyte activation receptor (SLAM) family (SLAMF) of receptors such as 2B4, and the Fc-binding receptors such as the IgG-binding receptor, CD16 (FcγRIII). Examples of NK cell immune-function responses modulated by NKRs comprise target cell killing (often referred to as cytotoxicity or cytolysis), cytokine secretion and/or proliferation. Typically, an NKR suitable for use in the methods and compositions described herein is a human NKR, (or hNKR). In an embodiment, the Ly49 receptor family in *Mus musculus*, which emerged by convergent evolution to provide the same function as a KIR in murine NK and T cells, is also included.

NKR-CAR, as that term is used herein, refers to a CAR which shares functional and structural properties with a NKR or adaptor molecule from a NK cell.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

TCAR, as that term is used herein, refers to a CAR which shares functional and structural properties with a cell immune-function receptor or adaptor molecule from a T cell.

A "tissue-specific" promoter is a nucleotide sequence which, when operably linked with a polynucleotide encodes or specified by a gene, causes the gene product to be produced in a cell substantially only if the cell is a cell of the tissue type A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000 (SEQ ID NO: 67), preferably greater than 64, more preferably greater than 100, most preferably greater than 300 or 400. poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the term "TCAR" comprises an antigen domain, an intracellular signaling domain, and optionally one or more costimulatory domains.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner protein present in a sample, but which antibody or ligand does not substantially recognize or bind other molecules in the sample.

By the term "stimulation," is meant a primary response induced by binding of a stimulatory molecule with its cognate ligand thereby mediating a signal transduction event, such as, but not limited to, signal transduction via the appropriate NK receptor.

"Xenogeneic" refers to a graft derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

NKR-CARs

Disclosed herein are compositions and methods for regulating the specificity and activity of cytotoxic cells, e.g., T cells or NK cells, e.g., with a non-naturally occurring chimeric antigen receptor (CAR). In an embodiment the CAR is an NKR-CAR. A NKR-CAR is a CAR which shares functional and structural properties with a NK cell immune-function receptor (or NKR). NKRs and NKR-CARs are described herein, e.g., in the section below. As is discussed below, a variety of NKRs can serve as the basis for an NKR-CAR.

NK Cell Immune-Function Receptors (NKRs) and NK Cells

As discussed herein, NK cell immune-function receptor (or NKR) refers to an endogenous naturally occurring transmembrane protein expressed in NK cells, which can engage with a ligand on an antigen presenting cell and modulate an NK cell immune-function response, e.g., it can modulate the cytolytic activity or cytokine secretion of the NK cell.

NK cells are mononuclear cells that develop in the bone marrow from lymphoid progenitors, and morphological features and biological properties typically include the expression of the cluster determinants (CDs) CD16, CD56, and/or CD57; the absence of the alpha/beta or gamma/delta TCR complex on the cell surface; the ability to bind to and kill target cells that fail to express "self" major histocompatibility complex (MHC)/human leukocyte antigen (HLA) proteins; and the ability to kill tumor cells or other diseased cells that express ligands for activating NK receptors. NK cells are characterized by their ability to bind and kill several types of tumor cell lines without the need for prior immunization or activation. NK cells can also release soluble proteins and cytokines that exert a regulatory effect on the immune system; and can undergo multiple rounds of cell division and produce daughter cells with similar biologic properties as the parent cell. Upon activation by interferons and/or cytokines, NK cells mediate the lysis of tumor cells and of cells infected with intracellular pathogens by mechanisms that require direct, physical contacts between the NK cell and the target cell. Lysis of target cells involves the release of cytotoxic granules from the NK cell onto the surface of the bound target, and effector proteins such as perforin and granzyme B that penetrate the target plasma membrane and induce apoptosis or programmed cell death. Normal, healthy cells are protected from lysis by NK cells. NK cell activity is regulated by a complex mechanism that involves both stimulating and inhibitory signals.

Briefly, the lytic activity of NK cells is regulated by various cell surface receptors that transduce either positive or negative intracellular signals upon interaction with ligands on the target cell. The balance between positive and negative signals transmitted via these receptors determines whether or not a target cell is lysed (killed) by a NK cell. NK cell stimulatory signals can be mediated by Natural Cytotoxicity Receptors (NCR) such as NKp30, NKp44, and NKp46; as well as NKG2C receptors, NKG2D receptors, certain activating killer cell immunoglobulin-like receptors (KIRs), and other activating NK receptors (Lanier, Annual Review of Immunology 2005; 23:225-74). NK cell inhibitory signals can be mediated by receptors like Ly49, CD94/NKG2A, as well as certain inhibitory KIRs, which recognize major histocompatibility complex (MHC) class I molecules (Kane et al., Nature 1986; 319:675-8; Ohlen et al, Science 1989; 246:666-8). These inhibitory receptors bind to polymorphic determinants of MHC class I molecules (including HLA class I) present on other cells and inhibit NK cell-mediated lysis.

KIR-CARs

Disclosed herein is a chimeric antigen receptor (CAR) molecule comprising an antigen binding moiety and a killer cell immunoglobulin-like receptor (KIR-CAR). In one embodiment, the KIR-CAR of the invention is expressed on the surface of a T cell.

KIR-CAR Based NKCARs

KIRs, referred to as killer cell immunoglobulin-like receptors, have been characterized in humans and non-human primates, and are polymorphic type 1 trans-membrane molecules present on certain subsets of lymphocytes, including NK cells and some T cells. KIRs interact with determinants in the alpha 1 and 2 domains of the MHC class I molecules and, as described elsewhere herein, distinct KIRs are either stimulatory or inhibitory for NK cells.

NKCARs described herein include KIR-CARs, which share functional and structural properties with KIRs.

KIRs are a family of cell surface proteins found on NK cells. They regulate the killing function of these cells by interacting with MHC class I molecules, which are expressed on all cell types. This interaction allows them to detect virally infected cells or tumor cells. Most KIRs are inhibitory, meaning that their recognition of MHC suppresses the cytotoxic activity of the NK cell that expresses them. Only a limited number of KIRs have the ability to activate cells.

The KIR gene family have at least 15 gene loci (KIR2DL1, KIR2DL2/L3, KIR2DL4, KIR2DL5A, KIR2DL5B, KIR2DS1, KIR2DS2, KIR2DS3, KIR2DS4, KIR2DS5, KIR3DL1/S1, KIR3DL2, KIR3DL3 and two pseudogenes, KIR2DP1 and KIR3DP1) encoded within a 100-200 Kb region of the Leukocyte Receptor Complex (LRC) located on chromosome 19 (19q13.4). The LRC constitutes a large, 1 Mb, and dense cluster of rapidly evolving immune genes which contains genes encoding other cell surface molecules with distinctive Ig-like extra-cellular domains. In addition, the extended LRC contains genes encoding the transmembrane adaptor molecules DAP10 and DAP12.

KIR genes vary in length from 4 to 16 Kb (full genomic sequence) and can contain four to nine exons. KIR genes are classified as belonging to one of three groups according to their structural features: (1) Type I KIR2D genes, which encode two extra-cellular domain proteins with a D1 and D2 conformation; (2) The structurally divergent Type II KIR2D genes which encode two extra-cellular domain proteins with a D0 and D2 conformation; and finally (3) KIR3D genes encoding proteins with three extra-cellular Ig-like domains (D0, D1 and D2).

Type I KIR2D genes, which include the pseudogene KIR2DP1 as well as KIR2DL1-3 and KIR2DS1-5 genes, possess eight exons as well as a pseudoexon 3 sequence. This pseudoexon is inactivated in Type I KIR2D. In some cases this is due to a nucleotide substitution located on the intron 2-exon 3 splice-site where its nucleotide sequence exhibits a high-degree of identity to KIR3D exon 3 sequences and possesses a characteristic three base pair deletion. In other cases a premature stop codon initiates differential splicing of exon 3. Within the Type I KIR2D group of genes, KIR2DL1 and KIR2DL2 share a common deletion in exon 7 distinguishing them from all other KIR in this exon, which results in a shorter exon 7 sequence. Similarly, within Type I KIR2D, KIR2DL1-3 differ from KIR2DS1-5 only in the length of their cytoplasmic tail encoding region in exon 9. The KIR2DP1 pseudogene structure differs from that of KIR2DL1-3 in that the former has a shorter exon 4 sequence, due to a single base pair deletion.

Type II KIR2D genes include KIR2DL4 and KIR2DL5. Unlike KIR3D and Type I KIR2D, Type II KIR2D characteristically have deleted the region corresponding to exon 4 in all other KIR. Additionally, Type II KIR2D genes differ from Type I KIR2D genes in that the former possess a translated exon 3, while Type I KIR2D genes have an untranslated pseudoexon 3 sequence in its place. Within the Type II KIR2D genes, KIR2DL4 is further differentiated from KIR2DL5 (as well as from other KIR genes) by the length of its exon 1 sequence. In KIR2DL4, exon 1 was found to be six nucleotides longer and to possess an initiation codon different from those present in the other KIR genes. This initiation codon is in better agreement with the 'Kozak transcription initiation consensus sequence' than the second potential initiation codon in KIR2DL4 that corresponds to the initiation codon present in other KIR genes.

KIR3D genes possess nine exons and include the structurally related KIR3DL1, KIR3DS1, KIR3DL2 and KIR3DL3 genes. KIR3DL2 nucleotide sequences are the longest of all KIR genes and span 16,256 bp in full genomic sequences and 1,368 bp in cDNA. Within the KIR3D group, the four KIR genes differ in the length of the region encoding the cytoplasmic tail in exon 9. The length of the cytoplasmic tail of KIR proteins can vary from 14 amino acid residues long (in some KIR3DS1 alleles) to 108 amino acid residues long (in KIR2DL4 proteins). Additionally, KIR3DS1 differs from KIR3DL1 or KIR3DL2 in that the former has a shorter exon 8 sequence. KIR3DL3 differs from other KIR sequences in that it completely lacks exon 6. The most extreme KIR gene structure difference observed was that of KIR3DP1. This gene fragment completely lacks exons 6 through 9, and occasionally also exon 2. The remaining portions of the gene which are present (exon 1, 3, 4 and 5) share a high level of sequence identity to other KIR3D sequences, in particular to KIR3DL3 sequences.

KIR proteins possess characteristic Ig-like domains on their extracellular regions, which in some KIR proteins are involved in HLA class I ligand binding. They also possess transmembrane and cytoplasmic regions which are functionally relevant as they define the type of signal which is transduced to the NK cell. KIR proteins can have two or three Ig-like domains (hence KIR2D or KIR3D) as well as short or long cytoplasmic tails (represented as KIR2DS or KIR2DL). Two domain KIR proteins are subdivided into two groups depending on the origin of the membrane distal Ig-like domains present. Type I KIR2D proteins (KIR2DL1, KIR2DL2, KIR2DL3, KIR2DS1, KIR2DS2, KIR2DS3, KIR2DS4 and KIR2DS5) possess a membrane-distal Ig-like domain similar in origin to the KIR3D D1 Ig-like domain but lack a D0 domain. This D1 Ig-like domain is encoded mainly by the fourth exon of the corresponding KIR genes. The Type II KIR2D proteins, KIR2DL4 and KIR2DL5, possess a membrane-distal Ig-like domain of similar sequence to the D0 domain present in KIR3D proteins, however, Type II KIR2D lack a D1 domain. Long cytoplasmic tails usually contain two Immune Tyrosine-based Inhibitory Motifs (ITIM) which transduce inhibitory signals to the NK cell. Short cytoplasmic tails possess a positively charged amino acid residue in their transmembrane region which allows them to associate with a DAP12 signaling molecule capable of generating an activation signal Exceptions to this is KIR2DL4, which contains only one N-terminus ITIM. In addition, KIR2DL4 also possesses a charged residue (arginine) in its transmembrane domain, a feature which allows this receptor to elicit both inhibitory and activating signals. KIR control the response of human NK cells by delivering inhibitory or activating signals upon recognition of MHC class I ligands on the surface of potential target cells.

KIR proteins vary in length from 306 to 456 amino acid residues. Although the differences in protein length are mostly the consequence of the number of Ig-like domains present, cytoplasmic region length diversity is also an influencing factor. The leader peptide of most KIR proteins is 21 amino acid residues long. However, the presence of a different initiation codon generates a correspondingly longer leader peptide in KIR2DL4 proteins.

The D0 Ig-like domain present in Type II KIR2D proteins and KIR3D proteins is approximately 96 amino acid residues in length. The D1 domain of Type I KIR2D and of KIR3D proteins is 102 amino acid residues long, while the D2 domain of all KIR proteins is 98 amino acid residues long. The length of the stem region varies from the 24 amino acid residues present in most KIR proteins, to only seven amino acid residues in the divergent KIR3DL3 protein. The transmembrane region is 20 amino acid residues long for most KIR proteins, but one residue shorter on KIR2DL1 and KIR2DL2 proteins as a result of a three base pair deletion in exon 7. Finally, the cytoplasmic region of KIR proteins exhibits greater length variations, ranging from 23 amino acid residues in some KIR3DS1 alleles to the 96 amino acid residues present in KIR3DL2 proteins.

Amino acid sequences for human KIR polypeptides (*Homo sapiens*) are available in the NCBI database, see e.g., accession number NP_037421.2 (GI:134268644), NP_703144.2 (GI:46488946), NP_001229796.1 (GI:338968852), NP_001229796.1 (GI:338968852), NP_006728.2 (GI:134268642), NP_065396.1 (GI:11968154), NP_001018091.1 (GI:66267727), NP_001077008.1 (GI:134133244), NP_036444.1 (GI:6912472), NP_055327.1 (GI:7657277), NP_056952.2 (GI:71143139), NP_036446.3 (GI:116517309), NP_001074239.1 (GI:124107610), NP_002246.5 (GI:124107606), NP_001074241.1 (GI: 124107604), NP_036445.1 (GI:6912474).

The nomenclature for KIRs is based upon the number of extracellular domains (KIR2D and KIR3D having two and three extracellular Ig-domains, respectively) and whether the cytoplasmic tail is long (KIR2DL or KIR3DL) or short (KIR2DS or KIR3DS). The presence or absence of a given KIR is variable from one NK cell to another within the NK population present in a single individual. Among humans, there is also a relatively high level of polymorphism of KIR genes, with certain KIR genes being present in some, but not all individuals. The expression of KIR alleles on NK cells is stochastically regulated, meaning that, in a given individual, a given lymphocyte may express one, two, or more different KIRs, depending on the genotype of the individual. The NK cells of a single individual typically express different combinations of KIRs, providing a repertoire of NK cells with different specificities for MHC class I molecules.

Certain KIR gene products cause stimulation of lymphocyte activity when bound to an appropriate ligand. The activating KIRs all have a short cytoplasmic tail with a charged trans-membrane residue that associates with an adapter molecule having an Immunoreceptor Tyrosine-based Activation Motifs (ITAMs) which transduce stimulatory signals to the NK cell. By contrast, inhibitory KIRs have a long cytoplasmic tail containing Immunoreceptor Tyrosine-based Inhibitory Motif (ITIM), which transduce inhibitory signals to the NK cell upon engagement of their MHC class I ligands. The known inhibitory KIRs include members of the KIR2DL and KIR3DL subfamilies. Inhibitory KIRs having two Ig domains (KIR2DL) recognize HLA-C allotypes: KIR2DL2 (formerly designated p58.2) and the closely related, allelic gene product KIR2DL3 both recognize "group 1" HLA-C allotypes (including HLA-Cw1, -3, -7, and -8), whereas KIR2DL1 (p58.1) recognizes "group 2" HLA-C allotypes (such as HLA-Cw2, -4, -5, and -6). The recognition by KIR2DL1 is dictated by the presence of a Lys residue at position 80 of HLA-C alleles. KIR2DL2 and KIR2DL3 recognition is dictated by the presence of an Asn residue at position 80 in HLA-C. Importantly, the great majority of HLA-C alleles have either an Asn or a Lys residue at position 80. Therefore, KIR2DL1, -2, and -3 collectively recognize essentially all HLA-C allotypes found in humans. One KIR with three Ig domains, KIR3DL1 (p70), recognizes an epitope shared by HLA-Bw4 alleles.

Finally, KIR3DL2 (p140), a homodimer of molecules with three Ig domains, recognizes HLA-A3 and -A11.

However, the invention should not be limited to inhibitory KIRs comprising a cytoplasmic tail containing ITIM. Rather, any inhibitory protein having a cytoplasmic domain that is associated with an inhibitory signal can be used in the construction of the CARs of the invention. Non-limiting examples of an inhibitory protein include but are not limited CTLA-4, PD-1, and the like. These proteins are known to inhibit T cell activation.

Accordingly, the invention provides a KIR-CAR comprising an extracellular domain that comprises a target-specific binding element otherwise referred to as an antigen binding domain fused to a KIR or fragment thereof. In one embodiment, the KIR is an activating KIR that comprises a short cytoplasmic tail that associates with an adapter molecule having an Immunoreceptor Tyrosine-based Activation Motifs (ITAMs) which transduce stimulatory signals to the NK cell (referred elsewhere herein as actKIR-CAR). In one embodiment, the KIR is an inhibitory KIR that comprises a long cytoplasmic tail containing Immunoreceptor Tyrosine-based Inhibitory Motif (ITIM), which transduce inhibitory signals (referred elsewhere herein as inhKIR-CAR). In some instances, it is desirable to remove the hinge region for the activating KIRs when construction an actKIR-CAR. This is because the invention is partly based on the discovery that an activating KIR CAR in which the KIR2DS2 hinge was removed to generate the KIR2S CAR, this KIRS2 CAR exhibited enhanced cytolytic activity compared to an actKIR-CAR comprising a full length wildtype KIR2DS2.

The nucleic acid sequences coding for the desired molecules of the invention can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The present invention includes retroviral and lentiviral vector constructs expressing a KIR-CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the KIR-CAR.

In an embodiment, a KIR-CAR comprises an antigen binding domain and a KIR transmembrane domain. In an embodiment, a KIR-CAR comprises an antigen binding domain and a KIR intracellular domain, e.g., an inhKIR intracellular domain.

KIR D domain, as that term is used herein, refers to a D0, D1, or D2 domain of a KIR.

KIR D domain, as that term is used herein, refers to a polypeptide domain having structural and functional properties of a D domain of a KIR.

KIR D0 domain, as that term is used herein, refers to a D0 domain of a KIR. In an embodiment the KIR D0 domain of a KIR-CAR has at least 70, 80, 85, 90, 95, or 99% homology with a reference sequence, e.g., a naturally occurring KIR D0 domain or a KIR D0 domain described herein. In embodiments the KIR D0 domain of a KIR-CAR differs at no more than 15, 10, 5, 2, or 1% of its residues from a reference sequence, e.g., a naturally occurring KIR D0 domain or a KIR D0 domain described herein. In embodiments the KIR D0 domain of a KIR-CAR differs at no more than 5, 4, 3, 2 or 1 residue from a reference sequence, e.g., a naturally occurring KIR D0 domain or a KIR D0 domain described herein. In embodiments the KIR D0 domain of a KIR-CAR does not differ from, or shares 100% homology with, a reference sequence, e.g., a naturally occurring KIR D0 domain or a KIR D0 domain described herein.

KIR D1 domain, as that term is used herein, refers to a polypeptide domain having structural and functional properties of a D1 domain of a KIR. In an embodiment the KIR D1 domain of a KIR-CAR has at least 70, 80, 85, 90, 95, or 99% homology with a reference sequence, e.g., a naturally occurring KIR D1 domain or a KIR D1 domain described herein. In embodiments the KIR D1 domain of a KIR-CAR differs at no more than 15, 10, 5, 2, or 1% of its residues from a reference sequence, e.g., a naturally occurring KIR D1 domain or a KIR D1 domain described herein. In embodiments the KIR D1 domain of a KIR-CAR differs at no more than 5, 4, 3, 2 or 1 residue from a reference sequence, e.g., a naturally occurring KIR D0 domain or a KIR D1 domain described herein. In embodiments the KIR D1 domain of a KIR-CAR does not differ from, or shares 100% homology with, a reference sequence, e.g., a naturally occurring KIR D1 domain or a KIR D1 domain described herein.

KIR D2 domain, as that term is used herein, refers to a polypeptide domain having structural and functional properties of a D2 domain of a KIR. In an embodiment the KIR D2 domain of a KIR-CAR has at least 70, 80, 85, 90, 95, or 99% homology with a reference sequence, e.g., a naturally occurring KIR D2 domain or a KIR D2 domain described herein. In embodiments the KIR D2 domain of a KIR-CAR differs at no more than 15, 10, 5, 2, or 1% of its residues from a reference sequence, e.g., a naturally occurring KIR D2 domain or a KIR D2 domain described herein. In embodiments the KIR D2 domain of a KIR-CAR differs at no more than 5, 4, 3, 2 or 1 residue from a reference sequence, e.g., a naturally occurring KIR D2 domain or a KIR D2 domain described herein. In embodiments the KIR D2 domain of a KIR-CAR does not differ from, or shares 100% homology with, a reference sequence, e.g., a naturally occurring KIR D2 domain or a KIR D0 domain described herein.

KIR hinge or stem domain, as that term is used herein, refers to a polypeptide domain having structural and functional properties of a hinge or stem domain of a KIR. In an embodiment the KIR hinge or stem domain of a KIR-CAR has at least 70, 80, 85, 90, 95, or 99% homology with a reference sequence, e.g., a naturally occurring KIR hinge or stem domain or a KIR hinge or stem domain described herein. In embodiments the KIR hinge or stem domain of a KIR-CAR differs at no more than 15, 10, 5, 2, or 1% of its residues from a reference sequence, e.g., a naturally occurring KIR hinge or stem domain or a KIR hinge or stem domain described herein. In embodiments the KIR hinge or stem domain of a KIR-CAR differs at no more than 5, 4, 3, 2 or 1 residue from a reference sequence, e.g., a naturally occurring KIR hinge or stem domain or a KIR hinge or stem domain described herein. In embodiments the KIR hinge or stem domain of a KIR-CAR does not differ from, or shares 100% homology with, a reference sequence, e.g., a naturally occurring KIR hinge or stem domain or a KIR hinge or stem domain described herein.

KIR transmembrane domain, as that term is used herein, refers to a polypeptide domain having structural and functional properties of a transmembrane domain of a KIR. In an embodiment the KIR transmembrane domain of a KIR-CAR has at least 70, 80, 85, 90, 95, or 99% homology with a reference sequence, e.g., a naturally occurring KIR transmembrane domain or a KIR transmembrane domain described herein. In embodiments the KIR transmembrane domain of a KIR-CAR differs at no more than 15, 10, 5, 2, or 1% of its residues from a reference sequence, e.g., a naturally occurring KIR transmembrane domain or a KIR transmembrane domain described herein. In embodiments the KIR transmembrane domain of a KIR-CAR differs at no more than 5, 4, 3, 2 or 1 residue from a reference sequence, e.g., a naturally occurring KIR transmembrane domain or a KIR transmembrane domain described herein. In embodiments the KIR transmembrane domain of a KIR-CAR does not differ from, or shares 100% homology with, a reference sequence, e.g., a naturally occurring KIR transmembrane domain or a KIR transmembrane domain described herein.

KIR intracelluar domain, as that term is used herein, refers to a polypeptide domain having structural and functional properties of an intracellular domain of a KIR. KIR intracellular domains comprise inhibitory KIR intracellular domains (referred to herein as inhKIR intracellular domains) and activating KIR intracellular domains (referred to herein as actKIR intracellular domains). In an embodiment the inhKIR intracellular domain comprises an ITIM sequence. In an embodiment the KIR intracellular domain of a KIR-CAR has at least 70, 80, 85, 90, 95, or 99% homology with a reference sequence, e.g., a naturally occurring KIR intracellular domain or a KIR intracellular domain described herein. In embodiments the KIR intracellular domain of a KIR-CAR differs at no more than 15, 10, 5, 2, or 1% of its residues from a reference sequence, e.g., a naturally occurring KIR intracellular domain or a KIR intracellular domain described herein. In embodiments the KIR intracellular domain of a KIR-CAR differs at no more than 5, 4, 3, 2 or 1 residue from a reference sequence, e.g., a naturally occurring KIR intracellular domain or a KIR intracellular domain described herein. In embodiments the KIR intracellular domain of a KIR-CAR does not differ from, or shares 100% homology with, a reference sequence, e.g., a naturally occurring KIR intracellular domain or a KIR intracellular domain described herein.

NCRs

NKCARs described herein include NCR-CARs, which share functional and structural properties with NCRs.

Natural killer (NK) cells are cytotoxic lymphoid cells specialized in destroying tumors and virus-infected cells. Unlike cytotoxic T lymphocytes, NK cells do not express antigen-specific receptors. The recognition of transformed cells occurs via the association of a multitude of cell-surface receptors with surface markers on the target cell. The NK cell surface receptors can be distinguished according to whether they activate or inhibit NK cell-mediated cytotoxicity. Numerous interactions between different receptors appear to lead to the formation of synapses between NK and target cells. The integration of activating and inhibiting signals at the synapse dictates whether or not the NK cells exert their cytolytic function on the target cell. Among the activating receptors, the family of Ig-like molecules is termed natural cytotoxicity receptors (NCRs). These natural cytotoxicity receptors include NKp30, NKp44 and NKp46 molecules. The NCRs are key activating receptors for NK cells in tumor cell recognition. All three NCRs are involved in the clearance of both tumor and virus-infected cells. In the latter, the antiviral activity is initiated by the interaction of NKp44 with hemagglutinin of influenza virus or Sendai virus. NKp46 targets virus-infected cells by binding to influenza virus hemagglutinin or Sendai virus hemagglutinin-neuraminidase. In contrast, it has been shown that NK cell-mediated cytotoxicity is inhibited by binding of NKp30 to the human cytomegaloviral protein pp65 (see, e.g., Arnon, et. al., Nat. Immunol. (2005) 6:515-523).

Amino acid sequences for a human NCR polypeptides (*Homo sapiens*) are available in the NCBI database, see e.g., accession number NP_004819.2 (GI:153945782), O14931.1 (GI:47605770), O95944.2 (GI:251757303), O76036.1 (GI:47605775), NP_001138939.1 (GI:224586865), and/or NP_001138938.1 (GI:224586860).

In an embodiment, a NCR-CAR comprises an antigen binding domain and a NCR transmembrane domain. In an embodiment, a KIR-CAR comprises an antigen binding domain and a NCR intracellular domain.

NCR extracellular domain, as that term is used herein, refers to a polypeptide domain having structural and functional properties of a extracellular domain of a NCR. In an embodiment the NCR extracellular domain of a NCR-CAR has at least 70, 80, 85, 90, 95, or 99% homology with a reference sequence, e.g., a naturally occurring NCR extracellular domain or a NCR extracellular domain described herein. In embodiments the NCR extracellular domain of a NCR-CAR differs at no more than 15, 10, 5, 2, or 1% of its residues from a reference sequence, e.g., a naturally occurring NCR extracellular domain or a NCR extracellular domain described herein. In embodiments the NCR extracellular domain of a NCR-CAR differs at no more than 5, 4, 3, 2 or 1 residue from a reference sequence, e.g., a naturally occurring NCR extracellular domain or a NCR extracellular domain described herein. In embodiments the NCR extracellular domain of a NCR-CAR does not differ from, or shares 100% homology with, a reference sequence, e.g., a naturally occurring NCR extracellular domain or a NCR extracellular domain described herein.

NCR hinge or stem domain, as that term is used herein, refers to a polypeptide domain having structural and functional properties of a hinge or stem domain of a NCR. In an embodiment the NCR hinge or stem domain of a NCR-CAR has at least 70, 80, 85, 90, 95, or 99% homology with a reference sequence, e.g., a naturally occurring NCR hinge or stem domain or a NCR hinge or stem domain described herein. In embodiments the NCR hinge or stem domain of a NCR-CAR differs at no more than 15, 10, 5, 2, or 1% of its residues from a reference sequence, e.g., a naturally occurring NCR hinge or stem domain or a NCR hinge or stem domain described herein. In embodiments the NCR hinge or stem domain of a NCR-CAR differs at no more than 5, 4, 3, 2 or 1 residue from a reference sequence, e.g., a naturally occurring NCR hinge or stem domain or a NCR hinge or stem domain described herein. In embodiments the NCR hinge or stem domain of a NCR-CAR does not differ from, or shares 100% homology with, a reference sequence, e.g., a naturally occurring NCR hinge or stem domain or a NCR hinge or stem domain described herein.

NCR transmembrane domain, as that term is used herein, refers to a polypeptide domain having structural and functional properties of a transmembrane domain of a NCR. In an embodiment the NCR transmembrane domain of a NCR-CAR has at least 70, 80, 85, 90, 95, or 99% homology with a reference sequence, e.g., a naturally occurring NCR transmembrane domain or a NCR transmembrane domain described herein. In embodiments the NCR transmembrane domain of a NCR-CAR differs at no more than 15, 10, 5, 2, or 1% of its residues from a reference sequence, e.g., a naturally occurring NCR transmembrane domain or a NCR transmembrane domain described herein. In embodiments the NCR transmembrane domain of a NCR-CAR differs at no more than 5, 4, 3, 2 or 1 residue from a reference sequence, e.g., a naturally occurring NCR transmembrane domain or a NCR transmembrane domain described herein. In embodiments the NCR transmembrane domain of a NCR-CAR does not differ from, or shares 100% homology with, a reference sequence, e.g., a naturally occurring NCR transmembrane domain or a NCR transmembrane domain described herein.

NCR intracelluar domain, as that term is used herein, refers to a polypeptide domain having structural and functional properties of an intracellular domain of a NCR. In an embodiment the NCR intracellular domain of a NCR-CAR has at least 70, 80, 85, 90, 95, or 99% homology with a reference sequence, e.g., a naturally occurring NCR intracellular domain or a NCR intracellular domain described herein. In embodiments the NCR intracellular domain of a NCR-CAR differs at no more than 15, 10, 5, 2, or 1% of its residues from a reference sequence, e.g., a naturally occurring NCR intracellular domain or a NCR intracellular domain described herein. In embodiments the NCR intracellular domain of a NCR-CAR differs at no more than 5, 4, 3, 2 or 1 residue from a reference sequence, e.g., a naturally occurring NCR intracellular domain or a NCR intracellular domain described herein. In embodiments the NCR intracellular domain of a NCR-CAR does not differ from, or shares 100% homology with, a reference sequence, e.g., a naturally occurring NCR intracellular domain or a NCR intracellular domain described herein.

SLAM Receptors

NKCARs described herein include SLAMF-CARs, which share functional and structural properties with SLAMFs.

The signaling lymphocyte activation molecule (SLAM) family of immune cell receptors is closely related to the CD2 family of the immunoglobulin (Ig) superfamily of molecules. The SLAM family (SLAMF) currently includes nine members named SLAM, CD48, CD229, 2B4, CD84, NTB-A, CRACC, BLAME, and CD2F-10. In general, SLAM molecules possess two to four extracellular Ig domains, a transmembrane segment, and an intracellular tyrosine-rich region. The molecules are differentially expressed on a variety of immune cell types. Several are self ligands and SLAM has been identified as the human measles virus receptor. Several small SH2-containing adaptor proteins are known to associate with the intracellular domains of SLAM family members and modulate receptor signaling including SH2D1A (also known as SLAM-associated protein [SAP]) and SH2D1B (also known as EAT2). For example, in T and NK cells, activated SLAM family receptors become tyrosine phosphorylated and recruit the adaptor SAP and subsequently the Src kinase Fyn. The ensuing signal transduction cascade influences the outcome of T cell-antigen presenting cell and NK cell-target cell interactions.

Amino acid sequences for human SLAM receptor polypeptides (*Homo sapiens*) are available in the NCBI database, see e.g., accession number NP_057466.1 (GI: 7706529), NP_067004.3 (GI: 19923572), NP_003028.1 (GI:4506969), NP_001171808.1 (GI: 296434285), NP_001171643.1 (GI: 296040491), NP_001769.2 (GI:21361571), NP_254273.2 (GI: 226342990), NP_064510.1 (GI: 9910342) and/or NP_002339.2 (GI: 55925578)

In an embodiment, a SLAMF-CAR comprises an antigen binding domain and a SLAMF transmembrane domain. In an embodiment, a SLAMF-CAR comprises an antigen binding domain and a NCR intracellular domain.

SLAMF extracellular domain, as that term is used herein, refers to a polypeptide domain having structural and functional properties of a extracellular domain of a SLAMF. In an embodiment the SLAMF extracellular domain of a SLAMF-CAR has at least 70, 80, 85, 90, 95, or 99% homology with a reference sequence, e.g., a naturally occurring SLAMF extracellular domain or a SLAMF extracellular domain described herein. In embodiments the SLAMF extracellular domain of a SLAMF-CAR differs at no more than 15, 10, 5, 2, or 1% of its residues from a reference sequence, e.g., a naturally occurring SLAMF extracellular domain or a SLAMF extracellular domain described herein. In embodiments the SLAMF extracellular domain of a SLAMF-CAR differs at no more than 5, 4, 3, 2 or 1 residue from a reference sequence, e.g., a naturally occurring SLAMF extracellular domain or a SLAMF extracellular domain described herein. In embodiments the SLAMF extracellular domain of a SLAMF-CAR does not differ from, or shares 100% homology with, a reference sequence, e.g., a naturally occurring SLAMF extracellular domain or a SLAMF extracellular domain described herein.

SLAMF hinge or stem domain, as that term is used herein, refers to a polypeptide domain having structural and functional properties of a hinge or stem domain of a SLAMF. In an embodiment the SLAMF hinge or stem domain of a SLAMF-CAR has at least 70, 80, 85, 90, 95, or 99% homology with a reference sequence, e.g., a naturally occurring SLAMF hinge or stem domain or a SLAMF hinge or stem domain described herein. In embodiments the SLAMF hinge or stem domain of a SLAMF-CAR differs at no more than 15, 10, 5, 2, or 1% of its residues from a reference sequence, e.g., a naturally occurring SLAMF hinge or stem domain or a SLAMF hinge or stem domain described herein. In embodiments the SLAMF hinge or stem domain of a SLAMF-CAR differs at no more than 5, 4, 3, 2 or 1 residue from a reference sequence, e.g., a naturally occurring SLAMF hinge or stem domain or a SLAMF hinge or stem domain described herein. In embodiments the SLAMF hinge or stem domain of a SLAMF-CAR does not differ from, or shares 100% homology with, a reference sequence, e.g., a naturally occurring SLAMF hinge or stem domain or a SLAMF hinge or stem domain described herein.

SLAMF transmembrane domain, as that term is used herein, refers to a polypeptide domain having structural and functional properties of a transmembrane domain of a SLAMF. In an embodiment the SLAMF transmembrane domain of a SLAMF-CAR has at least 70, 80, 85, 90, 95, or 99% homology with a reference sequence, e.g., a naturally occurring SLAMF transmembrane domain or a SLAMF transmembrane domain described herein. In embodiments the SLAMF transmembrane domain of a SLAMF-CAR differs at no more than 15, 10, 5, 2, or 1% of its residues from a reference sequence, e.g., a naturally occurring SLAMF transmembrane domain or a SLAMF transmembrane domain described herein. In embodiments the SLAMF transmembrane domain of a SLAMF-CAR differs at no more than 5, 4, 3, 2 or 1 residue from a reference sequence, e.g., a naturally occurring SLAMF transmembrane domain or a SLAMF transmembrane domain described herein. In embodiments the SLAMF transmembrane domain of a SLAMF-CAR does not differ from, or shares 100% homology with, a reference sequence, e.g., a naturally occurring SLAMF transmembrane domain or a SLAMF transmembrane domain described herein.

SLAMF intracelluar domain, as that term is used herein, refers to a polypeptide domain having structural and functional properties of an intracellular domain of a SLAMF. In an embodiment the SLAMF intracellular domain of a SLAMF-CAR has at least 70, 80, 85, 90, 95, or 99% homology with a reference sequence, e.g., a naturally occurring SLAMF intracellular domain or a SLAMF intracellular domain described herein. In embodiments the SLAMF intracellular domain of a SLAMF-CAR differs at no more than 15, 10, 5, 2, or 1% of its residues from a reference sequence, e.g., a naturally occurring SLAMF intracellular domain or a SLAMF intracellular domain described herein. In embodiments the SLAMF intracellular domain of a SLAMF-CAR differs at no more than 5, 4, 3, 2 or 1 residue from a reference sequence, e.g., a naturally occurring SLAMF intracellular domain or a SLAMF intracellular domain described herein. In embodiments the SLAMF intracellular domain of a SLAMF-CAR does not differ from, or shares 100% homology with, a reference sequence, e.g., a naturally occurring SLAMF intracellular domain or a SLAMF intracellular domain described herein.

Fc-Binding Receptors

NKCARs described herein include CARs based on the Fc receptors, FcR-CARs, e.g., CD16-CARs, and CD64-CARs, which share functional and structural properties with CD16 and CD64.

Upon activation, NK cells produce cytokines and chemokines abundantly and at the same time exhibit potent cytolytic activity. Activation of NK cells can occur through the direct binding of NK cell receptors to ligands on the target cell, as seen with direct tumor cell killing, or through the crosslinking of the Fc receptor (CD 16; FcγRIII) by binding to the Fc portion of antibodies bound to an antigen-bearing cell. This CD16 engagement (CD16 crosslinking) initiates NK cell responses via intracellular signals that are generated through one, or both, of the CD16-associated adaptor chains, FcRγ or CD3 ζ. Triggering of CD16 leads to phosphorylation of the γ or ζ chain, which in turn recruits tyrosine kinases, syk and ZAP-70, initiating a cascade of signal transduction leading to rapid and potent effector functions. The most well-known effector function is the release of cytoplasmic granules carrying toxic proteins to kill nearby target cells through the process of antibody-dependent cellular cytotoxicity. CD16 crosslinking also results in the production of cytokines and chemokines that, in turn, activate and orchestrate a series of immune responses.

However, unlike T and B lymphocytes, NK cells are thought to have only a limited capacity for target recognition using germline-encoded activation receptors (Bottino et al., Curr Top Microbiol Immunol. 298:175-182 (2006); Stewart et al., Curr Top Microbiol Immunol. 298:1-21 (2006)). NK cells express the activating Fc receptor CD 16, which recognizes IgG-coated target cells, thereby broadening target recognition (Ravetch & Bolland, Annu Rev Immunol. 19:275-290 (2001); Lanier Nat. Immunol. 9(5):495-502 (2008); Bryceson & Long, Curr Opin Immunol. 20(3):344-352 (2008)).

The expression and signal transduction activity of several NK cell activation receptors requires physically associated adaptors, which transduce signals through immunoreceptor tyrosine-based activation motifs (ITAMs). Among these adaptors, FcRγ and CD3 ζ chains can associate with CD16 and natural cytotoxicity receptors (NCRs) as either disulfide-linked homo-dimers or hetero-dimers, and these chains have been thought to be expressed by all mature NK cells.

Amino acid sequence for CD16 (*Homo sapiens*) is available in the NCBI database, see e.g., accession number NP_000560.5 (GI: 50726979), NP_001231682.1 (GI: 348041254)

In an embodiment, a FcR-CAR comprises an antigen binding domain and a FcR transmembrane domain. In an embodiment, a FcR-CAR comprises an antigen binding domain and a FcR intracellular domain.

CD16 extracellular domain, as that term is used herein, refers to a polypeptide domain having structural and functional properties of a extracellular domain of a CD 16. In an embodiment the CD16 extracellular domain of a CD16-CAR has at least 70, 80, 85, 90, 95, or 99% homology with a reference sequence, e.g., a naturally occurring CD16 extracellular domain or a CD16 extracellular domain described herein. In embodiments the CD16 extracellular domain of a CD16-CAR differs at no more than 15, 10, 5, 2, or 1% of its residues from a reference sequence, e.g., a naturally occurring CD16 extracellular domain or a CD16 extracellular domain described herein. In embodiments the CD16 extracellular domain of a CD16-CAR differs at no more than 5, 4, 3, 2 or 1 residue from a reference sequence, e.g., a naturally occurring CD16 extracellular domain or a CD16 extracellular domain described herein. In embodiments the CD16 extracellular domain of a CD16-CAR does not differ from, or shares 100% homology with, a reference sequence, e.g., a naturally occurring CD16 extracellular domain or a CD16 extracellular domain described herein.

CD16 hinge or stem domain, as that term is used herein, refers to a polypeptide domain having structural and functional properties of a hinge or stem domain of a CD16. In an embodiment the CD16 hinge or stem domain of a CD16-CAR has at least 70, 80, 85, 90, 95, or 99% homology with a reference sequence, e.g., a naturally occurring CD16 hinge or stem domain or a CD16 hinge or stem domain described herein. In embodiments the CD16 hinge or stem domain of a CD16-CAR differs at no more than 15, 10, 5, 2, or 1% of its residues from a reference sequence, e.g., a naturally occurring CD16 hinge or stem domain or a CD16 hinge or stem domain described herein. In embodiments the CD16 hinge or stem domain of a CD16-CAR differs at no more than 5, 4, 3, 2 or 1 residue from a reference sequence, e.g., a naturally occurring CD16 hinge or stem domain or a CD16 hinge or stem domain described herein. In embodiments the CD16 hinge or stem domain of a CD16-CAR does not differ from, or shares 100% homology with, a reference sequence, e.g., a naturally occurring CD16 hinge or stem domain or a CD16 hinge or stem domain described herein.

CD16 transmembrane domain, as that term is used herein, refers to a polypeptide domain having structural and functional properties of a transmembrane domain of a CD16. In an embodiment the CD16 transmembrane domain of a CD16-CAR has at least 70, 80, 85, 90, 95, or 99% homology with a reference sequence, e.g., a naturally occurring CD16 transmembrane domain or a CD16 transmembrane domain described herein. In embodiments the CD16 transmembrane domain of a CD16-CAR differs at no more than 15, 10, 5, 2, or 1% of its residues from a reference sequence, e.g., a naturally occurring CD16 transmembrane domain or a CD16 transmembrane domain described herein. In embodiments the CD16 transmembrane domain of a CD16-CAR differs at no more than 5, 4, 3, 2 or 1 residue from a reference sequence, e.g., a naturally occurring CD16 transmembrane domain or a CD16 transmembrane domain described herein. In embodiments the CD16 transmembrane domain of a CD16-CAR does not differ from, or shares 100% homology with, a reference sequence, e.g., a naturally occurring CD16 transmembrane domain or a CD16 transmembrane domain described herein.

CD16 intracelluar domain, as that term is used herein, refers to a polypeptide domain having structural and functional properties of an intracellular domain of a CD16. In an embodiment the CD16 intracellular domain of a CD16-CAR has at least 70, 80, 85, 90, 95, or 99% homology with a reference sequence, e.g., a naturally occurring CD16 intracellular domain or a CD16 intracellular domain described herein. In embodiments the CD16 intracellular domain of a CD16-CAR differs at no more than 15, 10, 5, 2, or 1% of its residues from a reference sequence, e.g., a naturally occurring CD16 intracellular domain or a CD16 intracellular domain described herein. In embodiments the CD16 intracellular domain of a CD16-CAR differs at no more than 5, 4, 3, 2 or 1 residue from a reference sequence, e.g., a naturally occurring CD16 intracellular domain or a CD16 intracellular domain described herein. In embodiments the CD16 intracellular domain of a CD16-CAR does not differ from, or shares 100% homology with, a reference sequence, e.g., a naturally occurring CD16 intracellular domain or a CD16 intracellular domain described herein.

CD64 extracellular domain, as that term is used herein, refers to a polypeptide domain having structural and functional properties of a extracellular domain of a CD64. In an embodiment the CD64 extracellular domain of a CD64-CAR has at least 70, 80, 85, 90, 95, or 99% homology with a reference sequence, e.g., a naturally occurring CD64 extracellular domain or a CD64 extracellular domain described herein. In embodiments the CD64 extracellular domain of a CD64-CAR differs at no more than 15, 10, 5, 2, or 1% of its residues from a reference sequence, e.g., a naturally occurring CD64 extracellular domain or a CD64 extracellular domain described herein. In embodiments the CD64 extracellular domain of a CD64-CAR differs at no more than 5, 4, 3, 2 or 1 residue from a reference sequence, e.g., a naturally occurring CD64 extracellular domain or a CD64 extracellular domain described herein. In embodiments the CD64 extracellular domain of a CD64-CAR does not differ from, or shares 100% homology with, a reference sequence, e.g., a naturally occurring CD64 extracellular domain or a CD64 extracellular domain described herein.

CD64 hinge or stem domain, as that term is used herein, refers to a polypeptide domain having structural and functional properties of a hinge or stem domain of a CD64. In an embodiment the CD64 hinge or stem domain of a CD64-CAR has at least 70, 80, 85, 90, 95, or 99% homology with a reference sequence, e.g., a naturally occurring CD64 hinge or stem domain or a CD64 hinge or stem domain described herein. In embodiments the CD64 hinge or stem domain of a CD64-CAR differs at no more than 15, 10, 5, 2, or 1% of its residues from a reference sequence, e.g., a naturally occurring CD64 hinge or stem domain or a CD64 hinge or stem domain described herein. In embodiments the CD64 hinge or stem domain of a CD64-CAR differs at no more than 5, 4, 3, 2 or 1 residue from a reference sequence, e.g., a naturally occurring CD64 hinge or stem domain or a CD64 hinge or stem domain described herein. In embodiments the CD64 hinge or stem domain of a CD64-CAR does not differ from, or shares 100% homology with, a reference sequence, e.g., a naturally occurring CD64 hinge or stem domain or a CD64 hinge or stem domain described herein.

CD64 transmembrane domain, as that term is used herein, refers to a polypeptide domain having structural and functional properties of a transmembrane domain of a CD64. In an embodiment the CD64 transmembrane domain of a CD64-CAR has at least 70, 80, 85, 90, 95, or 99% homology with a reference sequence, e.g., a naturally occurring CD64 transmembrane domain or a CD64 transmembrane domain described herein. In embodiments the CD64 transmembrane domain of a CD64-CAR differs at no more than 15, 10, 5, 2, or 1% of its residues from a reference sequence, e.g., a naturally occurring CD64 transmembrane domain or a CD64 transmembrane domain described herein. In embodiments the CD64 transmembrane domain of a CD64-CAR differs at no more than 5, 4, 3, 2 or 1 residue from a reference sequence, e.g., a naturally occurring CD64 transmembrane domain or a CD64 transmembrane domain described herein. In embodiments the CD64 transmembrane domain of a CD64-CAR does not differ from, or shares 100% homology with, a reference sequence, e.g., a naturally occurring CD64 transmembrane domain or a CD64 transmembrane domain described herein. CD64 intracelluar domain, as that term is used herein, refers to a polypeptide domain having structural and functional properties of an intracellular domain of a CD64. In an embodiment the CD64 intracellular domain of a CD64-CAR has at least 70, 80, 85, 90, 95, or 99% homology with a reference sequence, e.g., a naturally occurring CD64 intracellular domain or a CD64 intracellular domain described herein. In embodiments the CD64 intracellular domain of a CD64-CAR differs at no more than 15, 10, 5, 2, or 1% of its residues from a reference sequence, e.g., a naturally occurring CD64 intracellular domain or a CD64 intracellular domain described herein. In embodiments the CD64 intracellular domain of a CD64-CAR differs at no more than 5, 4, 3, 2 or 1 residue from a reference sequence, e.g., a naturally occurring CD64 intracellular domain or a CD64 intracellular domain described herein. In embodiments the CD64 intracellular domain of a CD64-CAR does not differ from, or shares 100% homology with, a reference sequence, e.g., a naturally occurring CD64 intracellular domain or a CD64 intracellular domain described herein.

Ly49 and Related Killer Cell Lectin-Like Receptors

NKCARs described herein include Ly49-CARs, which share functional and structural properties with Ly49.

The Ly49 receptors derive from at least 23 identified genes (Ly49A-W) in mice. These receptors share many of the same roles in mouse NK cells and T cells as that played by KIRs in humans despite their different structure (type II integral membrane proteins of the C-type lectin superfamily), and they also contain a considerable degree of genetic variation like human KIRs. The remarkable functional similarity between Ly49 and KIR receptors suggest that these groups of receptors have evolved independently yet convergently to perform the same physiologic functionals in NK cells and T cells.

Like KIRs in humans, different Ly49 receptors recognize different MHC class I alleles and are differentially expressed on subsets of NK cells. The original prototypic Ly49 receptors, Ly49A and Ly49C possess a cytoplasmic domain bearing two immunotyrosine-based inhibitory motifs (ITIM) similar to inhibitory KIRs such as KIR2DL3. These domains have been identified to recruit the phosphatase, SHP-1, and like the inhibitory KIRs, serve to limit the activation of NK cells and T cells. In addition to the inhibitory Ly49 molecules, several family members such as Ly49D and Ly49H have lost the ITIM-containing domains, and have instead acquired the capacity to interact with the signaling adaptor molecule, DAP12 similar to the activating KIRs such as KIR2DS2 in humans.

Amino acid sequence for Ly49 family members are available in the NCBI database, see e.g., accession numbers AAF82184.1 (GI: 9230810), AAF99547.1 (GI: 9801837), NP_034778.2 (GI: 133922593), NP_034779.1 (GI: 6754462), NP_001095090.1 (GI: 197333718), NP_034776.1 (GI: 21327665), AAK11559.1 (GI: 13021834) and/or NP_038822.3 (GI: 9256549).

In an embodiment, a Ly49-CAR comprises an antigen binding domain and a Ly49 transmembrane domain. In an embodiment, a Ly49-CAR comprises an antigen binding domain and a NCR intracellular domain.

LY49 extracellular domain, as that term is used herein, refers to a polypeptide domain having structural and functional properties of a extracellular domain of a LY49. In an embodiment the LY49 extracellular domain of a LY49-CAR has at least 70, 80, 85, 90, 95, or 99% homology with a reference sequence, e.g., a naturally occurring LY49 extracellular domain or a LY49 extracellular domain described herein. In embodiments the LY49 extracellular domain of a LY49-CAR differs at no more than 15, 10, 5, 2, or 1% of its residues from a reference sequence, e.g., a naturally occurring LY49 extracellular domain or a LY49 extracellular domain described herein. In embodiments the LY49 extracellular domain of a LY49-CAR differs at no more than 5, 4, 3, 2 or 1 residue from a reference sequence, e.g., a naturally occurring LY49 extracellular domain or a LY49 extracellular domain described herein. In embodiments the LY49 extracellular domain of a LY49-CAR does not differ from, or shares 100% homology with, a reference sequence, e.g., a naturally occurring LY49 extracellular domain or a LY49 extracellular domain described herein.

LY49 hinge or stem domain, as that term is used herein, refers to a polypeptide domain having structural and functional properties of a hinge or stem domain of a LY49. In an embodiment the LY49 hinge or stem domain of a LY49-CAR has at least 70, 80, 85, 90, 95, or 99% homology with a reference sequence, e.g., a naturally occurring LY49 hinge or stem domain or a LY49 hinge or stem domain described herein. In embodiments the LY49 hinge or stem domain of a LY49-CAR differs at no more than 15, 10, 5, 2, or 1% of its residues from a reference sequence, e.g., a naturally occurring LY49 hinge or stem domain or a LY49 hinge or stem domain described herein. In embodiments the LY49 hinge or stem domain of a LY49-CAR differs at no more than 5, 4, 3, 2 or 1 residue from a reference sequence, e.g., a naturally occurring LY49 hinge or stem domain or a LY49 hinge or stem domain described herein. In embodiments the LY49 hinge or stem domain of a LY49-CAR does not differ from, or shares 100% homology with, a reference sequence, e.g., a naturally occurring LY49 hinge or stem domain or a LY49 hinge or stem domain described herein.

LY49 transmembrane domain, as that term is used herein, refers to a polypeptide domain having structural and functional properties of a transmembrane domain of a LY49. In an embodiment the LY49 transmembrane domain of a LY49-CAR has at least 70, 80, 85, 90, 95, or 99% homology with a reference sequence, e.g., a naturally occurring LY49 transmembrane domain or a LY49 transmembrane domain described herein. In embodiments the LY49 transmembrane domain of a LY49-CAR differs at no more than 15, 10, 5, 2, or 1% of its residues from a reference sequence, e.g., a naturally occurring LY49 transmembrane domain or a LY49 transmembrane domain described herein. In embodiments the LY49 transmembrane domain of a LY49-CAR differs at no more than 5, 4, 3, 2 or 1 residue from a reference sequence, e.g., a naturally occurring LY49 transmembrane domain or a LY49 transmembrane domain described herein. In embodiments the LY49 transmembrane domain of a LY49-CAR does not differ from, or shares 100% homology with, a reference sequence, e.g., a naturally occurring LY49 transmembrane domain or a LY49 transmembrane domain described herein.

LY49 intracelluar domain, as that term is used herein, refers to a polypeptide domain having structural and functional properties of an intracellular domain of a LY49. In an embodiment the LY49 intracellular domain of a LY49-CAR has at least 70, 80, 85, 90, 95, or 99% homology with a reference sequence, e.g., a naturally occurring LY49 intracellular domain or a LY49 intracellular domain described herein. In embodiments the LY49 intracellular domain of a LY49-CAR differs at no more than 15, 10, 5, 2, or 1% of its residues from a reference sequence, e.g., a naturally occurring LY49 intracellular domain or a LY49 intracellular domain described herein. In embodiments the LY49 intracellular domain of a LY49-CAR differs at no more than 5, 4, 3, 2 or 1 residue from a reference sequence, e.g., a naturally occurring LY49 intracellular domain or a LY49 intracellular domain described herein. In embodiments the LY49 intracellular domain of a LY49-CAR does not differ from, or shares 100% homology with, a reference sequence, e.g., a naturally occurring LY49 intracellular domain or a LY49 intracellular domain described herein.

Intracelluar Signaling Domains or Adaptor Molecules, e.g., DAP12

Some NKR-CARs interact with other molecules, e.g., molecules comprising an intracellular signaling domain, e.g., an ITAM. In an embodiment a intracellular signaling domain is DAP12.

DAP12 is so named because of its structural features, and presumed function. Certain cell surface receptors lack intrinsic functionality, which hypothetically may interact with another protein partner, suggested to be a 12 kD protein. The mechanism of the signaling may involve an ITAM signal.

The DAP12 was identified from sequence databases based upon a hypothesized relationship to CD3 (see Olcese, et al. (1997) J. Immunol. 158:5083-5086), the presence of an ITAM sequence (see Thomas (1995) J. Exp. Med. 181:1953-1956), certain size predictions (see Olcese; and Takase, et al. (1997) J. Immunol. 159:741-747, and other features. In particular, the transmembrane domain was hypothesized to contain a charged residue, which would allow a salt bridge with the corresponding transmembrane segments of its presumed receptor partners, KIR CD94 protein, and possibly other similar proteins. See Daeron, et al. (1995) Immunity 3:635-646.

In fact, many of the known KIR, MIR, ILT, and CD94/NKG2 receptor molecules may actually function with an accessory protein which is part of the functional receptor complex. See Olcese, et al. (1997) J. Immunol. 158:5083-5086; and Takase, et al. (1997) J. Immunol. 159:741-747.

A DAP 12 domain, as that term is used herein, refers to a polypeptide domain having structural and functional properties of a cytoplasmic domain of a DAP 12, and will typically include an ITAM domain. In an embodiment a DAP 12 domain of a KIR-CAR has at least 70, 80, 85, 90, 95, or 99% homology with a reference sequence, e.g., a naturally occurring DAP 12 or a DAP 12 described herein. In embodiments the DAP 12 domain of a KIR-CAR differs at no more than 15, 10, 5, 2, or 1% of its residues from a reference sequence, e.g., a naturally occurring DAP 12 or a DAP 12 described herein. In embodiments the DAP 12 domain of a KIR-CAR differs at no more than 5, 4, 3, 2 or 1 residue from a reference sequence, e.g., a naturally occurring DAP 12 or a DAP 12 described herein. In embodiments the DAP 12 domain of a KIR-CAR does not differ from, or shares 100% homology with, a reference sequence, e.g., a naturally occurring DAP 12 or a DAP 12 described herein.

The DAP10 was identified partly by its homology to the DAP12, and other features. In particular, in contrast to the DAP12, which exhibits an ITAM activation motif, the DAP10 exhibits an ITIM inhibitory motif. The MDL-1 was identified by its functional association with DAP12.

The functional interaction between, e.g., DAP12 or DAP10, and its accessory receptor may allow use of the structural combination in receptors which normally are not found in a truncated receptor form. Thus, the mechanism of signaling through such accessory proteins as the DAP12 and DAP10 allow for interesting engineering of other KIR-like receptor complexes, e.g., with the KIR, MIR, ILT, and CD94 NKG2 type receptors. Truncated forms of intact receptors may be constructed which interact with a DAP12 or DAP10 to form a functional signaling complex.

The primate nucleotide sequence of DAP12 corresponds to SEQ ID NO: 6; the amino acid sequence corresponds to SEQ ID NO: 7. The signal sequence appears to run from met(−26) to gln(−1) or ala1; the mature protein should run from about ala1 (or gln2), the extracellular domain from about ala1 to pro14; the extracellular domain contains two cysteines at 7 and 9, which likely allow disulfide linkages to additional homotypic or heterotypic accessory proteins; the transmembrane region runs from about gly15 or val16 to about gly39; and an ITAM motif from tyr65 to leu79 (YxxL-6/8x-YxxL (SEQ ID NO: 68)). The LVA03A EST was identified and used to extract other overlapping sequences. See also Genbank Human ESTs that are part of human DAP12; some, but not all, inclusive Genbank Accession # AA481924; H39980; W60940; N41026; R49793; W60864; W92376; H12338; T52100; AA480109; H12392; W74783; and T55959

Inhibitory NKR-CARs

The present invention provides compositions and methods for limiting the depletion of non-cancerous cells by a type of CAR T cell therapy. As disclosed herein, a type of CAR T cell therapy comprises the use of NK receptors including but is not limited to activating and inhibitory receptors of NK cells known as killer cell immunoglobulin-like receptor (KIR). Accordingly the invention provides compositions and methods of using a NKR-CAR, e.g., a KIR-CAR, including but is not limited to an activating NKR-CAR (actNKR-CAR), e.g., an activating KIR-CAR (actKIR-CAR) and an inhibitory NKR-CAR (inhNKR-CAR), e.g., an inhibitory KIR-CAR (inhKIR-CAR).

In some embodiments, the KIR of an inhKIR-CARs is an inhibitory KIR that comprises a long cytoplasmic tail containing Immunoreceptor Tyrosine-based Inhibitory Motif (ITIM), which transduce inhibitory signals (referred elsewhere herein as inhKIR-CAR).

In some embodiments, an inhKIR-CAR comprises a cytoplasmic domain of an inhibitory molecule other than KIR. These inhibitory molecules can, in some embodiments, decrease the ability of a cell to mount an immune effector response. Cytoplasmic domains of inhibitory molecules may be coupled, e.g., by fusion, to transmembrane domains of KIR. Exemplary inhibitory molecules are shown in table 1:

TABLE 1

| Inhibitory molecules |
|---|
| CD160 |
| 2B4 |
| PD1 |
| TIM3 |
| LAG3 |
| TIGIT |
| CTLA-4 |
| BTLA |
| LAIR1 |
| PD-L1 |
| VISTA |

In some embodiments, an inhKIR-CAR comprises a PD1 cytoplasmic domain. A PD1 cytoplasmic domain, as that term is used herein, refers to a polypeptide domain having structural and functional properties of a cytoplasmic domain of a PD1. In an embodiment the PD1 cytoplasmic domain of a KIR-CAR has at least 70, 80, 85, 90, 95, or 99% homology with a reference sequence, e.g., a naturally occurring PD1 cytoplasmic domain or a PD1 cytoplasmic domain described herein (SEQ ID NO: 14). In embodiments the PD1 cytoplasmic domain of a KIR-CAR differs at no more than 15, 10, 5, 2, or 1% of its residues from a reference sequence, e.g., a naturally occurring PD1 cytoplasmic domain or a PD1 cytoplasmic domain described herein. In embodiments the PD1 cytoplasmic domain of a KIR-CAR differs at no more than 5, 4, 3, 2 or 1 residue from a reference sequence, e.g., a naturally occurring PD1 cytoplasmic domain or a PD1 cytoplasmic domain described herein. In embodiments the PD1 cytoplasmic domain of a KIR-CAR does not differ from, or shares 100% homology with, a reference sequence, e.g., a naturally occurring PD1 cytoplasmic domain or a PD1 cytoplasmic domain described herein.

In some embodiments, an inhKIR-CAR comprises a CTLA-4 cytoplasmic domain. A CTLA-4 cytoplasmic domain, as that term is used herein, refers to a polypeptide domain having structural and functional properties of a cytoplasmic domain of a CTLA-4. In an embodiment the CTLA-4 cytoplasmic domain of a KIR-CAR has at least 70, 80, 85, 90, 95, or 99% homology with a reference sequence, e.g., a naturally occurring CTLA-4 cytoplasmic domain or a CTLA-4 cytoplasmic domain described herein (SEQ ID NO: 15). In embodiments the CTLA-4 cytoplasmic domain of a KIR-CAR differs at no more than 15, 10, 5, 2, or 1% of its residues from a reference sequence, e.g., a naturally occurring CTLA-4 cytoplasmic domain or a CTLA-4 cytoplasmic domain described herein. In embodiments the CTLA-4 cytoplasmic domain of a KIR-CAR differs at no more than 5, 4, 3, 2 or 1 residue from a reference sequence, e.g., a naturally occurring CTLA-4 cytoplasmic domain or a CTLA-4 cytoplasmic domain described herein. In embodiments the CTLA-4 cytoplasmic domain of a KIR-CAR does not differ from, or shares 100% homology with, a reference sequence, e.g., a naturally occurring CTLA-4 cytoplasmic domain or a CTLA-4 cytoplasmic domain described herein.

In an embodiment, an inhNKR-CAR, e.g., an inhKIR-CAR, upon engagement with an antigen on a non-target or bystander cell, inactivates the cytotoxic cell comprising the inhNKR-CAR. While much of the description below relates to inhKIR-CARs, the invention includes the analogous application of other inhNKR-CARs.

In one embodiment, T cells expressing the actKIR-CAR exhibit an antitumor property when bound to its target, whereas T cells expressing an inhKIR-CAR results in inhibition of cell activity when the inhKIR-CAR is bound to its target.

Regardless of the type of KIR-CAR, KIR-CARs are engineered to comprise an extracellular domain having an antigen binding domain fused to a cytoplasmic domain. In one embodiment, KIR-CARs, when expressed in a T cell, are able to redirect antigen recognition based upon the antigen specificity. An exemplary antigen is CD19 because this antigen is expressed on B cell lymphoma. However, CD19 is also expressed on normal B cells, and thus CARs comprising an anti-CD19 domain may result in depletion of normal B cells. Depletion of normal B cells can make a treated subject susceptible to infection, as B cells normally aid T cells in the control of infection. The present invention provides for compositions and methods to limit the depletion of normal tissue during KIR-CAR T cell therapy. In one embodiment, the present invention provides methods to treat cancer and other disorders using KIR-CAR T cell therapy while limiting the depletion of healthy bystander cells.

In one embodiment, the invention comprises controlling or regulating KIR-CAR T cell activity. In one embodiment, the invention comprises compositions and methods related to genetically modifying T cells to express a plurality of types of KIR-CARs, where KIR-CAR T cell activation is dependent on the binding of a plurality of types of KIR-CARs to their target receptor. Dependence on the binding of a plurality of types of KIR-CARs improves the specificity of the lytic activity of the KIR-CAR T cell, thereby reducing the potential for depleting normal healthy tissue.

In another embodiment, the invention comprises compositions and methods related to genetically modifying T cells with an inhibitory KIR-CAR. In one embodiment, the inhibitory KIR-CAR comprises an extracellular antigen binding domain that recognizes an antigen associated with a normal, non-cancerous, cell and an inhibitory cytoplasmic domain.

In one embodiment, the invention provides a dual KIR-CAR where a T cell is genetically modified to express an inhKIR-CAR and an actKIR-CAR. In one embodiment, binding of the inhKIR-CAR to a normal, non-cancerous cell results in the inhibition of the dual KIR-CAR T cell. For example, in one embodiment, binding of the inhKIR-CAR to a normal, non-cancerous cell results in the death of the dual KIR-CAR T cell. In another embodiment, binding of the inhKIR-CAR to a normal, non-cancerous cell results in inhibiting the signal transduction of the actKIR-CAR. In yet another embodiment, binding of the inhKIR-CAR to a normal, non-cancerous cell results in the induction of a signal transduction signal that prevents the actKIR-CAR T cell from exhibiting its anti-tumor activity. Accordingly, the dual KIR-CAR comprising at least one inhKIR-CAR and at least one actKIR-CAR of the invention provides a mechanism to regulate the activity of the dual KIR-CAR T cell.

In one embodiment, the present invention provides methods for treating cancer and other disorders using KIR-CAR T cell therapies while minimizing the depletion of normal healthy tissue. The cancer may be a hematological malignancy, a solid tumor, a primary or a metastasizing tumor. Other diseases treatable using the compositions and methods of the invention include viral, bacterial and parasitic infections as well as autoimmune diseases.

Extracellular Hinge Domain

Extracellular hinge domain, as that term is used herein, refers to a polypeptide sequence of a NKCAR disposed between the transmembrane domain and antigen binding domain. In an embodiment the extracellular hinge domain allows sufficient distance from the outer surface of the cell and the antigen binding domain as well as flexibility to minimize steric hinderance between the cell and the antigen binding domain. In an embodiment the extracellular hinge domain is sufficiently short or flexible that it does not interfere with engagement of the cell that includes the NKCAR with an antigen bearing cell, e.g., a target cell. In an embodiment the extracellular hinge domain is from 2 to 20, 5 to 15, 7 to 12, or 8 to 10 amino acids in length. In an embodiment the hinge domain includes at least 50, 20, or 10 residues. In embodiments the hinge is 10 to 300, 10 to 250, or 10 to 200 residues in length. In an embodiment the distance from which the hinge extends from the cell is sufficiently short that the hinge does not hinder engagement with the surface of a target cell. In an embodiment the hinge extends less than 20, 15, or 10 nanometers from the surface of the cytotoxic cell. Thus, suitability for a hinge can be influenced by both linear length, the number of amino acid residues and flexibility of the hinge. An IgG4 hinge can be as long as 200 amino acids in length, but the distance it extends from the surface of the cytotoxic cell is smaller due to Ig-domain folding. A CD8alpha hinge, which is ~43 amino acids is rather linear at ~8 nm in length. In contrast, the IgG4 C2 & C3 hinge) is ~200 amino acids in length, but has a distance from the cytotoxic cell surface comparable to that of the CD8 alpha hinge. While not wishing to be bound by theory, the similarity in extension is influenced by flexibility.

In some instances, the extracellular hinge domain is, e.g., a hinge from a human protein, a fragment thereof, or a short oligo- or polypeptide linker.

In some embodiments, the hinge is an artificial sequence. In one embodiment, the hinge is a short oligopeptide linker comprising a glycine-serine doublet.

In some embodiments, the hinge is a naturally occurring sequence. In some embodiments, the hinge can be a human Ig (immunoglobulin) hinge, or fragment thereof. In one embodiment, for example, the hinge comprises (e.g., consists of) the amino acid sequence of the IgG4 hinge (SEQ ID NO: 49). In one embodiment, for example, the hinge comprises (e.g., consists of) the amino acid sequence of the IgD hinge (SEQ ID NO: 50). In some embodiments, the hinge can be a human CD8 hinge, or fragment thereof. In one embodiment, for example, the hinge comprises (e.g., consists of) the amino acid sequence of the CD8 hinge (SEQ ID NO: 51).

TCARS

In some embodiments, the CAR cell therapy of the present invention comprises NKR-CAR in combination with a TCAR. In one embodiment, a TCAR comprises an antigen binding domain fused to an intracellular domain. In embodiments, an intracellular signaling domain produces an intracellular signal when an extracellular domain, e.g., an antigen binding domain, to which it is fused binds a counter ligand. Intracellular signaling domains can include primary intracellular signaling domains and costimulatory signaling domains. In an embodiment, a TCAR molecule can be constructed for expression in an immune cell, e.g., a T cell, such that the TCAR molecule comprises a domain, e.g., a primary intracellular signaling domains, costimulatory signaling domain, inhibitory domains, etc., that is derived from a polypeptide that is typically associated with the immune cell. For example, a TCAR for expression in a T cell can comprise a 41BB domain and an CD3 zeta domain. In this instance, both the 41BB and CD3 zeta domains are derived from polypeptides associated with the T cell. In another embodiment, a TCAR molecule can be constructed for expression in an immune cell e.g., a T cell, such that the TCAR molecule comprises a domain that is derived from a polypeptide that is not typically associated with the immune cell. Alternatively, a TCAR for expression in a NK cell can comprise a 41BB domain and a CD3 zeta domain derived from a T cell (See e.g. WO2013/033626, incorporated herein by reference).

Primary Intracelluar Signaling Domain

In some embodiments a primary intracellular signaling domain produces an intracellular signal when an extracellular domain, e.g., an antigen binding domain, to which it is fused binds cognate antigen. It is derived from a primary stimulatory molecule, e.g., it comprises intracellular sequence of a primary stimulatory molecule. It comprises sufficient primary stimulatory molecule sequence to produce an intracellular signal, e.g., when an antigen binding domain to which it is fused binds cognate antigen.

A primary stimulatory molecule, is a molecule, that upon binding cognate ligand, mediates an immune effector response, e.g., in the cell in which it is expressed. Typically, it generates an intracellular signal that is dependent on binding to a cognate ligand that comprises antigen. The TCR/CD3 complex is an exemplary primary stimulatory molecule; it generates an intracellular signal upon binding to cognate ligand, e.g., an MHC molecule loaded with a peptide. Typically, e.g., in the case of the TCR/CD3 primary stimulatory molecule, the generation of an intracellular signal by a primary intracellular signaling domain is dependent on binding of the primary stimulatory molecule to antigen.

Primary stimulation can mediate altered expression of certain molecules, such as downregulation of TGF-β, and/or reorganization of cytoskeletal structures, and the like. Stimulation, can, e.g., in the presence of costimulation, result in an optimization, e.g., an increase, in an immune effector function of the T cell. Stimulation, e.g., in the context of a T cell, can mediate a T cell response, e.g., proliferation, activation, differentiation, and the like.

In an embodiment, the primary intracellular signaling domain comprises a signaling motif, e.g., an immunoreceptor tyrosine-based activation motif or ITAMs. A primary intracellular signaling domain can comprise ITAM containing cytoplasmic signaling sequences from TCR zeta (CD3 zeta), FcR gamma, FcR beta, CD3 gamma, CD3 delta, CD3 epsilon, CD5, CD22, CD79a, CD79b, CD278 (also known as "ICOS") and CD66d.

Exemplary primary intracellular signaling domains are provided in Table 2.

TABLE 2

| Primary Intracellular Signaling Domains In embodiments the domain comprises an ITAM |
|---|
| TCR zeta |
| FcR gamma |
| FcR beta |
| CD3 gamma |
| CD3 delta |
| CD3 epsilon |
| CD79a |
| CD79b |
| CD66d |
| DAP10 |
| DAP12 |

A primary intracellular signaling domain comprises a functional fragment, or analog, of a primary stimulatory molecule (e.g., CD3 zeta—GenBank Acc. No. BAG36664.1) It can comprise the entire intracellular region or a fragment of the intracellular region which is sufficient for generation of an intracellular signal when an antigen binding domain to which it is fused, or coupled by a dimerization switch, binds cognate antigen. In embodiments the primary intracellular signaling domain has at least 70, 75. 80. 85, 90, 95, 98, or 99% sequence identity with a naturally occurring primary stimulatory molecule, e.g., a human (GenBank Acc. No. BAG36664.1), or other mammalian, e.g., a nonhuman species, e.g., rodent, monkey, ape or murine intracelluar primary stimulatory molecule. In embodiments the primary intracellular signaling domain has at least 70, 75. 80. 85, 90, 95, 98, or 99% sequence identity with SEQ ID NO: 13.

In embodiments the primary intracellular signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human primary stimulatory molecule disclosed herein.

Costimulatory Signaling Domain

In an embodiment, a costimulatory signaling domain produces an intracellular signal when an extracellular domain, e.g., an antigen binding domain to which it is fused, or coupled by a dimerization switch, binds cognate ligand. It is derived from a costimulatory molecule. It comprises sufficient primary costimulatory molecule sequence to produce an intracellular signal, e.g., when an extracellular domain, e.g., an antigen binding domain, to which it is fused, or coupled by a dimerization switch, binds cognate ligand.

Costimulatory molecules are cell surface molecules, other than antigen receptors or their counter ligands, that promote an immune effector response. In some cases they are required for an efficient or enhanced immune response. Typically, a costimulatory molecule generates an intracellular signal that is dependent on binding to a cognate ligand that is, in embodiments, other than an antigen, e.g., the antigen recognized by an antigen binding domain of a T cell. Typically, signaling from a primary stimulatory molecule and a costimulatory molecule contribute to an immune effector response, and in some cases both are required for efficient or enhanced generation of an immune effector response.

A costimulatory domain comprises a functional fragment, or analog, of a costimulatory molecule (e.g., 4-1BB). It can comprise the entire intracellular region or a fragment of the intracellular region which is sufficient for generation of an intracellular signal, e.g., when an antigen binding domain to which it is fused, or coupled by a dimerization switch, binds cognate antigen. In embodiments the costimulatory domain has at least 70, 75. 80. 85, 90, 95, 98, or 99% sequence identity with a naturally occurring costimulatory molecule, e.g., a human, or other mammalian, e.g., a nonhuman species, e.g., rodent, monkey, ape or murine intracelluar costimulatory molecule. In embodiments the costimatory domain has at least 70, 75. 80. 85, 90, 95, 98, or 99% sequence identity with SEQ ID NO: 12.

Exemplary costimulatory signaling domains (intracellular signaling domains) are provided in Table 3.

TABLE 3

| Costimulatory Signaling Domains for RCARX (identified by the Costimulatory Molecules from which they are derived) |
|---|
| CD27 |
| CD28, |
| 4-1BB (CD137) |
| OX40 |
| CD30 |
| CD40 |
| ICOS (CD278) |
| ICAM-1 |
| LFA-1 (CD11a/CD18) |
| CD2 |
| CD7 |
| LIGHT |
| NKG2C |
| B7-H3 |
| a ligand that specifically binds with CD83 |

In embodiments the costimulatory signaling domain, has at least 70, 75, 80, 85, 90, 95, 96, 97, 98, or 99% identity with, or differs by no more than 30, 25, 20, 15, 10, 5, 4, 3, 2, or 1 amino acid residues from the corresponding residues of a naturally occurring human primary stimulatory molecule, e.g., a naturally occurring human costimulatory molecule disclosed herein.

Antigen Binding Domain

The CARs described herein, e.g., the KIR-CARs described herein, include an antigen binding domain in the extracellular region. An "antigen binding domain" as the term is used herein, refers to a molecule that has affinity for a target antigen, typically an antigen on a target cell, e.g., a cancer cell. An exemplary antigen binding domain comprises a polypeptide, e.g., an antibody molecule (which includes an antibody, and antigen binding fragments thereof, e.g., a immunoglobulin, single domain antibody (sdAb), and an scFv), or a non-antibody scaffold, e.g., a fibronectin, and the like. In embodiments, the antigen binding domain is a single polypeptide. In embodiments, the antigen binding domain comprises, one, two, or more, polypeptides.

The choice of an antigen binding domain can depend upon the type and number of ligands or receptors that define the surface of a target cell. For example, the antigen binding domain may be chosen to recognize a ligand or receptor that acts as a cell surface marker on target cells associated with a particular disease state. Examples of cell surface markers that may act as ligands or receptors include a cell surface marker associated with a particular disease state, e.g., cell surface makers for viral diseases, bacterial diseases parasitic infections, autoimmune diseases and disorders associated with unwanted cell proliferation, e.g., a cancer, e.g., a cancer described herein.

In the context of the present disclosure, "tumor antigen" or "proliferative disorder antigen" or "antigen associated with a proliferative disorder" refers to antigens that are common to specific proliferative disorders. In certain aspects, the proliferative disorder antigens of the present invention are derived from, cancers including but not limited to primary or metastatic melanoma, thymoma, lymphoma, sarcoma, lung cancer (e.g., NSCLC or SCLC), liver cancer, non-Hodgkin's lymphoma, Hodgkin's lymphoma, leukemias, multiple myeloma, glioblastoma, neuroblastoma, uterine cancer, cervical cancer, renal cancer, thyroid cancer, bladder cancer, kidney cancer and adenocarcinomas such as breast cancer, prostate cancer, ovarian cancer, pancreatic cancer, colon cancer and the like. In some embodiments, the cancer is B-cell acute lymphoid leukemia ("BALL"), T-cell acute lymphoid leukemia ("TALL"), acute lymphoid leukemia (ALL), acute myelogenous leukemia (AML); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, Marginal zone lymphoma, multiple myeloma, myelodysplasia and myelodysplastic syndrome, non-Hodgkin's lymphoma, plasmablastic lymphoma, plasmacytoid dendritic cell neoplasm, Waldenstrom macroglobulinemia, In one embodiment, the tumor antigen comprises one or more antigenic cancer epitopes immunologically recognized by tumor infiltrating lymphocytes (TIL) derived from a cancer tumor of a mammal.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), EGFRvIII, IL-11Ra, IL-13Ra, EGFR, B7H3, Kit, CA-IX, CS-1, MUC1, BCMA, bcr-abl, HER2, β-human chorionic gonadotropin, alphafetoprotein (AFP), ALK, CD19, CD123, cyclin B1, lectin-reactive AFP, Fos-related antigen 1, ADRB3, thyroglobulin, EphA2, RAGE-1, RU1, RU2, SSX2, AKAP-4, LCK, OY-TES1, PAX5, SART3, CLL-1, fucosyl GM1, GloboH, MN-CA IX, EPCAM, EVT6-AML, TGS5, human telomerase reverse transcriptase, plysialic acid, PLAC1, RU1, RU2 (AS), intestinal carboxyl esterase, lewisY, sLe, LY6K, mut hsp70-2, M-CSF, MYCN, RhoC, TRP-2, CYP1B1, BORIS, prostase, prostate-specific antigen (PSA), PAX3, PAP, NY-ESO-1, LAGE-1a, LMP2, NCAM, p53, p53 mutant, Ras mutant, gp100, prostein, OR51E2, PANX3, PSMA, PSCA, Her2/neu, hTERT, HMWMAA, HAVCR1, VEGFR2, PDGFR-beta, legumain, HPV E6, E7, survivin and telomerase, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART1, XAGE1, ELF2M, ERG (TMPRSS2 ETS fusion gene), NA17, neutrophil elastase, sarcoma translocation breakpoints, NY-BR-1, ephrinB2, CD20, CD22, CD24, CD30, CD33, CD38, CD44v6, CD97, CD171, CD179a, androgen receptor, insulin growth factor (IGF)-I, IGF-II, IGF-I receptor, GD2, o-acetyl-GD2, GD3, GM3, GPRC5D, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, CD33, BCMA, GD2, CLL-1, CA-IX, MUC1, HER2, and any combination thereof.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target antigens include transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

Non-limiting examples of tumor antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

Depending on the desired antigen to be targeted, the CAR of the invention can be engineered to include the appropriate antigen bind domain that is specific to the desired antigen target.

Antigen Binding Domains Derived from an Antibody Molecule

The antigen binding domain can be derived from an antibody molecule, e.g., one or more of monoclonal antibodies, polyclonal antibodies, recombinant antibodies, human antibodies, humanized antibodies, single-domain antibodies e.g., a heavy chain variable domain (VH), a light chain variable domain (VL) and a variable domain (VHH) from, e.g., human or camelid origin. In some instances, it is beneficial for the antigen binding domain to be derived from the same species in which the CAR will ultimately be used in, e.g., for use in humans, it may be beneficial for the antigen binding domain of the CAR, e.g., the KIR-CAR, e.g., described herein, to comprise a human or a humanized antigen binding domain. Antibodies can be obtained using known techniques known in the art.

The term "antibody," as used herein, refers to an immunoglobulin molecule which specifically binds with a target antigen. An antibody can be intact immunoglobulin derived from natural sources or from recombinant sources and can be an immunoreactive portion of intact immunoglobulin. Antibodies are typically tetramers of immunoglobulin molecules. The antibody molecule described herein may exist in a variety of forms where the antigen binding portion of the antibody is expressed as part of a contiguous polypeptide chain including, for example, a single domain antibody fragment (sdAb), a single chain antibody (scFv) and a humanized or human antibody, e.g., as described herein.

The term "antibody fragment" refers to a portion of an intact antibody and refers to the antigenic determining variable regions of an intact antibody. Examples of antibody fragments include, but are not limited to, a single chain domain antibody (sdAb), Fab, Fab', F(ab')2, and Fv fragments, linear antibodies, scFv antibodies, a linear antibody, single domain antibody such as an sdAb (either VL or VH), a camelid VHH domain, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody molecule which is generated using recombinant DNA technology, such as, for example, an antibody molecule expressed by a bacteriophage as described herein. The term should also be construed to mean an antibody molecule which has been generated by the synthesis of a DNA molecule encoding the antibody molecule and which DNA molecule expresses an antibody protein, or an amino acid sequence specifying the antibody, wherein the DNA or amino acid sequence has been obtained using synthetic DNA or amino acid sequence technology which is available and well known in the art.

In embodiments, the antigen binding domain comprises a fragment of an antibody that is sufficient to confer recognition and specific binding to the target antigen. Examples of an antibody fragment include, but are not limited to, an Fab, Fab', $F(ab')_2$, or Fv fragment, an scFv antibody fragment, a linear antibody, single domain antibody such as an sdAb (either VL or VH), a camelid VHH domain, and multi-specific antibodies formed from antibody fragments.

In an embodiment, the antigen binding domain is a "scFv," which can comprise a fusion protein comprising a VL chain and a VH chain of an antibody, where the VH and VL are, e.g., linked via a short flexible polypeptide linker, e.g., a linker described herein. The scFv is capable of being expressed as a single chain polypeptide and retains the specificity of the intact antibody from which it is derived. Moreover, the VL and VH variable chains can be linked in either order, e.g., with respect to the N-terminal and C-terminal ends of the polypeptide, the scFv may comprise VL-linker-VH or may comprise VH-linker-VL. An scFv that can be prepared according to method known in the art (see, for example, Bird et al., (1988) Science 242:423-426 and Huston et al., (1988) Proc. Natl. Acad. Sci. USA 85:5879-5883).

As described above and elsewhere, scFv molecules can be produced by linking VH and VL chains together using flexible polypeptide linkers. In some embodiments, the scFv molecules comprise flexible polypeptide linker with an optimized length and/or amino acid composition. The flexible polypeptide linker length can greatly affect how the variable regions of a scFv fold and interact. In fact, if a short polypeptide linker is employed (e.g., between 5-10 amino acids, intrachain folding is prevented. For examples of linker orientation and size see, e.g., Hollinger et al. 1993 Proc Natl Acad. Sci. U.S.A. 90:6444-6448, U.S. Patent Application Publication Nos. 2005/0100543, 2005/0175606, 2007/0014794, and PCT publication Nos. WO2006/020258 and WO2007/024715, is incorporated herein by reference. In one embodiment, the peptide linker of the scFv consists of amino acids such as glycine and/or serine residues used alone or in combination, to link variable heavy and variable light chain regions together. In one embodiment, the flexible polypeptide linker is a Gly/Ser linker and, e.g., comprises the amino acid sequence (Gly-Gly-Gly-Ser)n, where n is a positive integer equal to or greater than 1. For example, n=1, n=2, n=3. n=4, n=5 and n=6, n=7, n=8, n=9 and n=10 (SEQ ID NO: 69). In one embodiment, the flexible polypeptide linkers include, but are not limited to, (Gly4 Ser)4 (SEQ ID NO: 70) or (Gly4 Ser)3 (SEQ ID NO: 71). In another embodiment, the linkers include multiple repeats of (Gly2Ser), (GlySer) or (Gly3Ser) (SEQ ID NO: 72).

In some embodiments, the antigen binding domain is a single domain antigen binding (SDAB) molecules. A SDAB molecule includes molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies (e.g., described in more detail below). SDAB molecules may be any of the art, or any future single domain molecules. SDAB molecules may be derived from any species including, but not limited to mouse, human, camel, llama, fish, shark, goat, rabbit, and bovine. This term also includes naturally occurring single domain antibody molecules from species other than Camelidae and sharks.

In one aspect, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

According to another aspect, an SDAB molecule is a naturally occurring single domain antigen binding molecule known as a heavy chain devoid of light chains. Such single domain molecules are disclosed in WO 9404678 and Hamers-Casterman, C. et al. (1993) *Nature* 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

In certain embodiments, the SDAB molecule is a single chain fusion polypeptide comprising one or more single domain molecules (e.g., nanobodies), devoid of a complementary variable domain or an immunoglobulin constant, e.g., Fc, region, that binds to one or more target antigens.

The SDAB molecules can be recombinant, CDR-grafted, humanized, camelized, de-immunized and/or in vitro generated (e.g., selected by phage display).

In one embodiment, the antigen biding domain portion comprises a human antibody or a fragment thereof.

In some embodiments, a non-human antibody is humanized, where specific sequences or regions of the antibody are modified to increase similarity to an antibody naturally produced in a human. In an embodiment, the antigen binding domain is humanized.

Non human antibodies can be humanized using a variety of techniques known in the art, e.g., CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. No. 6,407,213, U.S. Pat. No. 5,766,886, International Publication No. WO 9317105, Tan et al., 2002, J. Immunol., 169:1119-25; Caldas et al., 2000, Protein Eng., 13(5):353-60; Morea et al., 2000, Methods, 20:267-79; Baca et al., 1997, J. Biol. Chem., 272:10678-84; Roguska et al., 1996, Protein Eng., 9(10):895-904; Couto et al., 1995, Cancer Res., 55:5973s-5977; Couto et al., 1995, Cancer Res., 55(8):1717-22; Sandhu 1994 Gene, 150(2): 409-10; and Pedersen et al., 1994, J. Mol. Biol., 235(3): 959-73, each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties). In preferred embodiments, the humanized antibody molecule comprises a sequence described herein, e.g., a variable light chain and/or a variable heavy chain described herein, e.g., a humanized variable light chain and/or variable heavy chain described in Table 4.

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816, 567; 6,331,415; 5,225,539; 5,530,101; 5,585,089; 6,548, 640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions.

In another aspect, the antigen binding domain is a T cell receptor ("TCR"), or a fragment thereof, for example, a single chain TCR (scTCR). Methods to make such TCRs is known in the art. See, e.g., Willemsen R A et al, Gene Therapy 7: 1369-1377 (2000); Zhang T et al, Cancer Gene Ther 11: 487-496 (2004); Aggen et al, Gene Ther. 19(4): 365-74 (2012) (references are incorporated herein by its entirety). For example, scTCR can be engineered that contains the Vα and Vβ genes from a T cell clone linked by a linker (e.g., a flexible peptide). This approach is very useful to cancer associated target that itself is intracellular, however, a fragment of such antigen (peptide) is presented on the surface of the cancer cells by MHC.

TABLE 4

Exemplary Antigen Binding Domains

| Target Antigen | Name | Amino Acid Sequence |
|---|---|---|
| CD19 | huscFv1 | EIVMTQSPATLSLSPGERATLSCRASQDISKYLNWYQQKPGQAPRL<br>LIYHTSRLHSGIPARFSGSGSGTDYTLTISSLQPEDFAVYFCQQGNT<br>LPYTFGQGTKLEIKGGGGSGGGGSGGGGSQVQLQESGPGLVKPSE<br>TLSLTCTVSGVSLPDYGVSWIRQPPGKGLEWIGVIWGSETTYYSSS<br>LKSRVTISKDNSKNQVSLKLSSVTAADTAVYYCAKHYYYGGSYA<br>MDYWGQGTLVTVSS (SEQ ID NO: 16) |
| CD19 | huscFv2 | eivmtqspatlslspgeratlscrasqdiskylnwyqqkpgqaprlliyhtsrlhsgiparfsgsgsgtdy<br>tltisslqpedfavyfcqqgntlpytfgqgtkleikggggsggggsggggsqvqlqesgpglvkpsetl<br>sltctvsgvslpdygvswirqppgkglewigviwgsettyyqsslksrvtiskdnsknqvslklssvta<br>adtavyycakhyyyggsyamdywgqgtlvtvss (SEQ ID NO: 17) |
| CD19 | huscFv3 | qvqlqesgpglvkpsetlsltctvsgvslpdygvswirqppgkglewigviwgsettyyssslksrvti<br>skdnsknqvslklssvtaadtavyycakhyyyggsyamdywgqgtlvtvssggggsggggsggg<br>gseivmtqspatlslspgeratlscrasqdiskylnwyqqkpgqaprlliyhtsrlhsgiparfsgsgsgt<br>dytltisslqpedfavyfcqqgntlpytfgqgtkleik (SEQ ID NO: 18) |
| CD19 | huscFv4 | qvqlqesgpglvkpsetlsltctvsgvslpdygvswirqppgkglewigviwgsettyyqsslksrvti<br>skdnsknqvslklssvtaadtavyycakhyyyggsyamdywgqgtlvtvssggggsggggsggg<br>gseivmtqspatlslspgeratlscrasqdiskylnwyqqkpgqaprlliyhtsrlhsgiparfsgsgsgt<br>dytltisslqpedfavyfcqqgntlpytfgqgtkleik (SEQ ID NO: 19) |
| CD19 | huscFv5 | eivmtqspatlslspgeratlscrasqdiskylnwyqqkpgqaprlliyhtsrlhsgiparfsgsgsgtdy<br>tltisslqpedfavyfcqqgntlpytfgqgtkleikggggsggggsggggsggggsqvqlqesgpglv<br>kpsetlsltctvsgvslpdygvswirqppgkglewigviwgsettyyssslksrvtiskdnsknqvslkl<br>ssvtaadtavyycakhyyyggsyamdywgqgtlvtvss (SEQ ID NO: 20) |
| CD19 | huscFv6 | eivmtqspatlslspgeratlscrasqdiskylnwyqqkpgqaprlliyhtsrlhsgiparfsgsgsgtdy<br>tltisslqpedfavyfcqqgntlpytfgqgtkleikggggsggggsggggsggggsqvqlqesgpglv<br>kpsetlsltctvsgvslpdygvswirqppgkglewigviwgsettyyqsslksrvtiskdnsknqvslk<br>lssvtaadtavyycakhyyyggsyamdywgqgtlvtvss (SEQ ID NO: 21) |
| CD19 | huscFv7 | qvqlqesgpglvkpsetlsltctvsgvslpdygvswirqppgkglewigviwgsettyyssslksrvti<br>skdnsknqvslklssvtaadtavyycakhyyyggsyamdywgqgtlvtvssggggsggggsggg<br>gsggggseivmtqspatlslspgeratlscrasqdiskylnwyqqkpgqaprlliyhtsrlhsgiparfs<br>gsgsgtdytltisslqpedfavyfcqqgntlpytfgqgtkleik (SEQ ID NO: 22) |
| CD19 | huscFv8 | qvqlqesgpglvkpsetlsltctvsgvslpdygvswirqppgkglewigviwgsettyyqsslksrvti<br>skdnsknqvslklssvtaadtavyycakhyyyggsyamdywgqgtlvtvssggggsggggsggg<br>gsggggseivmtqspatlslspgeratlscrasqdiskylnwyqqkpgqaprlliyhtsrlhsgiparfs<br>gsgsgtdytltisslqpedfavyfcqqgntlpytfgqgtkleik (SEQ ID NO: 23) |
| CD19 | huscFv9 | eivmtqspatlslspgeratlscrasqdiskylnwyqqkpgqaprlliyhtsrlhsgiparfsgsgsgtdy<br>tltisslqpedfavyfcqqgntlpytfgqgtkleikggggsggggsggggsggggsqvqlqesgpglv<br>kpsetlsltctvsgvslpdygvswirqppgkglewigviwgsettyynsslksrvtiskdnsknqvslk<br>lssvtaadtavyycakhyyyggsyamdywgqgtlvtvss (SEQ ID NO: 24) |
| CD19 | HuscFv10 | qvqlqesgpglvkpsetlsltctvsgvslpdygvswirqppgkglewigviwgsettyynsslksrvti<br>skdnsknqvslklssvtaadtavyycakhyyyggsyamdywgqgtlvtvssggggsggggsggg<br>gsggggseivmtqspatlslspgeratlscrasqdiskylnwyqqkpgqaprlliyhtsrlhsgiparfs<br>gsgsgtdytltisslqpedfavyfcqqgntlpytfgqgtkleik (SEQ ID NO: 25) |
| CD19 | HuscFv11 | eivmtqspatlslspgeratlscrasqdiskylnwyqqkpgqaprlliyhtsrlhsgiparfsgsgsgtdy<br>tltisslqpedfavyfcqqgntlpytfgqgtkleikggggsggggsggggsqvqlqesgpglvkpsetl<br>sltctvsgvslpdygvswirqppgkglewigviwgsettyynsslksrvtiskdnsknqvslklssvta<br>adtavyycakhyyyggsyamdywgqgtlvtvss (SEQ ID NO: 26) |
| CD19 | HuscFv12 | qvqlqesgpglvkpsetlsltctvsgvslpdygvswirqppgkglewigviwgsettyynsslksrvti<br>skdnsknqvslklssvtaadtavyycakhyyyggsyamdywgqgtlvtvssggggsggggsggg<br>gseivmtqspatlslspgeratlscrasqdiskylnwyqqkpgqaprlliyhtsrlhsgiparfsgsgsgt<br>dytltisslqpedfavyfcqqgntlpytfgqgtkleik (SEQ ID NO: 27) |
| CD19 | muCTL019 | diqmtqttsslsaslgdrvtiscrasqdiskylnwyqqkpdgtvklliyhtsrlhsgvpsrfsgsgsgtdy<br>sltisnleqediatyfcqqgntlpytfgggtkleitggggsggggsggggsevklqesgpglvapsqsls<br>vtctvsgvslpdygvswirqpprkglewlgviwgsettyynsalksrltiikdnsksqvflkmnslqtd<br>dtaiyycakhyyyggsyamdywgqgtsvtvss (SEQ ID NO: 28) |
| CD123 | Mu1172 | DIVLTQSPASLAVSLGQRATISCRASESVDNYGNTFMHWYQQKPG<br>QPPKLLIYRASNLESGIPARFSGSGSRTDFTLTINPVEADDVATYYC<br>QQSNEDPPTFGAGTKLELKGGGGSGGGGSSGGGSQIQLVQSGPEL<br>KKPGETVKISCKASGYIFTNYGMNWVKQAPGKSFKWMGWINTYT |

TABLE 4-continued

| Exemplary Antigen Binding Domains | | |
|---|---|---|
| Target Antigen | Name | Amino Acid Sequence |
| | | GESTYSADFKGRFAFSLETSASTAYLHINDLKNEDTATYFCARSGG<br>YDPMDYWGQGTSVTVSS (SEQ ID NO: 29) |
| CD123 | Mu1176 | DVQITQSPSYLAASPGETITINCRASKSISKDLAWYQEKPGKTNKLL<br>IYSGSTLQSGIPSRFSGSGSGTDFTLTISSLEPEDFAMYYCQQHNKY<br>PYTFGGGTKLEIKGGGGSGGGGSSGGGSQVQLQQPGAELVRPGAS<br>VKLSCKASGYTFTSYWMNWVKQRPDQGLEWIGRIDPYDSETHYN<br>QKFKDKAILTVDKSSSTAYMQLSSLTSEDSAVYYCARGNWDDYW<br>GQGTTLTVSS (SEQ ID NO: 30) |
| CD123 | huscFv1 | divltqspdslavslgeratincrasesvdnygntfmhwyqqkpgqppklliyrasnlesgvpdrfsgs<br>gsrtdftltisslqaedvavyycqqsnedpptfgqgtkleikggggsggggsggggsggggsqiqlvq<br>sgselkkpgasvkvsckasgyiftnygmnwvrqapgqglewmgwintytgestysadfkgrfvfsl<br>dtsystaylqinalkaedtavyycarsggydpmdywgqgttvtvss (SEQ ID NO: 31) |
| CD123 | huscFv2 | divltqspdslavslgeratincrasesvdnygntfmhwyqqkpgqppklliyrasnlesgvpdrfsgs<br>gsrtdftltisslqaedvavyycqqsnedpptfgqgtkleikggggsggggsggggsggggsqiqlvq<br>sgaevkkpgasvkvsckasgyiftnygmnwvrqapgqrlewmgwintytgestysadfkgrvtitl<br>dtsastaymelsslrsedtavyycarsggydpmdywgqgttvtvss (SEQ ID NO: 32) |
| CD123 | huscFv3 | eivltqspatlslspgeratlscrasesvdnygntfmhwyqqkpgqaprlliyrasnlesgiparfsgsgs<br>rtdftltisslepedvavyycqqsnedpptfgqgtkleikggggsggggsggggsggggsqiqlvqsg<br>selkkpgasvkvsckasgyiftnygmnwvrqapgqglewmgwintytgestysadfkgrfvfsldt<br>systaylqinalkaedtavyycarsggydpmdywgqgttvtvss (SEQ ID NO: 33) |
| CD123 | huscFv4 | eivliqspatlslspgeratlscrasesvdnygntfmhwyqqkpgqaprlliyrasnlesgiparfsgsgs<br>rtdftltisslepedvavyycqqsnedpptfgqgtkleikggggsggggsggggsggggsqiqlvqsg<br>aevkkpgasvkvsckasgyiftnygmnwvrqapgqrlewmgwintytgestysadfkgrvtitldt<br>sastaymelsslrsedtavyycarsggydpmdywgqgttvtvss (SEQ ID NO: 34) |
| CD123 | huscFv5 | qiqlvqsgselkkpgasvkvsckasgyiftnygmnwvrqapgqglewmgwintytgestysadfk<br>grfvfsldtsystaylqinalkaedtavyycarsggydpmdywgqgttvtvssggggsggggsgggg<br>sggggsdivltqspdslavslgeratincrasesvdnygntfmhwyqqkpgqppklliyrasnlesgv<br>pdrfsgsgsrtdftltisslqaedvavyycqqsnedpptfgqgtkleik (SEQ ID NO: 35) |
| CD123 | huscFv6 | qiqlvqsgselkkpgasvkvsckasgyiftnygmnwvrqapgqglewmgwintytgestysadfk<br>grfvfsldtsystaylqinalkaedtavyycarsggydpmdywgqgttvtvssggggsggggsgggg<br>sggggseivltqspatlslspgeratlscrasesvdnygntfmhwyqqkpgqaprlliyrasnlesgipa<br>rfsgsgsrtdftltisslepedvavyycqqsnedpptfgqgtkleik (SEQ ID NO: 36) |
| CD123 | huscFv7 | qiqlvqsgaevkkpgasvkvsckasgyiftnygmnwvrqapgqrlewmgwintytgestysadfk<br>grvtitldtsastaymelsslrsedtavyycarsggydpmdywgqgttvtvssggggsggggsgggg<br>sggggsdivltqspdslavslgeratincrasesvdnygntfmhwyqqkpgqppklliyrasnlesgv<br>pdrfsgsgsrtdftltisslqaedvavyycqqsnedpptfgqgtkleik (SEQ ID NO: 37) |
| CD123 | huscFv8 | qiqlvqsgaevkkpgasvkvsckasgyiftnygmnwvrqapgqrlewmgwintytgestysadfk<br>grvtitldtsastaymelsslrsedtavyycarsggydpmdywgqgttvtvssggggsggggsgggg<br>sggggseivltqspatlslspgeratlscrasesvdnygntfmhwyqqkpgqaprlliyrasnlesgipa<br>rfsgsgsrtdftltisslepedvavyycqqsnedpptfgqgtkleik (SEQ ID NO: 38) |
| EGFR vIII | huscFv1 | eiqlvqsgaevkkpgatvkisckgsgfniedyyihwvqqapgkglewmgridpendetkygpifq<br>grvtitadtstntvymelsslrsedtavyycafrggvywgqgttvtvssggggsggggsggggsgggg<br>sdvvmtqspdslavslgeratinckssqslldsdgktylnwlqqkpgqppkrlislvskldsgvpdrfs<br>gsgsgtdftltisslqaedvavyycwqgthfpgtfgggtkveik (SEQ ID NO: 39) |
| EGFR vIII | huscFv2 | dvvmtqspdslavslgeratinckssqslldsdgktylnwlqqkpgqppkrlislvskldsgvpdrfsg<br>sgsgtdftltisslqaedvavyycwqgthfpgtfgggtkveikggggsggggsggggsggggseiqlv<br>qsgaevkkpgatvkisckgsgfniedyyihwvqqapgkglewmgridpendetkygpifqgrvtit<br>adtstntvymelsslrsedtavyycafrggvywgqgttvtvss (SEQ ID NO: 40) |
| EGFR vIII | huscFv3 | eiqlvqsgaevkkpgeslrisckgsgfniedyyihwvrqmpgkglewmgridpendetkygpifq<br>ghvtisadtsintvylqwsslkasdtamyycafrggvywgqgttvtvssggggsggggsggggsgg<br>ggsdvvmtqsplslpvtlgqpasisckssqslldsdgktylnwlqqrpgqsprrlislvskldsgvpdrf<br>sgsgsgtdftlkisrveaedvgvyycwqgthfpgtfgggtkveik (SEQ ID NO: 41) |
| EGFR vIII | huscFv4 | dvvmtqsplslpvtlgqpasisckssqslldsdgktylnwlqqrpgqsprrlislvskldsgvpdrfsgs<br>gsgtdftlkisrveaedvgvyycwqgthfpgtfgggtkveikggggsggggsggggsggggseiqlv<br>qsgaevkkpgeslrisckgsgfniedyyihwvrqmpgkglewmgridpendetkygpifqghvti<br>sadtsintvylqwsslkasdtamyycafrggvywgqgttvtvss (SEQ ID NO: 42) |
| EGFR vIII | huscFv5 | eiqlvqsgaevkkpgatvkisckgsgfniedyyihwvqqapgkglewmgridpendetkygpifq<br>grvtitadtstntvymelsslrsedtavyycafrggvywgqgttvtvssggggsggggsggggsgggg<br>sdvvmtqsplslpvtlgqpasisckssqslldsdgktylnwlqqrpgqsprrlislvskldsgvpdrfsg<br>sgsgtdftlkisrveaedvgvyycwqgthfpgtfgggtkveik (SEQ ID NO: 43) |

TABLE 4-continued

Exemplary Antigen Binding Domains

| Target Antigen | Name | Amino Acid Sequence |
|---|---|---|
| EGFR vIII | huscFv6 | eiqlvqsgaevkkpgeslrisckgsgfniedyyihwvrqmpgkglewmgridpendetkygpifq ghvtisadtsintvylqwsslkasdtamyycafrggvywgqgttvtvssggggsggggsggggsgg ggsdvvmtqspdslavslgeratinckssqslldsdgktylnwlqqkpgqppkrlislvskldsgvpd rfsgsgsgtdftltisslqaedvavyycwqgthfpgtfgggtkveik (SEQ ID NO: 44) |
| EGFR vIII | huscFv7 | dvvmtqspdslayslgeratinckssqslldsdgktylnwlqqkpgqppkrlislvskldsgvpdrfsg sgsgtdftltisslqaedvavyycwqgthfpgtfgggtkveikggggsggggsggggsggggseiqlv qsgaevkkpgeslrisckgsgfniedyyihwvrqmpgkglewmgridpendetkygpifqghvti sadtsintvylqwsslkasdtamyycafrggvywgqgttvtvss (SEQ ID NO: 45) |
| EGFR vIII | huscFv8 | dvvmtqsplslpvtlgqpasisckssqslldsdgktylnwlqqrpgqsprrlislvskldsgvpdrfsgs gsgtdftlkisrveaedvgvyycwqgthfpgtfgggtkveikggggsggggsggggsggggseiqlv qsgaevkkpgatvkisckgsgfniedyyihwvqqapgkglewmgridpendetkygpifqgrvtit adtstntvymelsslrsedtavyycafrggvywgqgttvtvss (SEQ ID NO: 46) |
| EGFR vIII | Mu310C | eiqlqqsgaelvkpgasvklsctgsgfniedyyihwvkqrteqglewigridpendetkygpifqgra titadtssntvylqlssltsedtavyycafrggvywgpgttltvssggggsggggsggggshmdvvmt qspltlsvaigqsasisckssqslldsdgktylnwllqrpgqspkrlislvskldsgvpdrftgsgsgtdftl risrveaedlgiyycwqgthfpgtfgggtkleik (SEQ ID NO: 47) |
| mesothelin | ss1 | QVQLQQSGPELEKPGASVKISCKASGYSFTGYTMNWVKQS HGKSLEWIGLITPYNGASSYNQKFRGKATLTVDKSSSTAY MDLLSLTSEDSAVYFCARGGYDGRGFDYWGQGTTVTVSS GGGGSGGGGSGGGGSDIELTQSPAIMSASPGEKVTMTCSA SSSVSYMHWYQQKSGTSPKRWIYDTSKLASGVPGRFSGSG SGNSYSLTISSVEAEDDATYYCQQWSGYPLTFGAGTKLEI (SEQ ID NO: 48) |

Non-Antibody Scaffolds

In embodiments, the antigen binding domain comprises a non antibody scaffold, e.g., a fibronectin, ankyrin, domain antibody, lipocalin, small modular immuno-pharmaceutical, maxybody, Protein A, or affilin. The non antibody scaffold has the ability to bind to target antigen on a cell. In embodiments, the antigen binding domain is a polypeptide or fragment thereof of a naturally occurring protein expressed on a cell. In some embodiments, the antigen binding domain comprises a non-antibody scaffold. A wide variety of non-antibody scaffolds can be employed so long as the resulting polypeptide includes at least one binding region which specifically binds to the target antigen on a target cell.

Non-antibody scaffolds include: fibronectin (Novartis, MA), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (Scil Proteins GmbH, Halle, Germany).

Fibronectin scaffolds can be based on fibronectin type III domain (e.g., the tenth module of the fibronectin type III ($^{10}$Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). Because of this structure, this non-antibody scaffold mimics antigen binding properties that are similar in nature and affinity to those of antibodies. These scaffolds can be used in a loop randomization and shuffling strategy in vitro that is similar to the process of affinity maturation of antibodies in vivo.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

Avimers are derived from natural A-domain containing protein such as HER3. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Protein epitope mimetics (PEM) are medium-sized, cyclic, peptide-like molecules (MW 1-2 kDa) mimicking beta-hairpin secondary structures of proteins, the major secondary structure involved in protein-protein interactions Mismatched Antigen Binding Domains It has been discovered, that cells having a plurality of chimeric membrane embedded receptors each comprising an antigen binding domain (CMERs) that interactions between the antigen binding domain of the CMER can be undesirable, e.g., because it inhibits the ability of one or more of the antigen binding domains to bind its cognate antigen. Accordingly, disclosed herein are a first and a second non-naturally occurring CMER comprising antigen binding domains that minimize such interactions when expressed in the same cell. In an embodiment a plurality of CMERs comprises two TCARs. In an embodiment a plurality of CMERs comprises a TCAR and another CMER. In an embodiment a plurality of CMERs comprises two NKR-CARs. In an embodiment a plurality of CMERs comprises a NKR-CAR and another CMER. In an embodiment a plurality of CMERs comprises a TCAR and an NKR-CAR.

In some embodiments, the claimed invention comprises a first and second CMER, wherein the antigen binding domain of one of said first CMER said second CMER does not comprise a variable light domain and a variable heavy domain. In some embodiments, the antigen binding domain of one of said first CMER said second CMER is an scFv, and the other is not an scFv. In some embodiments, the antigen binding domain of one of said first CMER said second CMER comprises a single VH domain, e.g., a camelid, shark, or lamprey single VH domain, or a single VH domain derived from a human or mouse sequence or a non-antibody scaffold. In some embodiments, the antigen binding domain of one of said first CMER said second CMER comprises a nanobody. In some embodiments, the antigen binding domain of one of said first CMER said second CMER comprises a camelid VHH domain.

In some embodiments, the antigen binding domain of one of said first CMER said second CMER comprises an scFv, and the other comprises a single VH domain, e.g., a camelid, shark, or lamprey single VH domain, or a single VH domain derived from a human or mouse sequence. In some embodiments, the antigen binding domain of one of said first CMER said second CMER comprises an scFv, and the other comprises a nanobody. In some embodiments, the antigen binding domain of one of said first CMER said second CMER comprises an scFv, and the other comprises a camelid VHH domain.

In some embodiments, when present on the surface of a cell, binding of the antigen binding domain of said first CMER to its cognate antigen is not substantially reduced by the presence of said second CMER. In some embodiments, binding of the antigen binding domain of said first CMER to its cognate antigen in the presence of said second CMER is 85%, 90%, 95%, 96%, 97%, 98% or 99% of binding of the antigen binding domain of said first CMER to its cognate antigen in the absence of said second CMER.

In some embodiments, when present on the surface of a cell, the antigen binding domains of said first CMER said second CMER, associate with one another less than if both were scFv antigen binding domains. In some embodiments, the antigen binding domains of said first CMER said second CMER, associate with one another 85%, 90%, 95%, 96%, 97%, 98% or 99% less than if both were scFv antigen binding domains.

In some embodiments, the claimed invention comprises a first and second KIR-CAR, wherein the antigen binding domain of one of said first KIR-CAR said second KIR-CAR does not comprise a variable light domain and a variable heavy domain. In some embodiments, the antigen binding domain of one of said first KIR-CAR said second KIR-CAR is an scFv, and the other is not an scFv. In some embodiments, the antigen binding domain of one of said first KIR-CAR said second KIR-CAR comprises a single VH domain, e.g., a camelid, shark, or lamprey single VH domain, or a single VH domain derived from a human or mouse sequence or a non-antibody scaffold. In some embodiments, the antigen binding domain of one of said first KIR-CAR said second KIR-CAR comprises a nanobody. In some embodiments, the antigen binding domain of one of said first KIR-CAR said second KIR-CAR comprises a camelid VHH domain.

In some embodiments, the antigen binding domain of one of said first KIR-CAR said second KIR-CAR comprises an scFv, and the other comprises a single VH domain, e.g., a camelid, shark, or lamprey single VH domain, or a single VH domain derived from a human or mouse sequence. In some embodiments, the antigen binding domain of one of said first KIR-CAR said second KIR-CAR comprises an scFv, and the other comprises a nanobody. In some embodiments, the antigen binding domain of one of said first KIR-CAR said second KIR-CAR comprises an scFv, and the other comprises a camelid VHH domain.

In some embodiments, when present on the surface of a cell, binding of the antigen binding domain of said first KIR-CAR to its cognate antigen is not substantially reduced by the presence of said second KIR-CAR. In some embodiments, binding of the antigen binding domain of said first KIR-CAR to its cognate antigen in the presence of said second KIR-CAR is 85%, 90%, 95%, 96%, 97%, 98% or 99% of binding of the antigen binding domain of said first KIR-CAR to its cognate antigen in the absence of said second KIR-CAR.

In some embodiments, when present on the surface of a cell, the antigen binding domains of said first KIR-CAR said second KIR-CAR, associate with one another less than if both were scFv antigen binding domains. In some embodiments, the antigen binding domains of said first KIR-CAR said second KIR-CAR, associate with one another 85%, 90%, 95%, 96%, 97%, 98% or 99% less than if both were scFv antigen binding domains.

In some embodiments, the claimed invention comprises a first and second TCAR, wherein the antigen binding domain of one of said first TCAR said second TCAR does not comprise a variable light domain and a variable heavy domain. In some embodiments, the antigen binding domain of one of said first TCAR said second TCAR is an scFv, and the other is not an scFv. In some embodiments, the antigen binding domain of one of said first TCAR said second TCAR comprises a single VH domain, e.g., a camelid, shark, or lamprey single VH domain, or a single VH domain derived from a human or mouse sequence or a non-antibody scaffold. In some embodiments, the antigen binding domain of one of said first TCAR said second TCAR comprises a nanobody. In some embodiments, the antigen binding domain of one of said first TCAR said second TCAR comprises a camelid VHH domain.

In some embodiments, the antigen binding domain of one of said first TCAR said second TCAR comprises an scFv, and the other comprises a single VH domain, e.g., a camelid, shark, or lamprey single VH domain, or a single VH domain derived from a human or mouse sequence. In some embodiments, the antigen binding domain of one of said first TCAR said second TCAR comprises an scFv, and the other comprises a nanobody. In some embodiments, the antigen binding domain of one of said first TCAR said second TCAR comprises an scFv, and the other comprises a camelid VHH domain.

In some embodiments, when present on the surface of a cell, binding of the antigen binding domain of said first TCAR to its cognate antigen is not substantially reduced by the presence of said second TCAR. In some embodiments, binding of the antigen binding domain of said first TCAR to its cognate antigen in the presence of said second TCAR is 85%, 90%, 95%, 96%, 97%, 98% or 99% of binding of the antigen binding domain of said first TCAR to its cognate antigen in the absence of said second TCAR.

In some embodiments, when present on the surface of a cell, the antigen binding domains of said first TCAR said second TCAR, associate with one another less than if both were scFv antigen binding domains. In some embodiments, the antigen binding domains of said first TCAR said second TCAR, associate with one another 85%, 90%, 95%, 96%, 97%, 98% or 99% less than if both were scFv antigen binding domains.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1$\alpha$ promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In one embodiment, the vector is a lentivirus vector. In one embodiment, the vector further comprises a promoter. In one embodiment, the promoter is an EF-1 promoter.

In one embodiment, the vector is an in vitro transcribed vector, e.g., a vector that transcribes RNA of a nucleic acid molecule described herein. In one embodiment, the nucleic acid sequence in the vector further comprises a poly(A) tail, e.g., a poly A tail described herein, e.g., comprising about 150 adenosine bases. In one embodiment, the nucleic acid sequence in the vector further comprises a 3'UTR.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter.

Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Polynucleotides can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Disclosed herein are methods for producing an in vitro transcribed RNA NK-CAR. The present invention also includes an NK-CAR encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in. RNA so produced can efficiently transfect different kinds of cells. In one aspect, the template includes sequences for the NK-CAR.

In one aspect the NK-CAR is encoded by a messenger RNA (mRNA). In one aspect the mRNA encoding the NK-CAR is introduced into a T cell for production of a NK-CAR cell.

In one embodiment, the in vitro transcribed RNA NK-CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired temple for in vitro transcription is a NK-CAR of the present invention. For example, the template for the RNA NK-CAR comprises an extracellular region comprising a single chain variable domain of an anti-tumor antibody; a hinge region, a transmembrane domain (e.g., a transmembrane domain of KIR). In one embodiment, the desired temples for in vitro transcription comprises KIR-CAR and DAP12 on separate templates. In one embodiment, the desired temple for in vitro transcription comprises KIR-CAR and DAP12 on the same template. The template for DAP12 comprises a transmembrane domain and an intracellular region.

In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (SEQ ID NO: 73) (size can be 50-5000 T (SEQ ID NO: 74)), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines (SEQ ID NO: 75).

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides (SEQ ID NO: 76) to between 300 and 400 nucleotides (SEQ ID NO: 77) results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included. In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, $CD4^+$) that is greater than the cytotoxic or suppressor T cell population ($T_C$, $CD8^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a plurality of types of KIR-CARs, wherein each KIR-CAR combines an antigen recognition domain of a specific antibody with a component of a KIR.

In one embodiment, the KIR-CARs of the invention comprise an activating KIR which delivers its signal through an interaction with the immunotyrosine-based activation motif (ITAM) containing membrane protein, DAP12 that is mediated by residues within the transmembrane domains of these proteins.

In one embodiment, the KIR-CARs of the invention comprise an inhibitory KIR which delivers its signal through one or more immunotyrosine-based inhibitory motifs (ITIMs) that interact directly or indirectly with cytoplasmic signaling proteins such as SHP-1, SHP-2 and Vav family of proteins. KIRs bearing cytoplasmic domains that contain (ITIMs) abrogate the activating signal leading to inhibition of NK cytolytic and cytokine producing activity. In some instances, the modified T cell expressing a KIR-CAR of the invention can elicit a KIR-CAR-mediated T-cell response. In one embodiment, the dependence of the binding to more than one type of antigen allows the modified T cell to exhibit a heightened specificity to elicit a response upon binding of a tumor cell rather than a normal bystander cell.

The invention provides the use of a plurality of types of KIR-CARs to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a plurality of types of KIR-CARs, wherein each type of KIR-CAR comprises a binding moiety that specifically interacts with a predetermined target. In one embodiment, the cell comprises a first KIR-CAR comprising an activating KIR (actKIR-CAR), and a second KIR-CAR comprising an inhibitory KIR (inhKIR-CAR).

Without wishing to be bound by any particular theory, the anti-tumor immunity response elicited by the KIR-CAR-modified T cells may be an active or a passive immune response. In addition, the KIR-CAR mediated immune response may be part of an adoptive immunotherapy approach in which KIR-CAR-modified T cells induce an immune response specific to the antigen binding domain in the KIR-CAR.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the KIR-CAR T cells of the invention is designed to treat a particular cancer. In one embodiment, the KIR-CAR T cells of the invention are modified to express a first actKIR-CAR targeting a first antigen and a second inhKIR-CAR targeting a second antigen, where the first antigen is expressed on a particular tumor or cancer and the second antigen is not expressed on a particular tumor or cancer. In this manner, conditional activation of T cells is generated by engagement of actKIR-CAR (or standard TCR-zeta CAR bearing a scFv to an antigen on the malignant cell of interest) and the inhKIR-CAR bearing for example a scFv directed against an antigen that is present on normal, but not malignant tissue provides inhibition of the activating signal from the actKIR-CAR when the KIR-CAR T cell encounters normal cells. Examples of antigens that serve as useful targets for inhibitory CARs include the ephrin receptors (Pasquale, 2010, Nat Rev Cancer 10(3):165-80) and claudins (Singh et al., 2010, J Oncol, 2010:541957), which are expressed by epithelial cells from normal tissues, but often selectively lost by cancers (e.g. EPHA7).

With respect to ex vivo immunization, at least one of the following occurs in vitro prior to administering the cell into a mammal: i) expansion of the cells, ii) introducing a nucleic acid encoding a KIR-CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a KIR-CAR disclosed herein. The KIR-CAR-modified cell can be administered to a mammalian recipient to provide a therapeutic benefit. The mammalian recipient may be a human and the KIR-CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the KIR-CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the KIR-CAR-modified T cells of the invention.

The KIR-CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to draw blood (or have an apheresis performed), activate and genetically modify the T cells therefrom according to the present invention, and reinfuse the patient with these activated and expanded genetically modified T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. Strategies for CAR T cell dosing and scheduling have been discussed (Ertl et al, 2011, Cancer Res, 71:3175-81; Junghans, 2010, Journal of Translational Medicine, 8:55).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Chimeric NK Receptors

The results presented herein demonstrate an alternative approach to constructing CARs for T cells that can be more finely regulated compared with current CAR designs. Experiments were designed to develop a novel, regulated CAR system that comprises at least two or three chimeric fusion proteins. The primary T cell activating signal and inhibitory signals are based upon naturally occurring activating and inhibitory receptors of NK cells known as killer cell immunoglobulin-like receptors (KIRs).

KIRs exist as both activating and inhibitory forms that depend upon the intracellular domain of the receptor. Activating KIRs deliver their signals through an interaction with the immunotyrosine-based activation motif (ITAM) containing membrane protein, DAP12 that is recruited by residues within the transmembrane domains of these proteins. Inhibitory KIRs bear a cytoplasmic domain that contains immunotyrosine-based inhibitory motifs (ITIMs), which abrogate the activating signal leading to inhibition of NK cytolytic and cytokine producing activity. Similar to TCRs, KIRs belong to the immunoglobulin family of protein receptors, and many bind to invariant MHC and MHC-like ligands. Without wishing to be bound by any particular theory, it is believed that these interactions are utilized to naturally distinguish normal cells (usually expressing high density MHC class I) from malignant or virally infected cells (often with low or missing MHC class I).

KIR-like chimeric antigen receptors (KIR-CARs) have been constructed which fuse an scfv to a target antigen of interest with activating and inhibitory KIRs as shown in FIG. 1. Conditional activation of T cells is generated by engagement of an activating KIR-CAR (actKIR-CAR) or standard TCR-zeta CAR bearing an scfv to an antigen on the malignant cell of interest. An inhibitory CAR (inhCAR) bearing an scfv directed against an antigen that is present on normal, but not malignant tissue would provide dampening of the activating CAR primary signal when the T cell encounters normal cells. Examples of antigens that serve as useful targets for inhibitory CARs include the ephrin receptors (Pasquale, 2010, Nat Rev Cancer 10(3):165-80) and claudins (Singh et al., 2010, J Oncol, 2010:541957), which are expressed by epithelial cells from normal tissues, but often selectively lost by cancers (e.g. EPHA7).

Example 2: Activating KIR-CAR Construction and Activity

Figure 2:
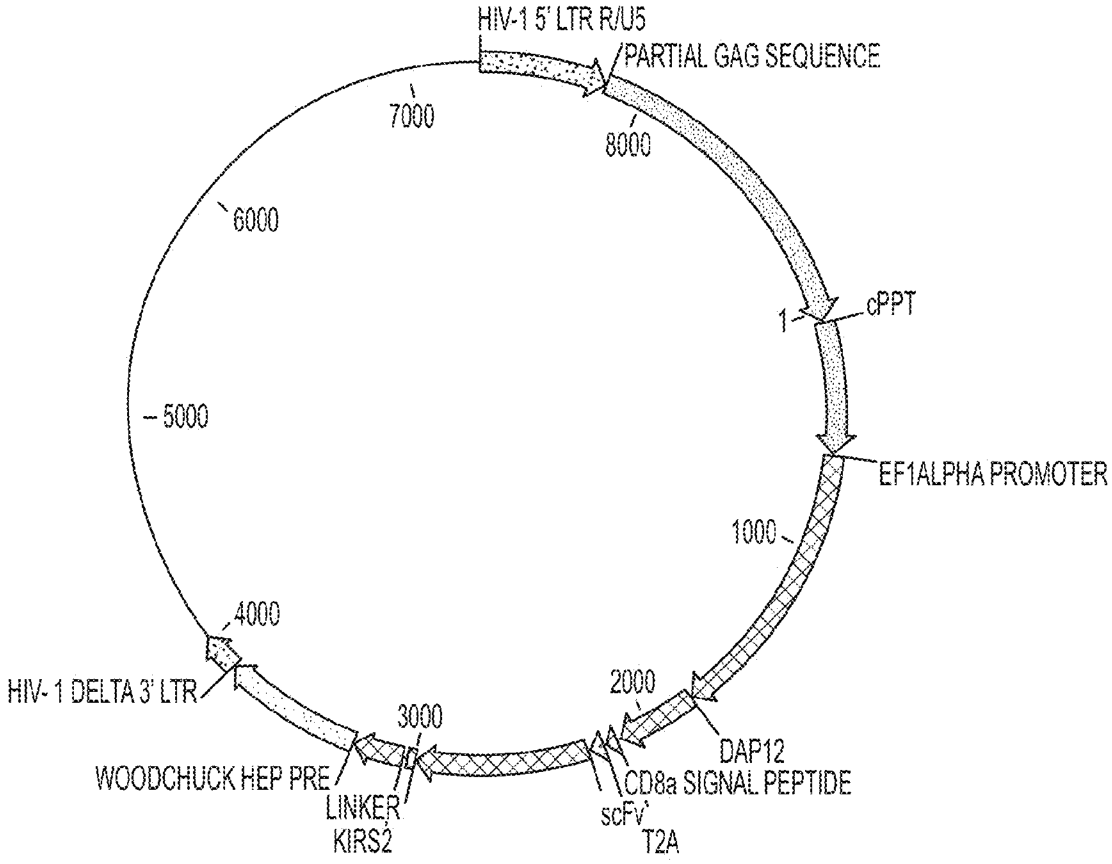
FIG. 2 is a schematic representation of the lentiviral vector used to deliver an activating KIR-based CAR in combination with the DAP12 signaling molecule.
Figure 3:
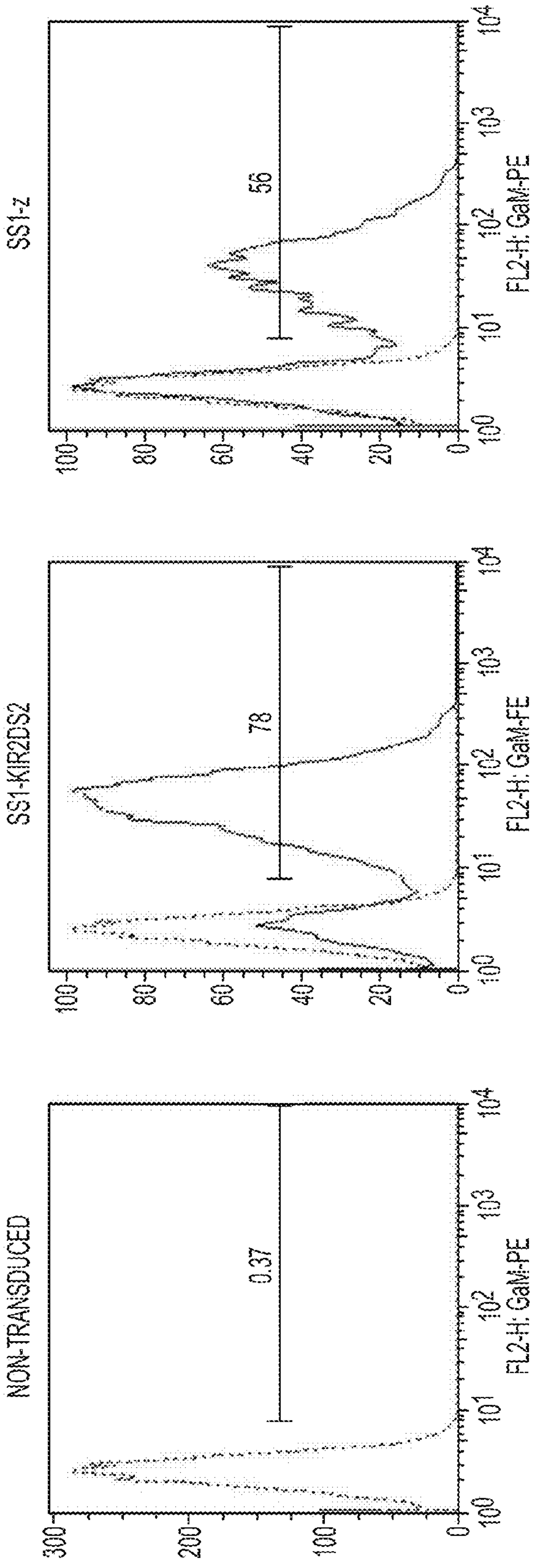
FIG. 3 is an image demonstrating that a mesothelin-specific actKIR-CARs can be efficiently expressed on the surface of primary human T cells. Human T cells were stimulated with anti-CD3/anti-CD28 microbeads and transduced with the indicated CAR or mock transduced and expanded ex vivo. The expression was detected using a biotinylated goat-anti-mouse F(ab)2-specific polyclonal IgG (Jackson Immunologics) followed by staining with streptavidin-PE.
Figure 4:
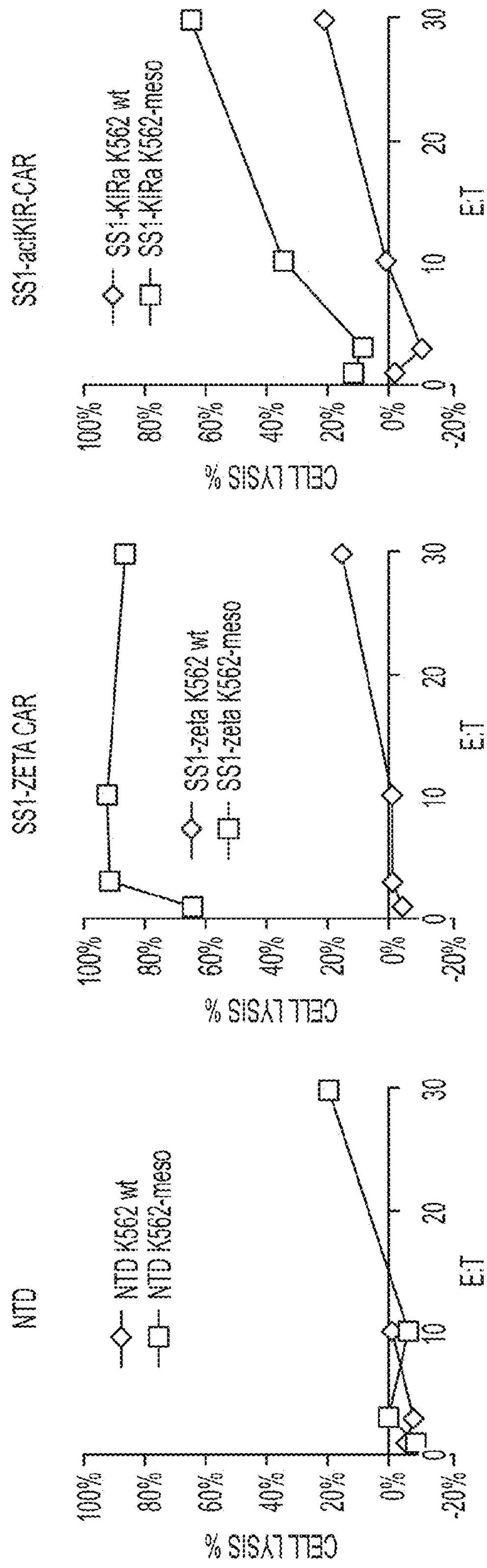
FIG. 4 is an image demonstrating that T cells expressing the SS1 actKIR-CAR exhibited cytotoxic activity towards target K562 cells engineered to express the mesothelin ligand (KT-meso). Human T cells were stimulated with anti-CD3/anti-CD28 microbeads, transduced with the indicated CAR or mock transduced and expanded ex vivo. $10^5$ CFSE-labeled K562 cells expressing mesothelin (KT-meso) or wild-type control K562 were incubated with varying ratios of CAR-expressing T cells for 16 hours at 37° C., 5% $CO_2$. The K562 target cells were then enumerated by flow cytometry using countbright beads and a viability stain (7AAD). The percentage of K562 cells lysed (percent lysis) was calculated by subtracting the number of viable target cells remaining after incubation with effector T cells from the number of viable K562 remaining after overnight culture without effector T cells, and then dividing by the number of viable K562 remaining after overnight culture without effector T cells.

Experiments were designed to construct activating KIR-CARs based upon fusion of the anti-CD19 or anti-mesothelin scFv (SS-1) that were previously incorporated into CARs based upon the TCR-zeta cytoplasmic domain that are currently in clinical trials. The human KIR2DS2 activating KIR receptor was chosen as the initial base receptor for the actKIR-CAR. In order to deliver activating signals, the actKIR-CARs required coexpression of DAP12, which is not expressed normally in T cells. Therefore, a lentiviral vector that expresses both the actKIR-CAR with human DAP12 using a "bicistronic" gene cassette based upon the 2A ribosomal skip peptide was constructed. A diagram of the lentiviral vector is illustrated in FIG. 2. Initial studies demonstrated that the actKIR-CARs were efficiently expressed in primary human T cells and the SS1 actKIR-CAR bound to mesothelin (FIG. 3). Similar to the previously developed and published SS1 scFv CD3 zeta (SS1-ζ) CAR (Carpenito et al., 2009, Proc Natl Acad Sci USA 106(9): 3360-5), T cells expressing the SS1 actKIR-CAR demonstrated cytotoxic activity towards target K562 cells engineered to express the mesothelin ligand (KT-meso) as shown in FIG. 4. Neither receptor exhibits killing of wild-type K562 lacking the mesothelin target.

Figure 5:
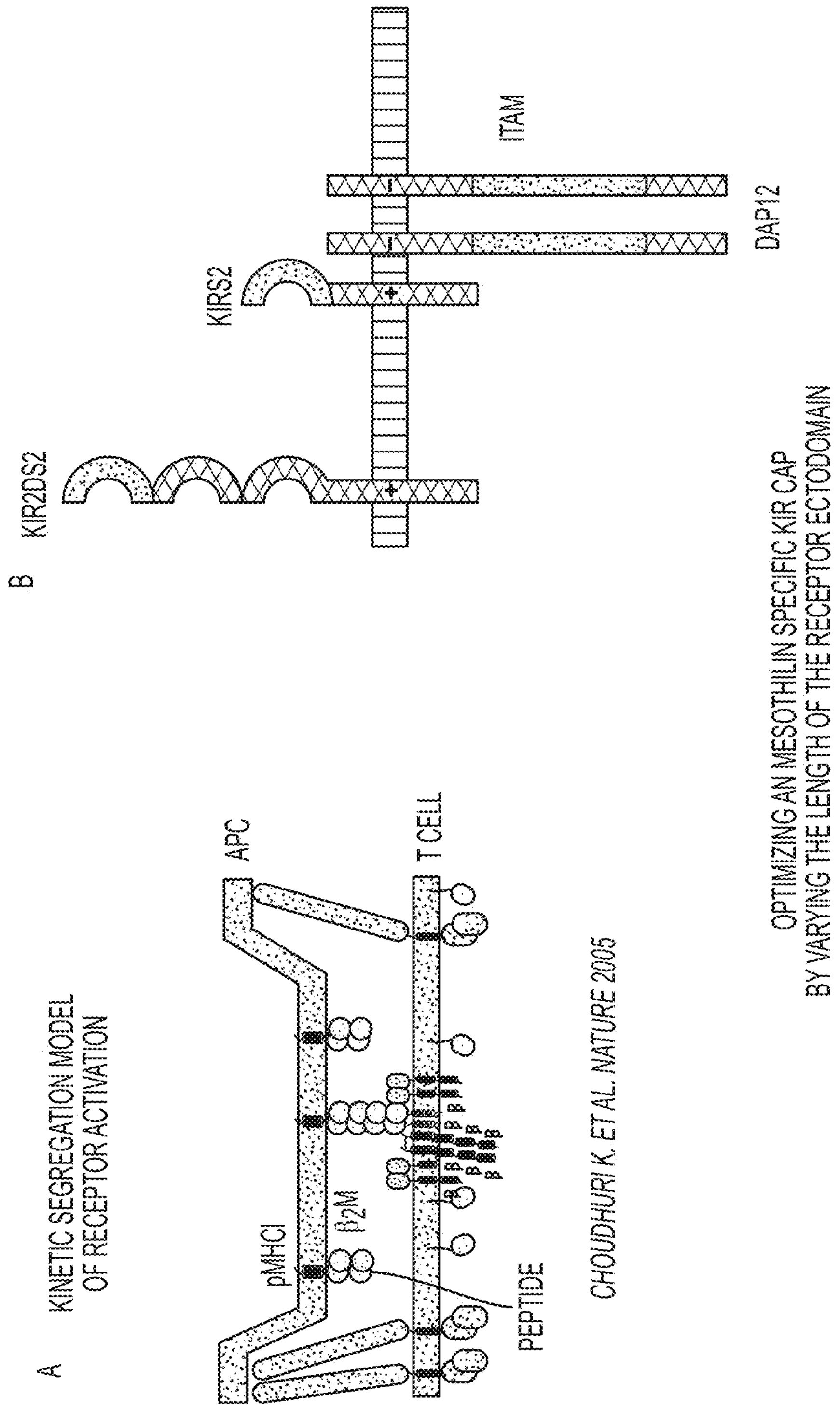
FIG. 5, comprising
Figure 6:
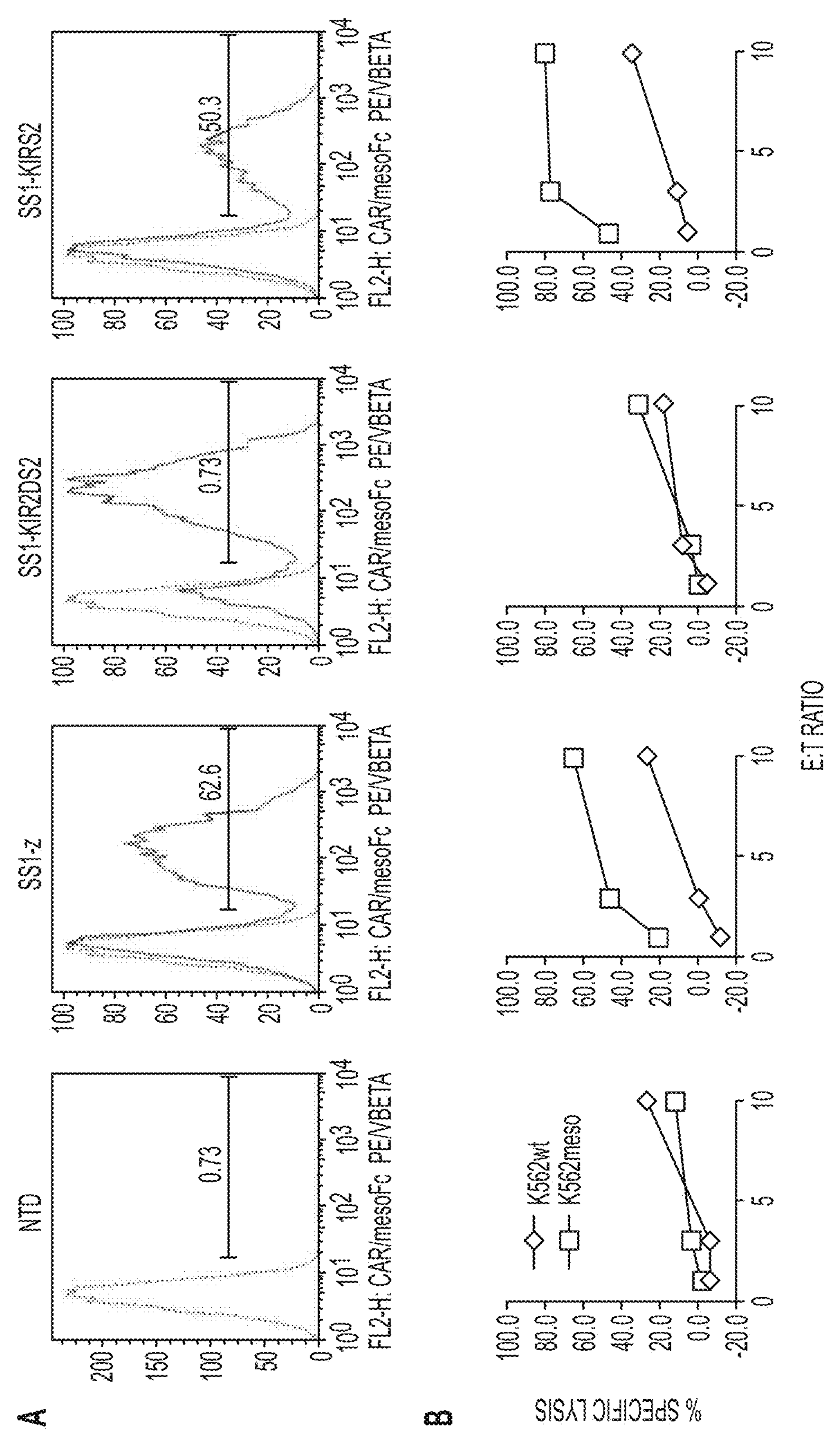
FIG. 6, comprising

Since the cytotoxic activity of the SS1 KIR CAR towards mesothelin-positive target cells was lower than the standard TCRzeta-based CAR targeting the same antigen with comparable CAR surface expression, it is believed that the mesothelin CAR may have an extracellular hinge (based upon wild-type KIR2DS2) that is non-optimal for segregation from CD45 due to its length. The kinetic segregation of activating ITAM-based receptors from CD45 is believed to be a key mechanisms for TCR activation, and dependent upon a length scale between the T cell and target cell membranes of ~14-15 nm (Choudhuri et al., 2005, Nature 436(7050):578-82). It is estimated that the KIR2DS2 based SS1 KIR-CAR to have a length scale of greater than 20 nm based upon the partial crystal structure of mesothelin demonstrating that the SS1 epitope is likely at an ~10 nm distance from the target cell membrane (Ma et al., 2012, J Biol Chem 287(40):33123-31) and CAR that is estimated to be ~10 nm assuming each Ig-like domain is ~3.5 nm in the KIR2DS2 hinge in addition to the scFv. Therefore an activating KIR CAR in which the KIR2DS2 hinge was removed (KIRS2 CAR) as shown schematically in FIG. 5 was constructed. It was shown that an SS1 scFv based KIRS2 CAR exhibited enhanced cytolytic activity towards mesothelin-expressing target cells compared with the CAR formed by fusion of the SS1 scFv onto full length wildtype KIR2DS2 (FIG. 6). This optimized KIRS2 CAR also showed enhanced activity over the SS1 scFv based TCRzeta CAR having a CD8 alpha extracellular hinge.

Example 3: InhKIR-CAR Construction and Activity

Figure 7:
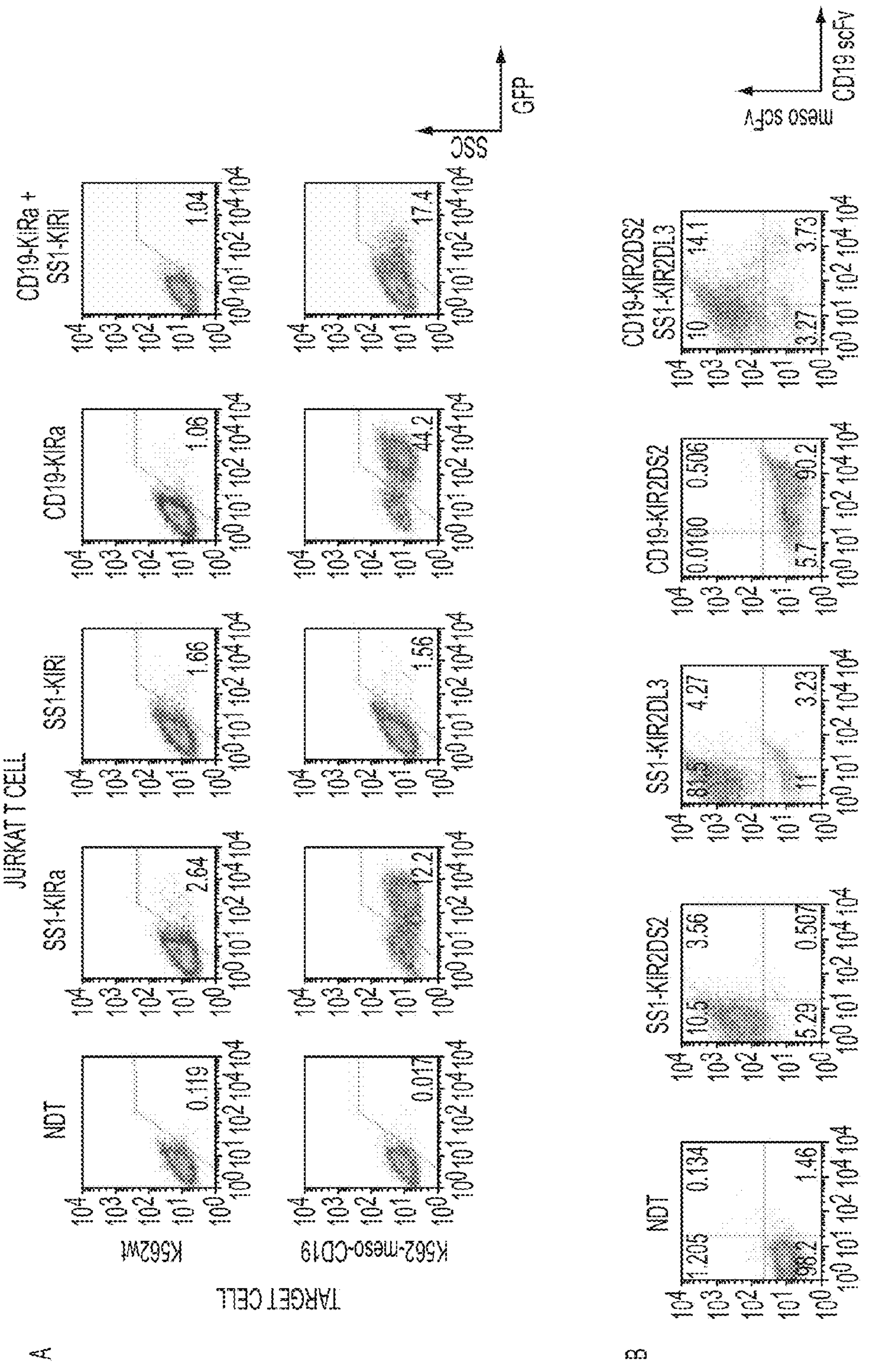
FIG. 7, comprising

An inhibitory KIR-CAR was constructed based upon the fusion of the anti-mesothelin SS1 scFv to the inhibitory KIR2DL3 receptor base. Initial studies demonstrated that the inhKIR-CARs efficiently expressed in primary human T cells. CD19 actKIR-CAR, SS1 actKIR-CAR and SS1 inhKIR-CAR alone or in combination have been introduced into Jurkat T cells bearing a dsGFP reporter under the control of an NFAT-driven promoter to monitor activation of this critical T cell signaling pathway. While Jurkat T cells expressing CD19 actKIR-CAR or SS1 actKIR-CAR alone are efficiently activated by K562 expressing both CD19 and mesothelin (KT-meso/CD19), Jurkat T cells co-expressing the CD19 actKIR-CAR and the SS1 inhKIR-CAR showed markedly reduced activation by the same KT-meso/CD19 target cells (FIG. 7A); however, analysis of the surface expression of the CD19 and mesothelin scFv binding using idiotype specific reagents surprisingly demonstrated that the expression of the different scFv target specificities were mutually exclusive (FIG. 7B).

Figure 8:
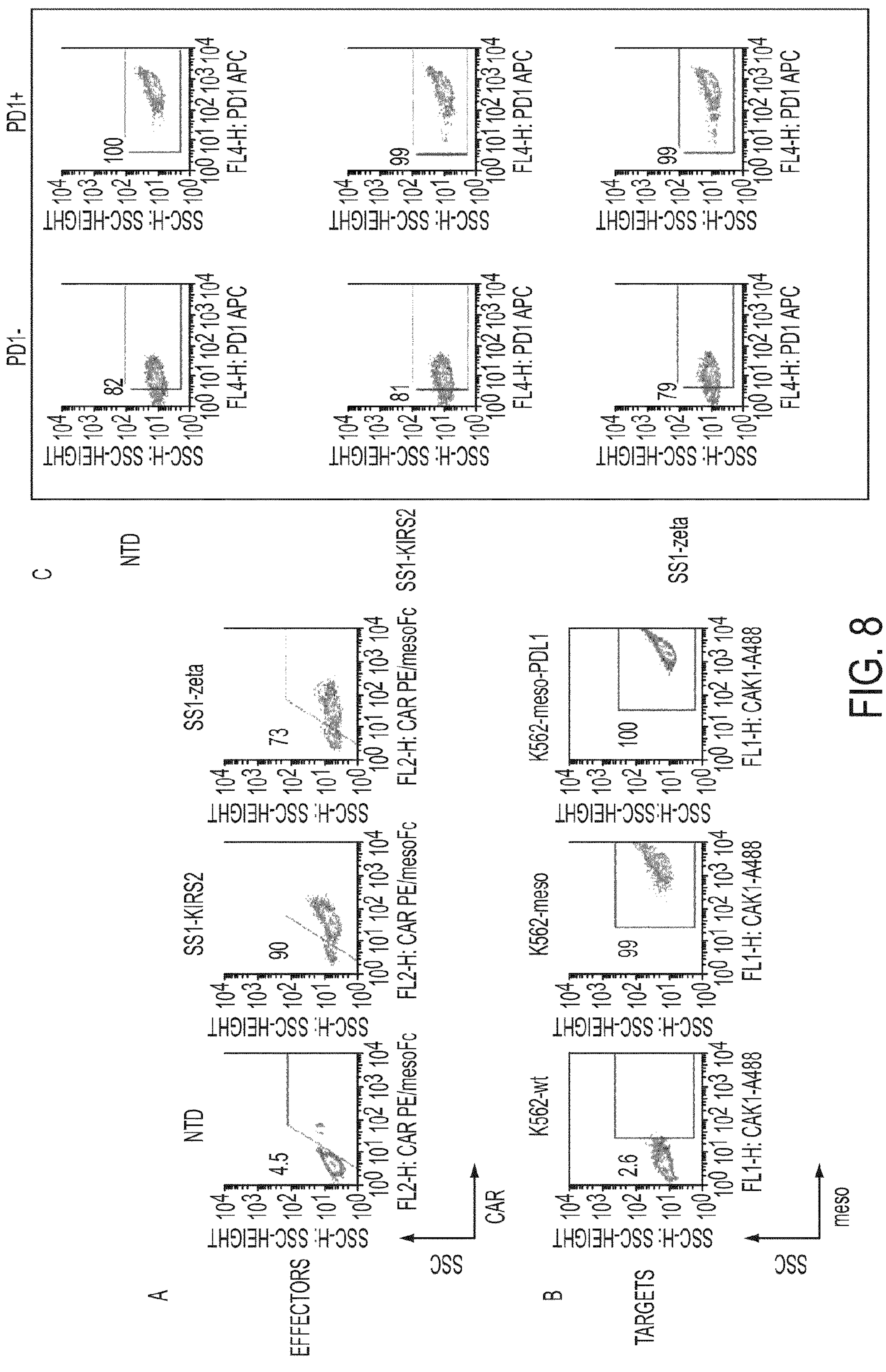
FIG. 8, comprising
Figure 9:
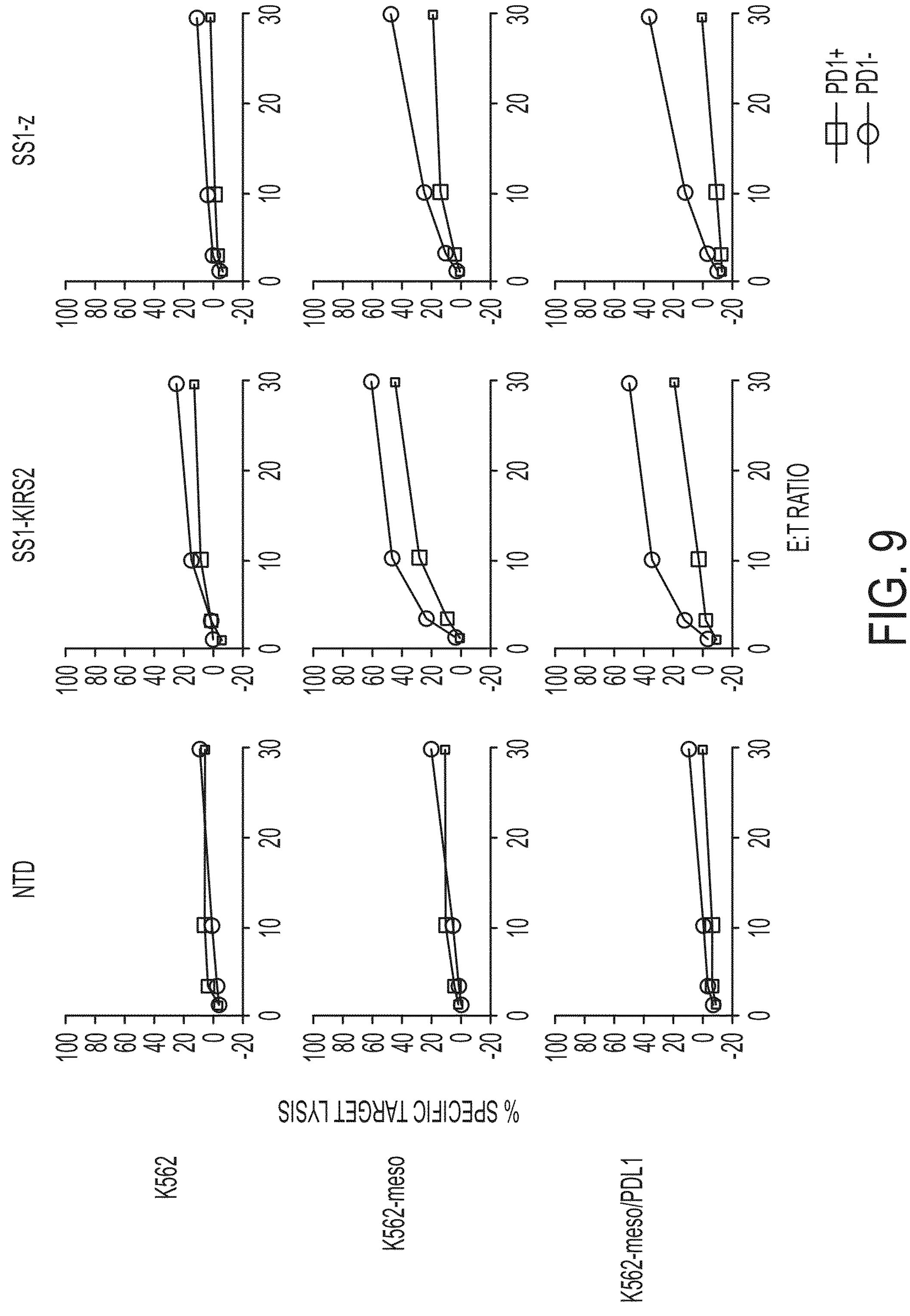
FIG. 9 is an image demonstrating that the combination of co-expressing wild-type PD-1 with both an activating KIR-based CAR and TCR-zeta based CAR targeting mesothelin led to PD-1 ligand 1 (PDL-1) dependent inhibition of the mesothelin-specific activating KIR-CAR cytotoxicity. Primary human T cells were stimulated with CD3/28 microbeads followed by lentiviral transduction with either the SS1-KIRS2 activating KIR CAR, the SS1-zeta CAR or mock transduced (NTD). The T cells were expanded over 9 days followed by electroporation of $5\times10^6$ T cells with 10 ug of in vitro transcribed RNA encoding wild-type PD1 using a BTX ECM830 electroporator (PD1+) or mock transfected (PD1−). The surface expression of the SS1-specific CAR and PD-1 was determined as shown in FIG. 8. K562 target cells with either no mesothelin or expressing mesothelin with or without PDL-1 were mixed with the different T cells conditions as indicated using varying effector T cell to target ratios of 30:1 to 1:1 as shown. Target K562 cell lysis was assessed using a calcein AM dye method to quantify the remaining viable cells following 4 hours of incubation. Data shown is calculated % target cell lysis compared against target cells without effector cells.
Figure 19:
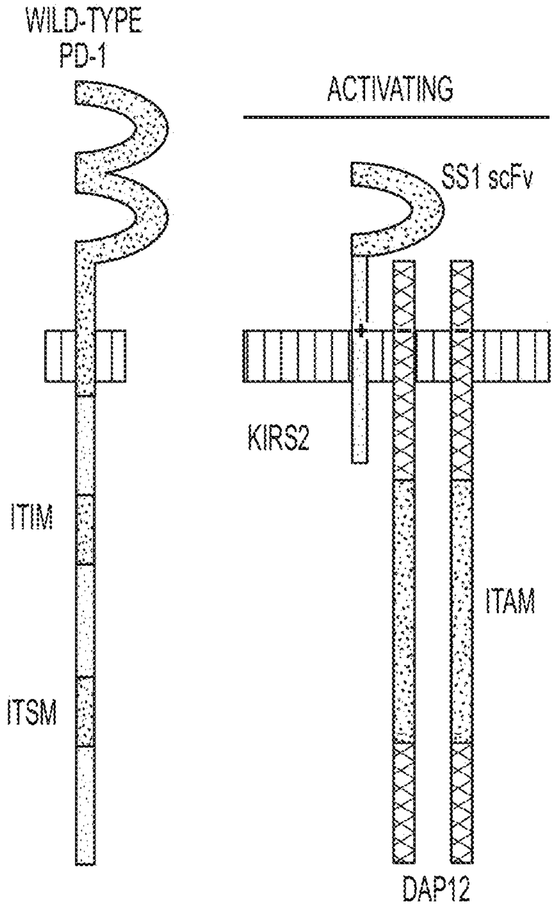
FIG. 19 shows a schematic representation of the receptors used in Experiments shown in FIGS. 21-23.

Example 4: Sensitivity of Activating KIR-CAR Designs to Natural Inhibitory Receptor Systems Since co-expression of two scFv CARs is limited, a strategy was pursued to evaluate the sensitivity of the KIR-based activating CARs to inhibitory signals derived from the PD-1 receptor. PD-1 is a natural receptor in T cells that uses an ITIM in the cytoplasmic domain similar to inhibitory KIRs to recruit phosphatases that negatively regulate TCR signaling. A schematic representation is shown in FIG. 19. The results presented herein demonstrate that wild-type PD-1 can be over-expressed with both an activating KIR-based CAR and a TCR-zeta based CAR targeting mesothelin (FIGS. 8A and 8C). The results also show that this combination led to PD-1 ligand 1 (PDL-1) dependent inhibition of the mesothelin-specific activating KIR-CAR cytotoxicity (FIG. 9). In the context of normal PD-1 expression by the T cells (i.e. T cells without PD-1 transfection), the KIR-CAR exhibits less inhibition when encountering PD-L1 overexpressing target cells compared with the TCR-zeta based CAR. Without wishing to be bound by any particular theory, it is believed that this may be an advantage of the KIR-CARs when encountering tumors that commonly express inhibitory receptor ligands.

Example 5: Co-Stimulation Dependent Activation of KIR CARs

Figure 14:
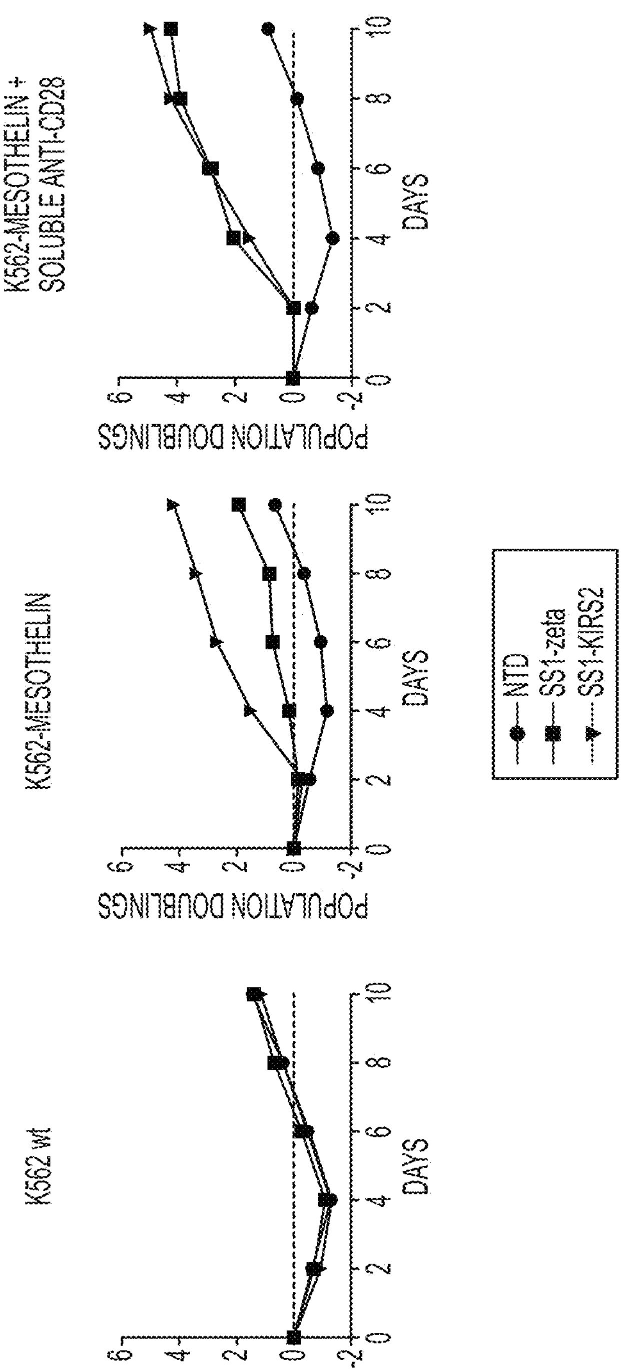
FIG. 14 illustrates the ability of a mesothelin-specific KIR-based CAR (SS1-KIRS2) to stimulate T cell proliferation that is antigen-dependent but independent of additional CD28 costimulation. Primary human T cells were stimulated with CD3/28 microbeads followed by lentiviral transduction of SS1-KIRS2 and DAP12 or the mesothelin-specific TCR-zeta CAR (SS1-zeta). Mock non-transduced cells (NTD) were used as a negative control. K562 target cells with either no mesothelin (K562 wt) or expressing mesothelin (K562-mesothelin) were mixed with the different T cells conditions as indicated at a 2:1 ratio of effector T cells to target cells. T cells stimulated with K562-mesothelin were further divided into a condition with or without a monoclonal anti-CD28 agonist antibody (clone 9.3) at 1 ug/mL. The number of viable T cells were enumerated by flow cytometry using bead-based counting at the indicated time points to calculate the number of population doublings following antigen stimulation.

Experiments were designed to evaluate the effects of chimeric co-stimulatory receptors (CCRs) in the KIR-CAR system compared to that described with standard CARs by Kloss et al. (Kloss et al., 2013, Nat Biotechnol 31(1):71-5). Experiments have also been designed to evaluate the costimulatory dependent activation requirements for KIRs by engaging the endogenous CD28 receptor in T cell using the agonist antibody, clone 9.3. As shown in FIG. 14, the KIRS2 CAR showed robust proliferation in response to mesothelin-positive targets in the absence of CD28 costimulation. This proliferation is superior to that observed with a TCR-zeta CAR where co-stimulation has been shown to be critical to proliferation. This data suggests that the KIR-based CAR may not have the same costimulation requirements as TCR-zeta CARs for antigen-specific proliferation (Milone et al., 2009, Mol Ther 17(8):1453-64; Carpenito et al., 2009, Proc Natl Acad Sci USA 106(9):3360-5), and this costimulation independence may be a significant advantage of KIR-based CARs to current TCR-zeta-based CARs. Experiments have been designed to evaluate the KIR-based CARs in humanized mice to test the KIR-based CAR against CARs with and without costimulatory domains in an in vivo pre-clinical setting (data and experiments in example 5 are also presented in example 6).

Example 6: Killer Immunoglobulin-Like Receptor (KIR)-Based Chimeric Antigen Receptors (CARs) Trigger Robust Cytotoxic Activity in Solid Tumors Chimeric antigen receptors (CARs) bearing an antigen-binding domain linked in cis to the cytoplasmic domains of CD3-ζ and costimulatory receptors provide a potent method for engineering T cell cytotoxicity towards tumors (Grupp et al., The New England journal of medicine, 368(16):1509-18, 2013; Brentjens et al., Science translational medicine, 5(177):177ra38, 2013; Porter et al., The New England journal of medicine, 365(8):725-33, 2011). An alternative chimeric receptor in which a single chain variable fragment (scFv) targeting mesothelin (SS1) was fused to the transmembrane and cytoplasmic domain of KIR2DS2, a stimulatory killer immunoglobulin-like receptor (KIR) normally expressed by natural killer (NK) cells is described herein. This SS1-KIRS2 KIR-based CAR triggers robust antigen-specific cytotoxic activity, cytokine secretion and proliferation when delivered to T cells in combination with adaptor molecule DAP12. Importantly, using a xenograft model of mesothelioma that is resistant to CD3ζ-based CAR-modified T cells bearing the cytoplasmic domains from the costimulatory receptors, CD28 or 4-1BB, the SS1-KIRS2/DAP12-modified T cells exhibit superior anti-tumor activity, suggesting that the KIR-based CAR can overcome inhibitory signals within tumors that limit second and third generation CD3ζ-based CARs. The data presented herein support future clinical evaluation of a KIR-based CAR in solid tumors.

"First generation" CARs were designed by the incorporation of a cytoplasmic domain containing the immunotyrosine-based activation motif (ITAM) into a single chimeric receptor that uses a single chain variable fragment (scFv) from an antibody for specific antigen targeting (Sadelain et al., Cancer discovery, 3(4):388-98, 2013). A number of different additional signaling domains from co-stimulatory receptors such as CD28, ICOS, 4-1BB and OX-40 were later incorporated in tandem into these receptors to enhance the proliferation and effector function of CARs (Finney H M et al. *J Immunol.* 1998; 161:2791-2797; Maher J. et al. Nat Biotech 2002; 20:70-75; Finney H M et al. J Immunol. 2004; 18:676-684; Milone et al., 2009, Mol Ther 17(8):1453-64; Carpenito et al., 2009, Proc Natl Acad Sci USA 106(9):3360-5). These "second generation" (one co-stimulatory domain) and "third generation" (2 co-stimulatory domains) CARs demonstrate significantly enhanced function in pre-clinical animal models of cancer, and these co-stimulation-enhanced CARs are currently in human clinical trials for hematologic malignancies and solid tumors (reviewed in Barrett D M et al. Ann Rev Med 2014; 65:333-347).

Although single-chain CARs trigger robust antigen-specific cytotoxic activity, natural receptors utilizing the highly conserved ITAM domains are generally structured into multi-chain complexes composed of separate ligand binding and ITAM-containing signaling chains, such as the T cell receptor (TCR)-CD3 complex, the B cell receptor (BCR)-Igα/β complex and the Fc receptor (FcR) complex. The benefits of a multi-chain immunoreceptor complex have been postulated to include: 1) greater diversity of signals available through the multiple chain interactions, 2) the use of one signaling domain for multiple ligand-binding receptors, and 3) sustained signaling by the ITAM-containing chain that is separable from the internalization of the ligand-binding chain (Sigalov et al., Advances in experimental medicine and biology, 640:ix-xi, 2008). The consequences of combining several homologous receptor components normally found in different receptors into a single CAR has not been fully elucidated; however, energy and antigen-independent signaling have been observed with some designs suggesting that these receptors may not fully recapitulate the function of the natural receptors upon which they are based (Brocker, Blood, 96(5):1999-2001, 2000; Brocker et al., The Journal of experimental medicine. 181(5):1653-9, 1995; Milone et al., Molecular therapy: the journal of the American Society of Gene Therapy, 17(8):1453-64, 2009).

The invention claimed herein describes CARs constructed upon a more "natural" split receptor design having greater potency in activating T cells due to the naturally-selected interactions between the subunits within the receptor complex. The killer immunoglobulin-like receptor (KIR) system was chosen, which represents one of the simplest ITAM-based receptor systems, as the foundation for a CAR (Thielens et al., Current opinion in immunology, 24(2):239-45, 2012). Although expressed by natural killer cells where they contribute to their natural cytotoxicity, KIR expression has also been observed in both CD4+ and CD8+ T cells (Moretta et al., Immunological reviews, 155:105-17, 1997; Falk et al., Human immunology; 61(12):1219-32, 2000; Remtoula et al., Journal of immunology, 180(5):2767-71, 2008). Activating KIRs, such as KIR2DS2, possess a short cytoplasmic domain with no known endogenous signaling capacity. Instead, these receptors form a non-covalent complex with dimers of DAP12, an ITAM-containing adaptor molecule capable of binding Syk and Zap70 kinases in NK cells (Lanier et al., Nature, 391(6668):703-7, 1998). In addition to stimulating cytotoxicity upon ligand binding, KIRs have also been shown to exhibit costimulatory effects within T cells in the absence of DAP12 suggesting that these molecules might be able to provide both primary triggering activity and costimulation in T cells (Snyder et al., Journal of immunology, 173(6):3725-31, 2004).

A KIR-based CAR was constructed by splicing the mesothelin-specific SS1 scFv onto the transmembrane and short cytoplasmic domain of the activating KIR, KIR2DS2 (SS1-KIRS2) as illustrated schematically in FIG. 1 (Hassan et al., Clinical cancer research: an official journal of the American Association for Cancer Research, 8(11):3520-6, 2002). The ITAM-containing adaptor molecule, DAP12 is constitutively expressed in natural killer (NK) cells, but it is only expressed in a subset of human T cells (Moretta et al.). Therefore, a bicistronic lentiviral vector encoding both the mesothelin-specific KIR-based CAR (SS1-KIRS2) and the DAP12 molecule separated by the Thoseaasigna virus 2A (T2A) sequence was generated in order to achieve co-expression of both molecules (FIG. 2). Transduction of primary human T cells with SS1-KIRS2 and DAP12 bicistroinic lentivirus following anti-CD3 and anti-CD28 activation demonstrated robust surface expression of SS1-KIRS2 that was comparable to the CD3ζ-based SS1ζ CAR (FIG. 6). SS1-KIRS2/DAP12 co-transduced T cells expanded following polyclonal anti-CD3/anti-CD28 stimulation with kinetics that was comparable to that observed with mock transduced T cells or T cells transduced with a mesothelin-specific CAR containing the CD3ζ cytoplasmic domain (data not shown). The cytotoxic activities of the KIR-based versus CD3ζ (SS1-z) CAR T cells was compared. SS1-KIRS2/DAP12-transduced T cells showed potent cytotoxic activity towards K562 cells that express human mesothelin (K-meso), but show no activity towards wild-type K562 (Kwt), similar in magnitude to the SS1ζ construct supporting the specific activation of the SS1-KIRS2 receptor by the cognate mesothelin target antigen (FIG. 6).

Figure 12:
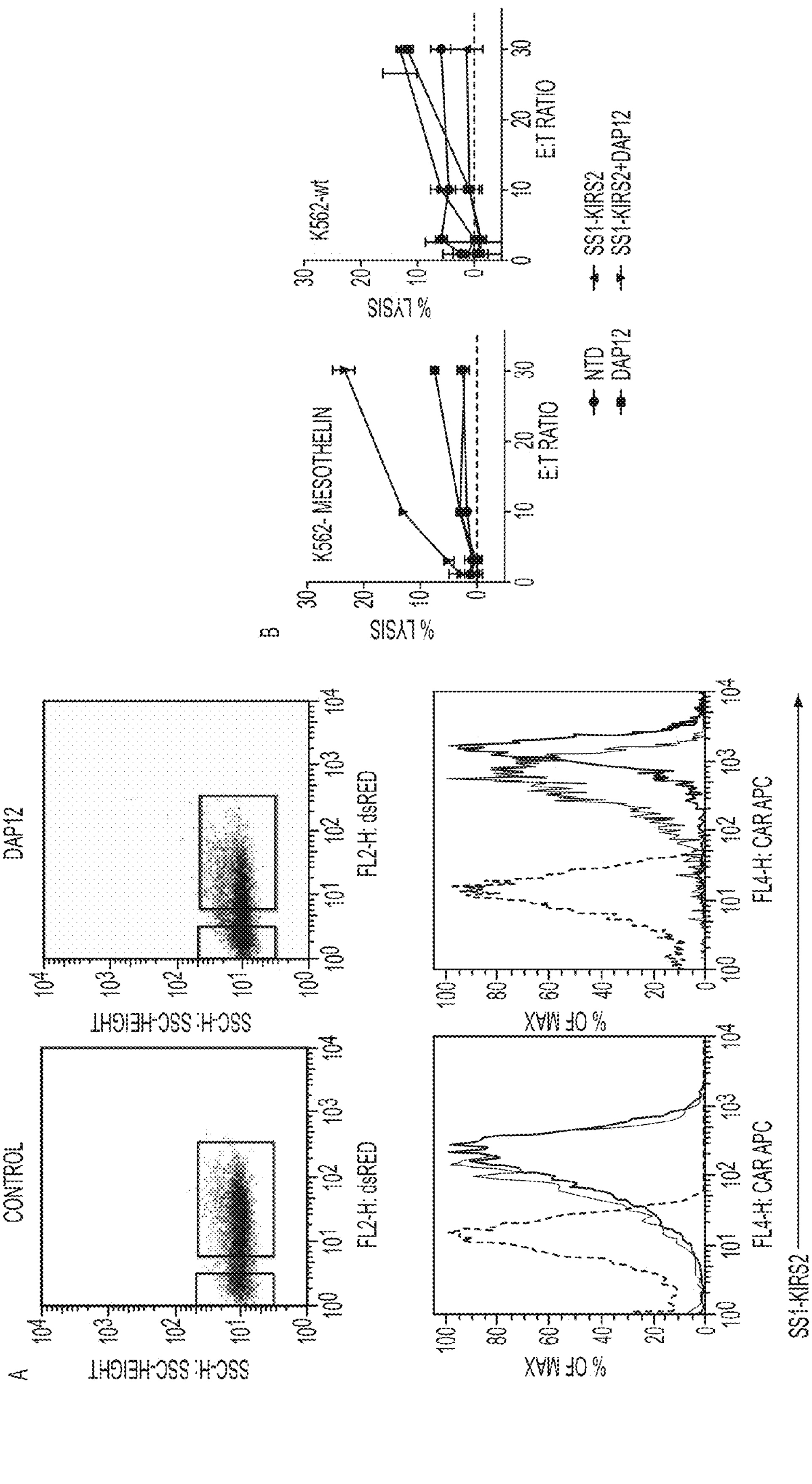
FIG. 12, comprising

Since expression of KIR2DS2 has been described in T cells in the absence of detectable DAP12 expression, the expression and function of the SS1-KIRS2 receptor with or without co-delivery of DAP12 was evaluated. Using a lentiviral vector that co-expressed DAP12 with the red fluorescent protein, dsRed (DAP12-dsRed) or a dsRed-expressing control vector (dsRed), T cells were transduced with the lentiviral DAP12 or control vector followed by transfection with in vitro transcribed RNA expressing SS1-KIRS2. SS1-KIRS2 was expressed at the surface of T cells without the addition of DAP12; however, the surface expression of SS1-KIRS2 increased by ~1-log with the addition of DAP12 (FIG. 12A). Despite the expression of SS1-KIRS2 in the absence of DAP12 co-delivery, these T cells showed no appreciable cytotoxic activity in response to mesothelin-expressing target cells compared with T cells that co-expressed SS1-KIRS2 and DAP12 (FIG. 12B). The data presented herein suggest that DAP12 is required for SS1-KIRS2 activity, but does not preclude the possibility that the KIR domain might also provide additional co-stimulatory activity independent of its association with DAP12 similarly to the natural KIR2DS2 receptor (Snyder et al.).

Figure 13:
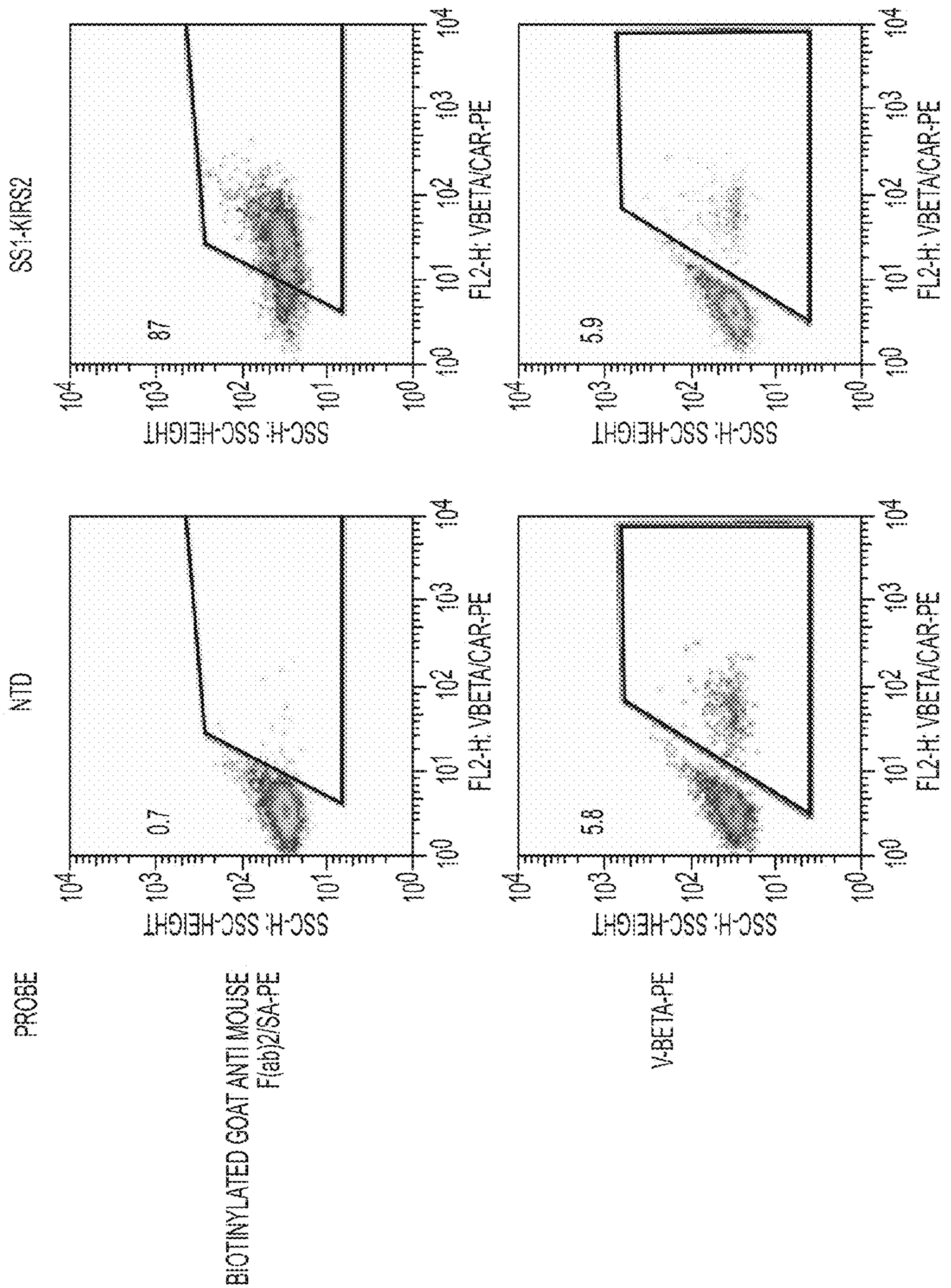
FIG. 13 shows that the expression of an endogenous TCR is unaffected by SS1-KIRS2 and DAP12 expression. $5\times10^6$ primary human T cells were electroporated with 10 ug of in vitro transcribed RNA encoding SS1-KIRS2 or mock transfected using a BTX ECM830 electroporator. After overnight incubation, the transfected T cells were stained for the expression of SS1-KIRS2 using a biotinylated goat anti-mouse F(ab)2 specific polyclonal antibody followed by streptavidin-PE. The expression of Vβ13.1 was assessed using a PE-conjugated monoclonal antibody specific to this Vβ chain of the TCR.

The non-covalent association of natural KIR2DS2 and DAP12 depends upon the electrostatic interactions between an aspartic acid residue in the KIR transmembrane (TM) domain and a lysine residue in the DAP12 TM domain (Feng et al., PLoS biology, 4(5):e142, 2006). Although the configuration of these ionizable amino acid residues in the TM domains of TCR and CD3 subunits are thought to differ from the KIRs and DAP12, providing some specificity for the interactions, the possibility that SS1-KIRS2 might be interacting with components of the CD3 complex in lieu of co-delivered DAP12 was investigated. Since the association between the CD3 complex and TCR chains is required for TCR expression on the cell surface, competition of the KIR for CD3 components would be expected to interfere with normal TCR expression as previously observed with expression of cloned TCRs (Varela-Rohena et al., Nature medicine, 14(12):1390-5, 2008). Therefore, the effect of SS1-KIRS2 expression on the expression of an endogenous TCR Vβ was evaluated. The frequency or intensity of TCR Vβ 14.3+ T cells were unaffected in T cells expressing the SS1-KIRS2. The data presented herein suggests an absence of a significant interaction between SS1-KIRS2 and members of the CD3 complex (FIG. 13).

Figure 10:
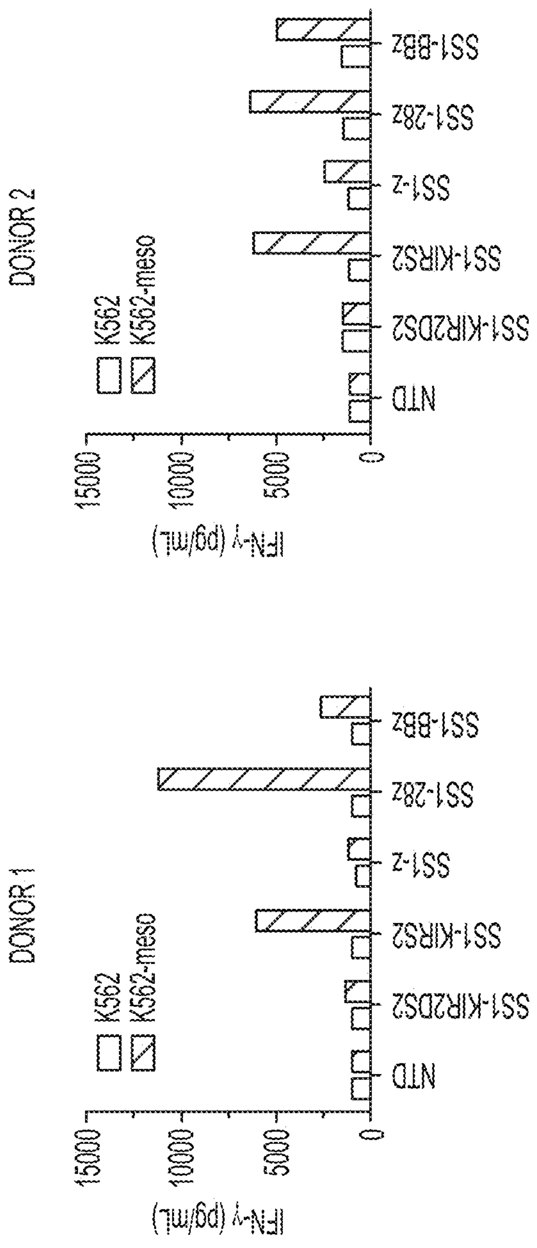
FIG. 10 is an image demonstrating the interferon-gamma (IFN-γ) production by T cells from two different donors expressing a mesothelin-specific activating KIR-based CAR (SS1-KIR2DS2 or SS1-KIRS2) or TCR-zeta based CAR with or without a costimulatory domain (SS1-z, SS1-28z or SS1-BBz). Primary human T cells were stimulated with CD3/28 microbeads followed by lentiviral transduction with the indicated activating KIR CAR or TCR-zeta based CAR. Mock non-transduced cells (NTD) were used as a negative control. K562 target cells with either no mesothelin (K562) or expressing mesothelin (K562-meso) were mixed with the different T cells conditions as indicated at a 2:1 ratio of effector T cells to target cells. Following 16 hours of incubation, IFN-γ was measured in the culture supernatants using a human IFN-gamma specific ELISA assay (R&D systems).
Figure 11:
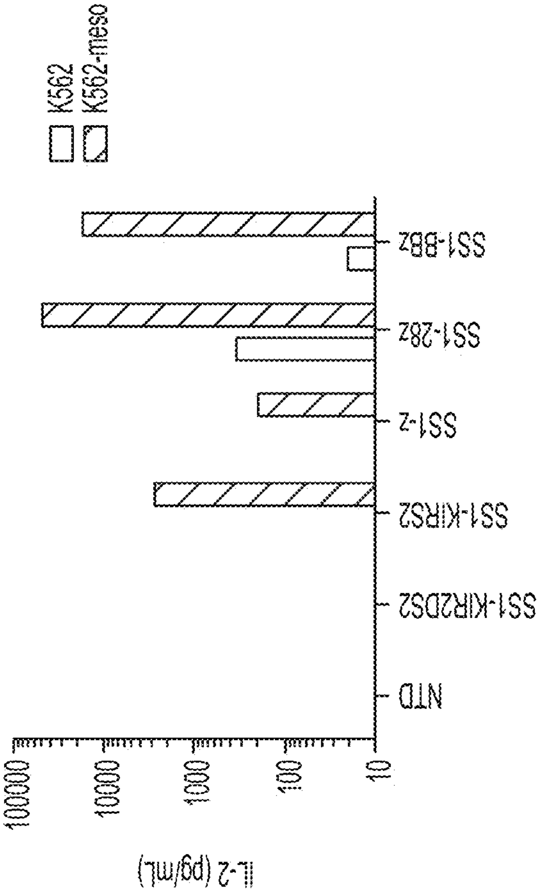
FIG. 11 is an image demonstrating the interleukin-2 (IL-2) production by T cells expressing a mesothelin-specific activating KIR-based CAR (SS1-KIR2DS2 or SS1-KIRS2) or TCR-zeta based CAR with or without a costimulatory domain (SS1-z, SS1-28z or SS1-BBz). Primary human T cells were stimulated with CD3/28 microbeads followed by lentiviral transduction with the indicated activating KIR CAR or TCR-zeta based CAR. Mock non-transduced cells (NTD) were used as a negative control. K562 target cells with either no mesothelin (K562) or expressing mesothelin (K562-meso) were mixed with the different T cells conditions as indicated at a 2:1 ratio of effector T cells to target cells. Following 16 hours of incubation, IL-2 was measured in the culture supernatants using a human IL-2 specific ELISA assay (R&D systems).

Although cytotoxic activity is an important effector function for in vivo anti-tumor activity of T cells, the ability of an antigen-receptor to trigger cytokine secretion and T cell proliferation are also important characteristics that generally correlate with robust anti-tumor activity in vivo. Therefore, the ability of T cells expressing SS1-KIRS2/DAP12 and CD3z-based CARs was compared without costimulatory domains (SS1-ζ) or with CD28 or 4-1BB co-stimulatory domains (SS1-28ζ and SS1-BBζ, respectively) to produce interferon-γ and IL-2 in response to mesothelin. The SS1-ζ construct produced the lowest levels of both IFN-γ and IL-2 (FIG. 10, 11). Interferon-γ production was higher and similarly elevated in the T cells expressing SS1-KIRS2/DAP12 or CD3ζ-based CARs bearing costimulatory domains (FIG. 10). T cells with the CD3ζ-based CARs bearing costimulatory domains produced greater quantities of IL-2 compared with T cells expressing SS1-ζ or SS1-KIRS2/DAP12 (FIG. 11). The SS1-KIRS2/DAP12 receptor was also a potent stimulator of T cell proliferation in response to cognate antigen (FIG. 14). Surprisingly, this proliferation was unaffected by the addition of agonist antibody to CD28 (clone 9.3) suggesting that additional costimulatory signals are not required. The data presented herein is consistent with a previously reported costimulatory function of naturally expressed KIR2DS2 in human CD8+ T cell clones in the absence of DAP12 (Snyder et al.). An alternative explanation is that additional receptors naturally expressed by T cells are also capable of utilizing the co-delivered DAP12 further contributing to T cell activation and proliferation.

Figure 15:
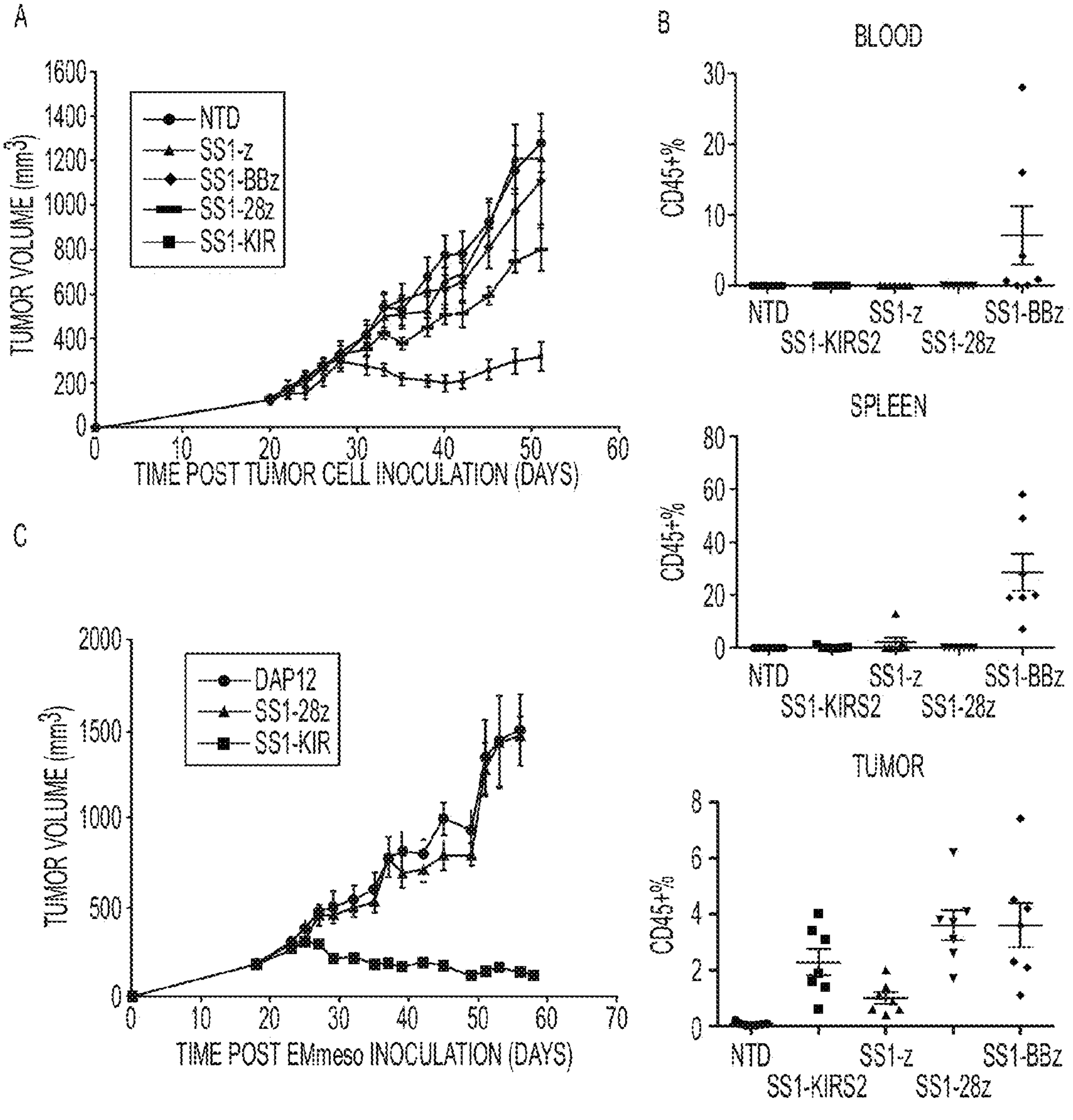
FIG. 15, comprising FIGS. 15A-15C, demonstrates that mesothelin-specific KIR-CAR modified T cells show enhanced anti-tumor activity in vivo compared with second generation TCR-ζ based CARs bearing CD28 or CD137 (4-1BB) costimulatory domains.

That in vivo anti-tumor activity of T cells modified with mesothelin-specific TCR-ζ based CARs is significantly enhanced by the incorporation of costimulatory domains including CD28 and 4-1BB was previously demonstrated (Carpenito et al., Proceedings of the National Academy of Sciences of the United States of America, 106(9):3360-5, 2009); however the efficacy of a single intravenous injection of these second or third generation CAR T cells into mice bearing established mesothelioma xenografts often failed to lead to complete tumor regression (Moon E K et al. Clin Cancer Res 2011; 17(14):4719-30; Riese M J et al. Cancer Res. 2013; 73(12):3566-77). Therefore, the activity of SS1-KIRS2/DAP12-modified T cells in this resistant subcutaneous model of mesothelioma was evaluated. The ability of SS1-KIRS2/DAP12-modified, DAP12-dsRed-modified T cells and SS1-28 T cells to kill EMMESO cells in vitro was first tested. As shown in FIG. 15A, all three types of CAR-modified T Cells showed similar in vitro killing efficacy, with minimal cytotoxicity induced by DAP12-dsRed-modified T cells. Mice bearing large established EM-meso tumors were intravenously injected with $10^7$ T cells that were either mock-transduced T cells (mock) or T cells transduced (at a similar level of transduction of ~80%) with SS1-z, SS1-BBz, SS1-28z, or SS1-KIR-DAP12 and tumor growth was followed (FIG. 15A). In this model, the mock, SS1ζ, and the SS1BBζ T cells had no significant anti-tumor efficacy. The growth of the tumors was significantly (data not shown), but only modestly slowed by injection of the SS1-28ζ CAR T cells. In contrast, after a 10 day lag period, the SS1-KIRS2/DAP12-modified T cells induced marked tumor regression inhibition of EM-meso tumor growth for up to 48 days. At this time, the animals were sacrificed and the blood, spleens, and tumors analyzed. Flow cytometry was used to detect the presence of the human CD45+ cells (FIG. 15B). Only mice receiving the SS1-BBz CAR T cells had detectable hCD45+ cells in the blood and spleen. Within the tumors, no hCD45+ cells were detected in mock T cell-treated mice and only a low percentage of T cells were observed in SS1z-treated mice. In contrast, the SS1-KIRS2/DAP12, SS1-28z, and SS1-41BB CARs had hCD45+ cells that comprised 2-4% of the total viable cells with comparable frequencies noted for each group (FIG. 15B). The data presented herein demonstrate that the markedly increased efficacy of the SS1-KIRS2/DAP12 was not due to larger frequency of T cells within the tumors.

To further explore the location of the T cells within the tumors, immunohistochemistry was performed. Staining showed CD8+ T cells and CD4+ T cells within the tumors within each group. Tumors from animals treated with SS1-BBζ and SS1-28ζ CAR-modified T cells demonstrated particularly dense T cell infiltrates; however, these infiltrates tended to be within the periphery of the tumor suggesting that the SS1-BBζ and SS1-28ζ CAR-modified T cells might be limited in their ability to traffic and/or function with the tumor microenvironment compared with the SS1-KIRS2/DAP12 CAR T cells.

Constitutive expression of DAP12 alone in murine T cells has been reported to confer NK-like activity to these T cells with the ability to control a solid tumor via NKG2D ligand-triggered effects (Teng et al., The Journal of biological chemistry, 280(46):38235-41, 2005). Although NKG2D has been reported to associate with DAP12 in mice, this association appears to be absent in humans (Rosen et al. Journal of immunology, 173(4):2470-8, 2004). Despite the lack of in vitro cytolytic activity by T cells expressing DAP12 only, a second in vivo experiment was performed to compare T cells expressing DAP12 alone to SS1-KIRS2/DAP12 and to SS1-28z engineered T cells. Similar to the in vitro results, DAP12-expressing T cells were unable to control EM-meso tumors in the absence of the mesothelin-specific SS1-KIR2S receptor (FIG. 15C). The data presented herein show an impressive anti-tumor response of the SS1-KIRS2/DAP12 T cells with frank tumor regression and almost elimination of the tumors by Day 48.

T cell persistence in tumors has been shown to be an important determinant of adoptive T cell transfer efficacy. However, the data presented herein show that the enhanced effects of the KIR-CAR are not due to increased numbers of T cells within the tumors; both the SS1-28z and SS1-41BBz constructs appear to persist at slightly higher numbers than the KIR CARs. The location of the CAR T cells may be important, however. The staining data presented herein suggests that SS1-KIRS2/DAP12 T cells may be more efficient in reaching the center of the tumors.

The mechanisms responsible for the markedly improved efficacy of the KIR-based CARs are under active investigation. Although both CD3 and KIR receptor systems rely upon ITAM-based recruitment and activation of downstream signal, the nature of the ensuing ITAM-mediated signaling may not be equivalent. Recently, a number of heterologous receptors with no known mechanism for interaction with ITAM-containing receptors including the cytokine receptors for type I interferon and IL-3, the chemokine receptors, CXCR4 and RANKL have been shown to depend upon ITAM-containing receptor for signaling (Wang et al., Nature immunology, 9(2):186-93, 2008; Hida et al., Nature immunology, 10(2):214-22, 2009; Koga et al., Nature, 428(6984):758-63, 2004; Kumar et al., Immunity, 25(2):213-24, 2006). It is therefore possible that the introduction of DAP12 into T cells may alter a number of additional signals that might be relevant to T cell function within the complex tumor microenvironment. The robust proliferation of T cells following KIR-based CAR activation without additional co-stimulation might also be an important part of the enhanced efficacy of T cells modified with SS1-KIRS2 and DAP12. The clonal expansion of T cells following TCR and co-stimulatory receptor engagement requires tremendous synthetic demands. Both CD28 and 4-1BB receptors are potent activators of the mTOR pathway that is an important regulator of the metabolism required to support clonal expansion (Colombetti et al., Journal of immunology, 176(5):2730-8, 2006; So et al., Frontiers in immunology, 4:139, 2013; Marelli-Berg et al. Immunology, 136(4):363-9, 2012). Interestingly, Berezhnoy et al. recently reported that interruption of mTOR using an siRNA to raptor directed by a 4-1BB-specific RNA aptamer significantly improved the anti-tumor activity of T cells following therapeutic vaccination of tumor-bearing mice (Berezhnoy et al., The Journal of clinical investigation. 124(1):188-97, 2014). Since costimulatory signals such as CD28 and 4-1BB are normally regulated both temporally and spatially during an immune response, this suggests that the unregulated costimulatory signals produced by the BBζ and 28ζ CARs, while critical for robust proliferation in response to CD3ζ CAR triggering, might have negative effects on T cell function in vivo, perhaps through persistent mTOR signaling.

In conclusion, the data presented herein demonstrate that the combination of KIR-based CAR and DAP12 provides a highly effective receptor system for conferring artificial antigen specificity to T cells. Despite relative equivalent in vitro activity, it has further been shown that this KIR-based CAR has much improved anti-tumor efficacy compared to CARs based on CD3ζ with one or more costimulatory domains in the model tumor system utilized herein, perhaps due to increased resistance to inactivation. Further exploration into the mechanisms of this increased efficacy and of chimeric receptor designs based upon other DAP12-associated ligand-binding receptors, as well as additional natural ITAM containing receptors systems such as FcRγ, will be pursued.

Example 7: A KIR-Based CAR can be Co-Expressed with a Natural Inhibitory KIR Permitting Regulation by HLA Expression on the Target Cells Generation and Characterization of a K562-Meso Cell Line that Express the KIR2DL3 Ligand HLA-Cw Material and Method:

Wild type K562 cells or a K562 line previously engineered to express mesothelin (K562-meso) were transduced with a lentiviral vector encoding the HLA-Cw3 allele. Cells were sorted for uniform expression of mesothelin and HLA-Cw3 by fluorescence-activated cell sorting. HLA-Cw3 expression was confirmed by flow cytometry following staining with the W6/32 anti-HLA A, B, C antibody conjugated to APC.

Figure 20:
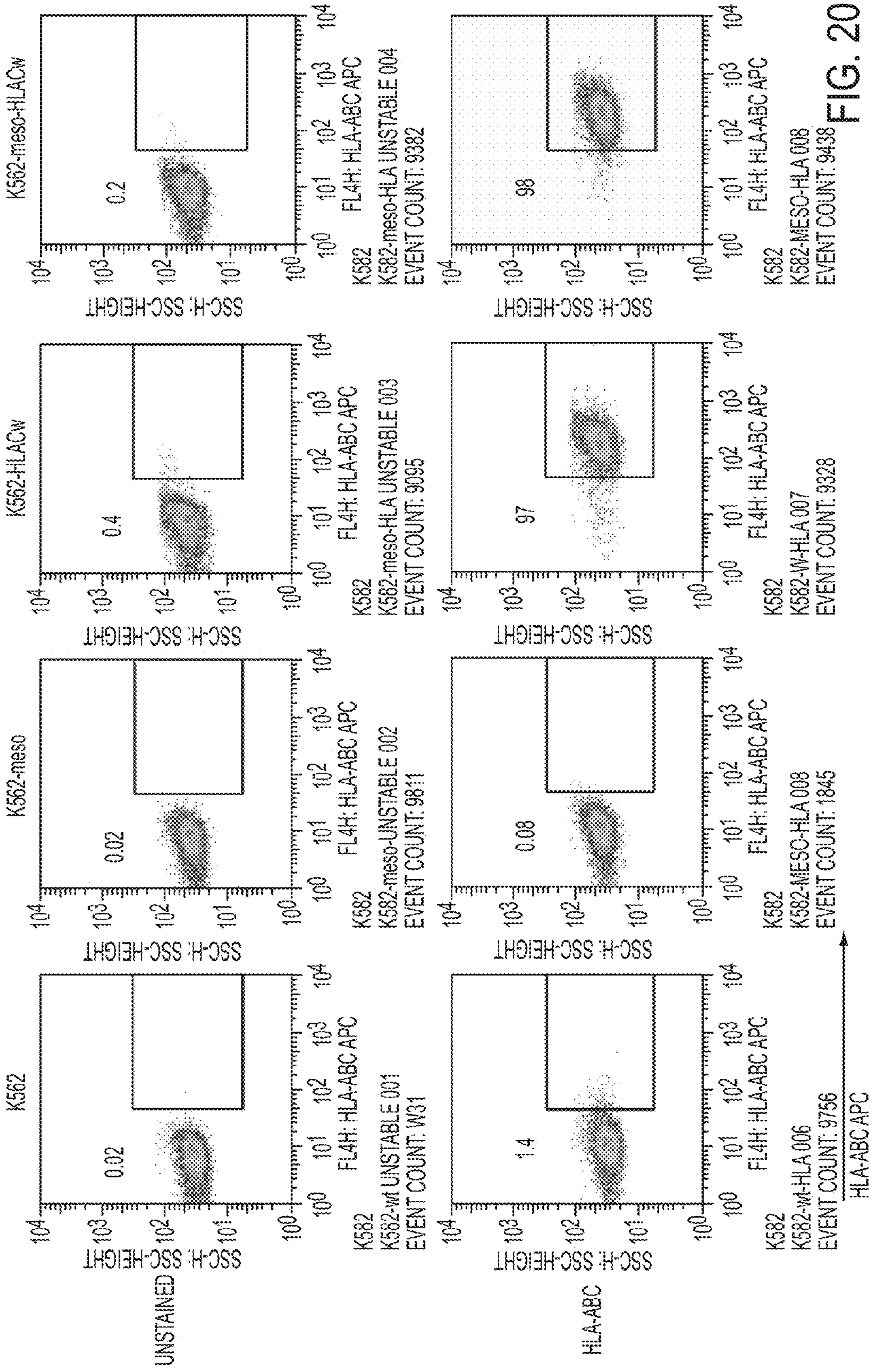
FIG. 20 demonstrates the generation and characterization of a K562-meso cell line that express the KIR2DL3 ligand HLA-Cw. K562 cells (K562) or K562 cells expressing mesothelin (K562-meso) were transduced with the HLA-Cw3 allele followed by fluorescence activated cell sorting to obtain K562 cells expressing HLA-Cw with (K562-meso-HLACw) or without (K562-HLACw) expression of mesothelin. HLA-Cw3 expression was assessed by flow cytometry using an APC-conjugated monoclonal antibody that recognizes HLA-A, B and C alleles (clone W6/32).

Result:

K562 cell lines expressing either mesothelin or HLA-Cw3 alone or in combination can be generated (FIG. 20).

Co-Expression of SS1-KIRS2 and KIR2DL3 in Primary Human T Cells

Material and Method:

Primary human T cells were stimulated with anti-CD3/28 microbeads followed by transduction with either a bicistronic lentiviral vector expressing DAP12 and SS1-KIRS2 alone or in combination with a lentiviral vector expressing KIR2DL3 on day 1 following activation. The expression of the SS1-KIRS2 CAR was assessed by flow cytometry using a biotinylated goat-anti-mouse F(ab)2 polyclonal antibody followed by SA-APC. KIR2DL3 expression was determined using a KIR2D specific monoclonal antibody.

Figure 21:
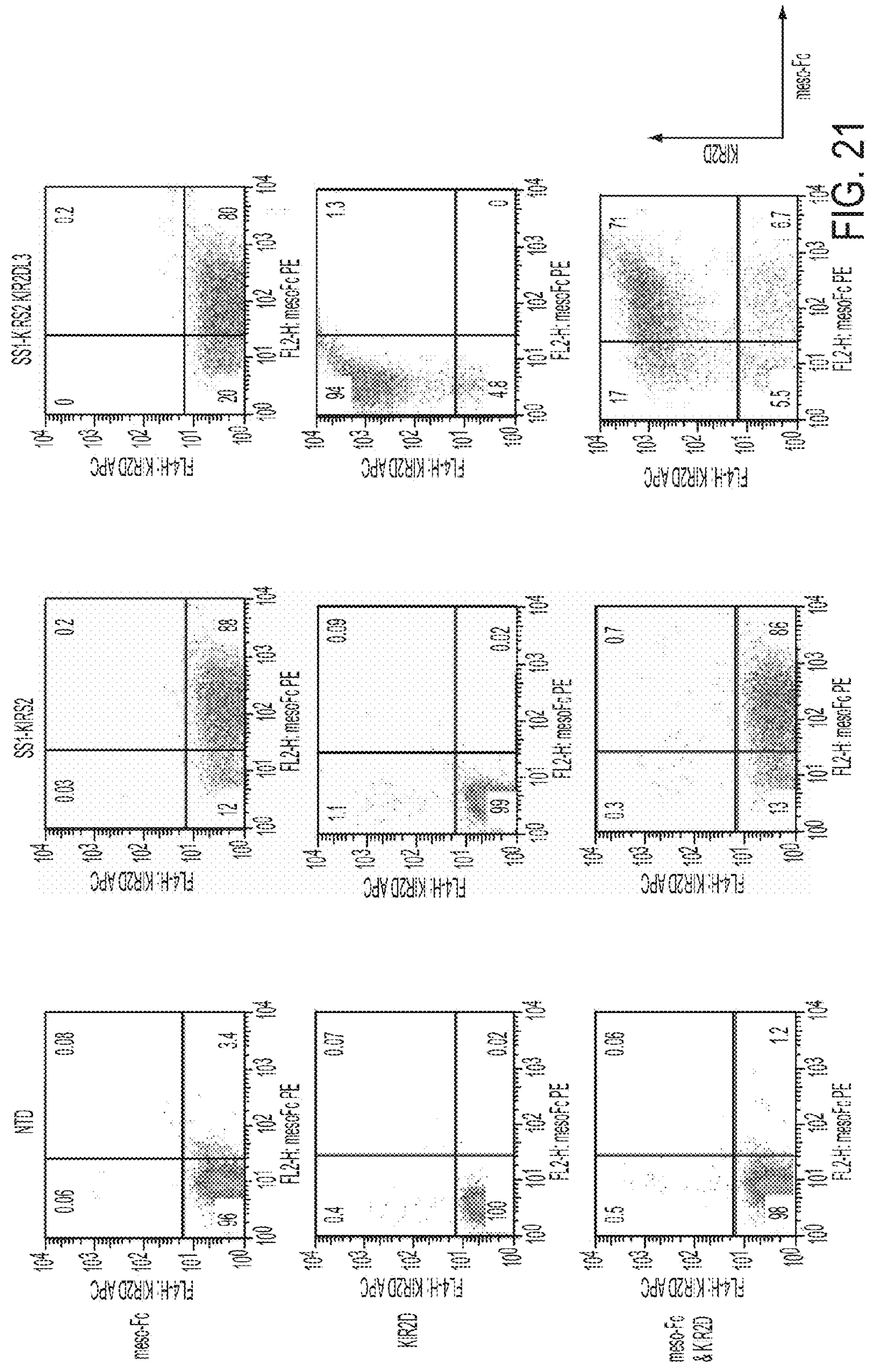
FIG. 21 demonstrates co-expression of SS1-KIRS2 and KIR2DL3 in primary human T cells. Primary human T cells were stimulated with CD3/28 microbeads followed by lentiviral transduction with SS1-KIRS2 and DAP12 (SS1-KIRS2) or mock transduced (NTD) in combination with wild-type KIR2DL3. The T cells were expanded until the end of log-phase growth. The surface expression of the mesothelin-specific CAR and KIR2DL3 was determined by staining with mesothelin-Fc followed by PE-conjugated goat-anti-human Fc and a monoclonal antibody to the KIR2DL3 ectodomain.

Result:

Primary human T cells expressing a mesothelin-specific KIR-based CAR with DAP12 (KIRS2) alone, KIR2DL3 alone or a combination of the two receptors can be generated (FIG. 21).

KIR2DL3 Coexpressed with a KIR CAR can Suppress Antigen Specific Cytotoxicity in the Presence of HLA-Cw on the Target Cells Material and Method:

Primary human T cells were stimulated with anti-CD3/28 microbeads followed by transduction with a bicistronic lentiviral vector expressing DAP12 and SS1-KIRS2. 5 μg of in vitro transcribed mRNA encoding KIR2DL3 was introduced into the lentivirally-transduced T cells by electroporation following 10 days of ex vivo expansion. These T cell populations were mixed with $^{51}$Cr-labeled K562 target cells (K562, K562-meso, K562-HLACw and K562-meso/HLACw) as indicated at varying ratios of effector T cells to target K562 cells (E:T ratio). Cytotoxicity was determined by measuring the fraction of $^{51}$Cr released into the supernatant at 4 hours.

Figure 22:
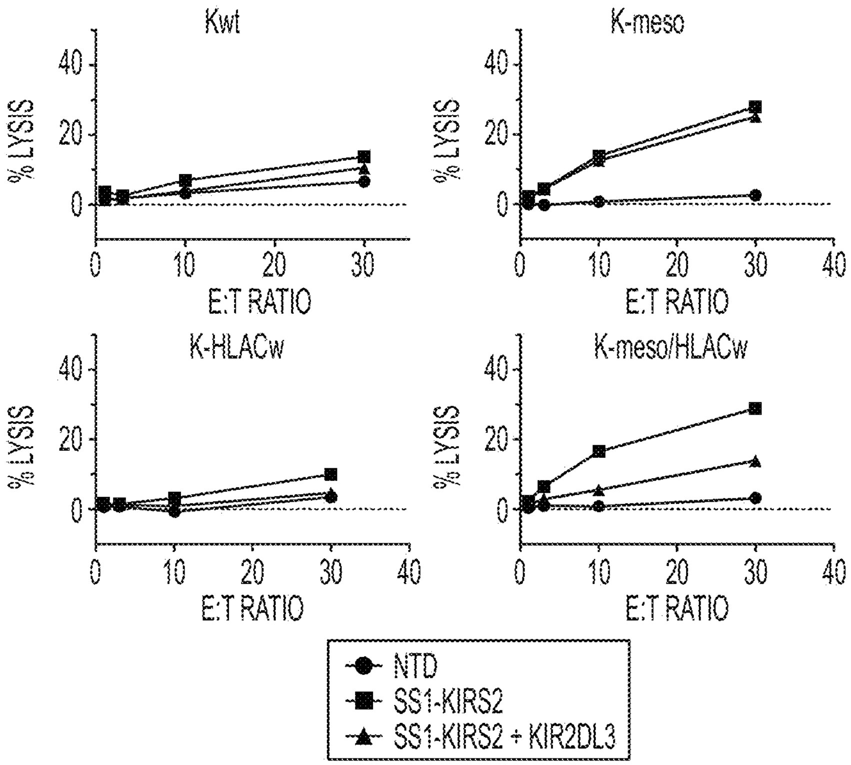
FIG. 22 demonstrates that KIR2DL3 coexpressed with a KIR CAR can suppress antigen specific cytotoxicity in the presence of HLA-Cw on the target cells. T cell that were generated and characterized as described in FIG. 21 were mixed with 51-Cr labeled target K562 cells that were generated and characterized as described in FIG. 22. Cytotoxicity was determined by measuring the fraction of $^{51}$Cr released into the supernatant at 4 hours compared target cells without effector cells.

Result:

SS1-KIRS2/DAP12-expressing T cells were capable of killing target K562 cells that express mesothelin regardless of HLA-Cw3 expression. In contrast, T cells co-expressing the SS1-KIRS2/DAP12 receptor complex and the inhibitory KIR, KIR2DL3 failed to exhibit robust cytotoxicity against K562 expressing mesothelin with HLA-Cw3; however, these cells demonstrated cytotoxic activity towards K562 cells expressing mesothelin alone that was comparable to SS1-KIRS2/DAP12-modified T cells. These results demonstrate the ability of inhibitory KIR receptors to regulate the functional activity of activating KIR-based CARs (FIG. 22).

Example 8: A KIR-Based CAR with CD19 Specificity can Trigger Antigen-Specific Target Cell Cytotoxicity In Vitro and In Vivo a KIR-Based CAR with CD19 Specificity can Trigger Antigen-Specific Target Cell Cytotoxicity In Vitro Material and Method:

Following anti-CD3/anti-CD28 bead activation, T cells were transduced with a bicistronic lentiviral vector expressing DAP12 along with either a CD19-specific KIR-based CAR in which the FMC63-derived scFv is fused to full length KIR2DS2 (CD19-KIR2DS2) or a KIR-based CAR generated by fusing the FMC63 scFv to the transmembrane and cytoplasmic domain of KIR2DS2 via a short linker $[Gly]_4$-Ser linker (SEQ ID NO: 66) (CD19-KIRS2). The transduced T cells were cultured until the end of the log phase growth, and the expression of the CD19-specific KIR-based CAR was assessed by flow cytometry using a biotinylated goat-anti-mouse $F(ab)_2$ polyclonal antibody followed by SA-PE. $^{51}$Cr-labeled K562 target cells with (K562-CD19) or without (K562-wt) CD19 expression were mixed at varying ratios with T cells to target cells (E:T ratio). Cytotoxicity was determined by measuring the fraction of $^{51}$Cr released into the supernatant at 4 hours. Control T cells that were either mock transduced (NTD) or transduced with a CD3-based CAR specific to CD19 (CD19-z) were also included as negative and positive controls, respectively.

Figure 16:
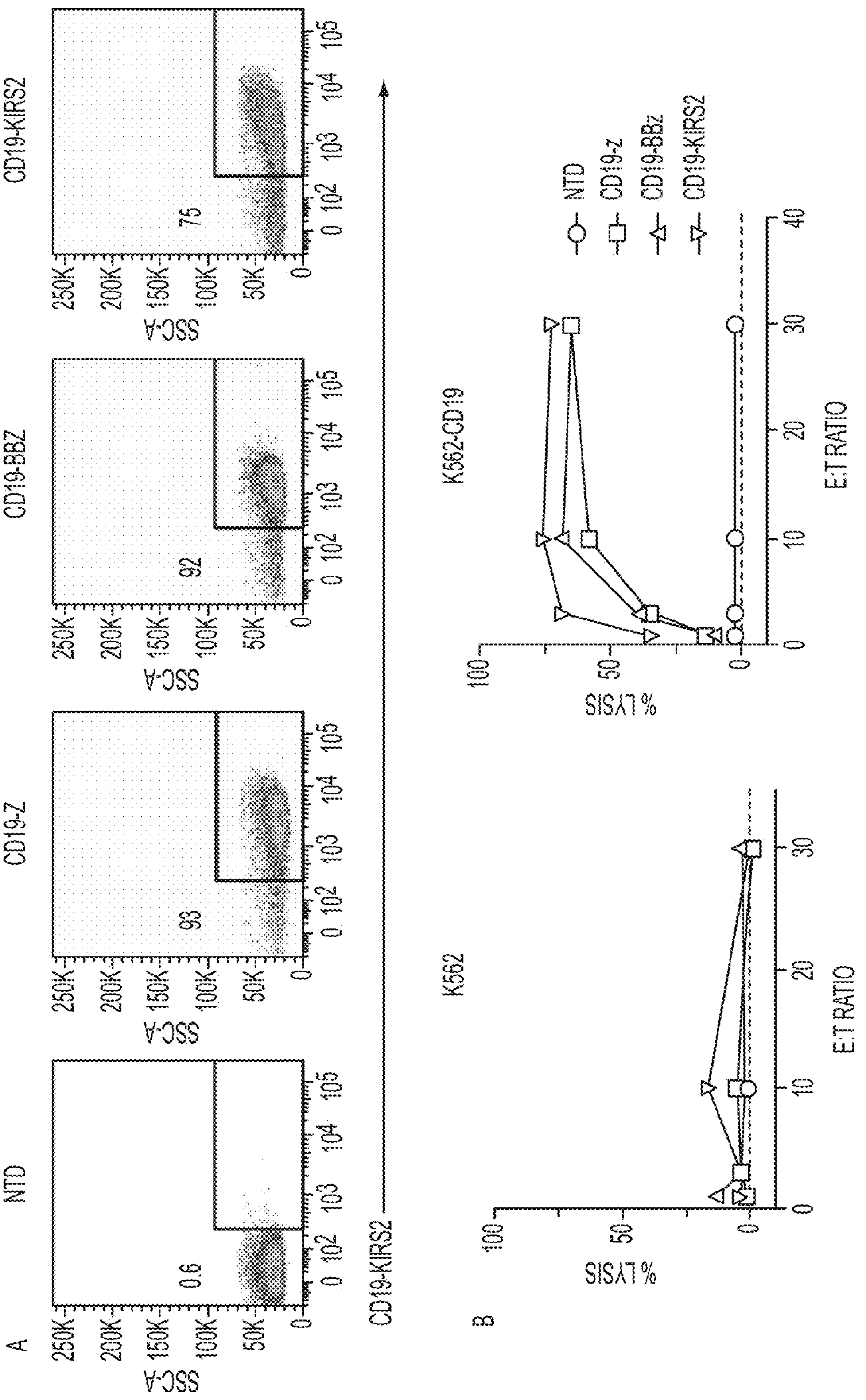
FIG. 16 comprising FIGS. 16A-16B, demonstrates a KIR-based CAR with CD19 specificity can trigger antigen-specific target cell cytotoxicity. Following anti-CD3/anti-CD28 bead activation, T cells were transduced with a bicistronic lentiviral vector expressing DAP12 along with either a CD19-specific KIR-based CAR in which the FMC63-derived scFv is fused to full length KIR2DS2 (CD19-KIR2DS2) or a KIR-based CAR generated by fusing the FMC63 scFv to the transmembrane and cytoplasmic domain of KIR2DS2 via a short linker $[Gly]_4$-Ser linker (SEQ ID NO: 66) (CD19-KIRS2). The transduced T cells were cultured until the end of the log phase growth, and the expression of the CD19-specific KIR-based CAR was assessed by flow cytometry using a biotinylated goat-anti-mouse $F(ab)_2$ polyclonal antibody followed by SA-PE. $^{51}$Cr-labeled K562 target cells with (K562-CD19) or without (K562-wt) CD19 expression were mixed at varying ratios with T cells to target cells (E:T ratio). Cytotoxicity was determined by measuring the fraction of $^{51}$Cr released into the supernatant at 4 hours. Control T cells that were either mock transduced (NTD) or transduced with a CD3ζ-based CAR specific to CD19 (CD19-z) were also included as negative and positive controls, respectively.

Result:

Flow cytometric analysis demonstrates expression of the CD19-specific scFv on the surface of the T cells transduced with CD19-KIR2DS2, CD19-KIRS2 and CD19-z (FIG. 16A). T cells expressing DAP12 with either CD19-KIR2DS2 or CD19-KIRS2 were capable of killing target cells in an antigen-specific manner (FIG. 16B). Cytotoxicity exhibited by the KIR-based CAR-modified T cells was comparable to or higher than T cells expressing a CD19-specific CD3-based CAR.

Figure 17:
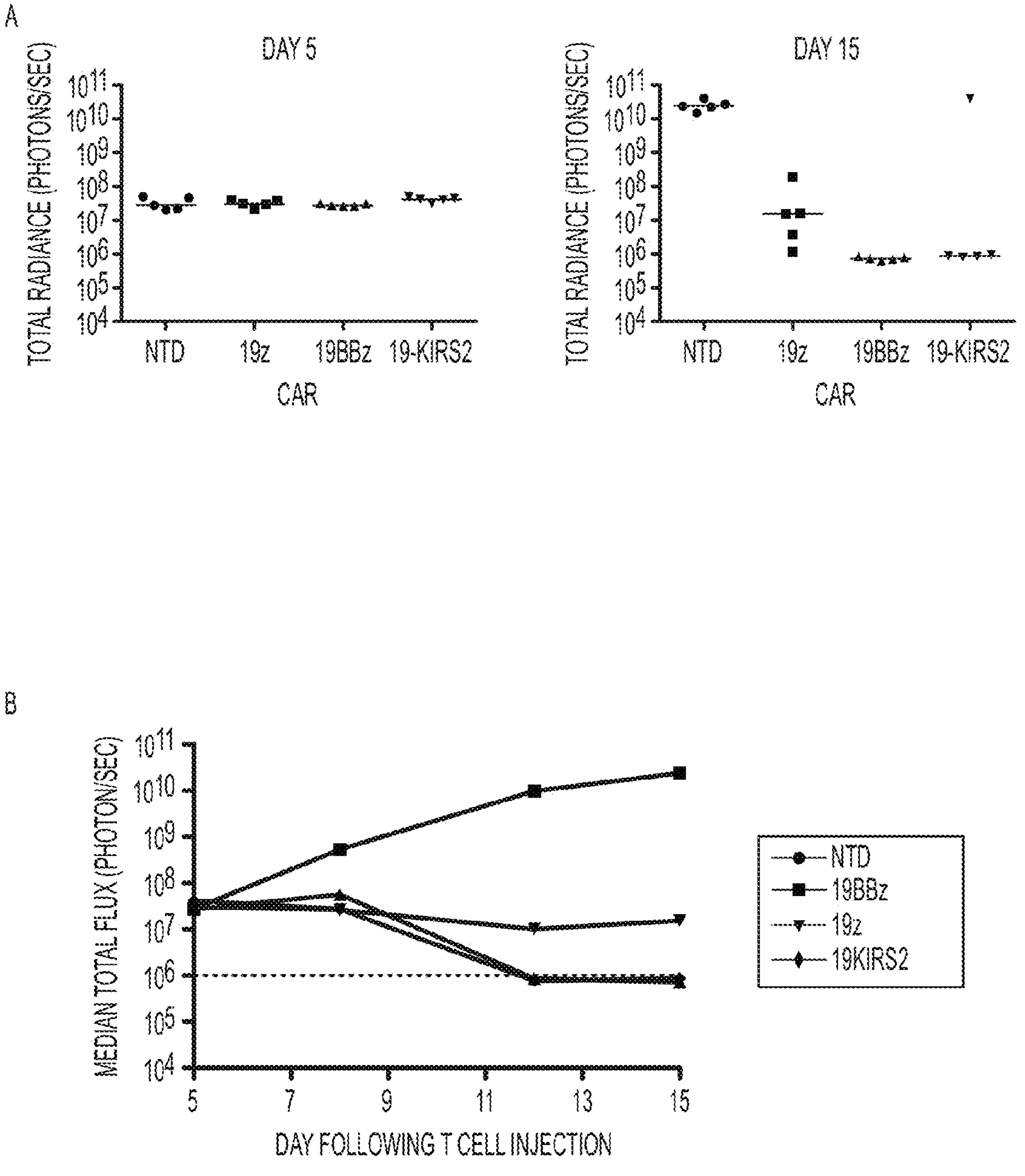
FIG. 17 comprising

T Cells Transduced with CD19-KIRS2/DAP12 Induce Tumor Regression in a Human Leukemia Xenograft Material and Method:

NOD-SCID-$\gamma_c^{-/-}$ (NSG) mice were engrafted intravenously by tail vein on day 0 with 1 million Nalm-6 CBG tumor cells, a leukemia cell line expressing CD19. In the experiment, T cells were stimulated with anti-CD3/anti-CD28 stimulator beads followed by lentiviral transduction on day 1 with a series of CD3-based CAR with or without a costimulatory domain (CD19-z, CD19-BBz) or the CD19-specific KIR-based CARs, CD19-KIRS2 with DAP12 as indicated in the figure. Mock transduced T cells (NTD) were used as a control. The T cells were expanded until the end of log-phase growth ex vivo and injected intravenously on day 5 post leukemia cell line injection with 2 million CAR T cells per mouse. Tumor burden was assessed via bioluminescent imaging. 5 animals were analyzed for each T cell condition (FIG. 17).

Result:

In the in vivo experiment presented (FIG. 17), the NTD T cells had no effect on tumor growth, while CD19z, CD19BBz and CD19-KIRS2-transduced T cells exhibit various anti-tumor effects. Mice infused with CD19z T cells showed a slight reduction in tumor burden but retained detectable levels of luminescence. In contrast, tumor cell luminescence in mice infused with either CD19BBz or CD19KIRS2 T cells dropped to the lower limit of detection (FIG. 17B, dotted line) only 7 days post T cell injection, exhibiting complete clearance outside of a small reservoir of leukemia cells in the T cell-inaccessible tooth root. By day 15, tumor burden in the mock T cell group surpassed the endpoint ($2\times10^{10}$ photons/second) and were sacrificed, while luminescence in the CD19BBz and CD19KIRS2 groups remained at the lower limit of detection.

Example 9: A Camelid Single VHH Domain-Based CAR can be Expressed on a T Cell Surface in Combination with a scFv-Based CAR without Appreciable Receptor Interaction Material and Method:

Jurkat T cells expressing GFP under an NFAT-dependent promoter (NF-GFP) were transduced with either a mesothelin-specific activating CAR (SS1-CAR), CD19-specific activating (19-CAR) or a CAR generated using a camelid VHH domain specific to EGFR (VHH-CAR). Following transduction with the activating CAR, the cells were then transduced with an additional inhibitory CAR recognizing CD19 (19-PD1) to generate cells co-expressing both the activating and inhibitory CAR (SS1+19PD1, 19+19PD1 or VHH+19PD1). The transduced Jurkat T cells were co-cultured for 24 hours with different cell lines that are either 1) devoid of all target antigens (K562), 2) express mesothelin (K-meso), CD19 (K-19) or EGFR (A431) only, 3) express a combination of EGFR and mesothelin (A431-mesothelin) or CD19 (A431-CD19) or 4) express a combination of CD19 and mesothelin (K-19/meso). Additional conditions that include either no stimulator cells (no stim) or K562 with 1 μg/mL of OKT3 (OKT3) were also included as negative and positive controls for NFAT activation, respectively. GFP expression, as a marker of NFAT activation, was assessed by flow cytometry.

Figure 25:
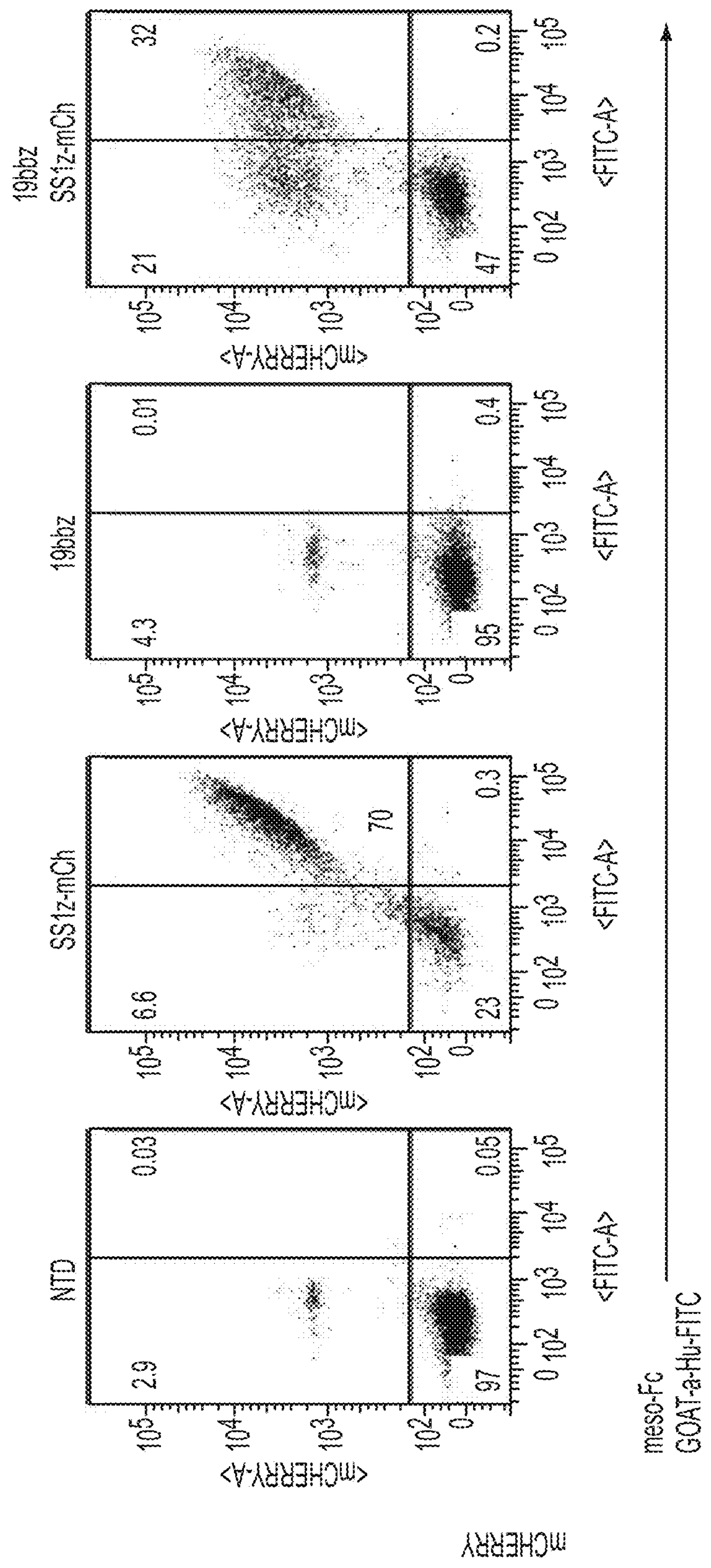
FIG. 25 is an image demonstrating that expression of a CD19-specific CAR also reduced the expression of mesothelin-binding sites on the surface of cells co-expressing an SS1-zeta-mCherry fusion CAR. Primary human T cells were stimulated with CD3/28 microbeads followed by lentiviral transduction with an SS1 scFv zeta CAR bearing a C-terminal mCherry fusion (SS1z-mCh) or the FMC63-derived CD19 specific 41BB-zeta CAR (19bbz) alone or combination. Mock-transduced cells were used as a control. The T cells were expanded until the end of log-phase growth, and dsRed as well as surface CAR expression was determined by flow cytometry after staining with mesothelin-Fc followed by a goat-anti-human Fc specific polyclonal antibody conjugated to FITC.
Figure 26:
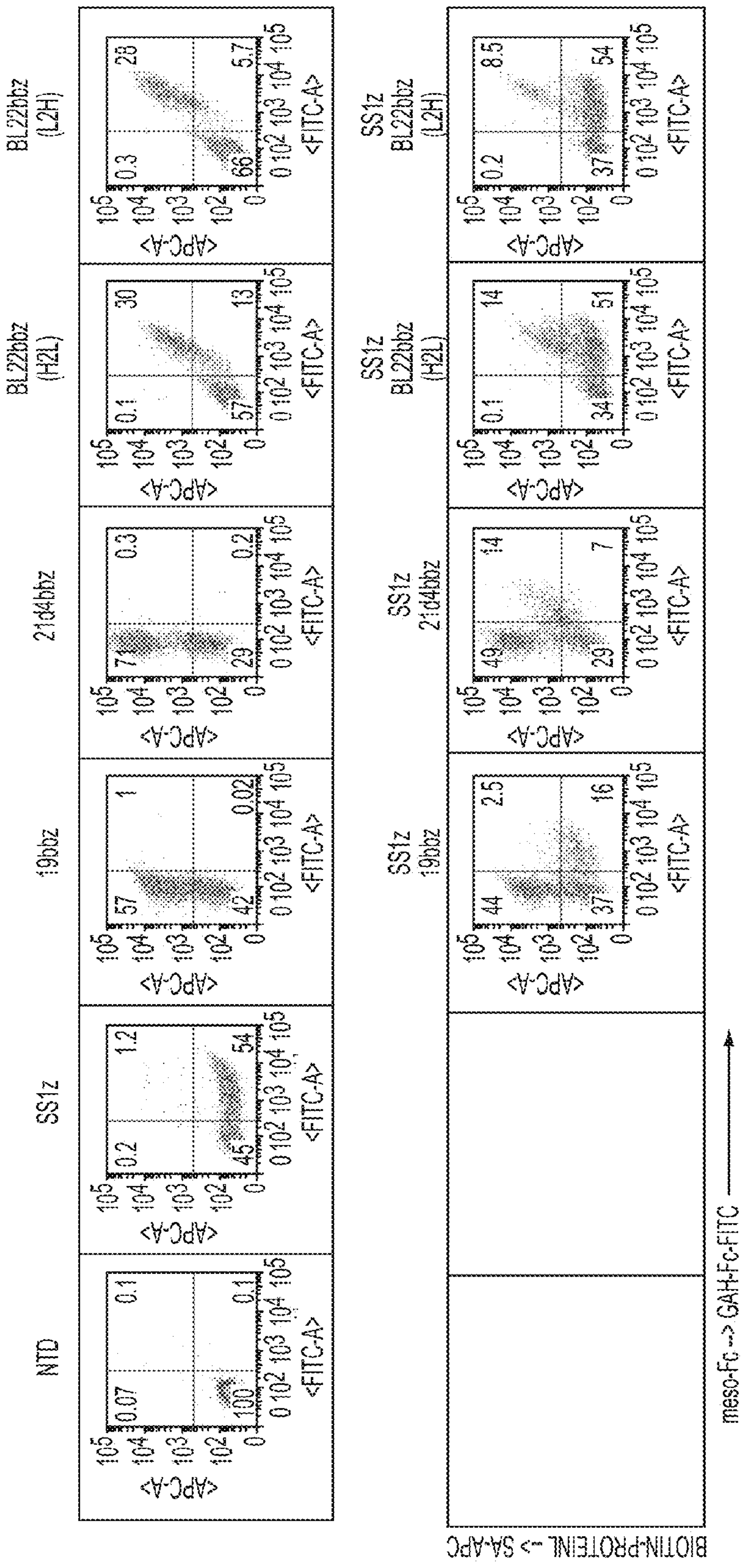
FIG. 26 is an image demonstrating that mutually exclusive expression of binding sites for the SS1 scFv is not unique to the FMC63 scFv. Primary human T cells were stimulated with CD3/28 microbeads followed by lentiviral transduction with either an SS1 scFv zeta CAR or various CD19 specific 41BB-zeta CARs (19BBz [FMC63 scFv, 214d scFv or the BL22 scFv CARs with alternate VH and VL orientations [H2L and L2H]). NTD represents mock-transduced cells used as a staining control. In addition, a separate set of T cells were co-transduced with the SS1 scFv zeta CAR and the different CD19 specific CARs as above. The T cells were expanded until the end of log phase growth, and surface CAR expression was determined by staining with biotinylated protein L (recognizes kappa light chain) followed by streptavidin APC simultaneously with mesothelin-Fc followed by a goat-anti-human Fc specific polyclonal antibody conjugated to PE. The cotransduced cells showed that the mutually exclusive expression observed with FMC63-based CAR is also observed with other scFv-CARs.
Figure 27:
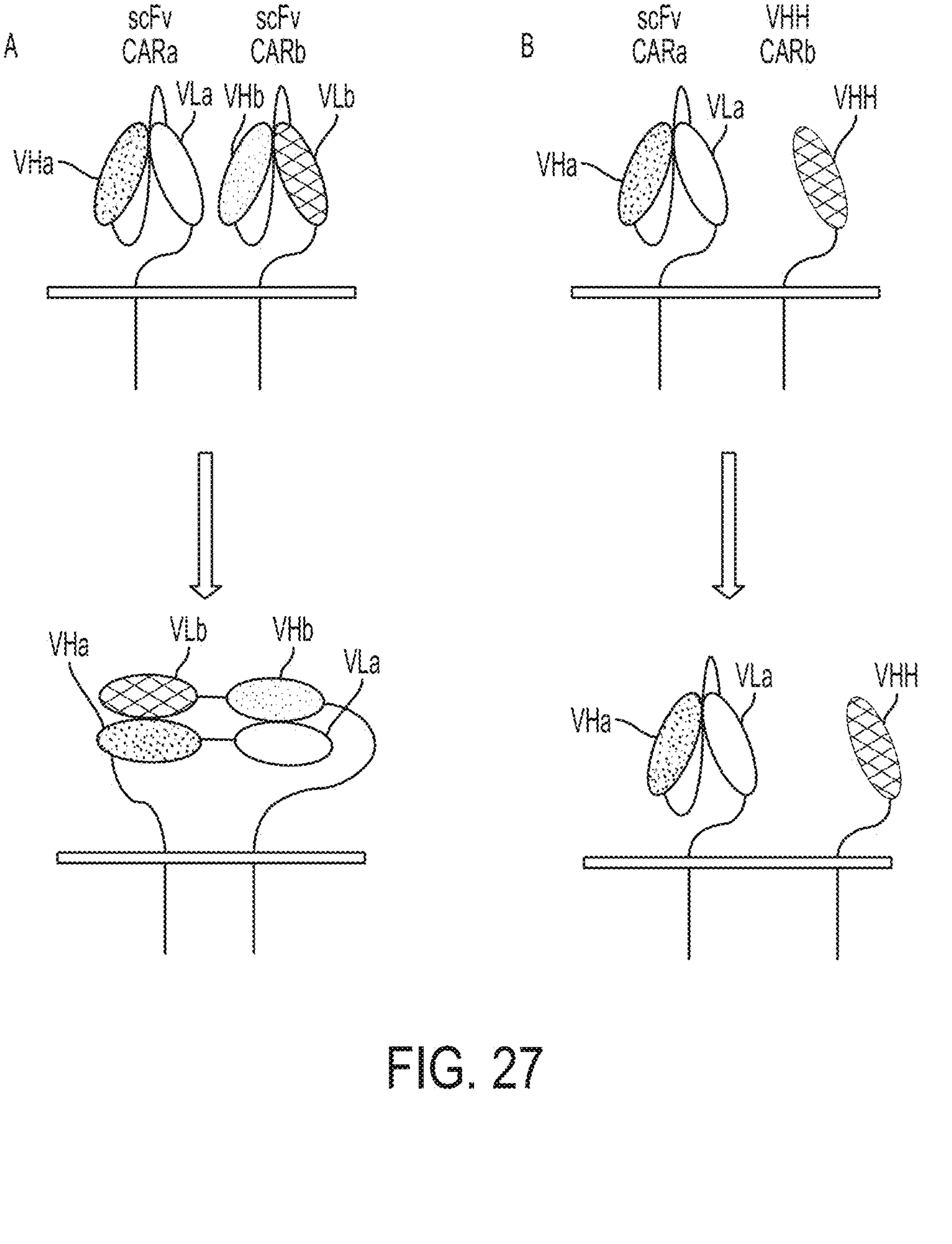
FIG. 27, comprising
Figure 28:
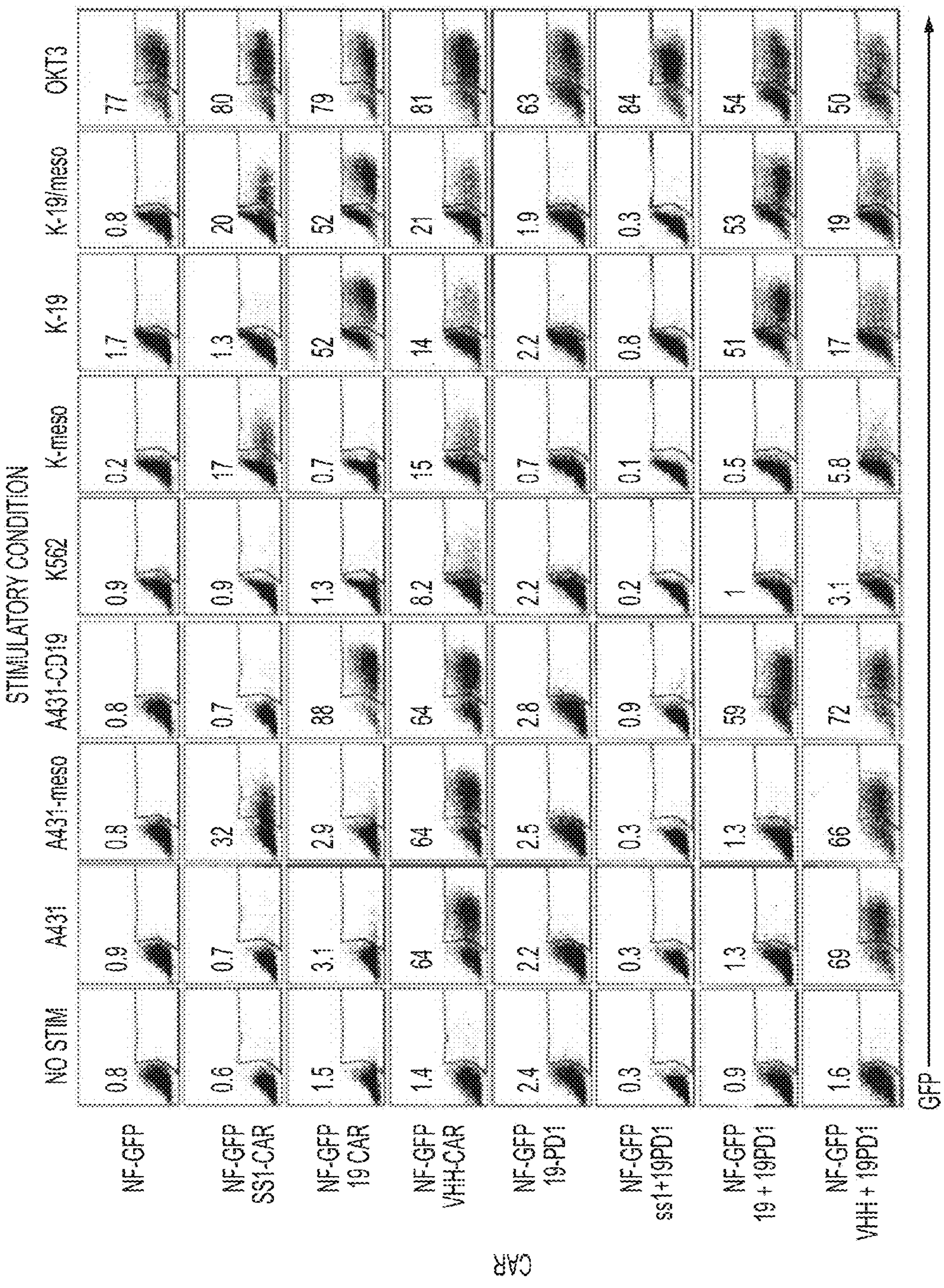
FIG. 28 demonstrates a camelid single VHH domain-based CAR can be expressed on a T cell surface in combination with a scFv-based CAR without appreciable receptor interaction. Jurkat T cells expressing GFP under an NFAT-dependent promoter (NF-GFP) were transduced with either a mesothelin-specific activating CAR (SS1-CAR), CD19-specific activating (19-CAR) or a CAR generated using a camelid VHH domain specific to EGFR (VHH-CAR). Following transduction with the activating CAR, the cells were then transduced with an additional inhibitory CAR recognizing CD19 (19-PD1) to generate cells co-expressing both the activating and inhibitory CAR (SS1+19PD1, 19+19PD1 or VHH+19PD1). The transduced Jurkat T cells were co-cultured for 24 hours with different cell lines that are either 1) devoid of all target antigens (K562), 2) express mesothelin (K-meso), CD19 (K-19) or EGFR (A431) only, 3) express a combination of EGFR and mesothelin (A431-mesothelin) or CD19 (A431-CD19) or 4) express a combination of CD19 and mesothelin (K-19/meso). Additional conditions that include either no stimulator cells (no stim) or K562 with 1 ug/mL of OKT3 (OKT3) were also included as negative and positive controls for NFAT activation, respectively. GFP expression, as a marker of NFAT activation, was assessed by flow cytometry.
Figure 29:
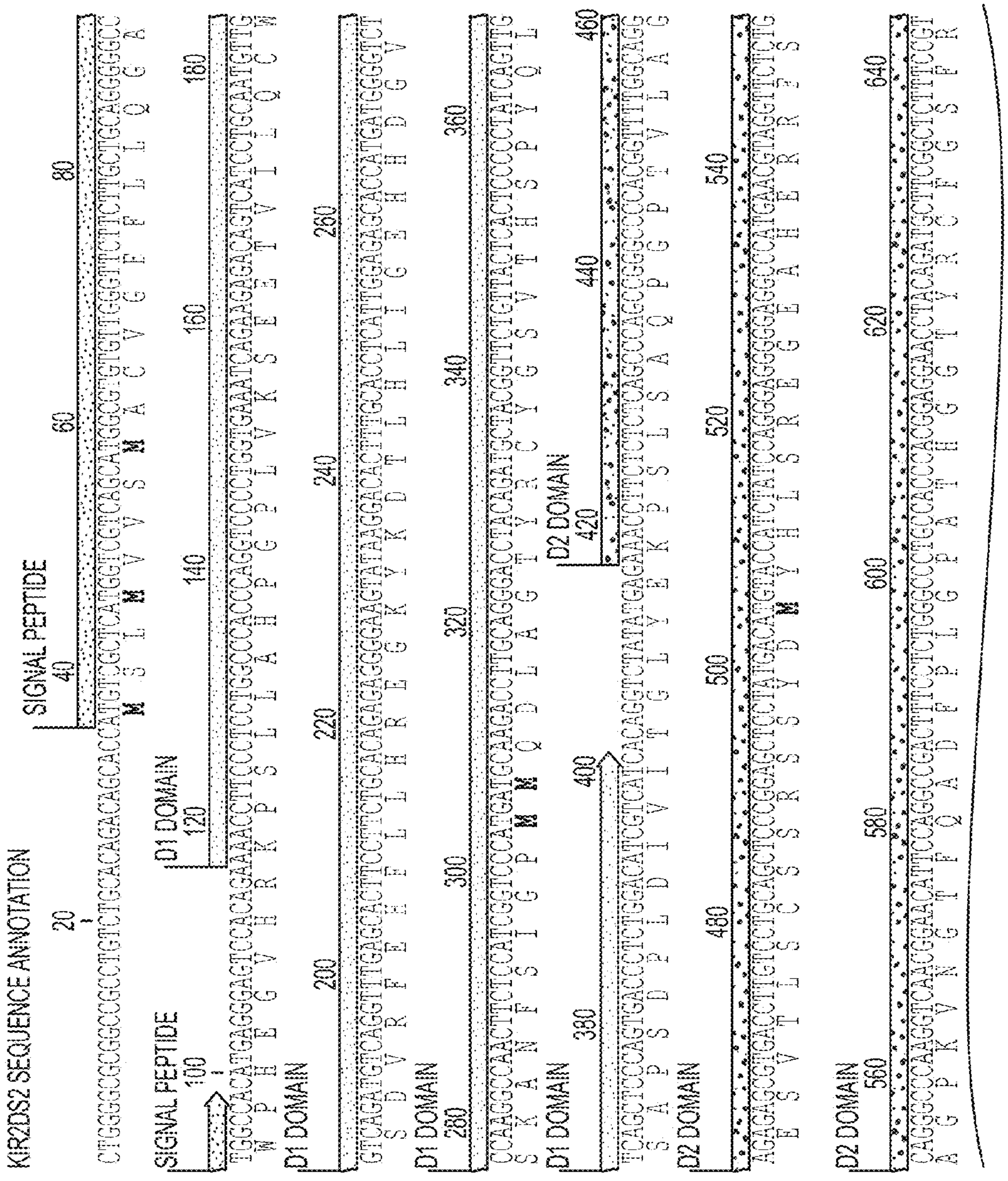
FIG. 29 shows a KIR2DS2 Sequence Annotation (SEQ ID NOS 52 and 53, respectively, in order of appearance).
Figure 29:
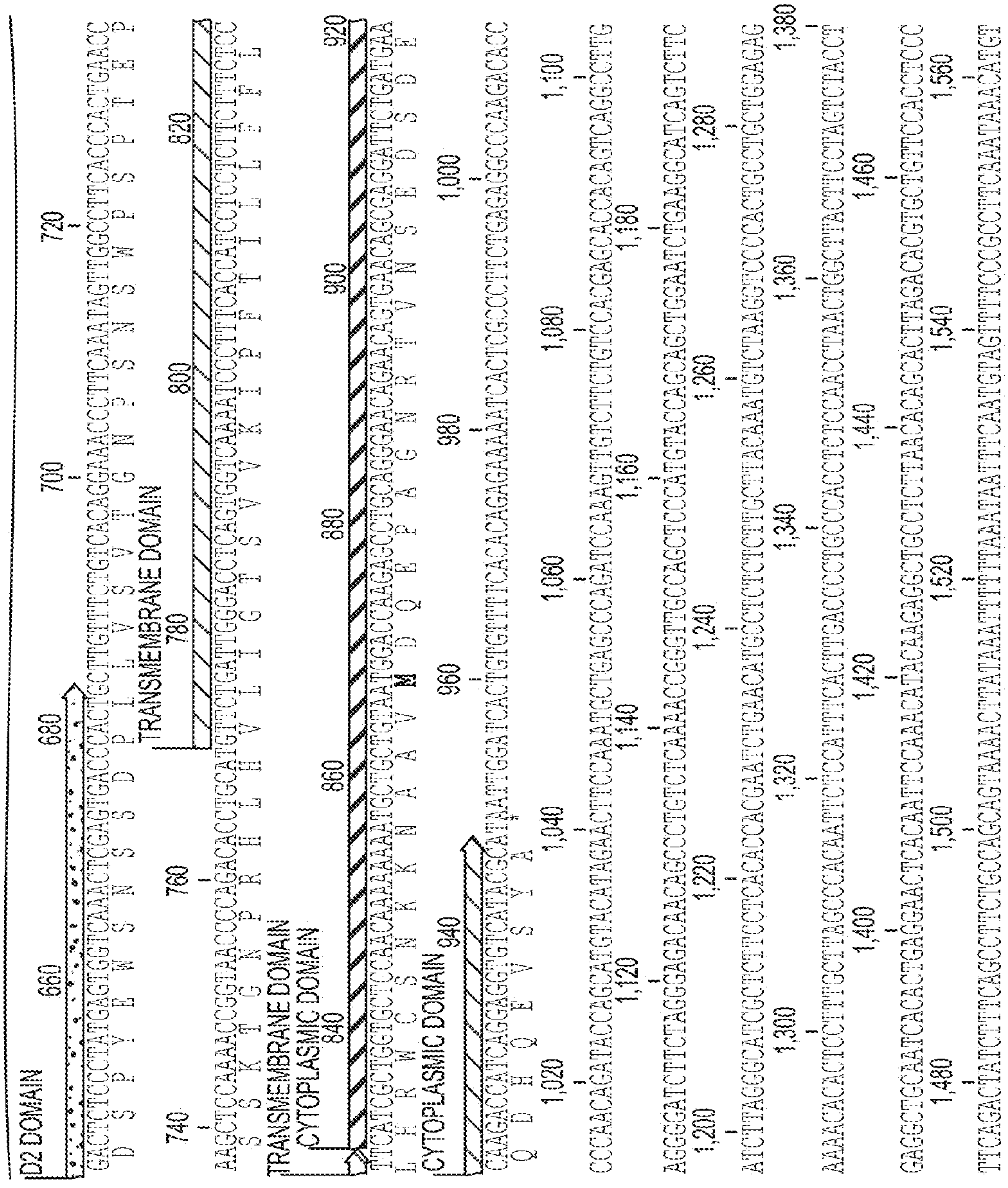
Figure 30:
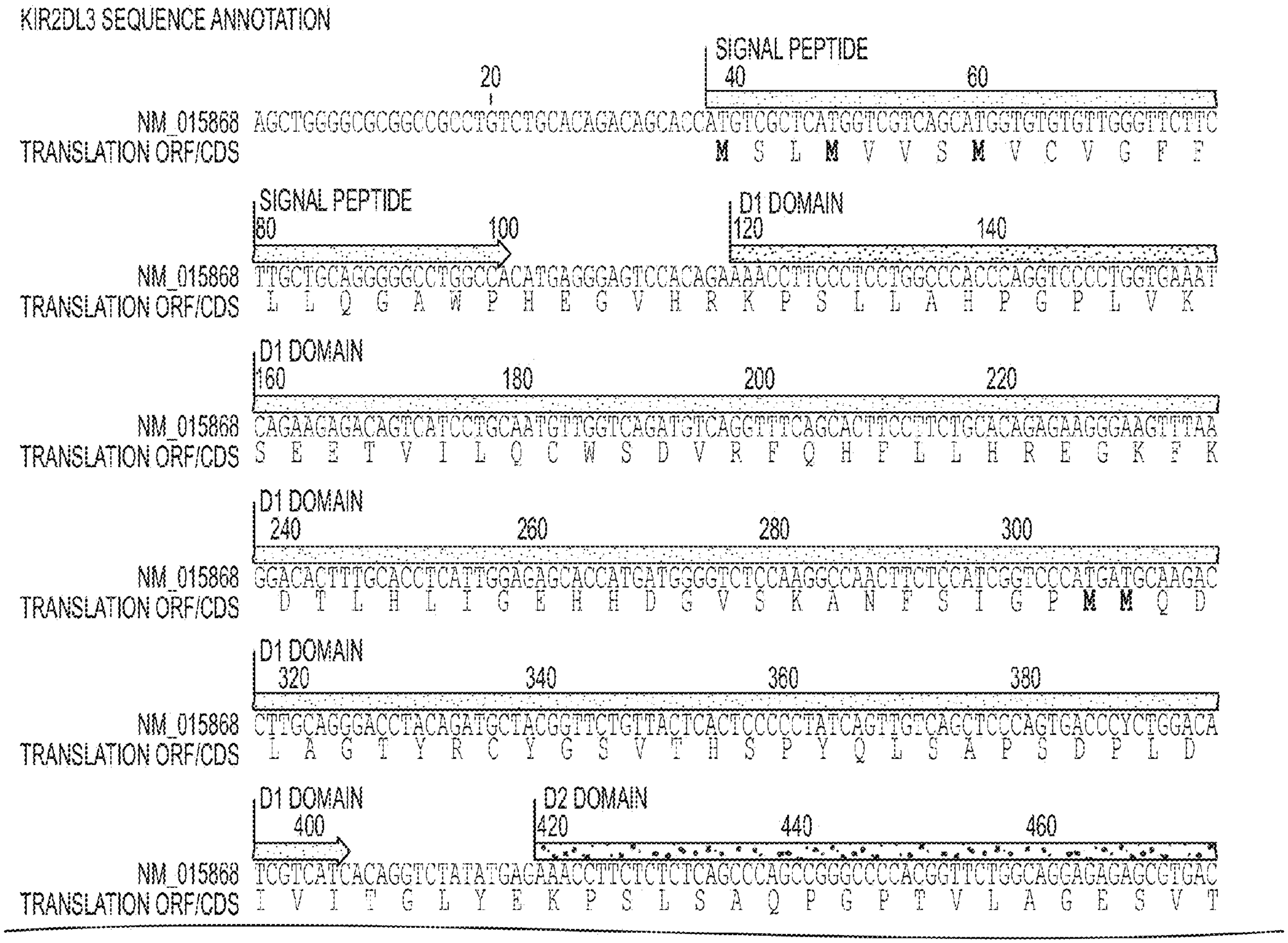
FIG. 30 shows a KIR2DL3 Sequence Annotation (SEQ ID NOS 54 and 55, respectively, in order of appearance).
Figure 30:
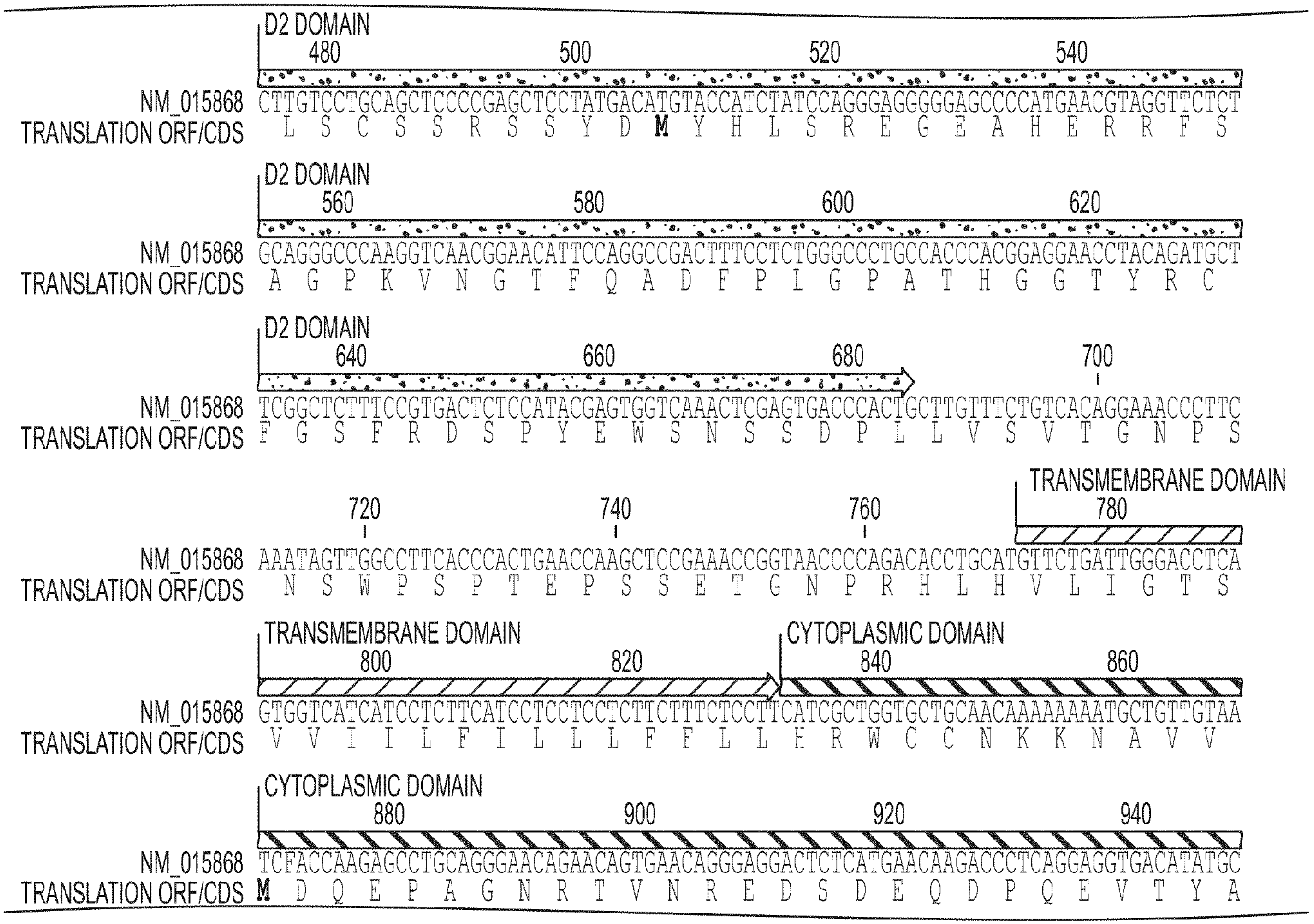
Figure 30:
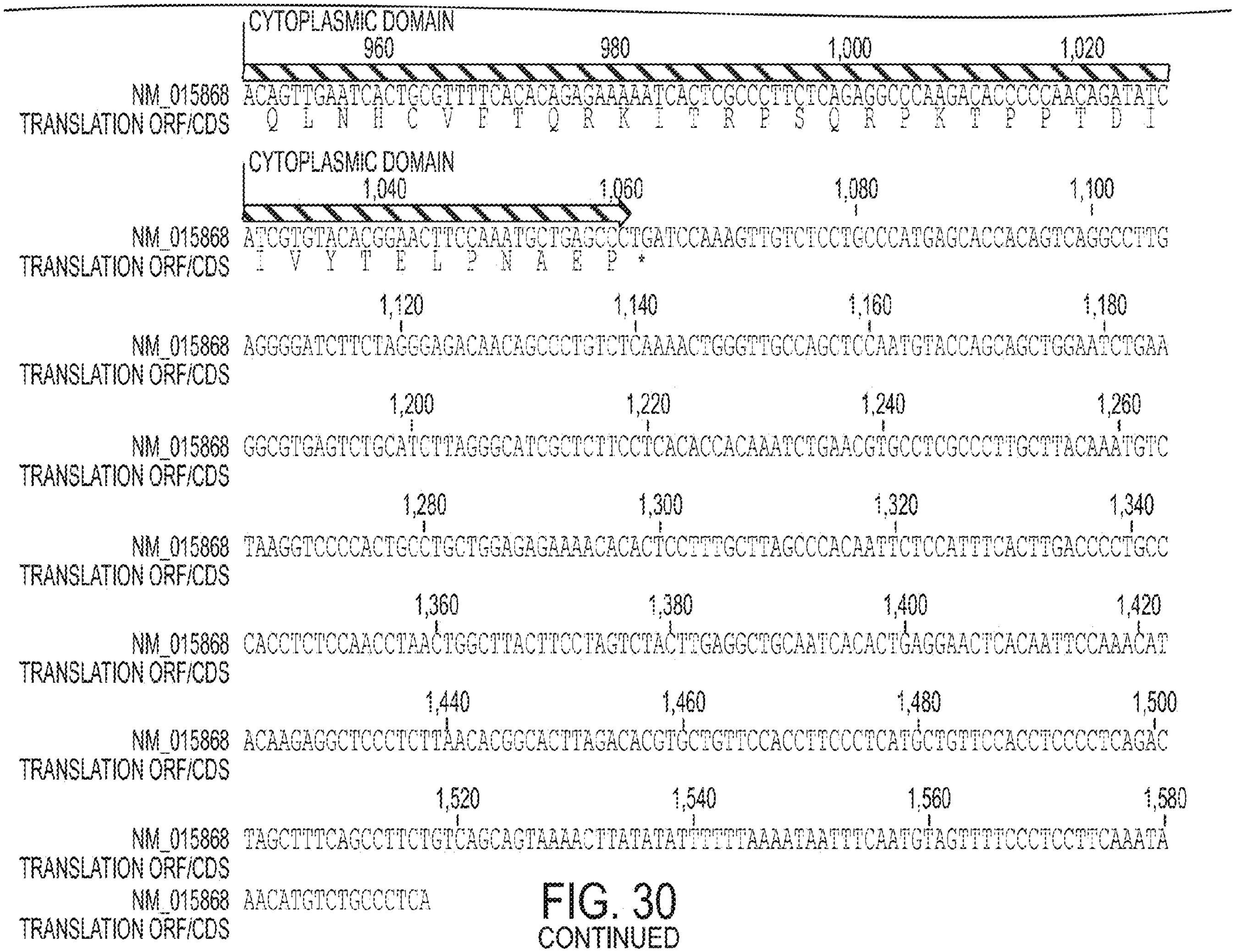
Figure 31:
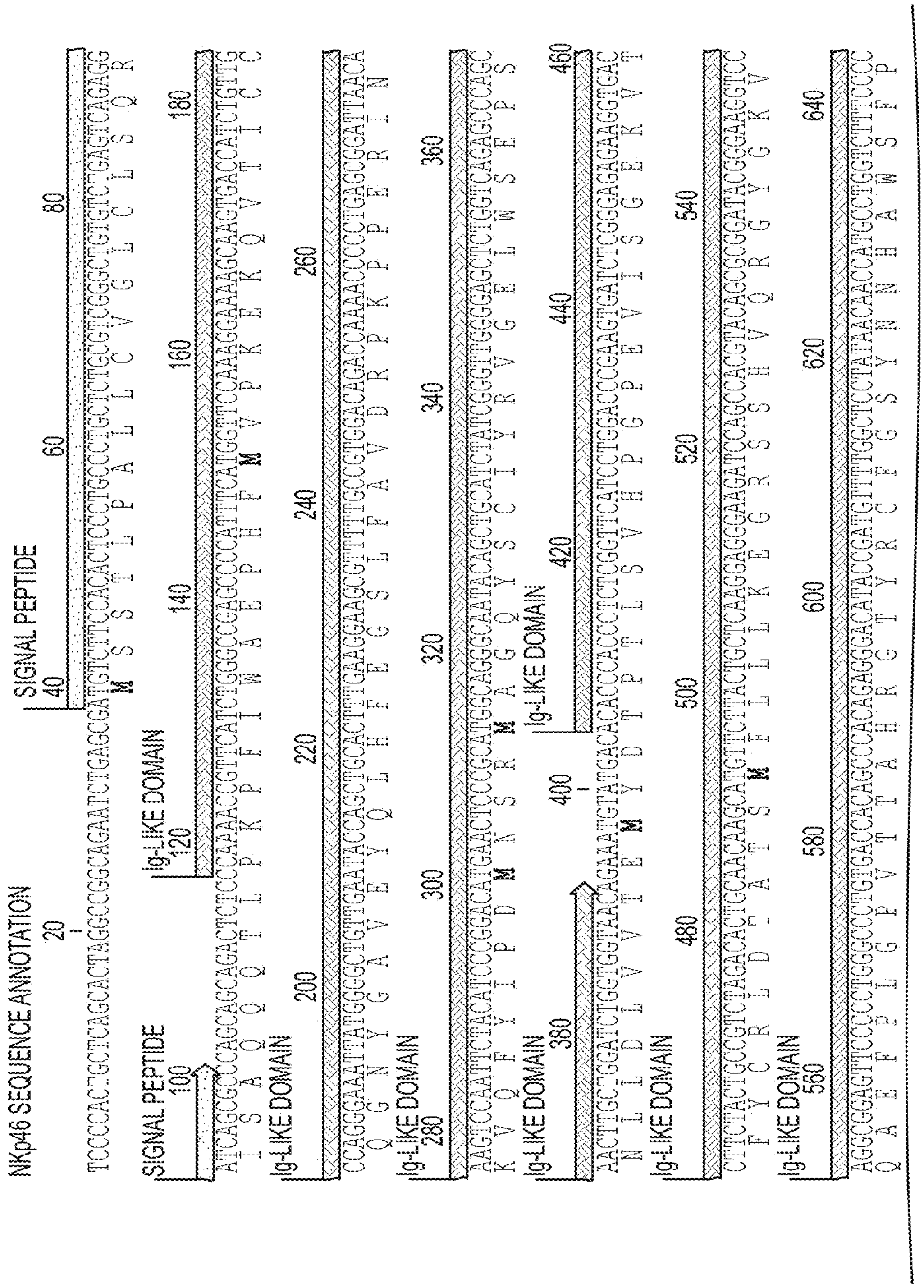
FIG. 31 shows a NKp46 Sequence Annotation (SEQ ID NOS 56 and 57, respectively, in order of appearance).
Figure 31:
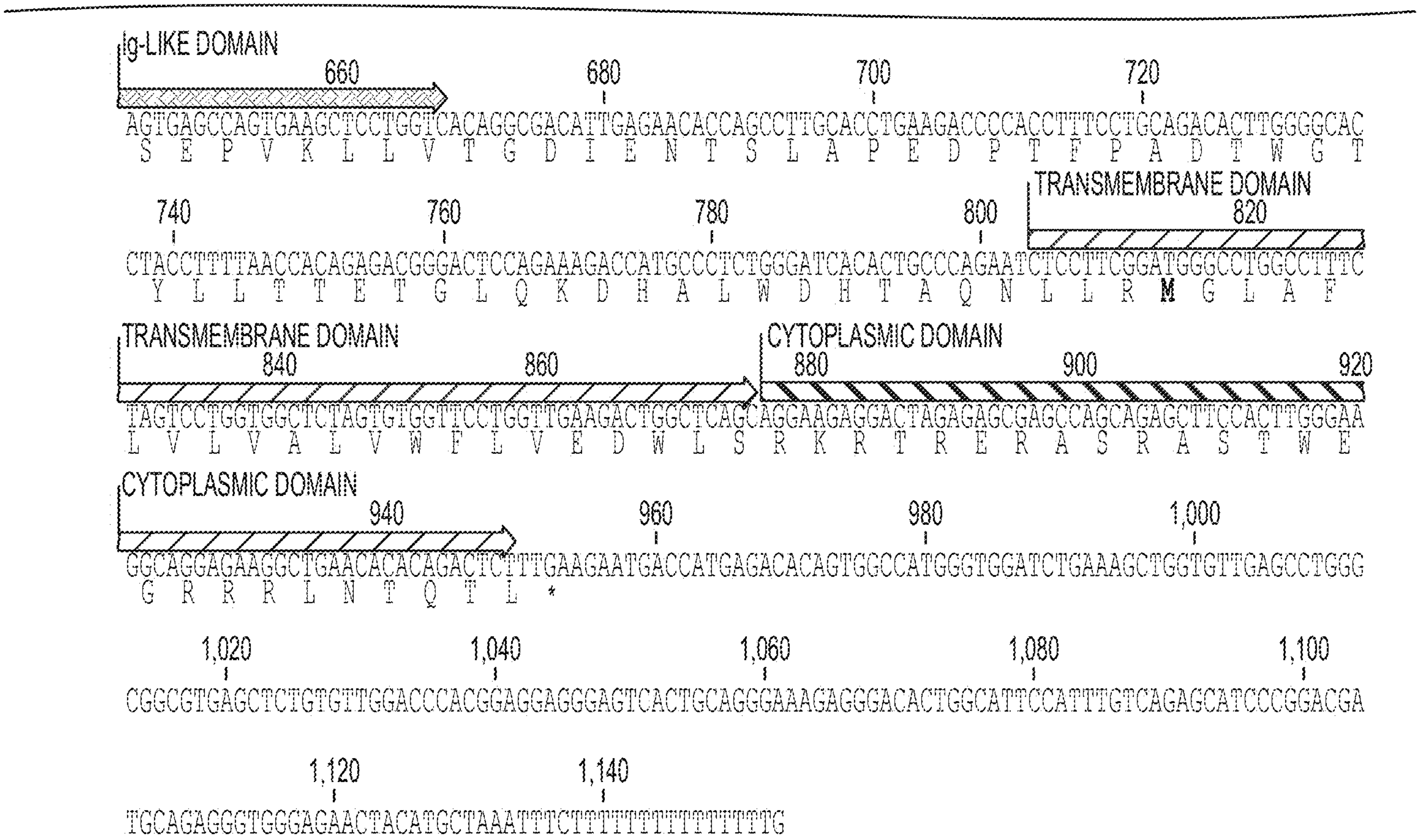
Figure 32:
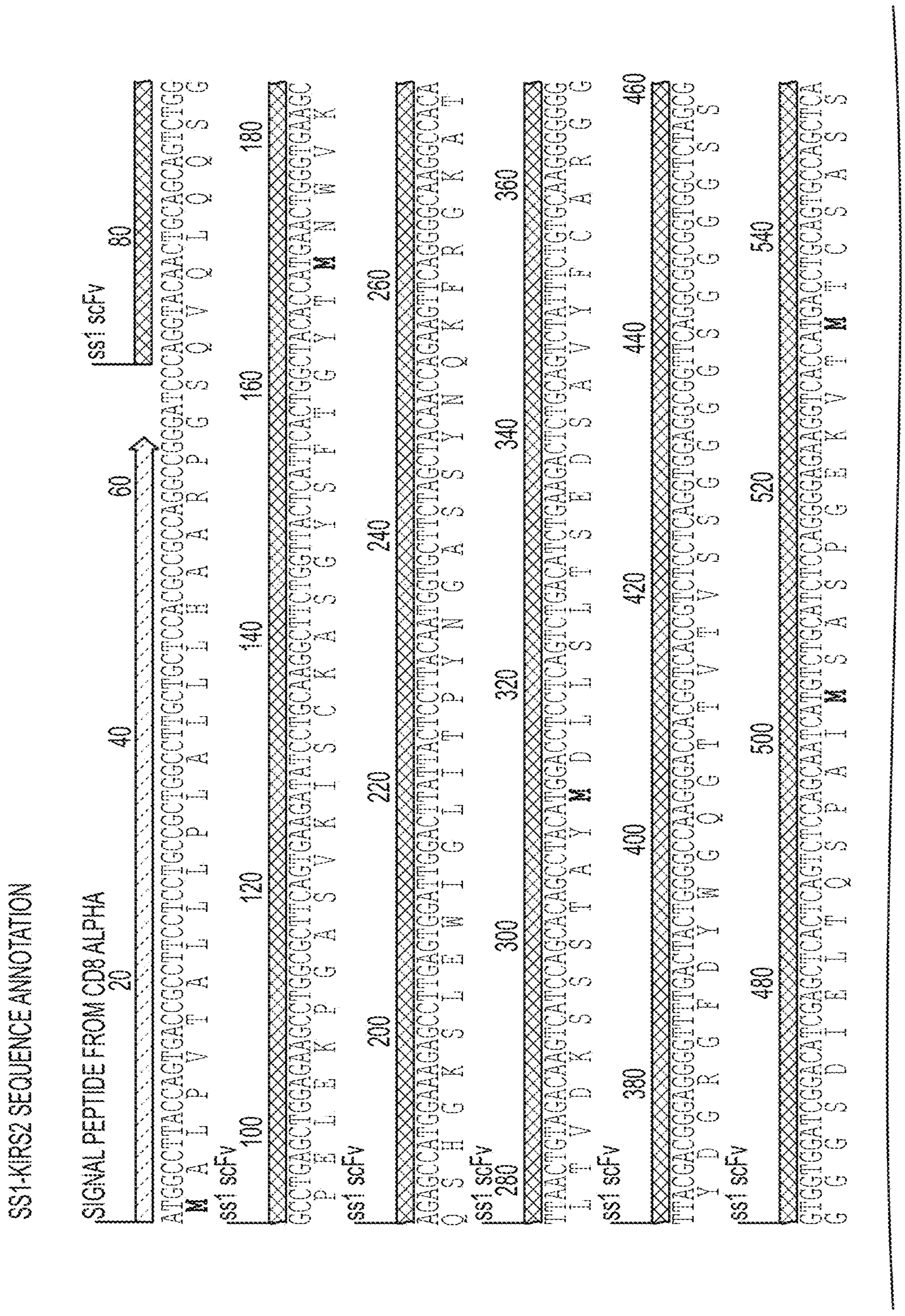
FIG. 32 shows a SS1-KIRS2 Sequence Annotation (SEQ ID NOS 58 and 59, respectively, in order of appearance).
Figure 32:
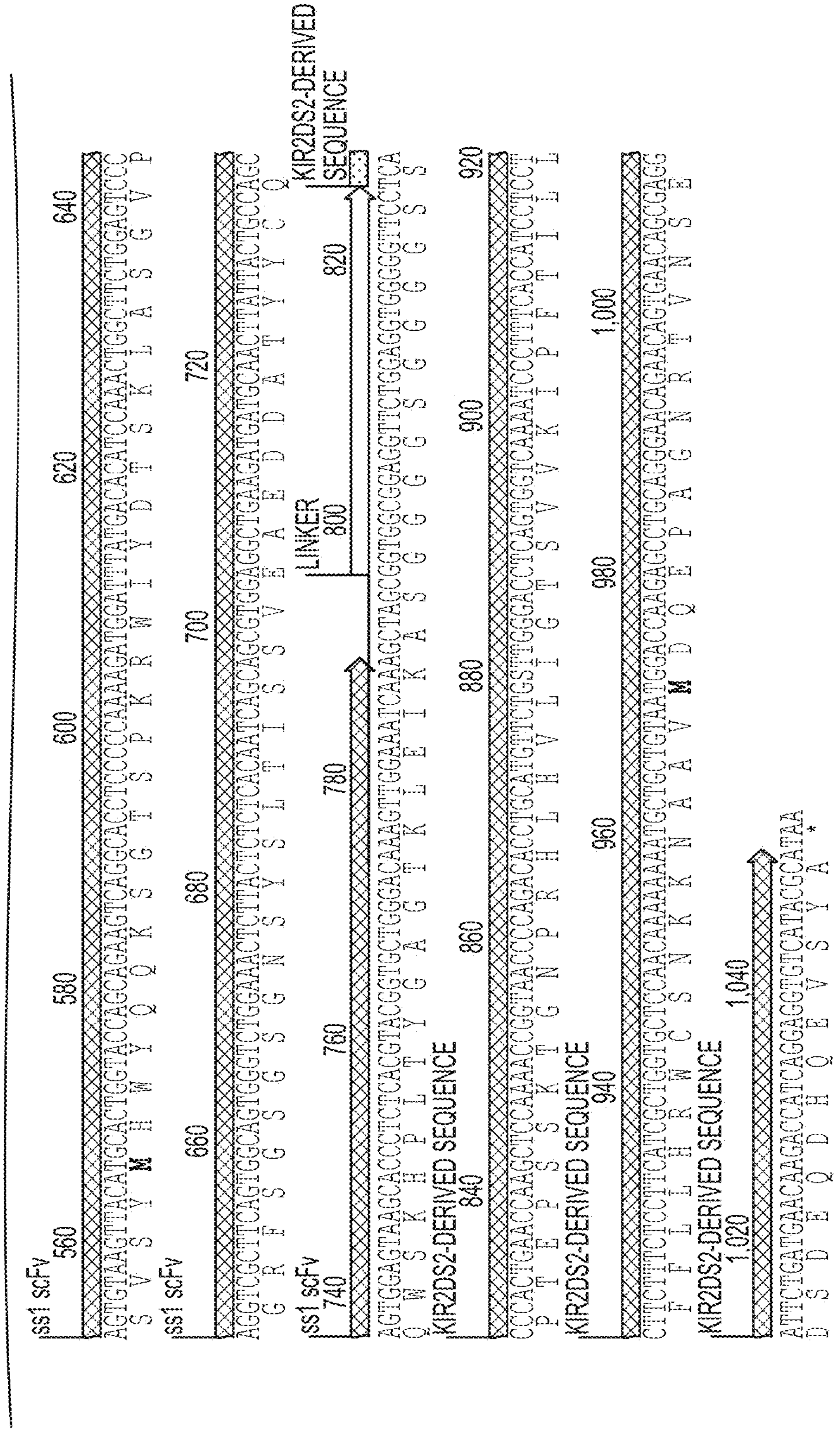
Figure 33:
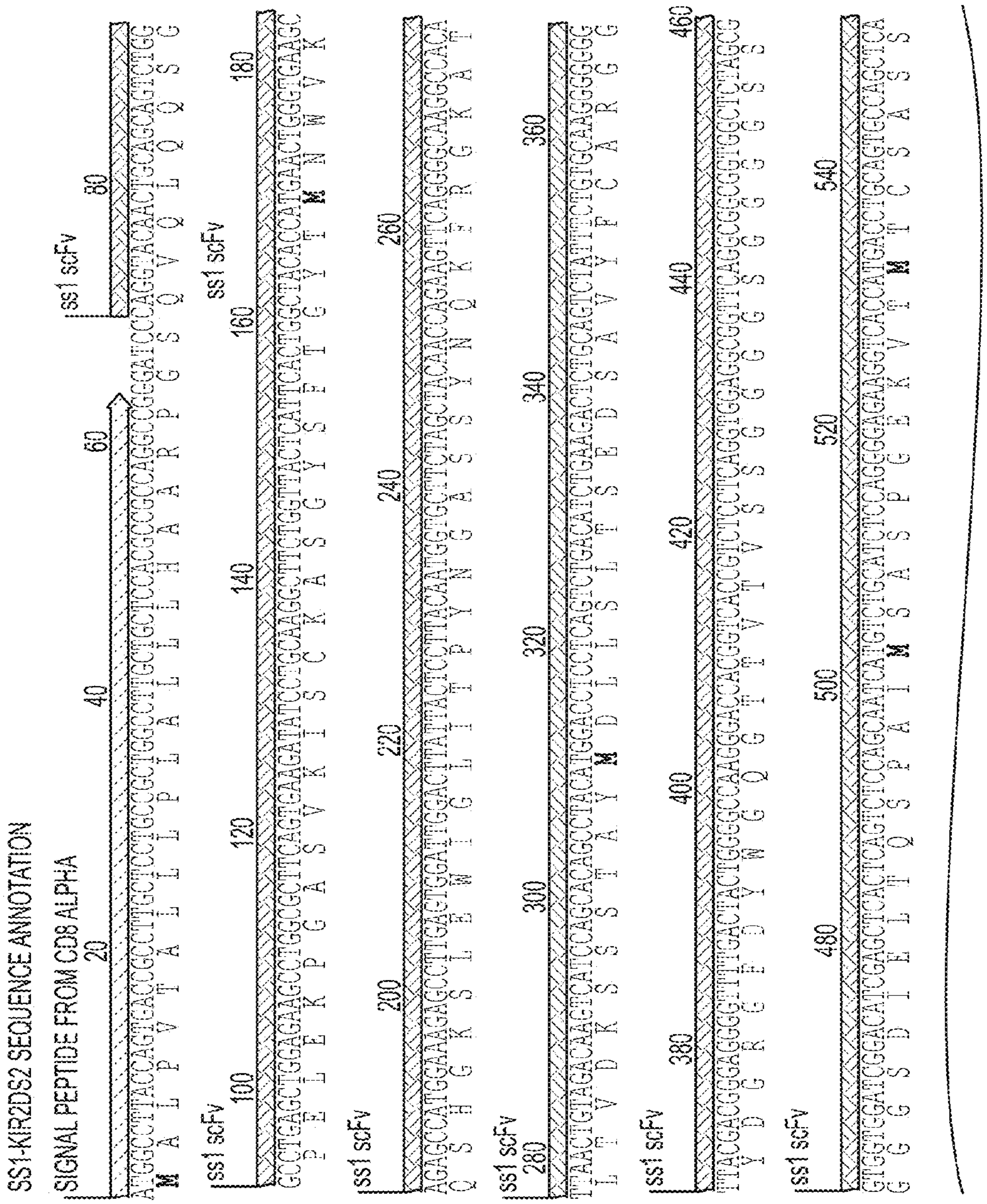
FIG. 33 shows a SS1-KIR2DS2 Sequence Annotation (SEQ ID NOS 60 and 61, respectively, in order of appearance).
Figure 33:
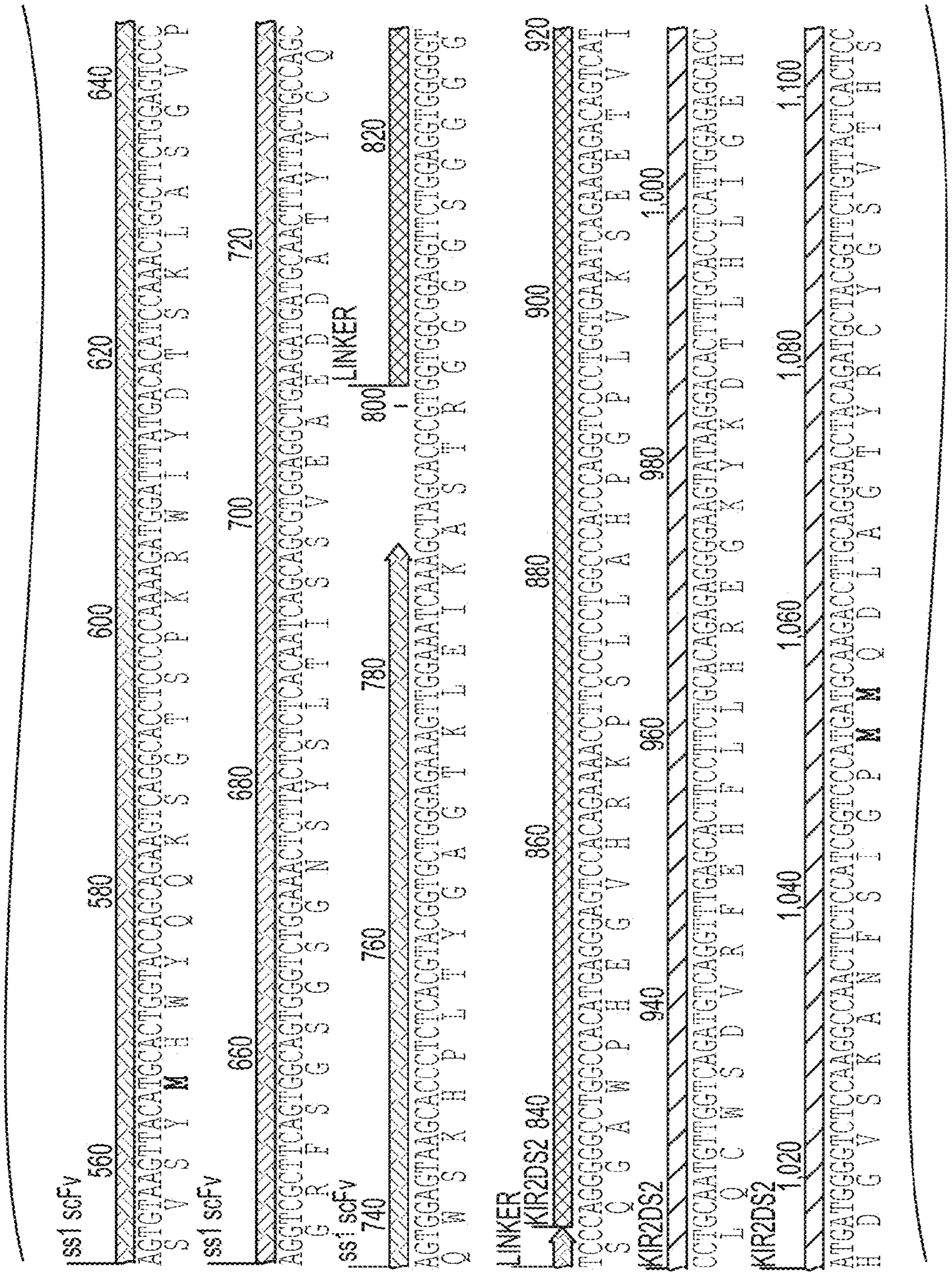
Figure 33:
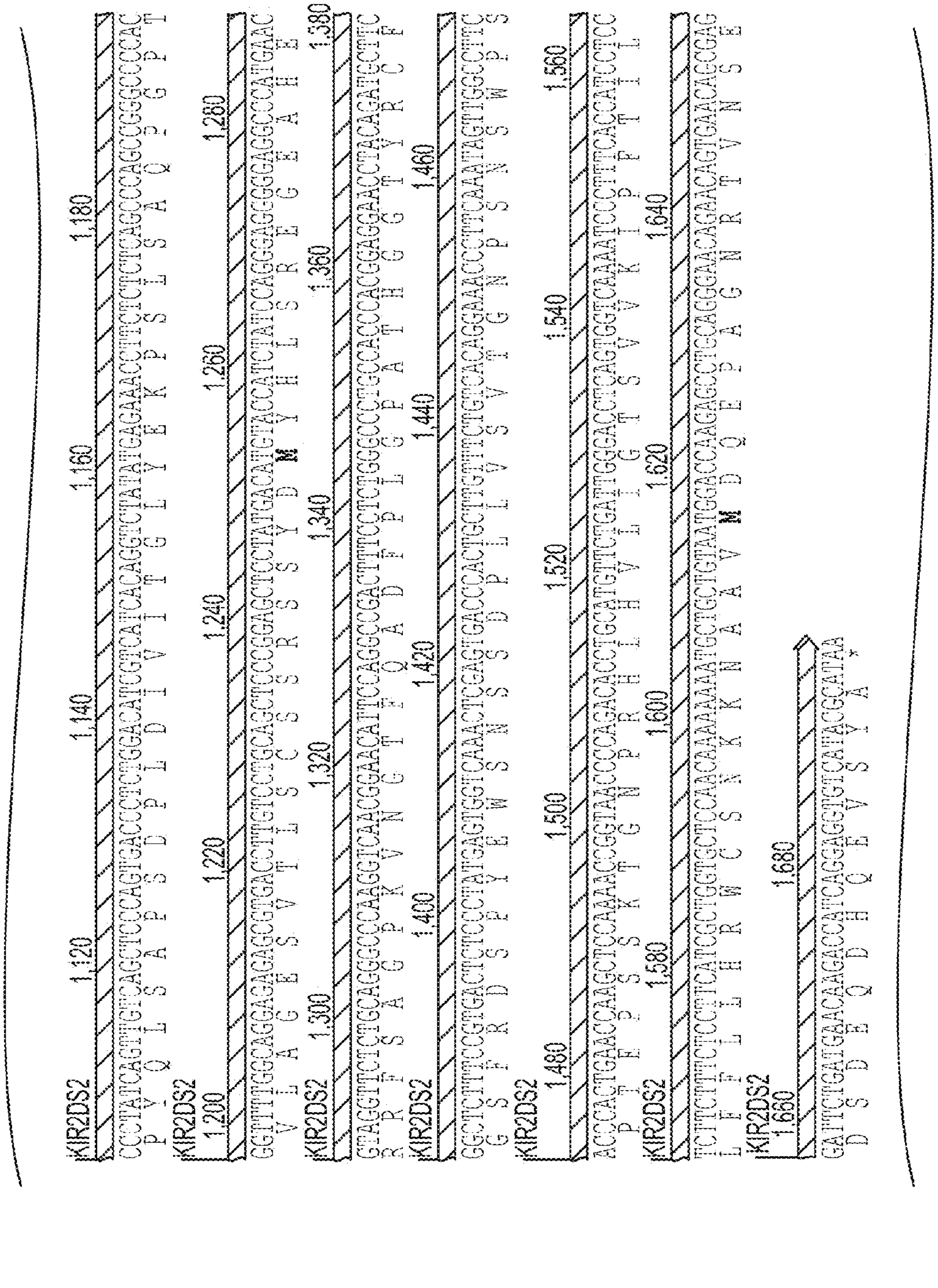
Figure 34:
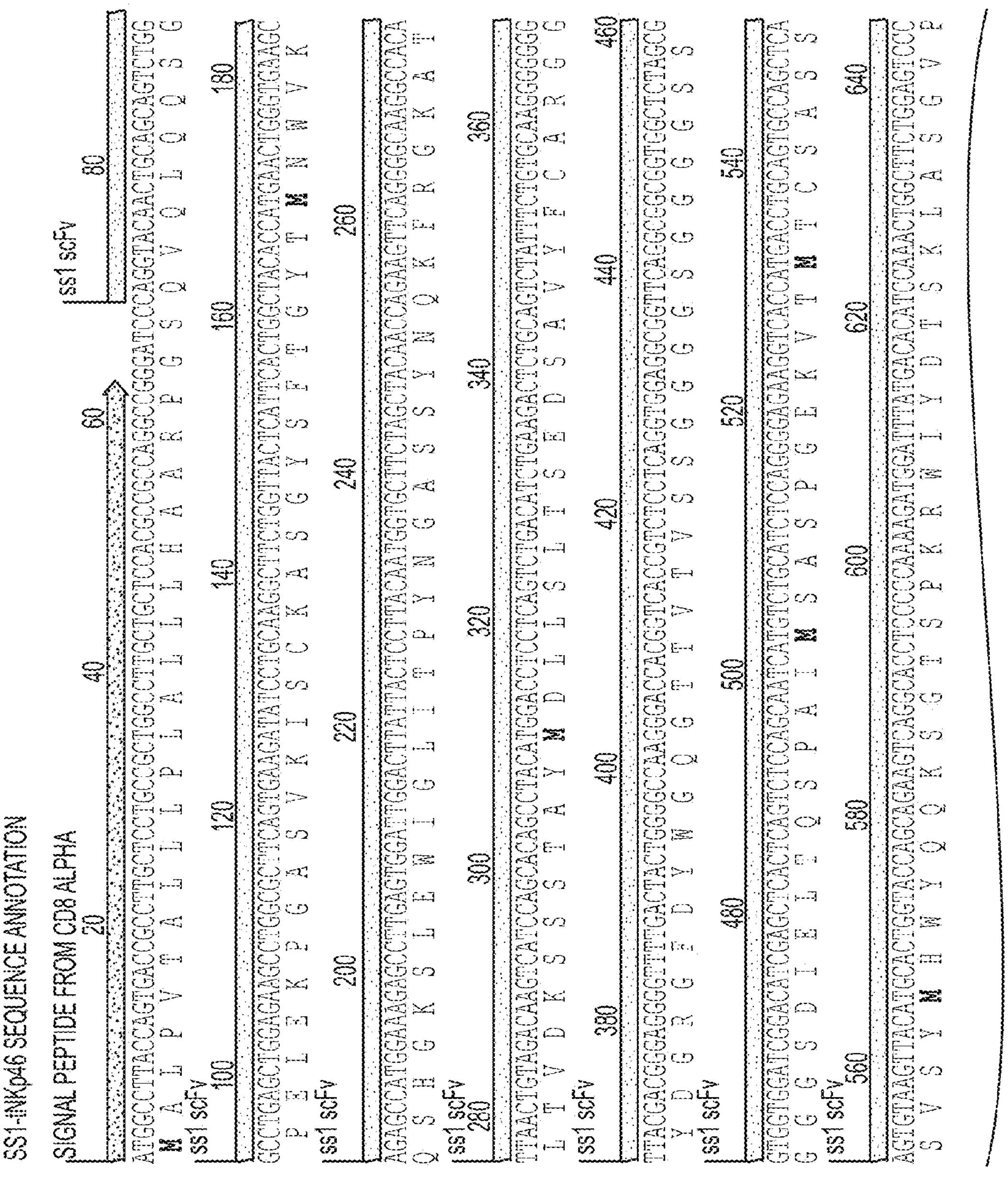
FIG. 34 shows a SS1-tNKp46 Sequence Annotation (SEQ ID NOS 62 and 63, respectively, in order of appearance).
Figure 34:
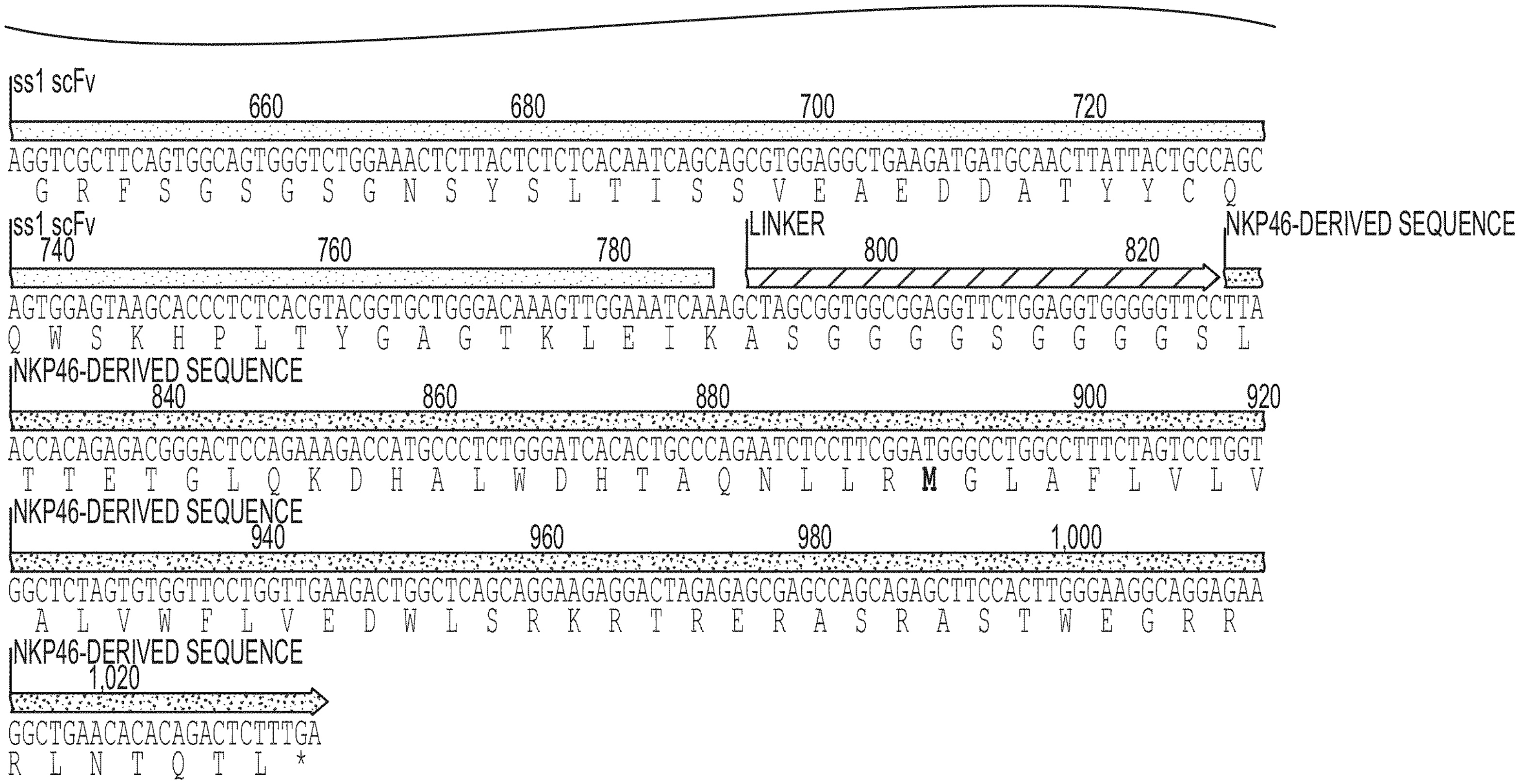
Figure 35:
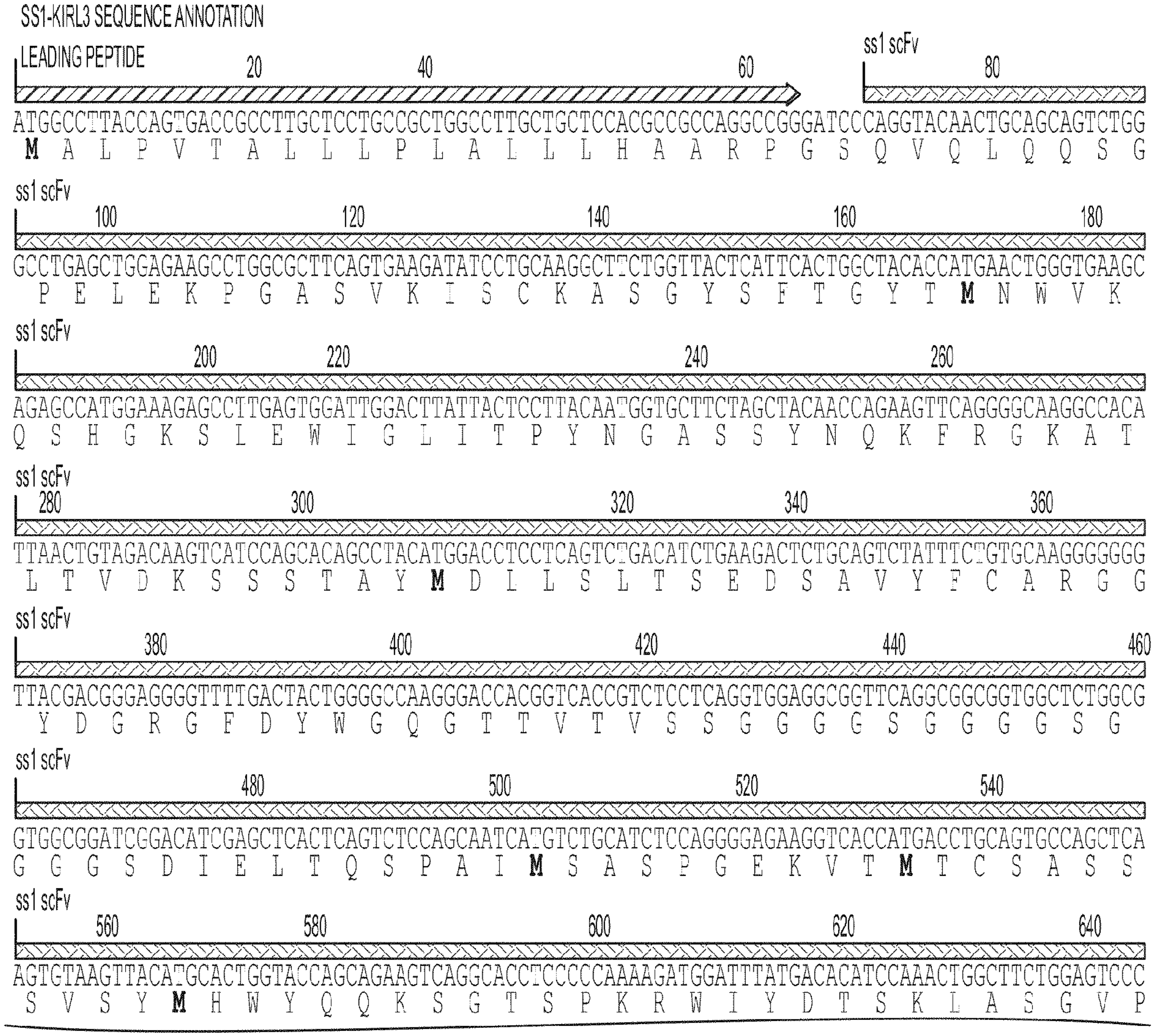
FIG. 35 shows a SS1-KIRL3 Sequence Annotation (SEQ ID NOS 64 and 65, respectively, in order of appearance).
Figure 35:
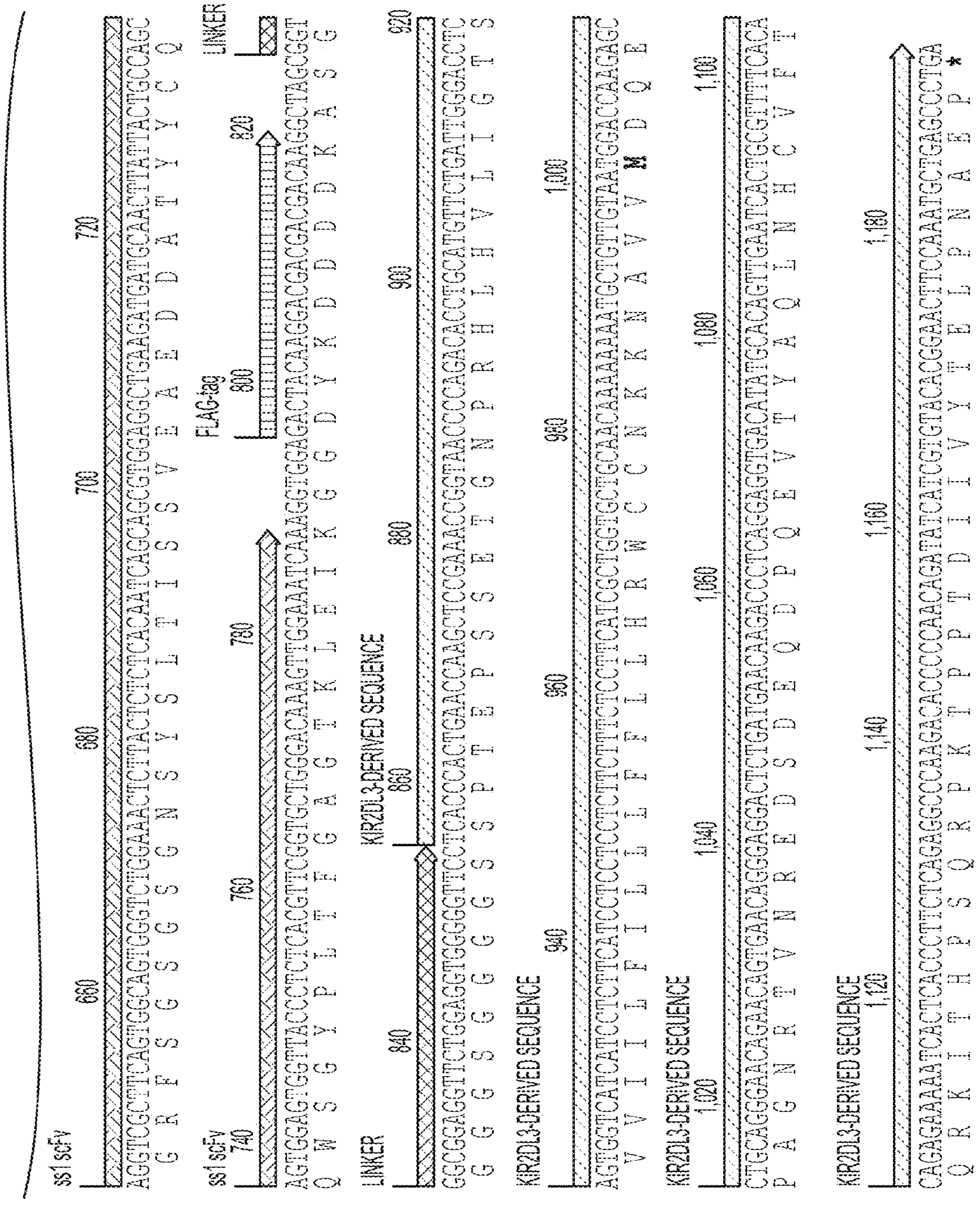

Result:

Camels and related species (e.g. Llama) naturally produce antibodies that have a single heavy-chain like variable domain. This domain, known as a camelid VHH domain, has evolved to exist without pairing to a light chain variable domain. FIG. 27A shows schematically the possibility that two heterologous scFv molecules can dissociate and re-associate with one another when displayed on the surface of a cell as demonstrated by the observed disruption in scFv binding to cognate ligand during receptor co-expression (FIG. 25 and FIG. 26). FIG. 27B shows a schematic representation of the expected reduced interaction between a scFv CAR displayed on the surface of a cell in combination with a VHH domain-based CAR. FIG. 28 demonstrates that coexpression of two scFv-based CARs (SS1-z activating CAR and CD19-PD1 inhibitory CAR) on the surface of a Jurkat leads to the inability of the activating CAR (SS1-z) to recognize its cognate ligand on the target cell and trigger T cell activation despite the absence of the inhibitory receptor's ligand. This is consistent with the observed reduced ligand binding on the surface (FIG. 25). In contrast, the coexpression of the same inhibitory CAR (CD19-PD1) with a camelid VHH-based activating CAR (VHH-z) has no impact on the ability of the VHH-based activating CAR to recognize its cognate EGFR ligand. These data support the model depicted in FIG. 27B that a VHH-based activating CAR can be expressed with an scFv-based CAR without significant interaction between the receptors due to the reduced ability of the scFv and VHH domains to interact.

Figure 18:
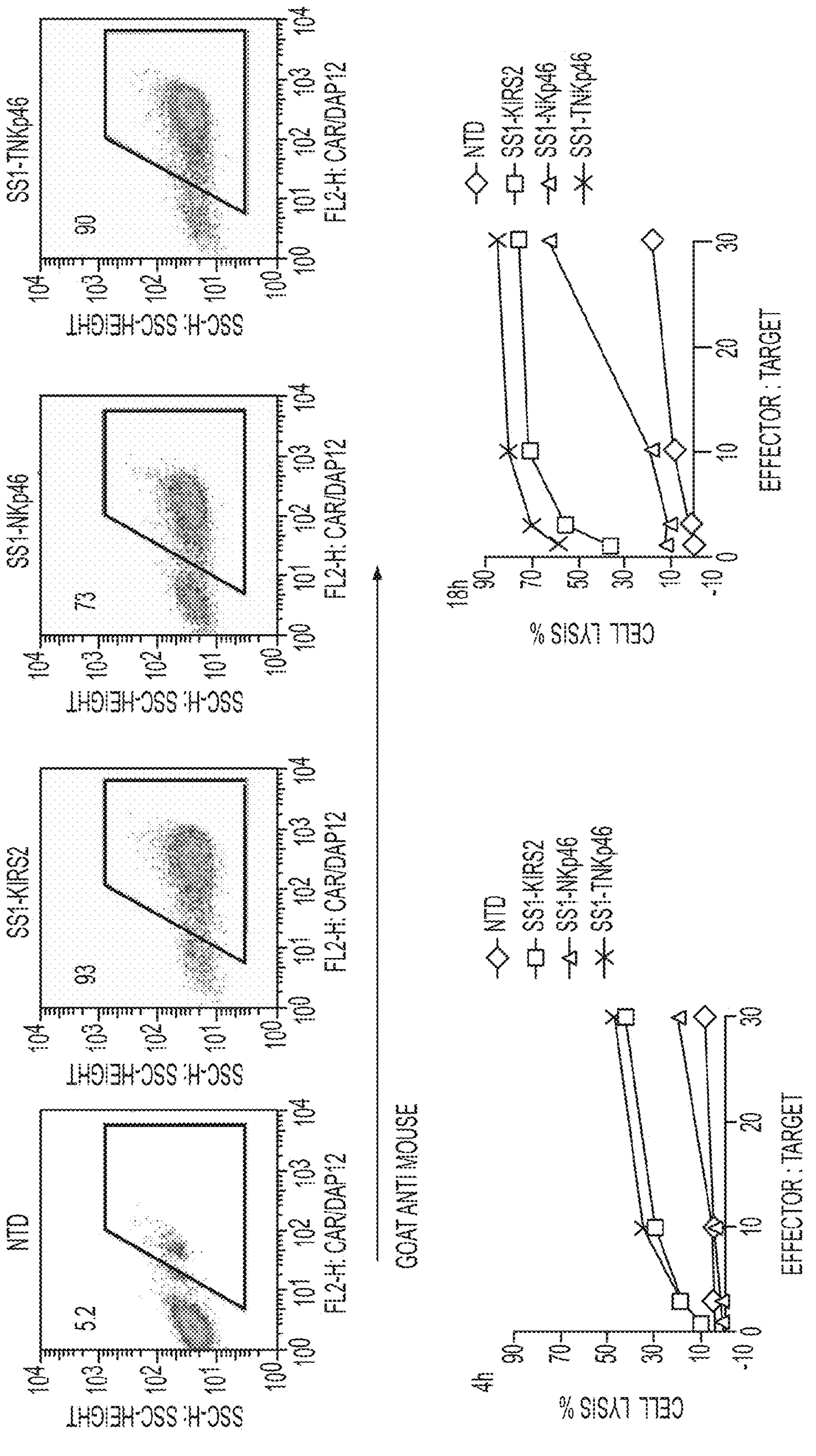
FIG. 18 demonstrates an NKp46-based NCR CAR with mesothelin specificity triggers antigen specific cytotoxicity. Following anti-CD3/anti-CD28 bead activation, T cells were transduced with a bi-cistronic lentiviral vector expressing either DAP12 and SS1-KIRS2 (control), or FcεRγ and a mesothelin specific NKp46-based CAR (SS1-NKp46) or FcεRγ and a mesothelin-specific NKp46 CAR in which the natural NKp46 extracellular domain was truncated (SS1-TNKp46). The expression of the mesothelin-specific CARs was assessed by flow cytometry using a biotinylated goat-anti-mouse F(ab)2 polyclonal antibody followed by SA-PE as shown in FIG. 18A. The T cells were mixed with $^{51}$Cr-labeled K562 target cells expressing mesothelin at varying ratios of effector T cells to target K562 cells (E:T ratio). Cytotoxicity was determined by measuring the fraction of $^{51}$Cr released into the supernatant at 4 hours compared with spontaneous release as shown in FIG. 18B.

Example 10: An NKp46-Based NCR CAR with Mesothelin Specificity Triggers Antigen Specific Cytotoxicity Material and Method:

Following anti-CD3/anti-CD28 bead activation, T cells were transduced with a bi-cistronic lentiviral vector expressing either DAP12 and SS1-KIRS2 (control), or FcϵRγ and a mesothelin specific NKp46-based CAR (SS1-NKp46) or FcϵRγ and a mesothelin-specific NKp46 CAR in which the natural NKp46 extracellular domain was truncated (SS1-TNKp46). The expression of the mesothelian-specific CARs was assessed by flow cytometry using a biotinylated goat-anti-mouse F(ab)2 polyclonal antibody followed by SA-PE (FIG. 18). The T cells were mixed with $^{51}$Cr-labeled K562 target cells expressing mesothelin at varying ratios of effector T cells to target K562 cells (E:T ratio). Cytotoxicity was determined by measuring the fraction of $^{51}$Cr released into the supernatant at 4 hours compared with spontaneous release.

Result:

Both the SS1-NKp46 and SS1-sNKp46 receptors exhibit surface expression on T cells. SS1-TNKp46 transduced T cells show robust target cell cytolysis that is comparable to the KIR-based SS1-KIRS2 CAR. SS1-NKp46 exhibited weaker cytotoxic activity that was evident only at high effector to target cell ratios (FIG. 18). These data demonstrate that an antigen-specific chimeric immunoreceptor for use in redirecting T cell cytolytic activity can be generated from natural cytotoxicity receptors (NCRs) using a design similar to that used to create a KIR-based CAR.

Example 11: Interaction of scFv Domains

Figure 23:
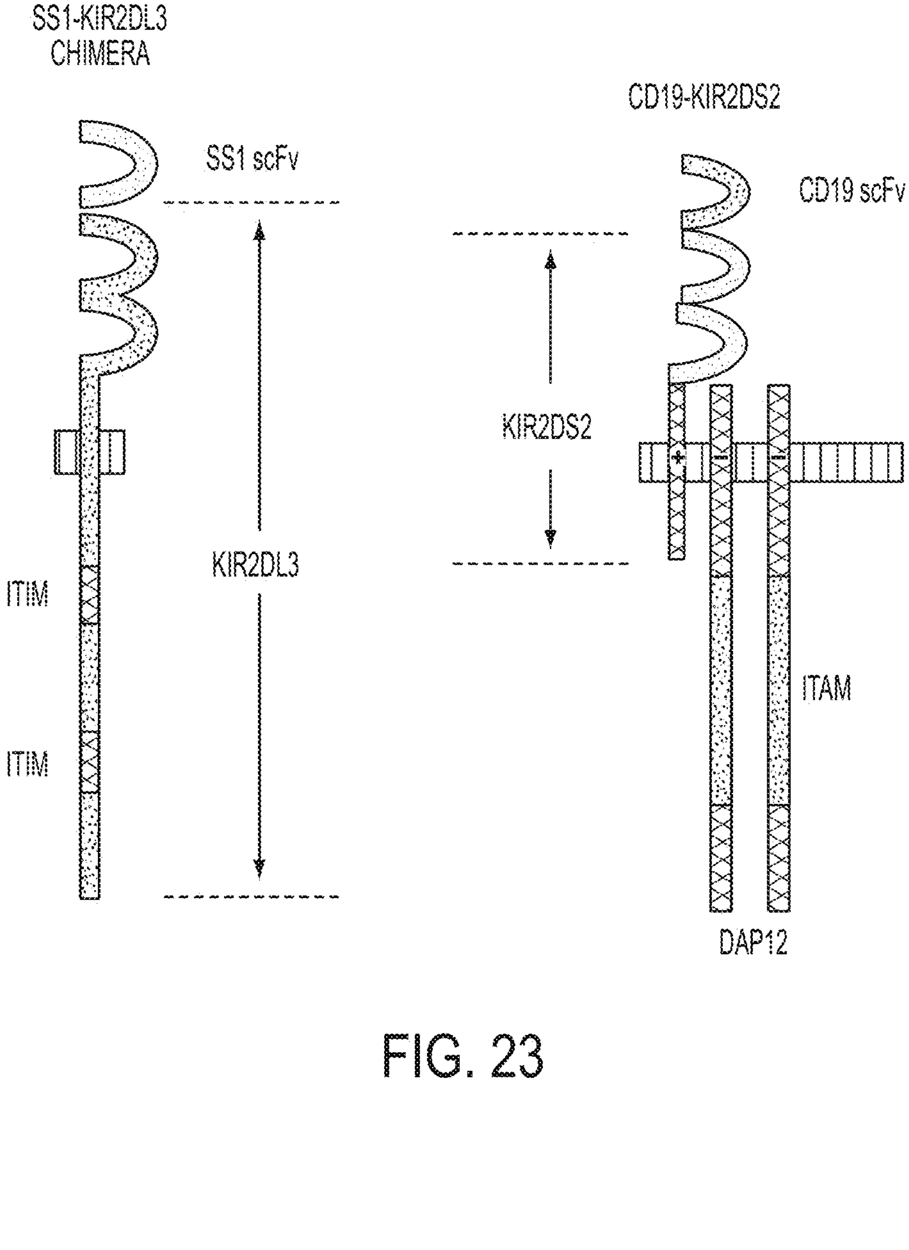
FIG. 23 shows a schematic representation of the receptors used in Experiments shown in FIG. 24.
Figure 24:
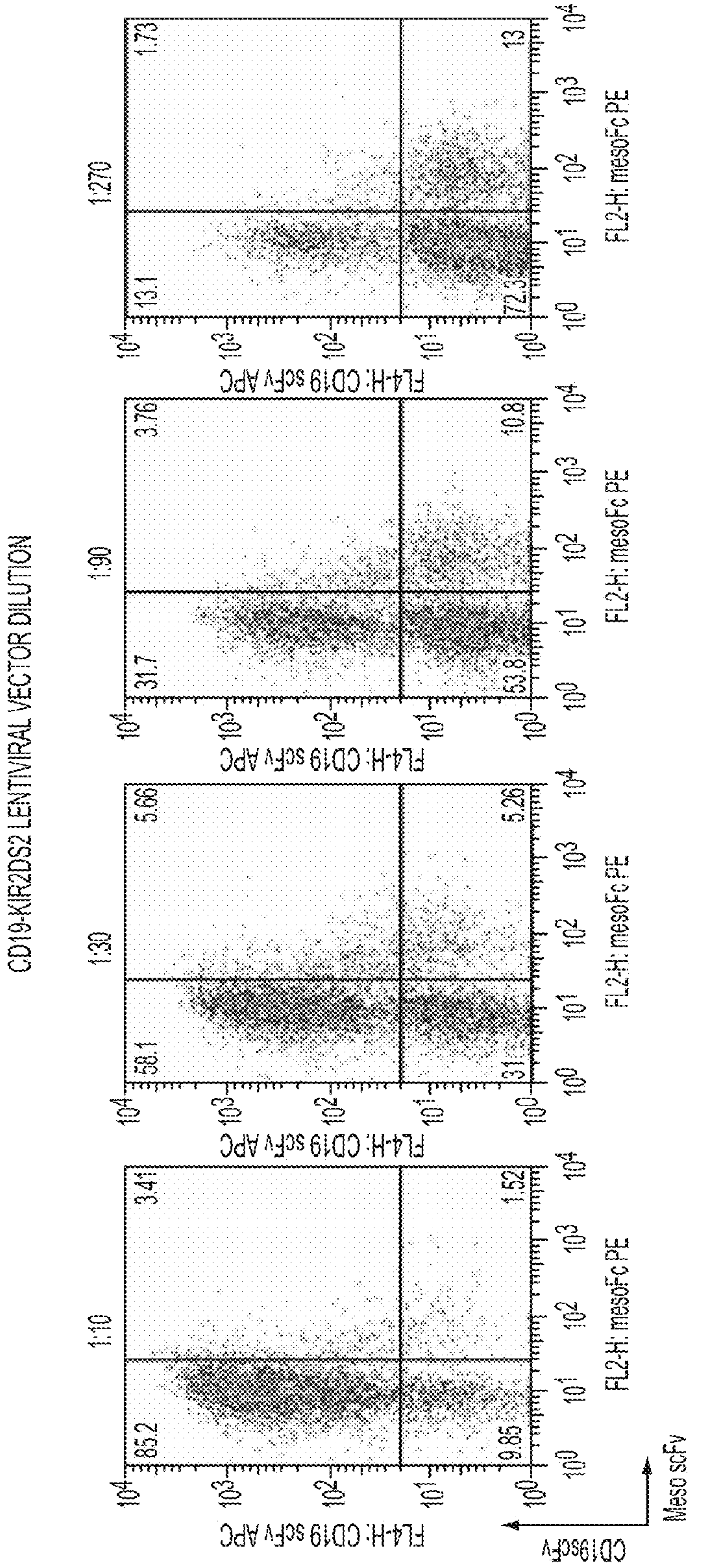
FIG. 24 demonstrates the inability to co-express two scFv-based chimeric receptors on the surface of the T cell while retaining each receptors' respective binding specificity. Jurkat T cells were transduced using a lentiviral vector encoding SS1-KIR2DL3. These cells were subsequently transduced with a second lentiviral vector encoding CD19-KIR2DS2 at varying dilutions of the vector. The expression of the SS1-specific scFv was assessed using mesothelin-Fc followed by PE-conjugated goat-anti-human Fc. The CD19-specific scFv expression was assessed using a PE-conjugated monoclonal antibody specific to the FMC63 idiotype.

Material and Method:

In FIG. 24, Jurkat T cells were transduced with lentiviral vector encoding a mesothelin-specific inhibitory KIR-based CAR (SS1-KIR2DL3). These transduced cells were then transduced with varying dilutions of a lentiviral vector encoding a CD19-specific activating KIR-based CAR (CD19-KIR2DS2). These KIR-CARs are shown schematically in FIG. 23. Following transduction with both CARs, the frequency of cells with surface expression of a CAR with an intact scFv capable of binding their target ligand was assessed by flow cytometry following staining with both a mesothelin-Fc fusion protein followed by a secondary anti-Fc antibody labeled with PE and an anti-CD19-specific (clone FMC63) anti-idiotype monoclonal antibody labeled with APC. In FIG. 25, anti-CD3/28-activated primary human T cells were transduced with different lentiviral vectors encoding either a mesothelin-specific CD3z-based CAR bearing an mCherry fusion to the C-terminus (SS1z-mCh), a CD19-specific CAR with CD3z and 4-1BB cytoplasmic domain (19bbz) or a combination of both SS1z-mCh and 19bbz. The expression of mCherry and a functional SS1 scFv was assessed by flow cytometry following staining with a mesothelin-Fc fusion protein followed by a secondary anti-Fc antibody labeled with FITC. In FIG. 26, anti-CD3/28-activated primary human T cells were transduced with different lentiviral vectors encoding either a mesothelin-specific CD3z-based CAR (SS1z), a CD19-specific CAR bearing the FMC63 scFv (19bbz) or a CD19-specific CAR bearing the 21d4 scFv (21d4bbz) or a CD19-specific CAR bearing the BL22 scFv (BL22bbz) in which the scFv was composed of either a heavy chain variable domain (VH) 5' to the light chain variable domain (VL) in the scFv (H2L) or the VL located 5' to the VH (L2H). Following transduction with each of the CD19-specific CAR, the T cells were then co-transduced with SS1z. The binding of the SS1z to mesothelin and the surface expression of the anti-CD19 scFv was assessed by flow cytometry following staining with a mesothelin-Fc fusion protein followed by a secondary anti-Fc antibody labeled with FITC or biotinylated protein L followed by streptavidin-conjugated APC.

Result:

FIG. 24 shows that coexpression of two intact, ligand-binding scFv-based CARs (SS1-KIR2DL3 and CD19-KIR2DS2) on the cell surface is mutually exclusive. FIG. 26 demonstrates the loss of ligand binding occurs despite expression of the CAR in the cell as illustrated by the presence of mCherry expressing cells with reduced mesothelin binding in cells co-transduced with SS1z-mCh and 19bbz. FIG. 26 demonstrates that the interaction between scFv leading to loss of scFv binding function can be observed using different scFv-based CARs supporting the universal nature of this effect. These observations are consistent with the model depicted in FIG. 27 Panel A in which the variable domain of one scFv can undergo intermolecular pairing with a heterologous scFv-based chimeric receptor leading to loss of binding by the scFv within a single CAR.

Example 12: KIR-CAR Sequences

SS1 KIR2DS2 gene sequence (SEQ ID NO: 1)

gtgcacgagtgggttacatcgaactggatctcaacagcggtaagatccttgagagttttcgccccgaagaacgttttccaatgatg
agcacttttaaagttctgctatgtggcgcggtattatcccgtattgacgccgggcaagagcaactcggtcgccgcatacactattct
cagaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtcagg
caactatggatgaacgaaatagacagatcgctgagataggtgcctcactgattaagcattggtaactgtcagaccaagtttactca
tatatactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagttac
cggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcaggg
tcggaacaggagagcgcacgagggagcttccagggggaaacgcctggtatctttatagtcctgtcgggtttcgccacctctgac
ttgagcgtcgatttttgtgatgctcgtcaggggggcggagcctatggaaaaacgccagcaacgcggcctttttacggttcctggc
cttttgctggccttttgctcacatgttctttcctgcgttatcccctgattctgtggataaccgtattaccgcctttgagtgagctgatacc
gctcgccgcagccgaacgaccgagcgcagcgagtcagtgagcgaggaagcggaagagcgcccaatacgcaaaccgcctct
ccccgcgcgttggccgattcattaatgcagctggcacgacaggtttcccgactggaaagcgggcagtgagcgcaacgcaatta
atgtgagttagctcactcattaggcaccccaggctttacactttatgcttccggctcgtatgttgtgtggaattgtgagcggataaca
atttcacacaggaaacagctatgaccatgattacgccaagcgcgcaattaaccctcactaaagggaacaaaagctggagctgca
agcttaatgtagtcttatgcaatactcttgtagtcttgcaacatggtaacgatgagttagcaacatgccttacaaggagagaaaaag
caccgtgcatgccgattggtggaagtaaggtggtacgatcgtgccttattaggaaggcaacagacgggtctgacatggattgga
cgaaccactgaattgccgcattgcagagatattgtatttaagtgcctagctcgatacaataaacgggtctctctggttagaccagat
ctgagcctgggagctctctggctaactagggaacccactgcttaagcctcaataaagcttgccttgagtgcttcaagtagtgtgtg
cccgtctgttgtgtgactctggtaactagagatccctcagacccttttagtcagtgtggaaaatctctagcagtggcgcccgaaca
gggacctgaaagcgaaagggaaaccagagctctctcgacgcaggactcggcttgctgaagcgcgcacggcaagaggcgag
gggcggcgactggtgagtacgccaaaaattttgactagcggaggctagaaggagagagatgggtgcgagagcgtcagtatta
agcgggggagaattagatcgcgatgggaaaaaattcggttaaggccagggggaaagaaaaaatataaattaaaacatatagtat
gggcaagcagggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgcatcaaaggata
gagataaaagacaccaaggaagctttagacaagatagaggaagagcaaaacaaaagtaagaccaccgcacagcaagcggc
cgctgatcttcagacctggaggaggagatatgagggacaattggagaagtgaattatataaatataaagtagtaaaaattgaacc
attaggagtagcacccaccaaggcaaagagaagagtggtgcagagagaaaaaagagcagtgggaataggagctttgttcctt
gggttcttgggagcagcaggaagcactatgggcgcagcctcaatgacgctgacggtacaggccagacaattattgtctggtata
gtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgca
ccactgctgtgccttggaatgctagttggagtaataaatctctggaacagattggaatcacacgacctggatggagtgggacaga
gaaattaacaattacacaagcttaatacactccttaattgaagaatcgcaaaaccagcaagaaaaagaatgaacaagaattattgga
attagataaatgggcaagtttgtggaattggtttaacataacaaattggctgtggtatataaaattattcataatgatagtaggaggctt
ggtaggtttaagaatagtttttgctgtactttctatagtgaatagagttaggcagggatattcaccattatcgtttcagacccacctccc
aaccccgaggggacccgacaggcccgaaggaatagaagaagaaggtggagagagagacagagacagatccattcgattag
tgaacggatctcgacggtatcgattagactgtagcccaggaatatggcagctagattgtacacatttagaaggaaaagttatcttg
gtagcagttcatgtagccagtggatatatagaagcagaagtaattccagcagagacagggcaagaaacagcatacttcctcttaa
aattagcaggaagatggccagtaaaaacagtacatacagacaatggcagcaatttcaccagtactacagttaaggccgcctgttg
gtgggcggggatcaagcaggaatttggcattccctacaatccccaaagtcaaggagtaatagaatctatgaataaagaattaaag
aaaattataggacaggtaagagatcaggctgaacatcttaagacagcagtacaaatggcagtattcatccacaattttaaaagaaa
aggggggattggggggtacagtgcaggggaaagaatagtagacataatagcaacagacatacaaactaaagaattacaaaaa
caaattacaaaaattcaaaattttcgggtttattacagggacagcagagatccagtttggctgcatacgcgtcgtgaggctccggt
gcccgtcagtgggcagagcgcacatcgcccacagtccccgagaagttggggggaggggtcggcaattgaaccggtgcctag
agaaggtggcgcggggtaaactgggaaagtgatgtcgtgtactggctccgcctttttcccgagggtgggggagaaccgtatata
agtgcagtagtcgccgtgaacgttctttttcgcaacgggtttgccgccagaacacaggtaagtgccgtgtgtggttcccgcgggc
ctggcctctttacgggttatggcccttgcgtgccttgaattacttccacctggctgcagtacgtgattcttgatcccgagcttcgggtt
ggaagtgggtgggagagttcgaggccttgcgcttaaggagccccttcgcctcgtgcttgagttgaggcctggcctgggcgctg
gggccgccgcgtgcgaatctggtggcaccttcgcgcctgtctcgctgctttcgataagtctctagccatttaaaatttttgatgacct
gctgcgacgcttttttctggcaagatagtcttgtaaatgcgggccaagatctgcacactggtatttcggtttttggggccgcgggc
ggcgacggggcccgtgcgtcccagcgcacatgttcggcgaggcggggcctgcgagcgcggccaccgagaatcggacggg
ggtagtctcaagctggccggcctgctctggtgcctggcctcgcgccgccgtgtatcgccccgccctgggcggcaaggctggc
ccggtcggcaccagttgcgtgagcggaaagatggccgcttcccggccctgctgcagggagctcaaaatggaggacgcggcg
ctcgggagagcgggcgggtgagtcacccacacaaaggaaaagggcctttccgtcctcagccgtcgcttcatgtgactccacgg
agtaccgggcgccgtccaggcacctcgattagttctcgtgcttttggagtacgtcgtctttaggttggggggaggggttttatgcg
atggagtttccccacactgagtgggtggagactgaagttaggccagcttggcacttgatgtaattctccttggaatttgccctttttg
agtttggatcttggttcattctcaagcctcagacagtggttcaaagtttttttcttccatttcaggtgtcgtgagctagaATGGGG
GGACTTGAACCCTGCAGCAGGCTCCTGCTCCTGCCTCTCCTGCTGGCTGTAAG
TGGTCTCCGTCCTGTCCAGGCCCAGGCCCAGAGCGATTGCAGTTGCTCTACGG
TGAGCCCGGGCGTGCTGGCAGGGATCGTGATGGGAGACCTGGTGCTGACAGT
GCTCATTGCCCTGGCCGTGTACTTCCTGGGCCGGCTGGTCCCTCGGGGGCGAG
GGGCTGCGGAGGCAGCGACCCGGAAACAGCGTATCACTGAGACCGAGTCGC
CTTATCAGGAGCTCCAGGGTCAGAGGTCGGATGTCTACAGCGACCTCAACAC
ACAGAGGCCGTATTACAAAgTCGAGGGCGGCGGAGAGGGCAGAGGAAGTCT
TCTAACATGCGGTGACGTGGAGGAGAATCCCGGCCCTAGGatggccttaccagtgaccg
ccttgctcctgccgctggccttgctgctccacgccgccaggccgggatcccaggtacaactgcagcagtctgggcctgagctg
gagaagcctggcgcttcagtgaagatatcctgcaaggcttctggttactcattcactggctacaccatgaactgggtgaagcaga
gccatggaaagagccttgagtggattggacttattactccttacaatggtgcttctagctacaaccagaagttcaggggcaaggcc
acattaactgtagacaagtcatccagcacagcctacatggacctcctcagtctgacatctgaagactctgcagtctatttctgtgca -continued agggggggttacgacgggaggggttttgactactggggccaagggaccacggtcaccgtctcctcaggtggaggcggttcag
gcggcggtggctctagcggtggtggatcggacatcgagctcactcagtctccagcaatcatgtctgcatctccaggggagaag
gtcaccatgacctgcagtgccagctcaagtgtaagttacatgcactggtaccagcagaagtcaggcacctcccccaaaagatgg
atttatgacacatccaaactggcttctggagtcccaggtcgcttcagtggcagtgggtctggaaactcttactctctcacaatcagc
agcgtggaggctgaagatgatgcaacttattactgccagcagtggagtaagcaccctctcacgtacggtgctgggacaaagttg
gaaatcaaagctagcACGCGTggtggcggaggttctggaggtgggggttcccaggggggcctggccacatgagggagtc
cacagaaaaccttccctcctggcccacccaggtcccctggtgaaatcagaagagacagtcatcctgcaatgttggtcagatgtca
ggtttgagcacttccttctgcacagagaggggaagtataaggacactttgcacctcattggagagcaccatgatggggtctccaa
ggccaacttctccatcggtcccatgatgcaagaccttgcagggacctacagatgctacggttctgttactcactcccccctatcagtt
gtcagctcccagtgaccctctggacatcgtcatcacaggtctatatgagaaaccttctctctcagcccagccgggccccacggttt
tggcaggagagagcgtgaccttgtcctgcagctcccggagctcctatgacatgtaccatctatccagggagggggaggcccat
gaacgtaggttctctgcagggcccaaggtcaacggaacattccaggccgactttcctctgggccctgccacccacggaggaac
ctacagatgcttcggctctttccgtgactctccctatgagtggtcaaactcgagtgacccactgcttgtttctgtcacaggaaaccct
tcaaatagttggccttcacccactgaaccaagctccaaaaccggtaaccccagacacctgcatgttctgattgggacctcagtggt
caaaatccctttcaccatcctcctcttctttctccttcatcgctggtgctccaacaaaaaaaatgctgctgtaatggaccaagagcct
gcagggaacagaacagtgaacagcgaggattctgatgaacaagaccatcaggaggtgtcatacgcataaGtcgacaatcaac
ctctggattacaaaatttgtgaaagattgactggtattcttaactatgttgctccttttacgctatgtggatacgctgctttaatgcctttgt
atcatgctattgcttcccgtatggctttcattttctcctccttgtataaatcctggttgctgtctctttatgaggagttgtggcccgttgtca
ggcaacgtggcgtggtgtgcactgtgtttgctgacgcaacccccactggttggggcattgccaccacctgtcagctcctttccgg
gactttcgctttccccctccctattgccacggcggaactcatcgccgcctgccttgcccgctgctggacaggggctcggctgttg
ggcactgacaattccgtggtgttgtcggggaagctgacgtcctttccatggctgctcgcctgtgttgccacctggattctgcgcgg
gacgtccttctgctacgtcccttcggccctcaatccagcggaccttccttcccgcggcctgctgccggctctgcggcctcttccgc
gtcttcgccttcgccctcagacgagtcggatctccctttgggccgcctccccgcctggaattcgagctcggtacctttaagaccaa
tgacttacaaggcagctgtagatcttagccactttttaaaagaaaaggggggactggaagggctaattcactcccaacgaagaca
agatctgcttttttgcttgtactgggtctctctggttagaccagatctgagcctgggagctctctggctaactagggaacccactgctt
aagcctcaataaagcttgccttgagtgcttcaagtagtgtgtgcccgtctgttgtgtgactctggtaactagagatccctcagaccct
tttagtcagtgtggaaaatctctagcagtagtagttcatgtcatcttattattcagtatttataacttgcaaagaaatgaatatcagaga
gtgagaggaacttgtttattgcagcttataatggttacaaataaagcaatagcatcacaaatttcacaaataaagcatttttttcactgc
attctagttgtggtttgtccaaactcatcaatgtatcttatcatgtctggctctagctatcccgcccctaactccgcccagttccgccca
ttctccgccccatggctgactaattttttttatttatgcagaggccgaggccgcctcggcctctgagctattccagaagtagtgagga
ggcttttttggaggcctacgcttttgcgtcgagacgtacccaattcgccctatagtgagtcgtattacgcgcgctcactggccgtcg
ttttacaacgtcgtgactgggaaaaccctggcgttacccaacttaatcgccttgcagcacatccccctttcgccagctggcgtaata
gcgaagaggcccgcaccgatcgcccttcccaacagttgcgcagcctgaatggcgaatggcgcgacgcgccctgtagcggcg
cattaagcgcggcgggtgtggtggttacgcgcagcgtgaccgctacacttgccagcgccctagcgcccgctcctttcgctttctt
cccttcctttctcgccacgttcgccggctttccccgtcaagctctaaatcgggggctccctttagggttccgatttagtgctttacggc
acctcgaccccaaaaaacttgattagggtgatggttcacgtagtgggccatcgccctgatagacggtttttcgccctttgacgttgg
agtccacgttctttaatagtggactcttgttccaaactggaacaacactcaaccctatctcggtctattcttttgatttataagggatttt
gccgatttcggcctattggttaaaaaatgagctgatttaacaaaaatttaacgcgaattttaacaaaatattaacgtttacaatttccca
ggtggcacttttcggggaaatgtgcgcggaacccctatttgtttatttttctaaatacattcaaatatgtatccgctcatgagacaataa
ccctgataaatgcttcaataatattgaaaaaggaagagtatgagtattcaacatttccgtgtcgcccttattcccttttttgcggcatttt
gccttcctgtttttgctcacccagaaacgctggtgaaagtaaaagatgctgaagatcagttgg SS1 KIRS2 gene sequence (SEQ ID NO: 2)

gtgcacgagtgggttacatcgaactggatctcaacagcggtaagatccttgagagttttcgccccgaagaacgttttccaatgatg
agcacttttaaagttctgctatgtggcgcggtattatcccgtattgacgccgggcaagagcaactcggtcgccgcatacactattct
cagaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtcagg
caactatggatgaacgaaatagacagatcgctgagataggtgcctcactgattaagcattggtaactgtcagaccaagtttactca
tatatactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagttac
cggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcaggg
tcggaacaggagagcgcacgagggagcttccagggggaaacgcctggtatctttatagtcctgtcgggtttcgccacctctgac
ttgagcgtcgatttttgtgatgctcgtcaggggggcggagcctatggaaaaacgccagcaacgcggcctttttacggttcctggc
cttttgctggccttttgctcacatgttctttcctgcgttatcccctgattctgtggataaccgtattaccgcctttgagtgagctgatacc
gctcgccgcagccgaacgaccgagcgcagcgagtcagtgagcgaggaagcggaagagcgcccaatacgcaaaccgcctct
ccccgcgcgttggccgattcattaatgcagctggcacgacaggtttcccgactggaaagcgggcagtgagcgcaacgcaatta
atgtgagttagctcactcattaggcaccccaggctttacactttatgcttccggctcgtatgttgtgtggaattgtgagcggataaca
atttcacacaggaaacagctatgaccatgattacgccaagcgcgcaattaaccctcactaaagggaacaaaagctggagctgca
agcttaatgtagtcttatgcaatactcttgtagtcttgcaacatggtaacgatgagttagcaacatgccttacaaggagagaaaaag
caccgtgcatgccgattggtggaagtaaggtggtacgatcgtgccttattaggaaggcaacagacgggtctgacatggattgga
cgaaccactgaattgccgcattgcagagatattgtatttaagtgcctagctcgatacaataaacgggtctctctggttagaccagat
ctgagcctgggagctctctggctaactagggaacccactgcttaagcctcaataaagcttgccttgagtgcttcaagtagtgtgtg
cccgtctgttgtgtgactctggtaactagagatccctcagacccttttagtcagtgtggaaaatctctagcagtggcgcccgaaca
gggacctgaaagcgaaagggaaaccagagctctctcgacgcaggactcggcttgctgaagcgcgcacggcaagaggcgag
gggcggcgactggtgagtacgccaaaaattttgactagcggaggctagaaggagagagatgggtgcgagagcgtcagtatta
agcgggggagaattagatcgcgatgggaaaaaattcggttaaggccagggggaaagaaaaaatataaattaaaacatatagtat
gggcaagcagggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgcatcaaaggata
gagataaaagacaccaaggaagctttagacaagatagaggaagagcaaaacaaaagtaagaccaccgcacagcaagcggc
cgctgatcttcagacctggaggaggagatatgagggacaattggagaagtgaattatataaatataaagtagtaaaaattgaacc
attaggagtagcacccaccaaggcaaagagaagagtggtgcagagagaaaaaagagcagtgggaataggagctttgttcctt
gggttcttgggagcagcaggaagcactatgggcgcagcctcaatgacgctgacggtacaggccagacaattattgtctggtata -continued gtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgca
ccactgctgtgccttggaatgctagttggagtaataaatctctggaacagattggaatcacacgacctggatggagtgggacaga
gaaattaacaattacacaagcttaatacactccttaattgaagaatcgcaaaaccagcaagaaaagaatgaacaagaattattgga
attagataaatgggcaagtttgtggaattggtttaacataacaaattggctgtggtatataaaattattcataatgatagtaggaggctt
ggtaggtttaagaatagtttttgctgtactttctatagtgaatagagttaggcagggatattcaccattatcgtttcagacccacctccc
aaccccgaggggacccgacaggcccgaaggaatagaagaagaaggtggagagagagacagagacagatccattcgattag
tgaacggatctcgacggtatcgattagactgtagcccaggaatatggcagctagattgtacacatttagaaggaaaagttatcttg
gtagcagttcatgtagccagtggatatatagaagcagaagtaattccagcagagacagggcaagaaacagcatacttcctcttaa
aattagcaggaagatggccagtaaaaacagtacatacagacaatggcagcaatttcaccagtactacagttaaggccgcctgttg
gtgggcggggatcaagcaggaatttggcattccctacaatccccaaagtcaaggagtaatagaatctatgaataaagaattaaag
aaaattataggacaggtaagagatcaggctgaacatcttaagacagcagtacaaatggcagtattcatccacaattttaaaagaaa
aggggggattggggggtacagtgcaggggaaagaatagtagacataatagcaacagacatacaaactaaagaattacaaaaa
caaattacaaaaattcaaaattttcgggtttattacagggacagcagagatccagtttggctgcatacgcgtcgtgaggctccggt
gcccgtcagtgggcagagcgcacatcgcccacagtccccgagaagttggggggaggggtcggcaattgaaccggtgcctag
agaaggtggcgcggggtaaactgggaaagtgatgtcgtgtactggctccgcctttttcccgagggtgggggagaaccgtatata
agtgcagtagtcgccgtgaacgttctttttcgcaacgggtttgccgccagaacacaggtaagtgccgtgtgtggttcccgcgggc
ctggcctctttacgggttatggcccttgcgtgccttgaattacttccacctggctgcagtacgtgattcttgatcccgagcttcgggtt
ggaagtgggtgggagagttcgaggccttgcgcttaaggagccccttcgcctcgtgcttgagttgaggcctggcctgggcgctg
ggccgccgcgtgcgaatctggtggcaccttcgcgcctgtctcgctgctttcgataagtctctagccatttaaaatttttgatgacct
gctgcgacgctttttttctggcaagatagtcttgtaaatgcgggccaagatctgcacactggtatttcggtttttggggccgcgggc
ggcgacggggcccgtgcgtcccagcgcacatgttcggcgaggcggggcctgcgagcgcggccaccgagaatcggacggg
ggtagtctcaagctggccggcctgctctggtgcctggcctcgcgccgccgtgtatcgccccgccctgggcggcaaggctggc
ccggtcggcaccagttgcgtgagcggaaagatggccgcttcccggccctgctgcagggagctcaaaatggaggacgcggcg
ctcgggagagcgggcgggtgagtcacccacacaaaggaaaagggcctttccgtcctcagccgtcgcttcatgtgactccacgg
agtaccgggcgccgtccaggcacctcgattagttctcgtgcttttggagtacgtcgtctttaggttggggggaggggttttatgcg
atggagtttccccacactgagtgggtggagactgaagttaggccagcttggcacttgatgtaattctccttggaatttgccctttttg
agtttggatcttggttcattctcaagcctcagacagtggttcaaagtttttttcttccatttcaggtgtcgtgagctagaATGGGG
GGACTTGAACCCTGCAGCAGGCTCCTGCTCCTGCCTCTCCTGCTGGCTGTAAG
TGGTCTCCGTCCTGTCCAGGCCCAGGCCCAGAGCGATTGCAGTTGCTCTACGG
TGAGCCCGGGCGTGCTGGCAGGGATCGTGATGGGAGACCTGGTGCTGACAGT
GCTCATTGCCCTGGCCGTGTACTTCCTGGGCCGGCTGGTCCCTCGGGGGCGAG
GGGCTGCGGAGGCAGCGACCCGGAAACAGCGTATCACTGAGACCGAGTCGC
CTTATCAGGAGCTCCAGGGTCAGAGGTCGGATGTCTACAGCGACCTCAACAC
ACAGAGGCCGTATTACAAAgTCGAGGGCGGCGGAGAGGGCAGAGGAAGTCT
TCTAACATGCGGTGACGTGGAGGAGAATCCCGGCCCTAGGatggccttaccagtgaccg
ccttgctcctgccgctggccttgctgctccacgccgccaggccgggatcccaggtacaactgcagcagtctgggcctgagctg
gagaagcctggcgcttcagtgaagatatcctgcaaggcttctggttactcattcactggctacaccatgaactgggtgaagcaga
gccatggaaagagccttgagtggattggacttattactccttacaatggtgcttctagctacaaccagaagttcaggggcaaggcc
acattaactgtagacaagtcatccagcacagcctacatggacctcctcagtctgacatctgaagactctgcagtctatttctgtgca
aggggggggttacgacgggaggggttttgactactggggccaagggaccacggtcaccgtctcctcaggtggaggcggttcag
gcggcggtggctctagcggtggtggatcggacatcgagctcactcagtctccagcaatcatgtctgcatctccaggggagaag
gtcaccatgacctgcagtgccagctcaagtgtaagttacatgcactggtaccagcagaagtcaggcacctcccccaaaagatgg
atttatgacacatccaaactggcttctggagtcccaggtcgcttcagtggcagtgggtctggaaactcttactctctcacaatcagc
agcgtggaggctgaagatgatgcaacttattactgccagcagtggagtaagcaccctctcacgtacggtgctgggacaaagttg
gaaatcaaagctagcggtggcggaggttctggaggtgggggttcctcacccactgaaccaagctccaaaaccggtaacccca
gacacctgcatgttctgattgggacctcagtggtcaaaatccctttcaccatcctcctcttctttctccttcatcgctggtgctccaaca
aaaaaaatgctgctgtaatggaccaagagcctgcagggaacagaacagtgaacagcgaggattctgatgaacaagaccatca
ggaggtgtcatacgcataaGtcgacaatcaacctctggattacaaaatttgtgaaagattgactggtattcttaactatgttgctcctt
ttacgctatgtggatacgctgctttaatgcctttgtatcatgctattgcttcccgtatggctttcattttctcctccttgtataaatcctggtt
gctgtctctttatgaggagttgtggcccgttgtcaggcaacgtggcgtggtgtgcactgtgtttgctgacgcaacccccactggttg
gggcattgccaccacctgtcagctcctttccgggactttcgctttccccctccctattgccacggcggaactcatcgccgcctgcct
tgcccgctgctggacaggggctcggctgttgggcactgacaattccgtggtgttgtcggggaagctgacgtcctttccatggctg
ctcgcctgtgttgccacctggattctgcgcgggacgtccttctgctacgtcccttcggccctcaatccagcggaccttccttcccgc
ggcctgctgccggctctgcggcctcttccgcgtcttcgccttcgccctcagacgagtcggatctccctttgggccgcctccccgc
ctggaattcgagctcggtacctttaagaccaatgacttacaaggcagctgtagatcttagccactttttaaaagaaaaggggggac
tggaagggctaattcactcccaacgaagacaagatctgctttttgcttgtactgggtctctctggttagaccagatctgagcctggg
agctctctggctaactagggaacccactgcttaagcctcaataaagcttgccttgagtgcttcaagtagtgtgtgcccgtctgttgtg
tgactctggtaactagagatccctcagacccttttagtcagtgtggaaaatctctagcagtagtagttcatgtcatcttattattcagta
tttataacttgcaaagaaatgaatatcagagagtgagaggaacttgtttattgcagcttataatggttacaaataaagcaatagcatc
acaaatttcacaaataaagcatttttttcactgcattctagttgtggtttgtccaaactcatcaatgtatcttatcatgtctggctctagcta
tcccgcccctaactccgcccagttccgcccattctccgccccatggctgactaattttttttatttatgcagaggccgaggccgcctc
ggcctctgagctattccagaagtagtgaggaggcttttttggaggcctacgcttttgcgtcgagacgtacccaattcgccctatagt
gagtcgtattacgcgcgctcactggccgtcgttttacaacgtcgtgactgggaaaaccctggcgttacccaacttaatcgccttgc
agcacatccccctttcgccagctggcgtaatagcgaagaggcccgcaccgatcgcccttcccaacagttgcgcagcctgaatg
gcgaatggcgcgacgcgccctgtagcggcgcattaagcgcggcgggtgtggtggttacgcgcagcgtgaccgctacacttgc
cagcgccctagcgcccgctcctttcgctttcttcccttcctttctcgccacgttcgccggctttccccgtcaagctctaaatcggggg
ctccctttagggttccgatttagtgctttacggcacctcgaccccaaaaaacttgattagggtgatggttcacgtagtgggccatcg
ccctgatagacggtttttcgccctttgacgttggagtccacgttctttaatagtggactcttgttccaaactggaacaacactcaaccc
tatctcggtctattcttttgatttataagggattttgccgatttcggcctattggttaaaaaatgagctgatttaacaaaaatttaacgcga
attttaacaaaatattaacgtttacaatttcccaggtggcacttttcggggaaatgtgcgcggaacccctatttgtttatttttctaaata
cattcaaatatgtatccgctcatgagacaataaccctgataaatgcttcaataatattgaaaaaggaagagtatgagtattcaacattt
ccgtgtcgcccttattcccttttttgcggcattttgccttcctgtttttgctcacccagaaacgctggtgaaagtaaaagatgctgaag
atcagttgg SS1 KIR2DL3 gene sequence (SEQ ID NO: 3)

gtgcacgagtgggttacatcgaactggatctcaacagcggtaagatccttgagagttttcgccccgaagaacgttttccaatgatg
agcacttttaaagttctgctatgtggcgcggtattatcccgtattgacgccgggcaagagcaactcggtcgccgcatacactattct
cagaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgctttttgcacaacat -continued

```
ggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtcagg
caactatggatgaacgaaatagacagatcgctgagataggtgcctcactgattaagcattggtaactgtcagaccaagtttactca
tatatactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagttac
cggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcaggg
tcggaacaggagagcgcacgagggagcttccagggggaaacgcctggtatctttatagtcctgtcgggtttcgccacctctgac
ttgagcgtcgatttttgtgatgctcgtcaggggggcggagcctatggaaaaacgccagcaacgcggcctttttacggttcctggc
cttttgctggccttttgctcacatgttctttcctgcgttatcccctgattctgtggataaccgtattaccgcctttgagtgagctgatacc
gctcgccgcagccgaacgaccgagcgcagcgagtcagtgagcgaggaagcggaagagcgcccaatacgcaaaccgcctct
ccccgcgcgttggccgattcattaatgcagctggcacgacaggtttcccgactggaaagcgggcagtgagcgcaacgcaatta
atgtgagttagctcactcattaggcaccccaggctttacactttatgcttccggctcgtatgttgtgtggaattgtgagcggataaca
atttcacacaggaaacagctatgaccatgattacgccaagcgcgcaattaaccctcactaaagggaacaaaagctggagctgca
agcttaatgtagtcttatgcaatactcttgtagtcttgcaacatggtaacgatgagttagcaacatgccttacaaggagagaaaaag
caccgtgcatgccgattggtggaagtaaggtggtacgatcgtgccttattaggaaggcaacagacgggtctgacatggattgga
cgaaccactgaattgccgcattgcagagatattgtatttaagtgcctagctcgatacaataaacgggtctctctggttagaccagat
ctgagcctgggagctctctggctaactagggaacccactgcttaagcctcaataaagcttgccttgagtgcttcaagtagtgtgtg
cccgtctgttgtgtgactctggtaactagagatccctcagacccttttagtcagtgtggaaaatctctagcagtggcgcccgaaca
gggacctgaaagcgaaagggaaaccagagctctctcgacgcaggactcggcttgctgaagcgcgcacggcaagaggcgag
gggcggcgactggtgagtacgccaaaaattttgactagcggaggctagaaggagagagatgggtgcgagagcgtcagtatta
agcgggggagaattagatcgcgatgggaaaaaattcggttaaggccagggggaaagaaaaaatataaattaaaacatatagtat
gggcaagcagggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgcatcaaaggata
gagataaaagacaccaaggaagctttagacaagatagaggaagagcaaaacaaaagtaagaccaccgcacagcaagcggc
cgctgatcttcagacctggaggaggagatatgagggacaattggagaagtgaattatataaatataaagtagtaaaaattgaacc
attaggagtagcacccaccaaggcaaagagaagagtggtgcagagagaaaaaagagcagtgggaataggagctttgttcctt
gggttcttgggagcagcaggaagcactatgggcgcagcctcaatgacgctgacggtacaggccagacaattattgtctggtata
gtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgca
ccactgctgtgccttggaatgctagttggagtaataaatctctggaacagattggaatcacacgacctggatggagtgggacaga
gaaattaacaattacacaagcttaatacactccttaattgaagaatcgcaaaaccagcaagaaaagaatgaacaagaattattgga
attagataaatgggcaagtttgtggaattggtttaacataacaaattggctgtggtatataaaattattcataatgatagtaggaggctt
ggtaggtttaagaatagtttttgctgtactttctatagtgaatagagttaggcagggatattcaccattatcgtttcagacccacctccc
aaccccgaggggacccgacaggcccgaaggaatagaagaagaaggtggagagagagacagagacagatccattcgattag
tgaacggatctcgacggtatcgattagactgtagcccaggaatatggcagctagattgtacacatttagaaggaaaagttatcttg
gtagcagttcatgtagccagtggatatatagaagcagaagtaattccagcagagacagggcaagaaacagcatacttcctcttaa
aattagcaggaagatggccagtaaaaacagtacatacagacaatggcagcaatttcaccagtactacagttaaggccgcctgttg
gtgggcggggatcaagcaggaatttggcattccctacaatccccaaagtcaaggagtaatagaatctatgaataaagaattaaag
aaaattataggacaggtaagagatcaggctgaacatcttaagacagcagtacaaatggcagtattcatccacaattttaaaagaaa
aggggggattggggggtacagtgcaggggaaagaatagtagacataatagcaacagacatacaaactaaagaattacaaaaa
caaattacaaaaattcaaaattttcgggtttattacagggacagcagagatccagtttggctgcatacgcgtcgtgaggctccggt
gcccgtcagtgggcagagcgcacatcgcccacagtccccgagaagttggggggaggggtcggcaattgaaccggtgcctag
agaaggtggcgcggggtaaactgggaaagtgatgtcgtgtactggctccgcctttttcccgagggtgggggagaaccgtatata
agtgcagtagtcgccgtgaacgttctttttcgcaacgggtttgccgccagaacacaggtaagtgccgtgtgtggttcccgcgggc
ctggcctctttacgggttatggcccttgcgtgccttgaattacttccacctggctgcagtacgtgattcttgatcccgagcttcgggtt
ggaagtgggtgggagagttcgaggccttgcgcttaaggagccccttcgcctcgtgcttgagttgaggcctggcctgggcgctg
gggccgccgcgtgcgaatctggtggcaccttcgcgcctgtctcgctgctttcgataagtctctagccatttaaaatttttgatgacct
gctgcgacgctttttttctggcaagatagtcttgtaaatgcgggccaagatctgcacactggtatttcggtttttggggccgcgggc
ggcgacggggcccgtgcgtcccagcgcacatgttcggcgaggcggggcctgcgagcgcggccaccgagaatcggacggg
ggtagtctcaagctggccggcctgctctggtgcctggcctcgcgccgccgtgtatcgccccgccctgggcggcaaggctggc
ccggtcggcaccagttgcgtgagcggaaagatggccgcttcccggccctgctgcagggagctcaaaatggaggacgcggcg
ctcgggagagcgggcgggtgagtcacccacacaaaggaaaagggcctttccgtcctcagccgtcgcttcatgtgactccacgg
agtaccgggcgccgtccaggcacctcgattagttctcgtgcttttggagtacgtcgtctttaggttggggggaggggttttatgcg
atggagtttccccacactgagtgggtggagactgaagttaggccagcttggcacttgatgtaattctccttggaatttgccctttttg
agtttggatcttggttcattctcaagcctcagacagtggttcaaagtttttttcttccatttcaggtgtcgtgagctagaATGGGG
GGACTTGAACCCTGCAGCAGGCTCCTGCTCCTGCCTCTCCTGCTGGCTGTAAG
TGGTCTCCGTCCTGTCCAGGCCCAGGCCCAGAGCGATTGCAGTTGCTCTACGG
TGAGCCCGGGCGTGCTGGCAGGGATCGTGATGGGAGACCTGGTGCTGACAGT
GCTCATTGCCCTGGCCGTGTACTTCCTGGGCCGGCTGGTCCCTCGGGGGCGAG
GGGCTGCGGAGGCAGCGACCCGGAAACAGCGTATCACTGAGACCGAGTCGC
CTTATCAGGAGCTCCAGGGTCAGAGGTCGGATGTCTACAGCGACCTCAACAC
ACAGAGGCCGTATTACAAAgTCGAGGGCGGCGGAGAGGGCAGAGGAAGTCT
TCTAACATGCGGTGACGTGGAGGAGAATCCCGGCCCTAGGatggccttaccagtgaccg
ccttgctcctgccgctggccttgctgctccacgccgccaggccgggatcccaggtacaactgcagcagtctgggcctgagctg
gagaagcctggcgcttcagtgaagatatcctgcaaggcttctggttactcattcactggctacaccatgaactgggtgaagcaga
gccatggaaagagccttgagtggattggacttattactccttacaatggtgcttctagctacaaccagaagttcaggggcaaggcc
acattaactgtagacaagtcatccagcacagcctacatggacctcctcagtctgacatctgaagactctgcagtctatttctgtgca
aggggggggttacgacgggaggggttttgactactggggccaagggaccacggtcaccgtctcctcaggtggaggcggttcag
gcggcggtggctctagcggtggtggatcggacatcgagctcactcagtctccagcaatcatgtctgcatctccaggggagaag
gtcaccatgacctgcagtgccagctcaagtgtaagttacatgcactggtaccagcagaagtcaggcacctcccccaaaagatgg
atttatgacacatccaaactggcttctggagtcccaggtcgcttcagtggcagtgggtctggaaactcttactctctcacaatcagc
agcgtggaggctgaagatgatgcaacttattactgccagcagtggagtaagcaccctctcacgtacggtgctgggacaaagttg
gaaatcaaagCTAGCggtggcggaggttctggaggtgggggttccCAGGGGGCCTGGCCACATGAG
GGAGTCCACAGAAAACCTTCCCTCCTGGCCCACCCAGGTCCCCTGGTGAAAT
CAGAAGAGACAGTCATCCTGCAATGTTGGTCAGATGTCAGGTTTCAGCACTT
```

-continued

```
CCTTCTGCACAGAGAAGGGAAGTTTAAGGACACTTTGCACCTCATTGGAGAG
CACCATGATGGGGTCTCCAAGGCCAACTTCTCCATCGGTCCCATGATGCAAG
ACCTTGCAGGGACCTACAGATGCTACGGTTCTGTTACTCACTCCCCCTATCAG
TTGTCAGCTCCCAGTGACCCTCTGGACATCGTCATCACAGGTCTATATGAGAA
ACCTTCTCTCTCAGCCCAGCCGGGCCCCACGGTTCTGGCAGGAGAGAGCGTG
ACCTTGTCCTGCAGCTCCCGGAGCTCCTATGACATGTACCATCTATCCAGGGA
GGGGGAGGCCCATGAACGTAGGTTCTCTGCAGGGCCCAAGGTCAACGGAAC
ATTCCAGGCCGACTTTCCTCTGGGCCCTGCCACCCACGGAGGAACCTACAGA
TGCTTCGGCTCTTTCCGTGACTCTCCATACGAGTGGTCAAACTCGAGTGACCC
ACTGCTTGTTTCTGTCACAGGAAACCCTTCAAATAGTTGGCTTTCACCCACTG
AACCAAGCTCCGAAACCGGTAACCCCAGACACCTGCATGTTCTGATTGGGAC
CTCAGTGGTCATCATCCTCTTCATCCTCCTCCTCTTCTTTCTCCTTCATCGCTG
GTGCTGCAACAAAAAAAATGCTGTTGTAATGGACCAAGAGCCTGCAGGGAAC
AGAACAGTGAACAGGGAGGACTCTGATGAACAAGACCCTCAGGAGGTGACA
TATGCACAGTTGAATCACTGCGTTTTCACACAGAGAAAAATCACTCACCCTTC
TCAGAGGCCCAAGACACCCCCAACAGATATCATCGTGTACACGGAACTTCCA
AATGCTGAGCCCTGAGtcgacaatcaacctctggattacaaaatttgtgaaagattgactggtattcttaactatgttg
ctccttttacgctatgtggatacgctgctttaatgcctttgtatcatgctattgcttcccgtatggctttcattttctcctccttgtataaatc
ctggttgctgtctctttatgaggagttgtggcccgttgtcaggcaacgtggcgtggtgtgcactgtgtttgctgacgcaacccccac
tggttggggcattgccaccacctgtcagctcctttccgggactttcgctttccccctccctattgccacggcggaactcatcgccgc
ctgccttgcccgctgctggacaggggctcggctgttgggcactgacaattccgtggtgttgtcggggaagctgacgtcctttccat
ggctgctcgcctgtgttgccacctggattctgcgcgggacgtccttctgctacgtcccttcggccctcaatccagcggaccttcctt
cccgcggcctgctgccggctctgcggcctcttccgcgtcttcgccttcgccctcagacgagtcggatctccctttgggccgcctc
cccgcctggaattcgagctcggtacctttaagaccaatgacttacaaggcagctgtagatcttagccactttttaaaagaaaaggg
gggactggaagggctaattcactcccaacgaagacaagatctgctttttgcttgtactgggtctctctggttagaccagatctgagc
ctgggagctctctggctaactagggaacccactgcttaagcctcaataaagcttgccttgagtgcttcaagtagtgtgtgcccgtct
gttgtgtgactctggtaactagagatccctcagacccttttagtcagtgtggaaaatctctagcagtagtagttcatgtcatcttattatt
cagtatttataacttgcaaagaaatgaatatcagagagtgagaggaacttgtttattgcagcttataatggttacaaataaagcaata
gcatcacaaatttcacaaataaagcatttttttcactgcattctagttgtggtttgtccaaactcatcaatgtatcttatcatgtctggctct
agctatcccgcccctaactccgcccagttccgcccattctccgccccatggctgactaattttttttatttatgcagaggccgaggcc
gcctcggcctctgagctattccagaagtagtgaggaggcttttttggaggcctacgcttttgcgtcgagacgtacccaattcgccct
atagtgagtcgtattacgcgcgctcactggccgtcgttttacaacgtcgtgactgggaaaaccctggcgttacccaacttaatcgc
cttgcagcacatccccctttcgccagctggcgtaatagcgaagaggcccgcaccgatcgcccttcccaacagttgcgcagcctg
aatggcgaatggcgcgacgcgccctgtagcggcgcattaagcgcggcgggtgtggtggttacgcgcagcgtgaccgctaca
cttgccagcgccctagcgcccgctcctttcgctttcttcccttcctttctcgccacgttcgccggctttccccgtcaagctctaaatcg
ggggctccctttagggttccgatttagtgctttacggcacctcgaccccaaaaaacttgattagggtgatggttcacgtagtgggc
catcgccctgatagacggtttttcgccctttgacgttggagtccacgttctttaatagtggactcttgttccaaactggaacaacactc
aaccctatctcggtctattcttttgatttataagggattttgccgatttcggcctattggttaaaaaatgagctgatttaacaaaaatttaa
cgcgaattttaacaaaatattaacgtttacaatttcccaggtggcacttttcggggaaatgtgcgcggaacccctatttgtttatttttct
aaatacattcaaatatgtatccgctcatgagacaataaccctgataaatgcttcaataatattgaaaaaggaagagtatgagtattca
acatttccgtgtcgcccttattcccttttttgcggcattttgccttcctgtttttgctcacccagaaacgctggtgaaagtaaaagatgct
gaagatcagttgg
```

CD19 KIR2DS2 construct sequence (SEQ ID NO: 4)

```
gtgcacgagtgggttacatcgaactggatctcaacagcggtaagatccttgagagttttcgccccgaagaacgttttccaatgatg
agcacttttaaagttctgctatgtggcgcggtattatcccgtattgacgccgggcaagagcaactcggtcgccgcatacactattct
cagaatgacttggttgagtactcaccagtcacagaaaagcatcttacggatggcatgacagtaagagaattatgcagtgctgcca
taaccatgagtgataacactgcggccaacttacttctgacaacgatcggaggaccgaaggagctaaccgcttttttgcacaacat
gggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatg
gaggcggataaagttgcaggaccacttctgcgctcggcccttccggctggctggtttattgctgataaatctggagccggtgagc
gtgggtctcgcggtatcattgcagcactggggccagatggtaagccctcccgtatcgtagttatctacacgacggggagtcagg
caactatggatgaacgaaatagacagatcgctgagataggtgcctcactgattaagcattggtaactgtcagaccaagtttactca
tatatactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactggctt
cagcagagcgcagataccaaatactgtccttctagtgtagccgtagttaggccaccacttcaagaactctgtagcaccgcctacat
acctcgctctgctaatcctgttaccagtggctgctgccagtggcgataagtcgtgtcttaccgggttggactcaagacgatagttac
cggataaggcgcagcggtcgggctgaacggggggttcgtgcacacagcccagcttggagcgaacgacctacaccgaactga
gatacctacagcgtgagctatgagaaagcgccacgcttcccgaagggagaaaggcggacaggtatccggtaagcggcaggg
tcggaacaggagagcgcacgagggagcttccagggggaaacgcctggtatctttatagtcctgtcgggtttcgccacctctgac
ttgagcgtcgatttttgtgatgctcgtcaggggggcggagcctatggaaaaacgccagcaacgcggcctttttacggttcctggc
cttttgctggccttttgctcacatgttctttcctgcgttatcccctgattctgtggataaccgtattaccgcctttgagtgagctgatacc
gctcgccgcagccgaacgaccgagcgcagcgagtcagtgagcgaggaagcggaagagcgcccaatacgcaaaccgcctct
ccccgcgcgttggccgattcattaatgcagctggcacgacaggtttcccgactggaaagcgggcagtgagcgcaacgcaatta
atgtgagttagctcactcattaggcaccccaggctttacactttatgcttccggctcgtatgttgtgtggaattgtgagcggataaca
atttcacacaggaaacagctatgaccatgattacgccaagcgcgcaattaaccctcactaaagggaacaaaagctggagctgca
agcttaatgtagtcttatgcaatactcttgtagtcttgcaacatggtaacgatgagttagcaacatgccttacaaggagagaaaaag
caccgtgcatgccgattggtggaagtaaggtggtacgatcgtgccttattaggaaggcaacagacgggtctgacatggattgga
cgaaccactgaattgccgcattgcagagatattgtatttaagtgcctagctcgatacaataaacgggtctctctggttagaccagat
ctgagcctgggagctctctggctaactagggaacccactgcttaagcctcaataaagcttgccttgagtgcttcaagtagtgtgtg
cccgtctgttgtgtgactctggtaactagagatccctcagacccttttagtcagtgtggaaaatctctagcagtggcgcccgaaca
gggacctgaaagcgaaagggaaaccagagctctctcgacgcaggactcggcttgctgaagcgcgcacggcaagaggcgag
gggcggcgactggtgagtacgccaaaaattttgactagcggaggctagaaggagagagatgggtgcgagagcgtcagtatta
agcgggggagaattagatcgcgatgggaaaaaattcggttaaggccagggggaaagaaaaaatataaattaaaacatatagtat
gggcaagcagggagctagaacgattcgcagttaatcctggcctgttagaaacatcagaaggctgtagacaaatactgggacag
ctacaaccatcccttcagacaggatcagaagaacttagatcattatataatacagtagcaaccctctattgtgtgcatcaaaggata
gagataaaagacaccaaggaagctttagacaagatagaggaagagcaaaacaaaagtaagaccaccgcacagcaagcggc
cgctgatcttcagacctggaggaggagatatgagggacaattggagaagtgaattatataaatataaagtagtaaaaattgaacc
attaggagtagcacccaccaaggcaaagagaagagtggtgcagagagaaaaaagagcagtgggaataggagctttgttcctt
```

-continued gggttcttgggagcagcaggaagcactatgggcgcagcctcaatgacgctgacggtacaggccagacaattattgtctggtata
gtgcagcagcagaacaatttgctgagggctattgaggcgcaacagcatctgttgcaactcacagtctggggcatcaagcagctc
caggcaagaatcctggctgtggaaagatacctaaaggatcaacagctcctggggatttggggttgctctggaaaactcatttgca
ccactgctgtgccttggaatgctagttggagtaataaatctctggaacagattggaatcacacgacctggatggagtgggacaga
gaaattaacaattacacaagcttaatacactccttaattgaagaatcgcaaaaccagcaagaaaagaatgaacaagaattattgga
attagataaatgggcaagtttgtggaattggtttaacataacaaattggctgtggtatataaaattattcataatgatagtaggaggctt
ggtaggtttaagaatagtttttgctgtactttctatagtgaatagagttaggcagggatattcaccattatcgtttcagacccacctccc
aaccccgaggggacccgacaggcccgaaggaatagaagaagaaggtggagagagagacagagacagatccattcgattag
tgaacggatctcgacggtatcgattagactgtagcccaggaatatggcagctagattgtacacatttagaaggaaaagttatcttg
gtagcagttcatgtagccagtggatatatagaagcagaagtaattccagcagagacagggcaagaaacagcatacttcctcttaa
aattagcaggaagatggccagtaaaaacagtacatacagacaatggcagcaatttcaccagtactacagttaaggccgcctgttg
gtgggcggggatcaagcaggaatttggcattccctacaatccccaaagtcaaggagtaatagaatctatgaataaagaattaaag
aaaattataggacaggtaagagatcaggctgaacatcttaagacagcagtacaaatggcagtattcatccacaattttaaaagaaa
aggggggattggggggtacagtgcaggggaaagaatagtagacataatagcaacagacatacaaactaaagaattacaaaaa
caaattacaaaaattcaaaattttcgggtttattacagggacagcagagatccagtttggctgcatacgcgtcgtgaggctccggt
gcccgtcagtgggcagagcgcacatcgcccacagtccccgagaagttggggggaggggtcggcaattgaaccggtgcctag
agaaggtggcgcggggtaaactgggaaagtgatgtcgtgtactggctccgcctttttcccgagggtgggggagaaccgtatata
agtgcagtagtcgccgtgaacgttctttttcgcaacgggtttgccgccagaacacaggtaagtgccgtgtgtggttcccgcgggc
ctggcctctttacgggttatggcccttgcgtgccttgaattacttccacctggctgcagtacgtgattcttgatcccgagcttcgggtt
ggaagtgggtgggagagttcgaggccttgcgcttaaggagccccttcgcctcgtgcttgagttgaggcctggcctgggcgctg
gggccgccgcgtgcgaatctggtggcaccttcgcgcctgtctcgctgctttcgataagtctctagccatttaaaatttttgatgacct
gctgcgacgctttttttctggcaagatagtcttgtaaatgcgggccaagatctgcacactggtatttcggtttttggggccgcgggc
ggcgacggggcccgtgcgtcccagcgcacatgttcggcgaggcggggcctgcgagcgcggccaccgagaatcggacggg
ggtagtctcaagctggccggcctgctctggtgcctggcctcgcgccgccgtgtatcgccccgccctgggcggcaaggctggc
ccggtcggcaccagttgcgtgagcggaaagatggccgcttcccggccctgctgcagggagctcaaaatggaggacgcggcg
ctcgggagagcgggcgggtgagtcacccacacaaaggaaaagggcctttccgtcctcagccgtcgcttcatgtgactccacgg
agtaccgggcgccgtccaggcacctcgattagttctcgtgcttttggagtacgtcgtctttaggttggggggaggggttttatgcg
atggagtttccccacactgagtgggtggagactgaagttaggccagcttggcacttgatgtaattctccttggaatttgccctttttg
agtttggatcttggttcattctcaagcctcagacagtggttcaaagtttttttcttccatttcaggtgtcgtgagctagaATGGGG
GGACTTGAACCCTGCAGCAGGCTCCTGCTCCTGCCTCTCCTGCTGGCTGTAAG
TGGTCTCCGTCCTGTCCAGGCCCAGGCCCAGAGCGATTGCAGTTGCTCTACGG
TGAGCCCGGGCGTGCTGGCAGGGATCGTGATGGGAGACCTGGTGCTGACAGT
GCTCATTGCCCTGGCCGTGTACTTCCTGGGCCGGCTGGTCCCTCGGGGGCGAG
GGGCTGCGGAGGCAGCGACCCGGAAACAGCGTATCACTGAGACCGAGTCGC
CTTATCAGGAGCTCCAGGGTCAGAGGTCGGATGTCTACAGCGACCTCAACAC
ACAGAGGCCGTATTACAAAgTCGAGGGCGGCGGAGAGGGCAGAGGAAGTCT
TCTAACATGCGGTGACGTGGAGGAGAATCCCGGCCCTAGGatggccttaccagtgaccg
ccttgctcctgccgctggccttgctgctccacgccgccaggccgggatccGACATCCAGATGACACAGACT
ACATCCTCCCTGTCTGCCTCTCTGGGAGACAGAGTCACCATCAGTTGCAGGGC
AAGTCAGGACATTAGTAAATATTTAAATTGGTATCAGCAGAAACCAGATGGA
ACTGTTAAACTCCTGATCTACCATACATCAAGATTACACTCAGGAGTCCCATC
AAGGTTCAGTGGCAGTGGGTCTGGAACAGATTATTCTCTCACCATTAGCAAC
CTGGAGCAAGAAGATATTGCCACTTACTTTTGCCAACAGGGTAATACGCTTCC
GTACACGTTCGGAGGGGGGACTAAGTTGGAAATAACAGGTGGCGGTGGCTCG
GGCGGTGGTGGGTCGGGTGGCGGCGGATCTGAGGTGAAACTGCAGGAGTCA
GGACCTGGCCTGGTGGCGCCCTCACAGAGCCTGTCCGTCACATGCACTGTCTC
AGGGGTCTCATTACCCGACTATGGTGTAAGCTGGATTCGCCAGCCTCCACGA
AAGGGTCTGGAGTGGCTGGGAGTAATATGGGGTAGTGAAACCACATACTATA
ATTCAGCTCTCAAATCCAGACTGACCATCATCAAGGACAACTCCAAGAGCCA
AGTTTTCTTAAAAATGAACAGTCTGCAAACTGATGACACAGCCATTTACTACT
GTGCCAAACATTATTACTACGGTGGTAGCTATGCTATGGACTACTGGGGTCA
AGGAACCTCAGTCACCGTCTCCTCAgctagcACGCGTggtggcggaggttctggaggtgggggtt
cccagggggcctggccacatgagggagtccacagaaaaccttccctcctggcccacccaggtcccctggtgaaatcagaaga
gacagtcatcctgcaatgttggtcagatgtcaggtttgagcacttccttctgcacagagaggggaagtataaggacactttgcacc
tcattggagagcaccatgatggggtctccaaggccaacttctccatcggtcccatgatgcaagaccttgcagggacctacagatg
ctacggttctgttactcactcccccctatcagttgtcagctcccagtgaccctctggacatcgtcatcacaggtctatatgagaaacct
tctctctcagcccagccgggccccacggttttggcaggagagagcgtgaccttgtcctgcagctcccggagctcctatgacatgt
accatctatccagggaggggggaggcccatgaacgtaggttctctgcagggcccaaggtcaacggaacattccaggccgacttt
cctctgggccctgccacccacggaggaacctacagatgcttcggctctttccgtgactctccctatgagtggtcaaactcgagtg
acccactgcttgtttctgtcacaggaaacccttcaaatagttggccttcacccactgaaccaagctccaaaaccggtaaccccaga
cacctgcatgttctgattgggacctcagtggtcaaaatccctttcaccatcctcctcttctttctccttcatcgctggtgctccaacaaa
aaaaatgctgctgtaatggaccaagagcctgcagggaacagaacagtgaacagcgaggattctgatgaacaagaccatcagg
aggtgtcatacgcataaGtcgacaatcaacctctggattacaaaatttgtgaaagattgactggtattcttaactatgttgctcctttta
cgctatgtggatacgctgctttaatgcctttgtatcatgctattgcttcccgtatggctttcattttctcctccttgtataaatcctggttgc
tgtctctttatgaggagttgtggcccgttgtcaggcaacgtggcgtggtgtgcactgtgtttgctgacgcaacccccactggttggg
gcattgccaccacctgtcagctcctttccgggactttcgctttccccctccctattgccacggcggaactcatcgccgcctgccttg
cccgctgctggacaggggctcggctgttgggcactgacaattccgtggtgttgtcggggaagctgacgtcctttccatggctgct
cgcctgtgttgccacctggattctgcgcgggacgtccttctgctacgtcccttcggccctcaatccagcggaccttccttcccgcg
gcctgctgccggctctgcggcctcttccgcgtcttcgccttcgccctcagacgagtcggatctccctttgggccgcctccccgcct
ggaattcgagctcggtacctttaagaccaatgacttacaaggcagctgtagatcttagccactttttaaaagaaaaggggggactg
gaagggctaattcactcccaacgaagacaagatctgcttttttgcttgtactgggtctctctggttagaccagatctgagcctgggag
ctctctggctaactagggaacccactgcttaagcctcaataaagcttgccttgagtgcttcaagtagtgtgtgcccgtctgttgtgtg
actctggtaactagagatccctcagacccttttagtcagtgtggaaaatctctagcagtagtagttcatgtcatcttattattcagtattt
ataacttgcaaagaaatgaatatcagagagtgagaggaacttgtttattgcagcttataatggttacaaataaagcaatagcatcac
aaatttcacaaataaagcatttttttcactgcattctagttgtggtttgtccaaactcatcaatgtatcttatcatgtctggctctagctatc
ccgcccctaactccgcccagttccgcccattctccgccccatggctgactaattttttttatttatgcagaggccgaggccgcctcg
gcctctgagctattccagaagtagtgaggaggcttttttggaggcctacgcttttgcgtcgagacgtacccaattcgccctatagtg
agtcgtattacgcgcgctcactggccgtcgttttacaacgtcgtgactgggaaaaccctggcgttacccaacttaatcgccttgca
gcacatccccctttcgccagctggcgtaatagcgaagaggcccgcaccgatcgcccttcccaacagttgcgcagcctgaatgg
cgaatggcgcgacgcgccctgtagcggcgcattaagcgcggcgggtgtggtggttacgcgcagcgtgaccgctacacttgcc
agcgccctagcgcccgctcctttcgctttcttcccttcctttctcgccacgttcgccggctttccccgtcaagctctaaatcgggggc -continued tccctttagggttccgatttagtgctttacggcacctcgaccccaaaaaacttgattagggtgatggttcacgtagtgggccatcgc
cctgatagacggtttttcgccctttgacgttggagtccacgttctttaatagtggactcttgttccaaactggaacaacactcaaccct
atctcggtctattcttttgatttataagggattttgccgatttcggcctattggttaaaaaatgagctgatttaacaaaaatttaacgcga
attttaacaaaatattaacgtttacaatttcccaggtggcacttttcggggaaatgtgcgcggaacccctatttgtttatttttctaaata
cattcaaatatgtatccgctcatgagacaataaccctgataaatgcttcaataatattgaaaaaggaagagtatgagtattcaacattt
ccgtgtcgcccttattcccttttttgcggcattttgccttcctgtttttgctcacccagaaacgctggtgaaagtaaaagatgctgaag
atcagttgg CD19-PD1 chimeric CAR sequence (SEQ ID NO: 5)

TGATGCGGTATTTTCTCCTTACGCATCTGTGCGGTATTTCACACCGCATATGG
TGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCC
GCTTACAGACAAGCTGTGACCGTCTCCGGGAGCTGCATGTGTCAGAGGTTTTC
ACCGTCATCACCGAAACGCGCGAGACGAAAGGGCCTCGTGATACGCCTATTT
TTATAGGTTAATGTCATGATAATAATGGTTTCTTAGACGTCAGGTGGCACTTT
TCGGGGAAATGTGCGCGGAACCCCTATTTGTTTATTTTTCTAAATACATTCAA
ATATGTATCCGCTCATGAGACAATAACCCTGATAAATGCTTCAATAATATTGA
AAAAGGAAGAGTATGAGTATTCAACATTTCCGTGTCGCCCTTATTCCCTTTTT
TGCGGCATTTTGCCTTCCTGTTTTTGCTCACCCAGAAACGCTGGTGAAAGTAA
AAGATGCTGAAGATCAGTTGGGTGCACGAGTGGGTTACATCGAACTGGATCT
CAACAGCGGTAAGATCCTTGAGAGTTTTCGCCCCGAAGAACGTTTTCCAATG
ATGAGCACTTTTAAAGTTCTGCTATGTGGCGCGGTATTATCCCGTATTGACGC
CGGGCAAGAGCAACTCGGTCGCCGCATACACTATTCTCAGAATGACTTGGTT
GAGTACTCACCAGTCACAGAAAAGCATCTTACGGATGGCATGACAGTAAGAG
AATTATGCAGTGCTGCCATAACCATGAGTGATAACACTGCGGCCAACTTACTT
CTGACAACGATCGGAGGACCGAAGGAGCTAACCGCTTTTTTGCACAACATGG
GGGATCATGTAACTCGCCTTGATCGTTGGGAACCGGAGCTGAATGAAGCCAT
ACCAAACGACGAGCGTGACACCACGATGCCTGTAGCAATGGCAACAACGTTG
CGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTT
CCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTT
ATCTACACGACGGGGAGTCAGGCAACTATGGATGAACGAAATAGACAGATC
GCTGAGATAGGTGCCTCACTGATTAAGCATTGGTAACTGTCAGACCAAGTTT
ACTCATATATACTTTAGATTGATTTAAAACTTCATTTTTAATTTAAAAGGATCT
AGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAG
ATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGT
AACTGGCTTCAGCAGAGCGCAGATACCAAATACTGTTCTTCTAGTGTAGCCGT
AGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACG
GGGGGTTCGTGCACACAGCCCAGCTTGGAGCGAACGACCTACACCGAACTGA
GATACCTACAGCGTGAGCTATGAGAAAGCGCCACGCTTCCCGAAGGGAGAA
AGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGC
CACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGC
CTTTTGCTCACATGTTCTTTCCTGCGTTATCCCCTGATTCTGTGGATAACCGTA
TTACCGCCTTTGAGTGAGCTGATACCGCTCGCCGCAGCCGAACGACCGAGCG
CAGCGAGTCAGTGAGCGAGGAAGCGGAAGAGCGCCCAATACGCAAACCGCC
TCTCCCCGCGCGTTGGCCGATTCATTAATGCAGCTGGCACGACAGGTTTCCCG
ACTGGAAAGCGGGCAGTGAGCGCAACGCAATTAATGTGAGTTAGCTCACTCA
TTAGGCACCCCAGGCTTTACACTTTATGCTTCCGGCTCGTATGTTGTGTGGAA
TTGTGAGCGGATAACAATTTCACACAGGAAACAGCTATGACCATGATTACGC
CAAGCTCTAATACGACTCACTATAGGGAGACAAGCTTGCATGCCTGCAGGTC
GACATGGCCTTACCAGTGACCGCCTTGCTCCTGCCGCTGGCCTTGCTGCTCCA
CGCCGCCAGGCCGGACATCCAGATGACACAGACTACATCCTCCCTGTCTGCC
TCTCTGGGAGACAGAGTCACCATCAGTTGCAGGGCAAGTCAGGACATTAGTA
AATATTTAAATTGGTATCAGCAGAAACCAGATGGAACTGTTAAACTCCTGAT
CTACCATACATCAAGATTACACTCAGGAGTCCCATCAAGGTTCAGTGGCAGT
GGGTCTGGAACAGATTATTCTCTCACCATTAGCAACCTGGAGCAAGAAGATA
TTGCCACTTACTTTTGCCAACAGGGTAATACGCTTCCGTACACGTTCGGAGGG
GGGACTAAGTTGGAAATAACAGGTGGCGGTGGCTCGGGCGGTGGTGGGTCG
GGTGGCGGCGGATCTGAGGTGAAACTGCAGGAGTCAGGACCTGGCCTGGTGG
CGCCCTCACAGAGCCTGTCCGTCACATGCACTGTCTCAGGGGTCTCATTACCC
GACTATGGTGTAAGCTGGATTCGCCAGCCTCCACGAAAGGGTCTGGAGTGGC
TGGGAGTAATATGGGGTAGTGAAACCACATACTATAATTCAGCTCTCAAATC
CAGACTGACCATCATCAAGGACAACTCCAAGAGCCAAGTTTTCTTAAAAATG
AACAGTCTGCAAACTGATGACACAGCCATTTACTACTGTGCCAAACATTATTA
CTACGGTGGTAGCTATGCTATGGACTACTGGGGTCAAGGAACCTCAGTCACC
GTCTCCTCAGctagcACGCGTggtggcggaggttctggaggtgggggttccaccctggtggttggtgtcgtgggc
ggcctgctgggcagcctggtgctgctagtctgggtcctggccgtcatctgctcccgggccgcacgagggacaataggagcca
ggcgcaccggccagcccctgaaggaggacccctcagccgtgcctgtgttctctgtggactatggggagctggatttccagtgg
cgagagaagaccccggagccccccgtgccctgtgtccctgagcagacggagtatgccaccattgtctttcctagcggaatggg
cacctcatcccccgcccgcaggggctcagctgacggccctcggagtgcccagccactgaggcctgaggatggacactgctct
tggcccctctgaGGATCCCCGGGTACCGAGCTCGAATTCAAAAAAAAAAAAAAAA
AAAAAAAAAAAAAAAAAAAAAAAAAAAAAAAAAAAAAAAAAAAAAAACTA
GTGGCGCC -continued

DAP12-T2A-SS1-KIRS2

(SEQ ID NO: 6)

1464 bp DNA

| FEATURES | Location |
|---|---|
| DAP12 | 1 . . . 339 |
| T2A sequence | 352 . . . 408 |
| SS1-scFv | 481 . . . 1200 |
| GS-linker | 1207 . . . 1236 |
| KIR2DS2-derived sequence | 1237 . . . 1464 |

ATGGGGGGAC TTGAACCCTG CAGCAGGTTC CTGCTCCTGC CTCTCCTGCT GGCTGTAAGT
GGTCTCCGTC CTGTCCAGGT CCAGGCCCAG AGCGATTGCA GTTGCTCTAC GGTGAGCCCG
GGCGTGCTGG CAGGGATCGT GATGGGAGAC CTGGTGCTGA CAGTGCTCAT TGCCCTGGCC
GTGTACTTCC TGGGCCGGCT GGTCCCTCGG GGGCGAGGGG CTGCGGAGGC AGCGACCCGG
AAACAGCGTA TCACTGAGAC CGAGTCGCCT TATCAGGAGC TCCAGGGTCA GAGGTCGGAT
GTCTACAGCG ACCTCAACAC ACAGAGGCCG TATTACAAAG TCGAGGGCGG CGGAGAGGGC
AGAGGAAGTC TTCTAACATG CGGTGACGTG GAGGAGAATC CCGGCCCTAG GATGGCCTTA
CCAGTGACCG CCTTGCTCCT GCCGCTGGCC TTGCTGCTCC ACGCCGCCAG GCCGGGATCC
CAGGTACAAC TGCAGCAGTC TGGGCCTGAG CTGGAGAAGC CTGGCGCTTC AGTGAAGATA
TCCTGCAAGG CTTCTGGTTA CTCATTCACT GGCTACACCA TGAACTGGGT GAAGCAGAGC
CATGGAAAGA GCCTTGAGTG GATTGGACTT ATTACTCCTT ACAATGGTGC TTCTAGCTAC
AACCAGAAGT TCAGGGGCAA GGCCACATTA ACTGTAGACA AGTCATCCAG CACAGCCTAC
ATGGACCTCC TCAGTCTGAC ATCTGAAGAC TCTGCAGTCT ATTTCTGTGC AAGGGGGGGT
TACGACGGGA GGGGTTTTGA CTACTGGGGC CAAGGGACCA CGGTCACCGT CTCCTCAGGT
GGAGGCGGTT CAGGCGGCGG TGGCTCTAGC GGTGGTGGAT CGGACATCGA GCTCACTCAG
TCTCCAGCAA TCATGTCTGC ATCTCCAGGG GAGAAGGTCA CCATGACCTG CAGTGCCAGC
TCAAGTGTAA GTTACATGCA CTGGTACCAG CAGAAGTCAG GCACCTCCCC CAAAAGATGG
ATTTATGACA CATCCAAACT GGCTTCTGGA GTCCCAGGTC GCTTCAGTGG CAGTGGGTCT
GGAAACTCTT ACTCTCTCAC AATCAGCAGC GTGGAGGCTG AAGATGATGC AACTTATTAC
TGCCAGCAGT GGAGTAAGCA CCCTCTCACG TACGGTGCTG GGACAAAGTT GGAAATCAAA
GCTAGCGGTG GCGGAGGTTC TGGAGGTGGG GGTTCCTCAC CCACTGAACC AAGCTCCAAA
ACCGGTAACC CCAGACACCT GCATGTTCTG ATTGGGACCT CAGTGGTCAA AATCCCTTTC
ACCATCCTCC TCTTCTTTCT CCTTCATCGC TGGTGCTCCA ACAAAAAAAA TGCTGCTGTA
ATGGACCAAG AGCCTGCAGG GAACAGAACA GTGAACAGCG AGGATTCTGA TGAACAAGAC
CATCAGGAGG TGTCATACGC ATAA

DAP12-T2A-SS1-KIRS2

(SEQ ID NO: 7)

488 aa Protein

| FEATURES | Location |
|---|---|
| DAP12 | 1 . . . 113 |
| T2A seq | 118 . . . 136 |
| Signal_peptide from CD8alpha | 138 . . . 158 |
| SS1-scFv | 161 . . . 400 |
| GS-linker | 403 . . . 412 |
| KIR2DS2-derived seq | 413 . . . 487 |

Sequence
MGGLEPCSRF LLLPLLLAVS GLRPVQVQAQ SDCSCSTVSP GVLAGIVMGD LVLTVLIALA
VYFLGRLVPR GRGAAEAATR KQRITETESP YQELQGQRSD VYSDLNTQRP YYKVEGGGEG
RGSLLTCGDV EENPGPRMAL PVTALLLPLA LLLHAARPGS QVQLQQSGPE LEKPGASVKI
SCKASGYSFT GYTMNWVKQS HGKSLEWIGL ITPYNGASSY NQKFRGKATL TVDKSSSTAY
MDLLSLTSED SAVYFCARGG YDGRGFDYWG QGTTVTVSSG GGGSGGGGSS GGGSDIELTQ
SPAIMSASPG EKVTMTCSAS SSVSYMHWYQ QKSGTSPKRW IYDTSKLASG VPGRFSGSGS
GNSYSLTISS VEAEDDATYY CQQWSKHPLT YGAGTKLEIK ASGGGGSGGG GSSPTEPSSK
TGNPRHLHVL IGTSVVKIPF TILLFFLLHR WCSNKKNAAV MDQEPAGNRT VNSEDSDEQD
HQEVSYA FCERG-T2A-SS1-TNKp46

(SEQ ID NO: 8)

1365 bp DNA

| FEATURES | Location |
|---|---|
| FCERG | 1 . . . 258 |
| T2A | 271 . . . 327 |
| Signal peptide from CD8alpha | 331 . . . 393 |
| SS1-scFv | 400 . . . 1119 |
| GS-linker | 1126 . . . 1155 |
| NKp46-derived sequence | 1156 . . . 1365 |

Sequence
ATGATTCCAG CAGTGGTCTT GCTCTTACTC CTTTTGGTTG AACAAGCAGC GGCCCTGGGA
GAGCCTCAGC TCTGCTATAT CCTGGATGCC ATCCTGTTTC TGTATGGAAT TGTCCTCACC
CTCCTCTACT GCCGACTGAA GATCCAAGTG CGAAAGGCAG CTATAACCAG CTATGAGAAA
TCAGATGGTG TTTACACGGG CCTGAGCACC AGGAACCAGG AGACTTACGA GACTCTGAAG
CATGAGAAAC CACCACAGTC CGGAGGCGGC GGAGAGGGCA GAGGAAGTCT TCTAACATGC
GGTGACGTGG AGGAGAATCC CGGCCCTAGG ATGGCCTTAC CAGTGACCGC CTTGCTCCTG
CCGCTGGCCT TGCTGCTCCA CGCCGCCAGG CCGGGATCCC AGGTACAACT GCAGCAGTCT
GGGCCTGAGC TGGAGAAGCC TGGCGCTTCA GTGAAGATAT CCTGCAAGGC TTCTGGTTAC
TCATTCACTG GCTACACCAT GAACTGGGTG AAGCAGAGCC ATGGAAAGAG CCTTGAGTGG
ATTGGACTTA TTACTCCTTA CAATGGTGCT TCTAGCTACA ACCAGAAGTT CAGGGGCAAG
GCCACATTAA CTGTAGACAA GTCATCCAGC ACAGCCTACA TGGACCTCCT CAGTCTGACA
TCTGAAGACT CTGCAGTCTA TTTCTGTGCA AGGGGGGGTT ACGACGGGAG GGGTTTTGAC
TACTGGGGCC AAGGGACCAC GGTCACCGTC TCCTCAGGTG GAGGCGGTTC AGGCGGCGGT -continued

```
GGCTCTAGCG GTGGTGGATC GGACATCGAG CTCACTCAGT CTCCAGCAAT CATGTCTGCA
TCTCCAGGGG AGAAGGTCAC CATGACCTGC AGTGCCAGCT CAAGTGTAAG TTACATGCAC
TGGTACCAGC AGAAGTCAGG CACCTCCCCC AAAAGATGGA TTTATGACAC ATCCAAACTG
GCTTCTGGAG TCCCAGGTCG CTTCAGTGGC AGTGGGTCTG GAAACTCTTA CTCTCTCACA
ATCAGCAGCG TGGAGGCTGA AGATGATGCA ACTTATTACT GCCAGCAGTG GAGTAAGCAC
CCTCTCACGT ACGGTGCTGG GACAAAGTTG GAAATCAAAG CTAGCGGTGG CGGAGGTTCT
GGAGGTGGGG GTTCCTTAAC CACAGAGACG GGACTCCAGA AAGACCATGC CCTCTGGGAT
CACACTGCCC AGAATCTCCT TCGGATGGGC CTGGCCTTTC TAGTCCTGGT GGCTCTAGTG
TGGTTCCTGG TTGAAGACTG GCTCAGCAGG AAGAGGACTA GAGAGCGAGC CAGCAGAGCT
TCCACTTGGG AAGGCAGGAG AAGGCTGAAC ACACAGACTC TTTGA
```

FCERG-T2A-SS1-TNKp46

(SEQ ID NO: 9)

455aa Protein

| FEATURES | Location |
|---|---|
| FCERG | 1 . . . 86 |
| T2A | 91 . . . 109 |
| Signal peptide from CD8alpha | 111 . . . 131 |
| SS1-scFv | 134 . . . 373 |
| GS-liner | 376 . . . 385 |
| NKp46-derived sequence | 386 . . . 454 |

Sequence

```
MIPAVVLLLL LLVEQAAALG EPQLCYILDA ILFLYGIVLT LLYCRLKIQV RKAAITSYEK
SDGVYTGLST RNQETYETLK HEKPPQSGGG GEGRGSLLTC GDVEENPGPR MALPVTALLL
PLALLLHAAR PGSQVQLQQS GPELEKPGAS VKISCKASGY SFTGYTMNWV KQSHGKSLEW
IGLITPYNGA SSYNQKFRGK ATLTVDKSSS TAYMDLLSLT SEDSAVYFCA RGGYDGRGFD
YWGQGTTVTV SSGGGGSGGG GSSGGGGSDIE LTQSPAIMSA SPGEKVTMTC SASSSVSYMH
WYQQKSGTSP KRWIYDTSKL ASGVPGRFSG SGSGNSYSLT ISSVEAEDDA TYYCQQWSKH
PLTYGAGTKL EIKASGGGGS GGGGSLTTET GLQKDHALWD HTAQNLLRMG LAFLVLVALV
WFLVEDWLSR KRTRERASRA STWEGRRRLN TQTL
```

DAP12-T2A-CD19-KIRS2

(SEQ ID NO: 10)

1470 bp DNA

| FEATURES | Location |
|---|---|
| DAP12 | 1 . . . 339 |
| T2A sequence | 352 . . . 408 |
| CD19-scFv | 481 . . . 481 |
| GS-linker | 1213 . . . 1242 |
| KIR2DS2-derived sequence | 1243 . . . 1470 |

Sequence

```
ATGGGGGGAC TTGAACCCTG CAGCAGGTTC CTGCTCCTGC CTCTCCTGCT GGCTGTAAGT
GGTCTCCGTC CTGTCCAGGT CCAGGCCCAG AGCGATTGCA GTTGCTCTAC GGTGAGCCCG
GGCGTGCTGG CAGGGATCGT GATGGGAGAC CTGGTGCTGA CAGTGCTCAT TGCCCTGGCC
GTGTACTTCC TGGGCCGGCT GGTCCCTCGG GGGCGAGGGG CTGCGGAGGC AGCGACCCGG
AAACAGCGTA TCACTGAGAC CGAGTCGCCT TATCAGGAGC TCCAGGGTCA GAGGTCGGAT
GTCTACAGCG ACCTCAACAC ACAGAGGCCG TATTACAAAG TCGAGGGCGG CGGAGAGGGC
AGAGGAAGTC TTCTAACATG CGGTGACGTG GAGGAGAATC CCGGCCCTAG GATGGCCTTA
CCAGTGACCG CCTTGCTCCT GCCGCTGGCC TTGCTGCTCC ACGCCGCCAG GCCGGGATCC
GACATCCAGA TGACACAGAC TACATCCTCC CTGTCTGCCT CTCTGGGAGA CAGAGTCACC
ATCAGTTGCA GGGCAAGTCA GGACATTAGT AAATATTTAA ATTGGTATCA GCAGAAACCA
GATGGAACTG TTAAACTCCT GATCTACCAT ACATCAAGAT TACACTCAGG AGTCCCATCA
AGGTTCAGTG GCAGTGGGTC TGGAACAGAT TATTCTCTCA CCATTAGCAA CCTGGAGCAA
GAAGATATTG CCACTTACTT TTGCCAACAG GGTAATACGC TTCCGTACAC GTTCGGAGGG
GGGACTAAGT TGGAAATAAC AGGTGGCGGT GGCTCGGGCG GTGGTGGGTC GGGTGGCGGC
GGATCTGAGG TGAAACTGCA GGAGTCAGGA CCTGGCCTGG TGGCGCCCTC ACAGAGCCTG
TCCGTCACAT GCACTGTCTC AGGGGTCTCA TTACCCGACT ATGGTGTAAG CTGGATTCGC
CAGCCTCCAC GAAAGGGTCT GGAGTGGCTG GGAGTAATAT GGGGTAGTGA AACCACATAC
TATAATTCAG CTCTCAAATC CAGACTGACC ATCATCAAGG ACAACTCCAA GAGCCAAGTT
TTCTTAAAAA TGAACAGTCT GCAAACTGAT GACACAGCCA TTTACTACTG TGCCAAACAT
TATTACTACG GTGGTAGCTA TGCTATGGAC TACTGGGGTC AAGGAACCTC AGTCACCGTC
TCCTCAGCTA GCGGTGGCGG AGGTTCTGGA GGTGGGGGTT CCTCACCCAC TGAACCAAGC
TCCAAAACCG GTAACCCCAG ACACCTGCAT GTTCTGATTG GGACCTCAGT GGTCAAAATC
CCTTTCACCA TCCTCCTCTT CTTTCTCCTT CATCGCTGGT GCTCCAACAA AAAAAATGCT
GCTGTAATGG ACCAAGAGCC TGCAGGGAAC AGAACAGTGA ACAGCGAGGA TTCTGATGAA
CAAGACCATC AGGAGGTGTC ATACGCATAA
```

DAP12-T2A-CD19-KIRS2

(SEQ ID NO: 11)

489 aa Protein

| FEATURES | Location |
|---|---|
| DAP12 | 1 . . . 113 |
| T2A seq | 118 . . . 136 |
| Signal_peptide from CD8alpha | 138 . . . 158 |
| CD19-scFv | 161 . . . 402 |
| GS-linker | 405 . . . 414 |
| KIR2DS2-derived seq | 415 . . . 489 |

Sequence

```
MGGLEPCSRF LLLPLLLAVS GLRPVQVQAQ SDCSCSTVSP GVLAGIVMGD LVLTVLIALA
VYFLGRLVPR GRGAAEAATR KQRITETESP YQELQGQRSD VYSDLNTQRP YYKVEGGGEG
RGSLLTCGDV EENPGPRMAL PVTALLLPLA LLLHAARPGS DIQMTQTTSS LSASLGDRVT
```

-continued

```
ISCRASQDIS KYLNWYQQKP DGTVKLLIYH TSRLHSGVPS RFSGSGSGTD YSLTISNLEQ
EDIATYFCQQ GNTLPYTFGG GTKLEITGGG GSGGGGSGGG GSEVKLQESG PGLVAPSQSL
SVTCTVSGVS LPDYGVSWIR QPPRKGLEWL GVIWGSETTY YNSALKSRLT IIKDNSKSQV
FLKMNSLQTD DTAIYYCAKH YYYGGSYAMD YWGQGTSVTV SSASGGGGSG GGGSSPTEPS
SKTGNPRHLH VLIGTSVVKI PFTILLFFLL HRWCSNKKNA AVMDQEPAGN RTVNSEDSDE
QDHQEVSYA*
```

4-1BB Intracellular domain (amino acid sequence)

(SEQ ID NO: 12)

KRGRKKLLYIFKQPFMRPVQTTQEEDGCSCRFPEEEEGGCEL

CD3 zeta domain (amino acid sequence)

(SEQ ID NO: 13)

```
RVKFSRSADAPAYKQGQNQLYNELNLGRREEYDVLDKRRGRDPEMGGKPRRK
NPQEGLYNELQKDKMAEAYSEIGMKGERRRGKGHDGLYQGLSTATKDTYDAL
HMQALPPR
```

Cytoplasmic Domain of PD1

(SEQ ID NO: 14)

Amino acids 192-288

```
CSRAARGTIGARRTGQPLKEDPSAVPVFSVDYGELDFQWREKTPEPPVPCVPEQT
EYATIVFPSGMGTSSPARRGSADGPRSAQPLRPEDGHCSWPL
```

Cytoplasmic Domain of CTLA-4

(SEQ ID NO: 15)

Amino acids 183-223

AVSLSKMLKKRSPLTTGVYVKMPPTEPECEKQFQPYFIPIN

IgG4H-hinge translation (SEQ ID NO: 49)

230 aa linear UNA

```
ESKYGPPCPP CPAPEFLGGP SVFLFPPKPK DTLMISRTPE VTCVVVDVSQ
EDPEVQFNWYVDGVEVHNAK TKPREEQFNS TYRVVSVLTV LHQDWLNGKE
YKCKVSNKGL PSSIEKTISK AKGQPREPQV YTLPPSQEEM TKNQVSLTCL
VKGFYPSDIA VEWESNGQPE NNYKTTPPVL DSDGSFFLYS RLTVDKSRWQ
EGNVFSCSVM HEALHNHYTQ KSLSLSLGKM
```

IgDH-hinge translation (SEQ ID NO: 50)

282 aa linear UNA

```
RWPESPKAQA SSVPTAQPQA EGSLAKATTA PATTRNTGRG GEEKKKEKEK
EEQEERETKT PECPSHTQPL GVYLLTPAVQ DLWLRDKATF TCFVVGSDLK
DAHLTWEVAG KVPTGGVEEG LLERHSNGSQ SQHSRLTLPR SLWNAGTSVT
CTLNHPSLPP QRLMALREPA AQAPVKLSLN LLASSDPPEA ASWLLCEVSG
FSPPNILLMW LEDQREVNTS GFAPARPPPQ PGSTTFWAWS VLRVPAPPSP
QPATYTCVVS HEDSRTLLNA SRSLEVSYVT DH
```

Human CD8 hinge (SEQ ID NO: 51)

43 aa linear UNA 10-FEB-2009

TTTPAPRPPT PAPTIASQPL SLRPEACRPA AGGAVHTRGL DFA

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A purified, or non-naturally occurring, activating killer cell immunoglobulin-like receptor chimeric antigen receptor (actKIR-CAR) comprising:

an extra-cellular antigen binding domain from an antibody molecule or a non-antibody scaffold;

an activating killer cell immunoglobulin-like receptor (actKIR) transmembrane domain; and a cytoplasmic domain.

2. The actKIR-CAR of claim 1, wherein said actKIR transmembrane domain can interact with the transmembrane domain of a DAP12 polypeptide.

3. The actKIR-CAR of claim 2, wherein said actKIR transmembrane domain comprises a positively charged moiety.

4. The actKIR-CAR of claim 1, wherein said cytoplasmic domain is a KIR-cytoplasmic domain.

5. The actKIR-CAR of claim 1, wherein said antigen binding domain from an antibody molecule comprises a scFv.

6. The actKIR-CAR of claim 1, further comprising an extracellular hinge domain.

7. The actKIR-CAR of claim 1, comprising an extracellular hinge domain that:

(i) is other than a KIR hinge domain;

(ii) is derived from a natural molecule;

(iii) comprises a non-naturally occurring polypeptide sequence;

(iv) is from human CD8-alpha subunit;

(v) is of less than 50, 20, or 10 amino acids in length, or (vi) has fewer amino acids than a KIR2DS2 hinge domain.

8. The actKIR-CAR of claim 1, wherein said actKIR-CAR comprises an actKIR cytoplasmic domain.

9. The actKIR-CAR of claim 1, wherein said actKIR-CAR can interact with and promote signaling from an Immunoreceptor Tyrosine-based Activation Motif (ITAM)-containing polypeptide.

10. The actKIR-CAR of claim 1, wherein said actKIR-CAR comprises a KIR D domain.

11. The actKIR-CAR of claim 1, wherein said actKIR-CAR comprises a KIR D1 domain or a KIR D2 domain.

12. The actKIR-CAR of claim 1, wherein said actKIR-CAR does not comprise a KIR D domain.

13. The actKIR-CAR of claim 1, wherein said KIR-CAR comprises a KIR2DS2 transmembrane domain or comprises a KIR2DS2 cytoplasmic domain.

14. The actKIR-CAR of claim 1, wherein said antigen binding domain from an antibody molecule binds an antigen present on a cancer cell.

15. The actKIR-CAR of claim 1, wherein said actKIR-CAR can interact with and promote signaling from a DAP12 or DAP10 polypeptide.

16. The actKIR-CAR of claim 1, wherein said actKIR-CAR can interact with and promote signaling from a DAP12 polypeptide.

17. The actKIR-CAR of claim 1, wherein said antigen binding domain from an antibody molecule comprises an immunoglobulin single domain antibody (sdAb).

18. The actKIR-CAR of claim 1, wherein said antigen binding domain from an antibody molecule comprises a single light chain variable domain (VL).

19. The actKIR-CAR of claim 1, wherein said antigen binding domain from an antibody molecule comprises a single heavy chain variable domain (VH).

20. The actKIR-CAR of claim 1, wherein said antigen binding domain from an antibody molecule comprises a nanobody.

21. The actKIR-CAR of claim 1, wherein said antigen binding domain from an antibody molecule binds an antigen present on a solid tumor cell.

22. The actKIR-CAR of claim 1, wherein said antigen binding domain from an antibody molecule binds an antigen present on a hematological tumor cell.

23. The actKIR-CAR of claim 1, wherein said antigen binding domain from an antibody molecule binds CD19, mesothelin, CD123, or BCMA.

* * * * *

SEQUENCE LISTING

```
<160> NUMBER OF SEQ ID NOS: 77

<210> SEQ ID NO 1
<211> LENGTH: 9810
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

gtgcacgagt gggttacatc gaactggatc tcaacagcgg taagatcctt gagagttttc      60

gccccgaaga acgttttcca atgatgagca cttttaaagt tctgctatgt ggcgcggtat     120

tatcccgtat tgacgccggg caagagcaac tcggtcgccg catacactat tctcagaatg     180
```

-continued

```
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga gatccttttt ttctgcgcgt aatctgctgc ttgcaaacaa    960
aaaaaccacc gctaccagcg gtggtttgtt tgccggatca agagctacca actctttttc   1020
cgaaggtaac tggcttcagc agagcgcaga taccaaatac tgtccttcta gtgtagccgt   1080
agttaggcca ccacttcaag aactctgtag caccgcctac atacctcgct ctgctaatcc   1140
tgttaccagt ggctgctgcc agtggcgata agtcgtgtct taccgggttg gactcaagac   1200
gatagttacc ggataaggcg cagcggtcgg gctgaacggg gggttcgtgc acacagccca   1260
gcttggagcg aacgacctac accgaactga gatacctaca gcgtgagcta tgagaaagcg   1320
ccacgcttcc cgaagggaga aaggcggaca ggtatccggt aagcggcagg gtcggaacag   1380
gagagcgcac gagggagctt ccagggggaa acgcctggta tctttatagt cctgtcgggt   1440
ttcgccacct ctgacttgag cgtcgatttt tgtgatgctc gtcagggggg cggagcctat   1500
ggaaaaacgc cagcaacgcg gcctttttac ggttcctggc cttttgctgg ccttttgctc   1560
acatgttctt tcctgcgtta tcccctgatt ctgtggataa ccgtattacc gcctttgagt   1620
gagctgatac cgctcgccgc agccgaacga ccgagcgcag cgagtcagtg agcgaggaag   1680
cggaagagcg cccaatacgc aaaccgcctc tccccgcgcg ttggccgatt cattaatgca   1740
gctggcacga caggtttccc gactggaaag cgggcagtga gcgcaacgca attaatgtga   1800
gttagctcac tcattaggca ccccaggctt tacactttat gcttccggct cgtatgttgt   1860
gtggaattgt gagcggataa caatttcaca caggaaacag ctatgaccat gattacgcca   1920
agcgcgcaat taaccctcac taaagggaac aaaagctgga gctgcaagct taatgtagtc   1980
ttatgcaata ctcttgtagt cttgcaacat ggtaacgatg agttagcaac atgccttaca   2040
aggagagaaa aagcaccgtg catgccgatt ggtggaagta aggtggtacg atcgtgcctt   2100
attaggaagg caacagacgg gtctgacatg gattggacga accactgaat tgccgcattg   2160
cagagatatt gtatttaagt gcctagctcg atacaataaa cgggtctctc tggttagacc   2220
agatctgagc ctgggagctc tctggctaac tagggaaccc actgcttaag cctcaataaa   2280
gcttgccttg agtgcttcaa gtagtgtgtg cccgtctgtt gtgtgactct ggtaactaga   2340
gatccctcag acccttttag tcagtgtgga aaatctctag cagtggcgcc cgaacaggga   2400
cctgaaagcg aaagggaaac cagagctctc tcgacgcagg actcggcttg ctgaagcgcg   2460
cacggcaaga ggcgaggggc ggcgactggt gagtacgcca aaaattttga ctagcggagg   2520
```

```
ctagaaggag agagatgggt gcgagagcgt cagtattaag cgggggagaa ttagatcgcg   2580
atgggaaaaa attcggttaa ggccaggggg aaagaaaaaa tataaattaa aacatatagt   2640
atgggcaagc agggagctag aacgattcgc agttaatcct ggcctgttag aaacatcaga   2700
aggctgtaga caaatactgg gacagctaca accatccctt cagacaggat cagaagaact   2760
tagatcatta tataatacag tagcaaccct ctattgtgtg catcaaagga tagagataaa   2820
agacaccaag gaagctttag acaagataga ggaagagcaa aacaaaagta agaccaccgc   2880
acagcaagcg gccgctgatc ttcagacctg gaggaggaga tatgagggac aattggagaa   2940
gtgaattata taaatataaa gtagtaaaaa ttgaaccatt aggagtagca cccaccaagg   3000
caaagagaag agtggtgcag agagaaaaaa gagcagtggg aataggagct ttgttccttg   3060
ggttcttggg agcagcagga agcactatgg gcgcagcctc aatgacgctg acggtacagg   3120
ccagacaatt attgtctggt atagtgcagc agcagaacaa tttgctgagg gctattgagg   3180
cgcaacagca tctgttgcaa ctcacagtct ggggcatcaa gcagctccag gcaagaatcc   3240
tggctgtgga aagataccta aaggatcaac agctcctggg gatttggggt tgctctggaa   3300
aactcatttg caccactgct gtgccttgga atgctagttg gagtaataaa tctctggaac   3360
agattggaat cacacgacct ggatggagtg ggacagagaa attaacaatt acacaagctt   3420
aatacactcc ttaattgaag aatcgcaaaa ccagcaagaa aagaatgaac aagaattatt   3480
ggaattagat aaatgggcaa gtttgtggaa ttggtttaac ataacaaatt ggctgtggta   3540
tataaaatta ttcataatga tagtaggagg cttggtaggt ttaagaatag tttttgctgt   3600
actttctata gtgaatagag ttaggcaggg atattcacca ttatcgtttc agacccacct   3660
cccaaccccg aggggacccg acaggcccga aggaatagaa gaagaaggtg gagagagaga   3720
cagagacaga tccattcgat tagtgaacgg atctcgacgg tatcgattag actgtagccc   3780
aggaatatgg cagctagatt gtacacattt agaaggaaaa gttatcttgg tagcagttca   3840
tgtagccagt ggatatatag aagcagaagt aattccagca gagacagggc aagaaacagc   3900
atacttcctc ttaaaattag caggaagatg gccagtaaaa acagtacata cagacaatgg   3960
cagcaatttc accagtacta cagttaaggc cgcctgttgg tgggcgggga tcaagcagga   4020
atttggcatt ccctacaatc cccaaagtca aggagtaata gaatctatga ataaagaatt   4080
aaagaaaatt ataggacagg taagagatca ggctgaacat cttaagacag cagtacaaat   4140
ggcagtattc atccacaatt ttaaaagaaa aggggggatt ggggggtaca gtgcagggga   4200
aagaatagta gacataatag caacagacat acaaactaaa gaattacaaa aacaaattac   4260
aaaaattcaa aattttcggg tttattacag ggacagcaga gatccagttt ggctgcatac   4320
gcgtcgtgag gctccggtgc ccgtcagtgg gcagagcgca catcgcccac agtccccgag   4380
aagttggggg gaggggtcgg caattgaacc ggtgcctaga gaaggtggcg cggggtaaac   4440
tgggaaagtg atgtcgtgta ctggctccgc ctttttcccg agggtggggg agaaccgtat   4500
ataagtgcag tagtcgccgt gaacgttctt tttcgcaacg ggtttgccgc cagaacacag   4560
gtaagtgccg tgtgtggttc ccgcgggcct ggcctcttta cgggttatgg cccttgcgtg   4620
ccttgaatta cttccacctg gctgcagtac gtgattcttg atcccgagct tcgggttgga   4680
agtgggtggg agagttcgag gccttgcgct taaggagccc cttcgcctcg tgcttgagtt   4740
gaggcctggc ctgggcgctg gggccgccgc gtgcgaatct ggtggcacct tcgcgcctgt   4800
ctcgctgctt tcgataagtc tctagccatt taaaattttt gatgacctgc tgcgacgctt   4860
tttttctggc aagatagtct tgtaaatgcg ggccaagatc tgcacactgg tatttcggtt   4920
```

```
tttggggccg cgggcggcga cggggcccgt gcgtcccagc gcacatgttc ggcgaggcgg   4980
ggcctgcgag cgcggccacc gagaatcgga cgggggtagt ctcaagctgg ccggcctgct   5040
ctggtgcctg gcctcgcgcc gccgtgtatc gccccgccct gggcggcaag gctggcccgg   5100
tcggcaccag ttgcgtgagc ggaaagatgg ccgcttcccg gccctgctgc agggagctca   5160
aaatggagga cgcggcgctc gggagagcgg gcgggtgagt cacccacaca aaggaaaagg   5220
gcctttccgt cctcagccgt cgcttcatgt gactccacgg agtaccgggc gccgtccagg   5280
cacctcgatt agttctcgtg cttttggagt acgtcgtctt taggttgggg ggaggggttt   5340
tatgcgatgg agtttcccca cactgagtgg gtggagactg aagttaggcc agcttggcac   5400
ttgatgtaat tctccttgga atttgccctt tttgagtttg gatcttggtt cattctcaag   5460
cctcagacag tggttcaaag tttttttctt ccatttcagg tgtcgtgagc tagaatgggg   5520
ggacttgaac cctgcagcag gctcctgctc ctgcctctcc tgctggctgt aagtggtctc   5580
cgtcctgtcc aggcccaggc ccagagcgat tgcagttgct ctacggtgag cccgggcgtg   5640
ctggcaggga tcgtgatggg agacctggtg ctgacagtgc tcattgccct ggccgtgtac   5700
ttcctgggcc ggctggtccc tcgggggcga ggggctgcgg aggcagcgac ccggaaacag   5760
cgtatcactg agaccgagtc gccttatcag gagctccagg gtcagaggtc ggatgtctac   5820
agcgacctca acacacagag gccgtattac aaagtcgagg gcggcggaga gggcagagga   5880
agtcttctaa catgcggtga cgtggaggag aatcccggcc ctaggatggc cttaccagtg   5940
accgccttgc tcctgccgct ggccttgctg ctccacgccg ccaggccggg atcccaggta   6000
caactgcagc agtctgggcc tgagctggag aagcctggcg cttcagtgaa gatatcctgc   6060
aaggcttctg gttactcatt cactggctac accatgaact gggtgaagca gagccatgga   6120
aagagccttg agtggattgg acttattact ccttacaatg gtgcttctag ctacaaccag   6180
aagttcaggg gcaaggccac attaactgta gacaagtcat ccagcacagc ctacatggac   6240
ctcctcagtc tgacatctga agactctgca gtctatttct gtgcaagggg gggttacgac   6300
gggaggggtt ttgactactg gggccaaggg accacggtca ccgtctcctc aggtggaggc   6360
ggttcaggcg gcggtggctc tagcggtggt ggatcggaca tcgagctcac tcagtctcca   6420
gcaatcatgt ctgcatctcc aggggagaag gtcaccatga cctgcagtgc cagctcaagt   6480
gtaagttaca tgcactggta ccagcagaag tcaggcacct cccccaaaag atggatttat   6540
gacacatcca aactggcttc tggagtccca ggtcgcttca gtggcagtgg gtctggaaac   6600
tcttactctc tcacaatcag cagcgtggag gctgaagatg atgcaactta ttactgccag   6660
cagtggagta agcaccctct cacgtacggt gctgggacaa agttggaaat caaagctagc   6720
acgcgtggtg gcggaggttc tggaggtggg ggttcccagg gggcctggcc acatgaggga   6780
gtccacagaa aaccttccct cctggcccac ccaggtcccc tggtgaaatc agaagagaca   6840
gtcatcctgc aatgttggtc agatgtcagg tttgagcact tccttctgca cagagagggg   6900
aagtataagg acactttgca cctcattgga gagcaccatg atggggtctc caaggccaac   6960
ttctccatcg gtcccatgat gcaagacctt gcagggacct acagatgcta cggttctgtt   7020
actcactccc cctatcagtt gtcagctccc agtgaccctc tggacatcgt catcacaggt   7080
ctatatgaga aaccttctct ctcagcccag ccgggcccca cggttttggc aggagagagc   7140
gtgaccttgt cctgcagctc ccggagctcc tatgacatgt accatctatc cagggagggg   7200
gaggcccatg aacgtaggtt ctctgcaggg cccaaggtca acggaacatt ccaggccgac   7260
```

```
tttcctctgg gccctgccac ccacggagga acctacagat gcttcggctc tttccgtgac   7320
tctccctatg agtggtcaaa ctcgagtgac ccactgcttg tttctgtcac aggaaaccct   7380
tcaaatagtt ggccttcacc cactgaacca agctccaaaa ccggtaaccc cagacacctg   7440
catgttctga ttgggacctc agtggtcaaa atccctttca ccatcctcct cttctttctc   7500
cttcatcgct ggtgctccaa caaaaaaaat gctgctgtaa tggaccaaga gcctgcaggg   7560
aacagaacag tgaacagcga ggattctgat gaacaagacc atcaggaggt gtcatacgca   7620
taagtcgaca atcaacctct ggattacaaa atttgtgaaa gattgactgg tattcttaac   7680
tatgttgctc cttttacgct atgtggatac gctgctttaa tgcctttgta tcatgctatt   7740
gcttcccgta tggctttcat tttctcctcc ttgtataaat cctggttgct gtctctttat   7800
gaggagttgt ggcccgttgt caggcaacgt ggcgtggtgt gcactgtgtt tgctgacgca   7860
acccccactg gttggggcat tgccaccacc tgtcagctcc tttccgggac tttcgctttc   7920
cccctcccta ttgccacggc ggaactcatc gccgcctgcc ttgcccgctg ctggacaggg   7980
gctcggctgt tgggcactga caattccgtg gtgttgtcgg ggaagctgac gtcctttcca   8040
tggctgctcg cctgtgttgc cacctggatt ctgcgcggga cgtccttctg ctacgtccct   8100
tcggccctca atccagcgga ccttccttcc cgcggcctgc tgccggctct gcggcctctt   8160
ccgcgtcttc gccttcgccc tcagacgagt cggatctccc tttgggccgc ctccccgcct   8220
ggaattcgag ctcggtacct ttaagaccaa tgacttacaa ggcagctgta gatcttagcc   8280
actttttaaa agaaaagggg ggactggaag ggctaattca ctcccaacga agacaagatc   8340
tgctttttgc ttgtactggg tctctctggt tagaccagat ctgagcctgg gagctctctg   8400
gctaactagg gaacccactg cttaagcctc aataaagctt gccttgagtg cttcaagtag   8460
tgtgtgcccg tctgttgtgt gactctggta actagagatc cctcagaccc ttttagtcag   8520
tgtggaaaat ctctagcagt agtagttcat gtcatcttat tattcagtat ttataacttg   8580
caaagaaatg aatatcagag agtgagagga acttgtttat tgcagcttat aatggttaca   8640
aataaagcaa tagcatcaca aatttcacaa ataaagcatt tttttcactg cattctagtt   8700
gtggtttgtc caaactcatc aatgtatctt atcatgtctg gctctagcta tcccgcccct   8760
aactccgccc agttccgccc attctccgcc ccatggctga ctaatttttt ttatttatgc   8820
agaggccgag gccgcctcgg cctctgagct attccagaag tagtgaggag gcttttttgg   8880
aggcctacgc ttttgcgtcg agacgtaccc aattcgccct atagtgagtc gtattacgcg   8940
cgctcactgg ccgtcgtttt acaacgtcgt gactgggaaa accctggcgt tacccaactt   9000
aatcgccttg cagcacatcc ccctttcgcc agctggcgta atagcgaaga ggcccgcacc   9060
gatcgccctt cccaacagtt gcgcagcctg aatggcgaat ggcgcgacgc gccctgtagc   9120
ggcgcattaa gcgcggcggg tgtggtggtt acgcgcagcg tgaccgctac acttgccagc   9180
gccctagcgc ccgctccttt cgctttcttc ccttcctttc tcgccacgtt cgccggcttt   9240
ccccgtcaag ctctaaatcg ggggctccct ttagggttcc gatttagtgc tttacggcac   9300
ctcgacccca aaaaacttga ttagggtgat ggttcacgta gtgggccatc gccctgatag   9360
acggtttttc gccctttgac gttggagtcc acgttcttta atagtggact cttgttccaa   9420
actggaacaa cactcaaccc tatctcggtc tattcttttg atttataagg gattttgccg   9480
atttcggcct attggttaaa aaatgagctg atttaacaaa aatttaacgc gaattttaac   9540
aaaatattaa cgtttacaat ttcccaggtg gcacttttcg gggaaatgtg cgcggaaccc   9600
ctatttgttt atttttctaa atacattcaa atatgtatcc gctcatgaga caataaccct   9660
```

gataaatgct tcaataatat tgaaaaagga agagtatgag tattcaacat ttccgtgtcg 9720
cccttattcc ctttttgcg gcattttgcc ttcctgtttt tgctcaccca gaaacgctgg 9780
tgaaagtaaa agatgctgaa gatcagttgg 9810

<210> SEQ ID NO 2
<211> LENGTH: 9165
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 2
gtgcacgagt gggttacatc gaactggatc tcaacagcgg taagatcctt gagagttttc 60
gccccgaaga acgttttcca atgatgagca cttttaaagt tctgctatgt ggcgcggtat 120
tatcccgtat tgacgccggg caagagcaac tcggtcgccg catacactat tctcagaatg 180
acttggttga gtactcacca gtcacagaaa agcatcttac ggatggcatg acagtaagag 240
aattatgcag tgctgccata accatgagtg ataacactgc ggccaactta cttctgacaa 300
cgatcggagg accgaaggag ctaaccgctt ttttgcacaa catgggggat catgtaactc 360
gccttgatcg ttgggaaccg gagctgaatg aagccatacc aaacgacgag cgtgacacca 420
cgatgcctgt agcaatggca acaacgttgc gcaaactatt aactggcgaa ctacttactc 480
tagcttcccg gcaacaatta atagactgga tggaggcgga taaagttgca ggaccacttc 540
tgcgctcggc ccttccggct ggctggttta ttgctgataa atctggagcc ggtgagcgtg 600
ggtctcgcgg tatcattgca gcactggggc cagatggtaa gccctcccgt atcgtagtta 660
tctacacgac ggggagtcag gcaactatgg atgaacgaaa tagacagatc gctgagatag 720
gtgcctcact gattaagcat tggtaactgt cagaccaagt ttactcatat atactttaga 780
ttgatttaaa acttcatttt taatttaaaa ggatctaggt gaagatcctt tttgataatc 840
tcatgaccaa aatcccttaa cgtgagtttt cgttccactg agcgtcagac cccgtagaaa 900
agatcaaagg atcttcttga gatccttttt ttctgcgcgt aatctgctgc ttgcaaacaa 960
aaaaaccacc gctaccagcg gtggtttgtt tgccggatca agagctacca actctttttc 1020
cgaaggtaac tggcttcagc agagcgcaga taccaaatac tgtccttcta gtgtagccgt 1080
agttaggcca ccacttcaag aactctgtag caccgcctac atacctcgct ctgctaatcc 1140
tgttaccagt ggctgctgcc agtggcgata agtcgtgtct taccgggttg gactcaagac 1200
gatagttacc ggataaggcg cagcggtcgg gctgaacggg gggttcgtgc acacagccca 1260
gcttggagcg aacgacctac accgaactga gatacctaca gcgtgagcta tgagaaagcg 1320
ccacgcttcc cgaagggaga aaggcggaca ggtatccggt aagcggcagg gtcggaacag 1380
gagagcgcac gagggagctt ccagggggaa acgcctggta tctttatagt cctgtcgggt 1440
ttcgccacct ctgacttgag cgtcgatttt tgtgatgctc gtcagggggg cggagcctat 1500
ggaaaaacgc cagcaacgcg gcctttttac ggttcctggc cttttgctgg ccttttgctc 1560
acatgttctt tcctgcgtta tcccctgatt ctgtggataa ccgtattacc gcctttgagt 1620
gagctgatac cgctcgccgc agccgaacga ccgagcgcag cgagtcagtg agcgaggaag 1680
cggaagagcg cccaatacgc aaaccgcctc tccccgcgcg ttggccgatt cattaatgca 1740
gctggcacga caggtttccc gactggaaag cgggcagtga gcgcaacgca attaatgtga 1800
gttagctcac tcattaggca ccccaggctt tacactttat gcttccggct cgtatgttgt 1860
gtggaattgt gagcggataa caatttcaca caggaaacag ctatgaccat gattacgcca 1920
agcgcgcaat taaccctcac taaagggaac aaaagctgga gctgcaagct taatgtagtc 1980
ttatgcaata ctcttgtagt cttgcaacat ggtaacgatg agttagcaac atgccttaca 2040
aggagagaaa aagcaccgtg catgccgatt ggtggaagta aggtggtacg atcgtgcctt 2100
attaggaagg caacagacgg gtctgacatg gattggacga accactgaat tgccgcattg 2160
cagagatatt gtatttaagt gcctagctcg atacaataaa cgggtctctc tggttagacc 2220
agatctgagc ctgggagctc tctggctaac tagggaaccc actgcttaag cctcaataaa 2280
gcttgccttg agtgcttcaa gtagtgtgtg cccgtctgtt gtgtgactct ggtaactaga 2340
gatccctcag acccttttag tcagtgtgga aaatctctag cagtggcgcc cgaacaggga 2400
cctgaaagcg aaagggaaac cagagctctc tcgacgcagg actcggcttg ctgaagcgcg 2460
cacggcaaga ggcgaggggc ggcgactggt gagtacgcca aaaattttga ctagcggagg 2520
ctagaaggag agagatgggt gcgagagcgt cagtattaag cgggggagaa ttagatcgcg 2580
atgggaaaaa attcggttaa ggccaggggg aaagaaaaaa tataaattaa aacatatagt 2640
atgggcaagc agggagctag aacgattcgc agttaatcct ggcctgttag aaacatcaga 2700
aggctgtaga caaatactgg gacagctaca accatccctt cagacaggat cagaagaact 2760
tagatcatta tataatacag tagcaaccct ctattgtgtg catcaaagga tagagataaa 2820
agacaccaag gaagctttag acaagataga ggaagagcaa aacaaaagta agaccaccgc 2880
acagcaagcg gccgctgatc ttcagacctg gaggaggaga tatgagggac aattggagaa 2940
gtgaattata taaatataaa gtagtaaaaa ttgaaccatt aggagtagca cccaccaagg 3000
caaagagaag agtggtgcag agagaaaaaa gagcagtggg aataggagct ttgttccttg 3060
ggttcttggg agcagcagga agcactatgg gcgcagcctc aatgacgctg acggtacagg 3120
ccagacaatt attgtctggt atagtgcagc agcagaacaa tttgctgagg gctattgagg 3180
cgcaacagca tctgttgcaa ctcacagtct ggggcatcaa gcagctccag gcaagaatcc 3240
tggctgtgga aagataccta aaggatcaac agctcctggg gatttggggt tgctctggaa 3300
aactcatttg caccactgct gtgccttgga atgctagttg gagtaataaa tctctggaac 3360
agattggaat cacacgacct ggatggagtg ggacagagaa attaacaatt acacaagctt 3420
aatacactcc ttaattgaag aatcgcaaaa ccagcaagaa aagaatgaac aagaattatt 3480
ggaattagat aaatgggcaa gtttgtggaa ttggtttaac ataacaaatt ggctgtggta 3540
tataaaatta ttcataatga tagtaggagg cttggtaggt ttaagaatag tttttgctgt 3600
actttctata gtgaatagag ttaggcaggg atattcacca ttatcgtttc agacccacct 3660
cccaaccccg aggggacccg acaggcccga aggaatagaa gaagaaggtg gagagagaga 3720
cagagacaga tccattcgat tagtgaacgg atctcgacgg tatcgattag actgtagccc 3780
aggaatatgg cagctagatt gtacacattt agaaggaaaa gttatcttgg tagcagttca 3840
tgtagccagt ggatatatag aagcagaagt aattccagca gagacagggc aagaaacagc 3900
atacttcctc ttaaaattag caggaagatg gccagtaaaa acagtacata cagacaatgg 3960
cagcaatttc accagtacta cagttaaggc cgcctgttgg tgggcgggga tcaagcagga 4020
atttggcatt ccctacaatc cccaaagtca aggagtaata gaatctatga ataaagaatt 4080
aaagaaaatt ataggacagg taagagatca ggctgaacat cttaagacag cagtacaaat 4140
ggcagtattc atccacaatt ttaaaagaaa aggggggatt ggggggtaca gtgcagggga 4200

```
aagaatagta gacataatag caacagacat acaaactaaa gaattacaaa aacaaattac   4260
aaaaattcaa aattttcggg tttattacag ggacagcaga gatccagttt ggctgcatac   4320
gcgtcgtgag gctccggtgc ccgtcagtgg gcagagcgca catcgcccac agtccccgag   4380
aagttggggg gaggggtcgg caattgaacc ggtgcctaga gaaggtggcg cggggtaaac   4440
tgggaaagtg atgtcgtgta ctggctccgc ctttttcccg agggtggggg agaaccgtat   4500
ataagtgcag tagtcgccgt gaacgttctt tttcgcaacg ggtttgccgc cagaacacag   4560
gtaagtgccg tgtgtggttc ccgcgggcct ggcctcttta cgggttatgg cccttgcgtg   4620
ccttgaatta cttccacctg gctgcagtac gtgattcttg atcccgagct tcgggttgga   4680
agtgggtggg agagttcgag gccttgcgct taaggagccc cttcgcctcg tgcttgagtt   4740
gaggcctggc ctgggcgctg gggccgccgc gtgcgaatct ggtggcacct tcgcgcctgt   4800
ctcgctgctt tcgataagtc tctagccatt taaaattttt gatgacctgc tgcgacgctt   4860
tttttctggc aagatagtct tgtaaatgcg ggccaagatc tgcacactgg tatttcggtt   4920
tttggggccg cgggcggcga cggggcccgt gcgtcccagc gcacatgttc ggcgaggcgg   4980
ggcctgcgag cgcggccacc gagaatcgga cgggggtagt ctcaagctgg ccggcctgct   5040
ctggtgcctg gcctcgcgcc gccgtgtatc gccccgccct gggcggcaag gctggcccgg   5100
tcggcaccag ttgcgtgagc ggaaagatgg ccgcttcccg gccctgctgc agggagctca   5160
aaatggagga cgcggcgctc gggagagcgg gcgggtgagt cacccacaca aaggaaaagg   5220
gcctttccgt cctcagccgt cgcttcatgt gactccacgg agtaccgggc gccgtccagg   5280
cacctcgatt agttctcgtg cttttggagt acgtcgtctt taggttgggg ggaggggttt   5340
tatgcgatgg agtttcccca cactgagtgg gtggagactg aagttaggcc agcttggcac   5400
ttgatgtaat tctccttgga atttgccctt tttgagtttg gatcttggtt cattctcaag   5460
cctcagacag tggttcaaag tttttttctt ccatttcagg tgtcgtgagc tagaatgggg   5520
ggacttgaac cctgcagcag gctcctgctc ctgcctctcc tgctggctgt aagtggtctc   5580
cgtcctgtcc aggcccaggc ccagagcgat tgcagttgct ctacggtgag cccgggcgtg   5640
ctggcaggga tcgtgatggg agacctggtg ctgacagtgc tcattgccct ggccgtgtac   5700
ttcctgggcc ggctggtccc tcgggggcga ggggctgcgg aggcagcgac ccggaaacag   5760
cgtatcactg agaccgagtc gccttatcag gagctccagg gtcagaggtc ggatgtctac   5820
agcgacctca acacacagag gccgtattac aaagtcgagg gcggcggaga gggcagagga   5880
agtcttctaa catgcggtga cgtggaggag aatcccggcc ctaggatggc cttaccagtg   5940
accgccttgc tcctgccgct ggccttgctg ctccacgccg ccaggccggg atcccaggta   6000
caactgcagc agtctgggcc tgagctggag aagcctggcg cttcagtgaa gatatcctgc   6060
aaggcttctg gttactcatt cactggctac accatgaact gggtgaagca gagccatgga   6120
aagagccttg agtggattgg acttattact ccttacaatg gtgcttctag ctacaaccag   6180
aagttcaggg gcaaggccac attaactgta gacaagtcat ccagcacagc ctacatggac   6240
ctcctcagtc tgacatctga agactctgca gtctatttct gtgcaagggg gggttacgac   6300
gggagggggt ttgactactg gggccaaggg accacggtca ccgtctcctc aggtggaggc   6360
ggttcaggcg gcggtggctc tagcggtggt ggatcggaca tcgagctcac tcagtctcca   6420
gcaatcatgt ctgcatctcc aggggagaag gtcaccatga cctgcagtgc cagctcaagt   6480
gtaagttaca tgcactggta ccagcagaag tcaggcacct cccccaaaag atggatttat   6540
gacacatcca aactggcttc tggagtccca ggtcgcttca gtggcagtgg gtctggaaac   6600
```

-continued

```
tcttactctc tcacaatcag cagcgtggag gctgaagatg atgcaactta ttactgccag   6660
cagtggagta agcaccctct cacgtacggt gctgggacaa agttggaaat caaagctagc   6720
ggtggcggag gttctggagg tgggggttcc tcacccactg aaccaagctc caaaaccggt   6780
aaccccagac acctgcatgt tctgattggg acctcagtgg tcaaaatccc tttcaccatc   6840
ctcctcttct ttctccttca tcgctggtgc tccaacaaaa aaaatgctgc tgtaatggac   6900
caagagcctg cagggaacag aacagtgaac agcgaggatt ctgatgaaca agaccatcag   6960
gaggtgtcat acgcataagt cgacaatcaa cctctggatt acaaaatttg tgaaagattg   7020
actggtattc ttaactatgt tgctcctttt acgctatgtg gatacgctgc tttaatgcct   7080
ttgtatcatg ctattgcttc ccgtatggct ttcattttct cctccttgta taaatcctgg   7140
ttgctgtctc tttatgagga gttgtggccc gttgtcaggc aacgtggcgt ggtgtgcact   7200
gtgtttgctg acgcaacccc cactggttgg ggcattgcca ccacctgtca gctcctttcc   7260
gggactttcg ctttcccct ccctattgcc acggcggaac tcatcgccgc ctgccttgcc   7320
cgctgctgga caggggctcg gctgttgggc actgacaatt ccgtggtgtt gtcggggaag   7380
ctgacgtcct ttccatggct gctcgcctgt gttgccacct ggattctgcg cgggacgtcc   7440
ttctgctacg tcccttcggc cctcaatcca gcggaccttc cttcccgcgg cctgctgccg   7500
gctctgcggc ctcttccgcg tcttcgcctt cgccctcaga cgagtcggat ctccctttgg   7560
gccgcctccc cgcctggaat tcgagctcgg tacctttaag accaatgact tacaaggcag   7620
ctgtagatct tagccacttt ttaaaagaaa aggggggact ggaagggcta attcactccc   7680
aacgaagaca agatctgctt tttgcttgta ctgggtctct ctggttagac cagatctgag   7740
cctgggagct ctctggctaa ctagggaacc cactgcttaa gcctcaataa agcttgcctt   7800
gagtgcttca agtagtgtgt gcccgtctgt tgtgtgactc tggtaactag agatccctca   7860
gaccctttta gtcagtgtgg aaaatctcta gcagtagtag ttcatgtcat cttattattc   7920
agtatttata acttgcaaag aaatgaatat cagagagtga gaggaacttg tttattgcag   7980
cttataatgg ttacaaataa agcaatagca tcacaaattt cacaaataaa gcattttttt   8040
cactgcattc tagttgtggt ttgtccaaac tcatcaatgt atcttatcat gtctggctct   8100
agctatcccg cccctaactc cgcccagttc cgcccattct ccgccccatg gctgactaat   8160
ttttttatt tatgcagagg ccgaggccgc ctcggcctct gagctattcc agaagtagtg   8220
aggaggcttt tttggaggcc tacgcttttg cgtcgagacg tacccaattc gccctatagt   8280
gagtcgtatt acgcgcgctc actggccgtc gttttacaac gtcgtgactg ggaaaaccct   8340
ggcgttaccc aacttaatcg ccttgcagca catcccctt tcgccagctg gcgtaatagc   8400
gaagaggccc gcaccgatcg cccttcccaa cagttgcgca gcctgaatgg cgaatggcgc   8460
gacgcgccct gtagcggcgc attaagcgcg gcgggtgtgg tggttacgcg cagcgtgacc   8520
gctacacttg ccagcgccct agcgcccgct cctttcgctt tcttcccttc ctttctcgcc   8580
acgttcgccg gctttccccg tcaagctcta aatcgggggc tccctttagg gttccgattt   8640
agtgctttac ggcacctcga ccccaaaaaa cttgattagg gtgatggttc acgtagtggg   8700
ccatcgccct gatagacggt ttttcgccct ttgacgttgg agtccacgtt ctttaatagt   8760
ggactcttgt tccaaactgg aacaacactc aaccctatct cggtctattc ttttgattta   8820
taagggattt tgccgatttc ggcctattgg ttaaaaaatg agctgattta acaaaaattt   8880
aacgcgaatt ttaacaaaat attaacgttt acaatttccc aggtggcact tttcggggaa   8940
```

```
atgtgcgcgg aacccctatt tgtttatttt tctaaataca ttcaaatatg tatccgctca   9000

tgagacaata accctgataa atgcttcaat aatattgaaa aaggaagagt atgagtattc   9060

aacatttccg tgtcgccctt attccctttt ttgcggcatt ttgccttcct gtttttgctc   9120

acccagaaac gctggtgaaa gtaaaagatg ctgaagatca gttgg                   9165
```

<210> SEQ ID NO 3
<211> LENGTH: 9915
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gtgcacgagt gggttacatc gaactggatc tcaacagcgg taagatcctt gagagttttc     60

gccccgaaga acgttttcca atgatgagca cttttaaagt tctgctatgt ggcgcggtat    120

tatcccgtat tgacgccggg caagagcaac tcggtcgccg catacactat tctcagaatg    180

acttggttga gtactcacca gtcacagaaa agcatcttac ggatggcatg acagtaagag    240

aattatgcag tgctgccata accatgagtg ataacactgc ggccaactta cttctgacaa    300

cgatcggagg accgaaggag ctaaccgctt ttttgcacaa catgggggat catgtaactc    360

gccttgatcg ttgggaaccg gagctgaatg aagccatacc aaacgacgag cgtgacacca    420

cgatgcctgt agcaatggca acaacgttgc gcaaactatt aactggcgaa ctacttactc    480

tagcttcccg gcaacaatta atagactgga tggaggcgga taaagttgca ggaccacttc    540

tgcgctcggc ccttccggct ggctggttta ttgctgataa atctggagcc ggtgagcgtg    600

ggtctcgcgg tatcattgca gcactggggc cagatggtaa gccctcccgt atcgtagtta    660

tctacacgac ggggagtcag gcaactatgg atgaacgaaa tagacagatc gctgagatag    720

gtgcctcact gattaagcat tggtaactgt cagaccaagt ttactcatat atactttaga    780

ttgatttaaa acttcatttt taatttaaaa ggatctaggt gaagatcctt tttgataatc    840

tcatgaccaa aatcccttaa cgtgagtttt cgttccactg agcgtcagac cccgtagaaa    900

agatcaaagg atcttcttga gatccttttt ttctgcgcgt aatctgctgc ttgcaaacaa    960

aaaaaccacc gctaccagcg gtggtttgtt tgccggatca agagctacca actctttttc   1020

cgaaggtaac tggcttcagc agagcgcaga taccaaatac tgtccttcta gtgtagccgt   1080

agttaggcca ccacttcaag aactctgtag caccgcctac atacctcgct ctgctaatcc   1140

tgttaccagt ggctgctgcc agtggcgata agtcgtgtct taccgggttg gactcaagac   1200

gatagttacc ggataaggcg cagcggtcgg gctgaacggg gggttcgtgc acacagccca   1260

gcttggagcg aacgacctac accgaactga gatacctaca gcgtgagcta tgagaaagcg   1320

ccacgcttcc cgaagggaga aaggcggaca ggtatccggt aagcggcagg gtcggaacag   1380

gagagcgcac gagggagctt ccagggggaa acgcctggta tctttatagt cctgtcgggt   1440

ttcgccacct ctgacttgag cgtcgatttt tgtgatgctc gtcagggggg cggagcctat   1500

ggaaaaacgc cagcaacgcg gcctttttac ggttcctggc cttttgctgg ccttttgctc   1560

acatgttctt tcctgcgtta tcccctgatt ctgtggataa ccgtattacc gcctttgagt   1620

gagctgatac cgctcgccgc agccgaacga ccgagcgcag cgagtcagtg agcgaggaag   1680

cggaagagcg cccaatacgc aaaccgcctc tccccgcgcg ttggccgatt cattaatgca   1740

gctggcacga caggtttccc gactggaaag cgggcagtga gcgcaacgca attaatgtga   1800
```

-continued

```
gttagctcac tcattaggca ccccaggctt tacactttat gcttccggct cgtatgttgt   1860

gtggaattgt gagcggataa caatttcaca caggaaacag ctatgaccat gattacgcca   1920

agcgcgcaat taaccctcac taaagggaac aaaagctgga gctgcaagct taatgtagtc   1980

ttatgcaata ctcttgtagt cttgcaacat ggtaacgatg agttagcaac atgccttaca   2040

aggagagaaa aagcaccgtg catgccgatt ggtggaagta aggtggtacg atcgtgcctt   2100

attaggaagg caacagacgg gtctgacatg gattggacga accactgaat tgccgcattg   2160

cagagatatt gtatttaagt gcctagctcg atacaataaa cgggtctctc tggttagacc   2220

agatctgagc ctgggagctc tctggctaac tagggaaccc actgcttaag cctcaataaa   2280

gcttgccttg agtgcttcaa gtagtgtgtg cccgtctgtt gtgtgactct ggtaactaga   2340

gatccctcag acccttttag tcagtgtgga aaatctctag cagtggcgcc cgaacaggga   2400

cctgaaagcg aaagggaaac cagagctctc tcgacgcagg actcggcttg ctgaagcgcg   2460

cacggcaaga ggcgaggggc ggcgactggt gagtacgcca aaaattttga ctagcggagg   2520

ctagaaggag agagatgggt gcgagagcgt cagtattaag cgggggagaa ttagatcgcg   2580

atgggaaaaa attcggttaa ggccaggggg aaagaaaaaa tataaattaa aacatatagt   2640

atgggcaagc agggagctag aacgattcgc agttaatcct ggcctgttag aaacatcaga   2700

aggctgtaga caaatactgg gacagctaca accatccctt cagacaggat cagaagaact   2760

tagatcatta tataatacag tagcaaccct ctattgtgtg catcaaagga tagagataaa   2820

agacaccaag gaagctttag acaagataga ggaagagcaa aacaaaagta agaccaccgc   2880

acagcaagcg gccgctgatc ttcagacctg gaggaggaga tatgagggac aattggagaa   2940

gtgaattata taaatataaa gtagtaaaaa ttgaaccatt aggagtagca cccaccaagg   3000

caaagagaag agtggtgcag agagaaaaaa gagcagtggg aataggagct ttgttccttg   3060

ggttcttggg agcagcagga agcactatgg gcgcagcctc aatgacgctg acggtacagg   3120

ccagacaatt attgtctggt atagtgcagc agcagaacaa tttgctgagg gctattgagg   3180

cgcaacagca tctgttgcaa ctcacagtct ggggcatcaa gcagctccag gcaagaatcc   3240

tggctgtgga aagataccta aaggatcaac agctcctggg gatttggggt tgctctggaa   3300

aactcatttg caccactgct gtgccttgga atgctagttg gagtaataaa tctctggaac   3360

agattggaat cacacgacct ggatggagtg ggacagagaa attaacaatt acacaagctt   3420

aatacactcc ttaattgaag aatcgcaaaa ccagcaagaa aagaatgaac aagaattatt   3480

ggaattagat aaatgggcaa gtttgtggaa ttggtttaac ataacaaatt ggctgtggta   3540

tataaaatta ttcataatga tagtaggagg cttggtaggt ttaagaatag tttttgctgt   3600

actttctata gtgaatagag ttaggcaggg atattcacca ttatcgtttc agacccacct   3660

cccaaccccg aggggacccg acaggcccga aggaatagaa gaagaaggtg gagagagaga   3720

cagagacaga tccattcgat tagtgaacgg atctcgacgg tatcgattag actgtagccc   3780

aggaatatgg cagctagatt gtacacattt agaaggaaaa gttatcttgg tagcagttca   3840

tgtagccagt ggatatatag aagcagaagt aattccagca gagacagggc aagaaacagc   3900

atacttcctc ttaaaattag caggaagatg gccagtaaaa acagtacata cagacaatgg   3960

cagcaatttc accagtacta cagttaaggc cgcctgttgg tgggcgggga tcaagcagga   4020

atttggcatt ccctacaatc cccaaagtca aggagtaata gaatctatga ataaagaatt   4080

aaagaaaatt ataggacagg taagagatca ggctgaacat cttaagacag cagtacaaat   4140

ggcagtattc atccacaatt ttaaaagaaa aggggggatt ggggggtaca gtgcagggga   4200
```

```
aagaatagta gacataatag caacagacat acaaactaaa gaattacaaa aacaaattac   4260
aaaaattcaa aattttcggg tttattacag ggacagcaga gatccagttt ggctgcatac   4320
gcgtcgtgag gctccggtgc ccgtcagtgg gcagagcgca catcgcccac agtccccgag   4380
aagttggggg gaggggtcgg caattgaacc ggtgcctaga gaaggtggcg cggggtaaac   4440
tgggaaagtg atgtcgtgta ctggctccgc ctttttcccg agggtggggg agaaccgtat   4500
ataagtgcag tagtcgccgt gaacgttctt tttcgcaacg ggtttgccgc cagaacacag   4560
gtaagtgccg tgtgtggttc ccgcgggcct ggcctcttta cgggttatgg cccttgcgtg   4620
ccttgaatta cttccacctg gctgcagtac gtgattcttg atcccgagct tcgggttgga   4680
agtgggtggg agagttcgag gccttgcgct taaggagccc cttcgcctcg tgcttgagtt   4740
gaggcctggc ctgggcgctg gggccgccgc gtgcgaatct ggtggcacct tcgcgcctgt   4800
ctcgctgctt tcgataagtc tctagccatt taaaattttt gatgacctgc tgcgacgctt   4860
tttttctggc aagatagtct tgtaaatgcg ggccaagatc tgcacactgg tatttcggtt   4920
tttggggccg cgggcggcga cggggcccgt gcgtcccagc gcacatgttc ggcgaggcgg   4980
ggcctgcgag cgcggccacc gagaatcgga cgggggtagt ctcaagctgg ccggcctgct   5040
ctggtgcctg gcctcgcgcc gccgtgtatc gccccgccct gggcggcaag gctggcccgg   5100
tcggcaccag ttgcgtgagc ggaaagatgg ccgcttcccg gccctgctgc agggagctca   5160
aaatggagga cgcggcgctc gggagagcgg gcgggtgagt cacccacaca aaggaaaagg   5220
gcctttccgt cctcagccgt cgcttcatgt gactccacgg agtaccgggc gccgtccagg   5280
cacctcgatt agttctcgtg cttttggagt acgtcgtctt taggttgggg ggaggggttt   5340
tatgcgatgg agtttcccca cactgagtgg gtggagactg aagttaggcc agcttggcac   5400
ttgatgtaat tctccttgga atttgccctt tttgagtttg gatcttggtt cattctcaag   5460
cctcagacag tggttcaaag tttttttctt ccatttcagg tgtcgtgagc tagaatgggg   5520
ggacttgaac cctgcagcag gctcctgctc ctgcctctcc tgctggctgt aagtggtctc   5580
cgtcctgtcc aggcccaggc ccagagcgat tgcagttgct ctacggtgag cccgggcgtg   5640
ctggcaggga tcgtgatggg agacctggtg ctgacagtgc tcattgccct ggccgtgtac   5700
ttcctgggcc ggctggtccc tcgggggcga ggggctgcgg aggcagcgac ccggaaacag   5760
cgtatcactg agaccgagtc gccttatcag gagctccagg gtcagaggtc ggatgtctac   5820
agcgacctca acacacagag gccgtattac aaagtcgagg gcggcggaga gggcagagga   5880
agtcttctaa catgcggtga cgtggaggag aatcccggcc ctaggatggc cttaccagtg   5940
accgccttgc tcctgccgct ggccttgctg ctccacgccg ccaggccggg atcccaggta   6000
caactgcagc agtctgggcc tgagctggag aagcctggcg cttcagtgaa gatatcctgc   6060
aaggcttctg gttactcatt cactggctac accatgaact gggtgaagca gagccatgga   6120
aagagccttg agtggattgg acttattact ccttacaatg gtgcttctag ctacaaccag   6180
aagttcaggg gcaaggccac attaactgta gacaagtcat ccagcacagc ctacatggac   6240
ctcctcagtc tgacatctga agactctgca gtctatttct gtgcaagggg gggttacgac   6300
gggaggggtt ttgactactg gggccaaggg accacggtca ccgtctcctc aggtggaggc   6360
ggttcaggcg gcggtggctc tagcggtggt ggatcggaca tcgagctcac tcagtctcca   6420
gcaatcatgt ctgcatctcc aggggagaag gtcaccatga cctgcagtgc cagctcaagt   6480
gtaagttaca tgcactggta ccagcagaag tcaggcacct cccccaaaag atggatttat   6540
```

-continued

```
gacacatcca aactggcttc tggagtccca ggtcgcttca gtggcagtgg gtctggaaac   6600
tcttactctc tcacaatcag cagcgtggag gctgaagatg atgcaactta ttactgccag   6660
cagtggagta agcaccctct cacgtacggt gctgggacaa agttggaaat caaagctagc   6720
ggtggcggag gttctggagg tgggggttcc caggggggcct ggccacatga gggagtccac   6780
agaaaacctt ccctcctggc ccacccaggt cccctggtga aatcagaaga gacagtcatc   6840
ctgcaatgtt ggtcagatgt caggtttcag cacttccttc tgcacagaga agggaagttt   6900
aaggacactt tgcacctcat tggagagcac catgatgggg tctccaaggc caacttctcc   6960
atcggtccca tgatgcaaga ccttgcaggg acctacagat gctacggttc tgttactcac   7020
tcccccctatc agttgtcagc tcccagtgac cctctggaca tcgtcatcac aggtctatat   7080
gagaaacctt ctctctcagc ccagccgggc cccacggttc tggcaggaga gagcgtgacc   7140
ttgtcctgca gctcccggag ctcctatgac atgtaccatc tatccaggga gggggaggcc   7200
catgaacgta ggttctctgc agggcccaag gtcaacggaa cattccaggc cgactttcct   7260
ctgggccctg ccacccacgg aggaacctac agatgcttcg gctctttccg tgactctcca   7320
tacgagtggt caaactcgag tgacccactg cttgtttctg tcacaggaaa cccttcaaat   7380
agttggcttt cacccactga accaagctcc gaaaccggta accccagaca cctgcatgtt   7440
ctgattggga cctcagtggt catcatcctc ttcatcctcc tcctcttctt tctccttcat   7500
cgctggtgct gcaacaaaaa aaatgctgtt gtaatggacc aagagcctgc agggaacaga   7560
acagtgaaca gggaggactc tgatgaacaa gaccctcagg aggtgacata tgcacagttg   7620
aatcactgcg ttttcacaca gagaaaaatc actcaccctt ctcagaggcc caagacaccc   7680
ccaacagata tcatcgtgta cacggaactt ccaaatgctg agccctgagt cgacaatcaa   7740
cctctggatt acaaaatttg tgaaagattg actggtattc ttaactatgt tgctcctttt   7800
acgctatgtg gatacgctgc tttaatgcct ttgtatcatg ctattgcttc ccgtatggct   7860
ttcattttct cctccttgta taaatcctgg ttgctgtctc tttatgagga gttgtggccc   7920
gttgtcaggc aacgtggcgt ggtgtgcact gtgtttgctg acgcaacccc cactggttgg   7980
ggcattgcca ccacctgtca gctcctttcc gggactttcg ctttcccct ccctattgcc   8040
acggcggaac tcatcgccgc ctgccttgcc cgctgctgga caggggctcg gctgttgggc   8100
actgacaatt ccgtggtgtt gtcggggaag ctgacgtcct ttccatggct gctcgcctgt   8160
gttgccacct ggattctgcg cgggacgtcc ttctgctacg tcccttcggc cctcaatcca   8220
gcggaccttc cttcccgcgg cctgctgccg gctctgcggc ctcttccgcg tcttcgcctt   8280
cgccctcaga cgagtcggat ctccctttgg gccgcctccc cgcctggaat tcgagctcgg   8340
tacctttaag accaatgact tacaaggcag ctgtagatct tagccacttt ttaaaagaaa   8400
agggggggact ggaagggcta attcactccc aacgaagaca agatctgctt tttgcttgta   8460
ctgggtctct ctggttagac cagatctgag cctgggagct ctctggctaa ctagggaacc   8520
cactgcttaa gcctcaataa agcttgcctt gagtgcttca agtagtgtgt gcccgtctgt   8580
tgtgtgactc tggtaactag agatccctca gacccttta gtcagtgtgg aaaatctcta   8640
gcagtagtag ttcatgtcat cttattattc agtatttata acttgcaaag aaatgaatat   8700
cagagagtga gaggaacttg tttattgcag cttataatgg ttacaaataa agcaatagca   8760
tcacaaattt cacaaataaa gcattttttt cactgcattc tagttgtggt ttgtccaaac   8820
tcatcaatgt atcttatcat gtctggctct agctatcccg cccctaactc cgcccagttc   8880
cgcccattct ccgccccatg gctgactaat tttttttatt tatgcagagg ccgaggccgc   8940
```

ctcggcctct gagctattcc agaagtagtg aggaggcttt tttggaggcc tacgcttttg 9000
cgtcgagacg tacccaattc gccctatagt gagtcgtatt acgcgcgctc actggccgtc 9060
gttttacaac gtcgtgactg ggaaaaccct ggcgttaccc aacttaatcg ccttgcagca 9120
catccccctt tcgccagctg gcgtaatagc gaagaggccc gcaccgatcg cccttcccaa 9180
cagttgcgca gcctgaatgg cgaatggcgc gacgcgccct gtagcggcgc attaagcgcg 9240
gcgggtgtgg tggttacgcg cagcgtgacc gctacacttg ccagcgccct agcgcccgct 9300
cctttcgctt tcttcccttc ctttctcgcc acgttcgccg gctttccccg tcaagctcta 9360
aatcgggggc tccctttagg gttccgattt agtgctttac ggcacctcga ccccaaaaaa 9420
cttgattagg gtgatggttc acgtagtggg ccatcgccct gatagacggt ttttcgccct 9480
ttgacgttgg agtccacgtt ctttaatagt ggactcttgt tccaaactgg aacaacactc 9540
aaccctatct cggtctattc ttttgattta taagggattt tgccgatttc ggcctattgg 9600
ttaaaaaatg agctgattta acaaaaattt aacgcgaatt ttaacaaaat attaacgttt 9660
acaatttccc aggtggcact tttcggggaa atgtgcgcgg aacccctatt tgtttatttt 9720
tctaaataca ttcaaatatg tatccgctca tgagacaata accctgataa atgcttcaat 9780
aatattgaaa aaggaagagt atgagtattc aacatttccg tgtcgccctt attccctttt 9840
ttgcggcatt ttgccttcct gtttttgctc acccagaaac gctggtgaaa gtaaaagatg 9900
ctgaagatca gttgg 9915

<210> SEQ ID NO 4
<211> LENGTH: 9816
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4
gtgcacgagt gggttacatc gaactggatc tcaacagcgg taagatcctt gagagttttc 60
gccccgaaga acgttttcca atgatgagca cttttaaagt tctgctatgt ggcgcggtat 120
tatcccgtat tgacgccggg caagagcaac tcggtcgccg catacactat tctcagaatg 180
acttggttga gtactcacca gtcacagaaa agcatcttac ggatggcatg acagtaagag 240
aattatgcag tgctgccata accatgagtg ataacactgc ggccaactta cttctgacaa 300
cgatcggagg accgaaggag ctaaccgctt ttttgcacaa catgggggat catgtaactc 360
gccttgatcg ttgggaaccg gagctgaatg aagccatacc aaacgacgag cgtgacacca 420
cgatgcctgt agcaatggca acaacgttgc gcaaactatt aactggcgaa ctacttactc 480
tagcttcccg gcaacaatta atagactgga tggaggcgga taaagttgca ggaccacttc 540
tgcgctcggc ccttccggct ggctggttta ttgctgataa atctggagcc ggtgagcgtg 600
ggtctcgcgg tatcattgca gcactggggc cagatggtaa gccctcccgt atcgtagtta 660
tctacacgac ggggagtcag gcaactatgg atgaacgaaa tagacagatc gctgagatag 720
gtgcctcact gattaagcat tggtaactgt cagaccaagt ttactcatat atactttaga 780
ttgatttaaa acttcatttt taatttaaaa ggatctaggt gaagatcctt tttgataatc 840
tcatgaccaa aatcccttaa cgtgagtttt cgttccactg agcgtcagac cccgtagaaa 900
agatcaaagg atcttcttga gatccttttt ttctgcgcgt aatctgctgc ttgcaaacaa 960
aaaaaccacc gctaccagcg gtggtttgtt tgccggatca agagctacca actctttttc 1020

```
cgaaggtaac tggcttcagc agagcgcaga taccaaatac tgtccttcta gtgtagccgt   1080
agttaggcca ccacttcaag aactctgtag caccgcctac atacctcgct ctgctaatcc   1140
tgttaccagt ggctgctgcc agtggcgata agtcgtgtct taccgggttg gactcaagac   1200
gatagttacc ggataaggcg cagcggtcgg gctgaacggg gggttcgtgc acacagccca   1260
gcttggagcg aacgacctac accgaactga gatacctaca gcgtgagcta tgagaaagcg   1320
ccacgcttcc cgaagggaga aaggcggaca ggtatccggt aagcggcagg gtcggaacag   1380
gagagcgcac gagggagctt ccagggggaa acgcctggta tctttatagt cctgtcgggt   1440
ttcgccacct ctgacttgag cgtcgatttt tgtgatgctc gtcagggggg cggagcctat   1500
ggaaaaacgc cagcaacgcg gcctttttac ggttcctggc cttttgctgg ccttttgctc   1560
acatgttctt tcctgcgtta tcccctgatt ctgtggataa ccgtattacc gcctttgagt   1620
gagctgatac cgctcgccgc agccgaacga ccgagcgcag cgagtcagtg agcgaggaag   1680
cggaagagcg cccaatacgc aaaccgcctc tccccgcgcg ttggccgatt cattaatgca   1740
gctggcacga caggtttccc gactggaaag cgggcagtga gcgcaacgca attaatgtga   1800
gttagctcac tcattaggca ccccaggctt tacactttat gcttccggct cgtatgttgt   1860
gtggaattgt gagcggataa caatttcaca caggaaacag ctatgaccat gattacgcca   1920
agcgcgcaat taaccctcac taaagggaac aaaagctgga gctgcaagct taatgtagtc   1980
ttatgcaata ctcttgtagt cttgcaacat ggtaacgatg agttagcaac atgccttaca   2040
aggagagaaa aagcaccgtg catgccgatt ggtggaagta aggtggtacg atcgtgcctt   2100
attaggaagg caacagacgg gtctgacatg gattggacga accactgaat tgccgcattg   2160
cagagatatt gtatttaagt gcctagctcg atacaataaa cgggtctctc tggttagacc   2220
agatctgagc ctgggagctc tctggctaac tagggaaccc actgcttaag cctcaataaa   2280
gcttgccttg agtgcttcaa gtagtgtgtg cccgtctgtt gtgtgactct ggtaactaga   2340
gatccctcag acccttttag tcagtgtgga aaatctctag cagtggcgcc cgaacaggga   2400
cctgaaagcg aaagggaaac cagagctctc tcgacgcagg actcggcttg ctgaagcgcg   2460
cacggcaaga ggcgaggggc ggcgactggt gagtacgcca aaaattttga ctagcggagg   2520
ctagaaggag agagatgggt gcgagagcgt cagtattaag cgggggagaa ttagatcgcg   2580
atgggaaaaa attcggttaa ggccaggggg aaagaaaaaa tataaattaa aacatatagt   2640
atgggcaagc agggagctag aacgattcgc agttaatcct ggcctgttag aaacatcaga   2700
aggctgtaga caaatactgg gacagctaca accatccctt cagacaggat cagaagaact   2760
tagatcatta tataatacag tagcaaccct ctattgtgtg catcaaagga tagagataaa   2820
agacaccaag gaagctttag acaagataga ggaagagcaa aacaaaagta agaccaccgc   2880
acagcaagcg gccgctgatc ttcagacctg gaggaggaga tatgagggac aattggagaa   2940
gtgaattata taaatataaa gtagtaaaaa ttgaaccatt aggagtagca cccaccaagg   3000
caaagagaag agtggtgcag agagaaaaaa gagcagtggg aataggagct ttgttccttg   3060
ggttcttggg agcagcagga agcactatgg gcgcagcctc aatgacgctg acggtacagg   3120
ccagacaatt attgtctggt atagtgcagc agcagaacaa tttgctgagg gctattgagg   3180
cgcaacagca tctgttgcaa ctcacagtct ggggcatcaa gcagctccag gcaagaatcc   3240
tggctgtgga aagataccta aaggatcaac agctcctggg gatttggggt tgctctggaa   3300
aactcatttg caccactgct gtgccttgga atgctagttg gagtaataaa tctctggaac   3360
```

```
agattggaat cacacgacct ggatggagtg ggacagagaa attaacaatt acacaagctt   3420
aatacactcc ttaattgaag aatcgcaaaa ccagcaagaa aagaatgaac aagaattatt   3480
ggaattagat aaatgggcaa gtttgtggaa ttggtttaac ataacaaatt ggctgtggta   3540
tataaaatta ttcataatga tagtaggagg cttggtaggt ttaagaatag tttttgctgt   3600
actttctata gtgaatagag ttaggcaggg atattcacca ttatcgtttc agacccacct   3660
cccaaccccg aggggacccg acaggcccga aggaatagaa gaagaaggtg gagagagaga   3720
cagagacaga tccattcgat tagtgaacgg atctcgacgg tatcgattag actgtagccc   3780
aggaatatgg cagctagatt gtacacattt agaaggaaaa gttatcttgg tagcagttca   3840
tgtagccagt ggatatatag aagcagaagt aattccagca gagacagggc aagaaacagc   3900
atacttcctc ttaaaattag caggaagatg gccagtaaaa acagtacata cagacaatgg   3960
cagcaatttc accagtacta cagttaaggc cgcctgttgg tgggcgggga tcaagcagga   4020
atttggcatt ccctacaatc cccaaagtca aggagtaata gaatctatga ataaagaatt   4080
aaagaaaatt ataggacagg taagagatca ggctgaacat cttaagacag cagtacaaat   4140
ggcagtattc atccacaatt ttaaaagaaa aggggggatt ggggggtaca gtgcagggga   4200
aagaatagta gacataatag caacagacat acaaactaaa gaattacaaa aacaaattac   4260
aaaaattcaa aattttcggg tttattacag ggacagcaga gatccagttt ggctgcatac   4320
gcgtcgtgag gctccggtgc ccgtcagtgg gcagagcgca catcgcccac agtccccgag   4380
aagttggggg gaggggtcgg caattgaacc ggtgcctaga gaaggtggcg cggggtaaac   4440
tgggaaagtg atgtcgtgta ctggctccgc ctttttcccg agggtggggg agaaccgtat   4500
ataagtgcag tagtcgccgt gaacgttctt tttcgcaacg ggtttgccgc cagaacacag   4560
gtaagtgccg tgtgtggttc ccgcgggcct ggcctcttta cgggttatgg cccttgcgtg   4620
ccttgaatta cttccacctg gctgcagtac gtgattcttg atcccgagct tcgggttgga   4680
agtgggtggg agagttcgag gccttgcgct taaggagccc cttcgcctcg tgcttgagtt   4740
gaggcctggc ctgggcgctg gggccgccgc gtgcgaatct ggtggcacct tcgcgcctgt   4800
ctcgctgctt tcgataagtc tctagccatt taaaattttt gatgacctgc tgcgacgctt   4860
tttttctggc aagatagtct tgtaaatgcg ggccaagatc tgcacactgg tatttcggtt   4920
tttggggccg cgggcggcga cggggcccgt gcgtcccagc gcacatgttc ggcgaggcgg   4980
ggcctgcgag cgcggccacc gagaatcgga cgggggtagt ctcaagctgg ccggcctgct   5040
ctggtgcctg gcctcgcgcc gccgtgtatc gccccgccct gggcggcaag gctggcccgg   5100
tcggcaccag ttgcgtgagc ggaaagatgg ccgcttcccg gccctgctgc agggagctca   5160
aaatggagga cgcggcgctc gggagagcgg gcgggtgagt cacccacaca aaggaaaagg   5220
gcctttccgt cctcagccgt cgcttcatgt gactccacgg agtaccgggc gccgtccagg   5280
cacctcgatt agttctcgtg cttttggagt acgtcgtctt taggttgggg ggaggggttt   5340
tatgcgatgg agtttcccca cactgagtgg gtggagactg aagttaggcc agcttggcac   5400
ttgatgtaat tctccttgga atttgccctt tttgagtttg gatcttggtt cattctcaag   5460
cctcagacag tggttcaaag tttttttctt ccatttcagg tgtcgtgagc tagaatgggg   5520
ggacttgaac cctgcagcag gctcctgctc ctgcctctcc tgctggctgt aagtggtctc   5580
cgtcctgtcc aggcccaggc ccagagcgat tgcagttgct ctacggtgag cccgggcgtg   5640
ctggcaggga tcgtgatggg agacctggtg ctgacagtgc tcattgccct ggccgtgtac   5700
ttcctgggcc ggctggtccc tcgggggcga ggggctgcgg aggcagcgac ccggaaacag   5760
```

cgtatcactg agaccgagtc gccttatcag gagctccagg gtcagaggtc ggatgtctac 5820
agcgacctca acacacagag gccgtattac aaagtcgagg gcggcggaga gggcagagga 5880
agtcttctaa catgcggtga cgtggaggag aatcccggcc ctaggatggc cttaccagtg 5940
accgccttgc tcctgccgct ggccttgctg ctccacgccg ccaggccggg atccgacatc 6000
cagatgacac agactacatc ctccctgtct gcctctctgg gagacagagt caccatcagt 6060
tgcagggcaa gtcaggacat tagtaaatat ttaaattggt atcagcagaa accagatgga 6120
actgttaaac tcctgatcta ccatacatca agattacact caggagtccc atcaaggttc 6180
agtggcagtg ggtctggaac agattattct ctcaccatta gcaacctgga gcaagaagat 6240
attgccactt acttttgcca acagggtaat acgcttccgt acacgttcgg aggggggact 6300
aagttggaaa taacaggtgg cggtggctcg ggcggtggtg ggtcgggtgg cggcggatct 6360
gaggtgaaac tgcaggagtc aggacctggc ctggtggcgc cctcacagag cctgtccgtc 6420
acatgcactg tctcaggggt ctcattaccc gactatggtg taagctggat tcgccagcct 6480
ccacgaaagg gtctggagtg gctgggagta atatggggta gtgaaaccac atactataat 6540
tcagctctca aatccagact gaccatcatc aaggacaact ccaagagcca agttttctta 6600
aaaatgaaca gtctgcaaac tgatgacaca gccatttact actgtgccaa acattattac 6660
tacggtggta gctatgctat ggactactgg ggtcaaggaa cctcagtcac cgtctcctca 6720
gctagcacgc gtggtggcgg aggttctgga ggtgggggtt cccagggggc ctggccacat 6780
gagggagtcc acagaaaacc ttccctcctg gcccacccag gtcccctggt gaaatcagaa 6840
gagacagtca tcctgcaatg ttggtcagat gtcaggtttg agcacttcct tctgcacaga 6900
gaggggaagt ataaggacac tttgcacctc attggagagc accatgatgg ggtctccaag 6960
gccaacttct ccatcggtcc catgatgcaa gaccttgcag ggacctacag atgctacggt 7020
tctgttactc actcccccta tcagttgtca gctcccagtg accctctgga catcgtcatc 7080
acaggtctat atgagaaacc ttctctctca gcccagccgg gccccacggt tttggcagga 7140
gagagcgtga ccttgtcctg cagctcccgg agctcctatg acatgtacca tctatccagg 7200
gagggggagg cccatgaacg taggttctct gcagggccca aggtcaacgg aacattccag 7260
gccgactttc ctctgggccc tgccacccac ggaggaacct acagatgctt cggctctttc 7320
cgtgactctc cctatgagtg gtcaaactcg agtgacccac tgcttgtttc tgtcacagga 7380
aacccttcaa atagttggcc ttcacccact gaaccaagct ccaaaaccgg taaccccaga 7440
cacctgcatg ttctgattgg gacctcagtg gtcaaaatcc ctttcaccat cctcctcttc 7500
tttctccttc atcgctggtg ctccaacaaa aaaaatgctg ctgtaatgga ccaagagcct 7560
gcagggaaca gaacagtgaa cagcgaggat tctgatgaac aagaccatca ggaggtgtca 7620
tacgcataag tcgacaatca acctctggat tacaaaattt gtgaaagatt gactggtatt 7680
cttaactatg ttgctccttt tacgctatgt ggatacgctg ctttaatgcc tttgtatcat 7740
gctattgctt cccgtatggc tttcattttc tcctccttgt ataaatcctg gttgctgtct 7800
ctttatgagg agttgtggcc cgttgtcagg caacgtggcg tggtgtgcac tgtgtttgct 7860
gacgcaaccc ccactggttg gggcattgcc accacctgtc agctcctttc cgggactttc 7920
gctttccccc tccctattgc cacggcggaa ctcatcgccg cctgccttgc ccgctgctgg 7980
acaggggctc ggctgttggg cactgacaat tccgtggtgt tgtcggggaa gctgacgtcc 8040
tttccatggc tgctcgcctg tgttgccacc tggattctgc gcgggacgtc cttctgctac 8100

-continued

```
gtcccttcgg ccctcaatcc agcggacctt ccttcccgcg gcctgctgcc ggctctgcgg   8160
cctcttccgc gtcttcgcct tcgccctcag acgagtcgga tctccctttg ggccgcctcc   8220
ccgcctggaa ttcgagctcg gtacctttaa gaccaatgac ttacaaggca gctgtagatc   8280
ttagccactt tttaaaagaa aaggggggac tggaagggct aattcactcc caacgaagac   8340
aagatctgct ttttgcttgt actgggtctc tctggttaga ccagatctga gcctgggagc   8400
tctctggcta actagggaac ccactgctta agcctcaata aagcttgcct tgagtgcttc   8460
aagtagtgtg tgcccgtctg ttgtgtgact ctggtaacta gagatccctc agaccctttt   8520
agtcagtgtg gaaaatctct agcagtagta gttcatgtca tcttattatt cagtatttat   8580
aacttgcaaa gaaatgaata tcagagagtg agaggaactt gtttattgca gcttataatg   8640
gttacaaata aagcaatagc atcacaaatt tcacaaataa agcatttttt tcactgcatt   8700
ctagttgtgg tttgtccaaa ctcatcaatg tatcttatca tgtctggctc tagctatccc   8760
gcccctaact ccgcccagtt ccgcccattc tccgccccat ggctgactaa ttttttttat   8820
ttatgcagag gccgaggccg cctcggcctc tgagctattc cagaagtagt gaggaggctt   8880
ttttggaggc ctacgctttt gcgtcgagac gtacccaatt cgccctatag tgagtcgtat   8940
tacgcgcgct cactggccgt cgttttacaa cgtcgtgact gggaaaaccc tggcgttacc   9000
caacttaatc gccttgcagc acatccccct ttcgccagct ggcgtaatag cgaagaggcc   9060
cgcaccgatc gcccttccca acagttgcgc agcctgaatg gcgaatggcg cgacgcgccc   9120
tgtagcggcg cattaagcgc ggcgggtgtg gtggttacgc gcagcgtgac cgctacactt   9180
gccagcgccc tagcgcccgc tcctttcgct ttcttccctt cctttctcgc cacgttcgcc   9240
ggctttcccc gtcaagctct aaatcggggg ctccctttag ggttccgatt tagtgcttta   9300
cggcacctcg accccaaaaa acttgattag ggtgatggtt cacgtagtgg gccatcgccc   9360
tgatagacgg tttttcgccc tttgacgttg gagtccacgt tctttaatag tggactcttg   9420
ttccaaactg gaacaacact caaccctatc tcggtctatt cttttgattt ataagggatt   9480
ttgccgattt cggcctattg gttaaaaaat gagctgattt aacaaaaatt taacgcgaat   9540
tttaacaaaa tattaacgtt tacaatttcc caggtggcac ttttcgggga aatgtgcgcg   9600
gaacccctat ttgtttattt ttctaaatac attcaaatat gtatccgctc atgagacaat   9660
aaccctgata aatgcttcaa taatattgaa aaaggaagag tatgagtatt caacatttcc   9720
gtgtcgccct tattcccttt tttgcggcat tttgccttcc tgtttttgct cacccagaaa   9780
cgctggtgaa agtaaaagat gctgaagatc agttgg                             9816
```

```
<210> SEQ ID NO 5
<211> LENGTH: 3821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
```

```
tgatgcggta ttttctcctt acgcatctgt gcggtatttc acaccgcata tggtgcactc     60
tcagtacaat ctgctctgat gccgcatagt taagccagcc ccgacacccg ccaacacccg    120
ctgacgcgcc ctgacgggct tgtctgctcc cggcatccgc ttacagacaa gctgtgaccg    180
tctccgggag ctgcatgtgt cagaggtttt caccgtcatc accgaaacgc gcgagacgaa    240
agggcctcgt gatacgccta tttttatagg ttaatgtcat gataataatg gtttcttaga    300
```

-continued

```
cgtcaggtgg cacttttcgg ggaaatgtgc gcggaacccc tatttgttta tttttctaaa    360
tacattcaaa tatgtatccg ctcatgagac aataaccctg ataaatgctt caataatatt    420
gaaaaaggaa gagtatgagt attcaacatt tccgtgtcgc ccttattccc ttttttgcgg    480
cattttgcct tcctgttttt gctcacccag aaacgctggt gaaagtaaaa gatgctgaag    540
atcagttggg tgcacgagtg ggttacatcg aactggatct caacagcggt aagatccttg    600
agagttttcg ccccgaagaa cgttttccaa tgatgagcac ttttaaagtt ctgctatgtg    660
gcgcggtatt atcccgtatt gacgccgggc aagagcaact cggtcgccgc atacactatt    720
ctcagaatga cttggttgag tactcaccag tcacagaaaa gcatcttacg gatggcatga    780
cagtaagaga attatgcagt gctgccataa ccatgagtga taacactgcg gccaacttac    840
ttctgacaac gatcggagga ccgaaggagc taaccgcttt tttgcacaac atgggggatc    900
atgtaactcg ccttgatcgt tgggaaccgg agctgaatga agccatacca aacgacgagc    960
gtgacaccac gatgcctgta gcaatggcaa caacgttgcg caaactatta actggcgaac   1020
tacttactct agcttcccgg caacaattaa tagactggat ggaggcggat aaagttgcag   1080
gaccacttct gcgctcggcc cttccggctg gctggtttat tgctgataaa tctggagccg   1140
gtgagcgtgg gtctcgcggt atcattgcag cactggggcc agatggtaag ccctcccgta   1200
tcgtagttat ctacacgacg gggagtcagg caactatgga tgaacgaaat agacagatcg   1260
ctgagatagg tgcctcactg attaagcatt ggtaactgtc agaccaagtt tactcatata   1320
tactttagat tgatttaaaa cttcattttt aatttaaaag gatctaggtg aagatccttt   1380
ttgataatct catgaccaaa atcccttaac gtgagttttc gttccactga gcgtcagacc   1440
ccgtagaaaa gatcaaagga tcttcttgag atcctttttt tctgcgcgta atctgctgct   1500
tgcaaacaaa aaaaccaccg ctaccagcgg tggtttgttt gccggatcaa gagctaccaa   1560
ctctttttcc gaaggtaact ggcttcagca gagcgcagat accaaatact gttcttctag   1620
tgtagccgta gttaggccac cacttcaaga actctgtagc accgcctaca tacctcgctc   1680
tgctaatcct gttaccagtg gctgctgcca gtggcgataa gtcgtgtctt accgggttgg   1740
actcaagacg atagttaccg gataaggcgc agcggtcggg ctgaacgggg ggttcgtgca   1800
cacagcccag cttggagcga acgacctaca ccgaactgag atacctacag cgtgagctat   1860
gagaaagcgc cacgcttccc gaagggagaa aggcggacag gtatccggta agcggcaggg   1920
tcggaacagg agagcgcacg agggagcttc caggggggaaa cgcctggtat ctttatagtc   1980
ctgtcgggtt tcgccacctc tgacttgagc gtcgattttt gtgatgctcg tcaggggggc   2040
ggagcctatg gaaaaacgcc agcaacgcgg cctttttacg gttcctggcc ttttgctggc   2100
cttttgctca catgttcttt cctgcgttat cccctgattc tgtggataac cgtattaccg   2160
cctttgagtg agctgatacc gctcgccgca gccgaacgac cgagcgcagc gagtcagtga   2220
gcgaggaagc ggaagagcgc ccaatacgca aaccgcctct ccccgcgcgt tggccgattc   2280
attaatgcag ctggcacgac aggtttcccg actggaaagc gggcagtgag cgcaacgcaa   2340
ttaatgtgag ttagctcact cattaggcac cccaggcttt acactttatg cttccggctc   2400
gtatgttgtg tggaattgtg agcggataac aatttcacac aggaaacagc tatgaccatg   2460
attacgccaa gctctaatac gactcactat agggagacaa gcttgcatgc ctgcaggtcg   2520
acatggcctt accagtgacc gccttgctcc tgccgctggc cttgctgctc cacgccgcca   2580
ggccggacat ccagatgaca cagactacat cctccctgtc tgcctctctg ggagacagag   2640
tcaccatcag ttgcagggca agtcaggaca ttagtaaata tttaaattgg tatcagcaga   2700
```

aaccagatgg aactgttaaa ctcctgatct accatacatc aagattacac tcaggagtcc 2760
catcaaggtt cagtggcagt gggtctggaa cagattattc tctcaccatt agcaacctgg 2820
agcaagaaga tattgccact tacttttgcc aacagggtaa tacgcttccg tacacgttcg 2880
gaggggggac taagttggaa ataacaggtg gcggtggctc gggcggtggt gggtcgggtg 2940
gcggcggatc tgaggtgaaa ctgcaggagt caggacctgg cctggtggcg ccctcacaga 3000
gcctgtccgt cacatgcact gtctcagggg tctcattacc cgactatggt gtaagctgga 3060
ttcgccagcc tccacgaaag ggtctggagt ggctgggagt aatatggggt agtgaaacca 3120
catactataa ttcagctctc aaatccagac tgaccatcat caaggacaac tccaagagcc 3180
aagttttctt aaaaatgaac agtctgcaaa ctgatgacac agccatttac tactgtgcca 3240
aacattatta ctacggtggt agctatgcta tggactactg gggtcaagga acctcagtca 3300
ccgtctcctc agctagcacg cgtggtggcg gaggttctgg aggtgggggt tccaccctgg 3360
tggttggtgt cgtgggcggc ctgctgggca gcctggtgct gctagtctgg gtcctggccg 3420
tcatctgctc ccgggccgca cgagggacaa taggagccag gcgcaccggc cagcccctga 3480
aggaggaccc ctcagccgtg cctgtgttct ctgtggacta tggggagctg gatttccagt 3540
ggcgagagaa gaccccggag ccccccgtgc cctgtgtccc tgagcagacg gagtatgcca 3600
ccattgtctt tcctagcgga atgggcacct catcccccgc ccgcaggggc tcagctgacg 3660
gccctcggag tgcccagcca ctgaggcctg aggatggaca ctgctcttgg cccctctgag 3720
gatccccggg taccgagctc gaattcaaaa aaaaaaaaaa aaaaaaaaaa aaaaaaaaaa 3780
aaaaaaaaaa aaaaaaaaaa aaaaaaaaaa ctagtggcgc c 3821

<210> SEQ ID NO 6
<211> LENGTH: 1464
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
atggggggac ttgaaccctg cagcaggttc ctgctcctgc ctctcctgct ggctgtaagt 60
ggtctccgtc ctgtccaggt ccaggcccag agcgattgca gttgctctac ggtgagcccg 120
ggcgtgctgg cagggatcgt gatgggagac ctggtgctga cagtgctcat tgccctggcc 180
gtgtacttcc tgggccggct ggtccctcgg gggcgagggg ctgcggaggc agcgacccgg 240
aaacagcgta tcactgagac cgagtcgcct tatcaggagc tccagggtca gaggtcggat 300
gtctacagcg acctcaacac acagaggccg tattacaaag tcgagggcgg cggagagggc 360
agaggaagtc ttctaacatg cggtgacgtg gaggagaatc ccggccctag gatggcctta 420
ccagtgaccg ccttgctcct gccgctggcc ttgctgctcc acgccgccag gccgggatcc 480
caggtacaac tgcagcagtc tgggcctgag ctggagaagc ctggcgcttc agtgaagata 540
tcctgcaagg cttctggtta ctcattcact ggctacacca tgaactgggt gaagcagagc 600
catggaaaga gccttgagtg gattggactt attactcctt acaatggtgc ttctagctac 660
aaccagaagt tcaggggcaa ggccacatta actgtagaca agtcatccag cacagcctac 720
atggacctcc tcagtctgac atctgaagac tctgcagtct atttctgtgc aagggggggt 780
tacgacggga ggggttttga ctactggggc caagggacca cggtcaccgt ctcctcaggt 840
ggaggcggtt caggcggcgg tggctctagc ggtggtggat cggacatcga gctcactcag 900

```
tctccagcaa tcatgtctgc atctccaggg gagaaggtca ccatgacctg cagtgccagc    960

tcaagtgtaa gttacatgca ctggtaccag cagaagtcag gcacctcccc caaaagatgg   1020

atttatgaca catccaaact ggcttctgga gtcccaggtc gcttcagtgg cagtgggtct   1080

ggaaactctt actctctcac aatcagcagc gtggaggctg aagatgatgc aacttattac   1140

tgccagcagt ggagtaagca ccctctcacg tacggtgctg ggacaaagtt ggaaatcaaa   1200

gctagcggtg gcggaggttc tggaggtggg ggttcctcac ccactgaacc aagctccaaa   1260

accggtaacc ccagacacct gcatgttctg attgggacct cagtggtcaa aatccctttc   1320

accatcctcc tcttctttct ccttcatcgc tggtgctcca acaaaaaaaa tgctgctgta   1380

atggaccaag agcctgcagg gaacagaaca gtgaacagcg aggattctga tgaacaagac   1440

catcaggagg tgtcatacgc ataa                                          1464
```

```
<210> SEQ ID NO 7
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu Leu His Ala Ala Arg Pro Gly Ser
145                 150                 155                 160

Gln Val Gln Leu Gln Gln Ser Gly Pro Glu Leu Glu Lys Pro Gly Ala
                165                 170                 175

Ser Val Lys Ile Ser Cys Lys Ala Ser Gly Tyr Ser Phe Thr Gly Tyr
            180                 185                 190

Thr Met Asn Trp Val Lys Gln Ser His Gly Lys Ser Leu Glu Trp Ile
        195                 200                 205

Gly Leu Ile Thr Pro Tyr Asn Gly Ala Ser Ser Tyr Asn Gln Lys Phe
    210                 215                 220

Arg Gly Lys Ala Thr Leu Thr Val Asp Lys Ser Ser Ser Thr Ala Tyr
225                 230                 235                 240

Met Asp Leu Leu Ser Leu Thr Ser Glu Asp Ser Ala Val Tyr Phe Cys
                245                 250                 255
```

```
Ala Arg Gly Gly Tyr Asp Gly Arg Gly Phe Asp Tyr Trp Gly Gln Gly
            260                 265                 270

Thr Thr Val Thr Val Ser Ser Gly Gly Gly Gly Ser Gly Gly Gly Gly
        275                 280                 285

Ser Ser Gly Gly Gly Ser Asp Ile Glu Leu Thr Gln Ser Pro Ala Ile
    290                 295                 300

Met Ser Ala Ser Pro Gly Glu Lys Val Thr Met Thr Cys Ser Ala Ser
305                 310                 315                 320

Ser Ser Val Ser Tyr Met His Trp Tyr Gln Gln Lys Ser Gly Thr Ser
                325                 330                 335

Pro Lys Arg Trp Ile Tyr Asp Thr Ser Lys Leu Ala Ser Gly Val Pro
            340                 345                 350

Gly Arg Phe Ser Gly Ser Gly Ser Gly Asn Ser Tyr Ser Leu Thr Ile
        355                 360                 365

Ser Ser Val Glu Ala Glu Asp Asp Ala Thr Tyr Tyr Cys Gln Gln Trp
    370                 375                 380

Ser Lys His Pro Leu Thr Tyr Gly Ala Gly Thr Lys Leu Glu Ile Lys
385                 390                 395                 400

Ala Ser Gly Gly Gly Gly Ser Gly Gly Gly Gly Ser Ser Pro Thr Glu
                405                 410                 415

Pro Ser Ser Lys Thr Gly Asn Pro Arg His Leu His Val Leu Ile Gly
            420                 425                 430

Thr Ser Val Val Lys Ile Pro Phe Thr Ile Leu Leu Phe Phe Leu Leu
        435                 440                 445

His Arg Trp Cys Ser Asn Lys Lys Asn Ala Ala Val Met Asp Gln Glu
    450                 455                 460

Pro Ala Gly Asn Arg Thr Val Asn Ser Glu Asp Ser Asp Glu Gln Asp
465                 470                 475                 480

His Gln Glu Val Ser Tyr Ala
                485
```

<210> SEQ ID NO 8
<211> LENGTH: 1365
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
atgattccag cagtggtctt gctcttactc cttttggttg aacaagcagc ggccctggga     60

gagcctcagc tctgctatat cctggatgcc atcctgtttc tgtatggaat tgtcctcacc    120

ctcctctact gccgactgaa gatccaagtg cgaaaggcag ctataaccag ctatgagaaa    180

tcagatggtg tttacacggg cctgagcacc aggaaccagg agacttacga gactctgaag    240

catgagaaac caccacagtc cggaggcggc ggagagggca gaggaagtct tctaacatgc    300

ggtgacgtgg aggagaatcc cggccctagg atggccttac cagtgaccgc cttgctcctg    360

ccgctggcct tgctgctcca cgccgccagg ccgggatccc aggtacaact gcagcagtct    420

gggcctgagc tggagaagcc tggcgcttca gtgaagatat cctgcaaggc ttctggttac    480

tcattcactg gctacaccat gaactgggtg aagcagagcc atggaaagag ccttgagtgg    540

attggactta ttactcctta caatggtgct tctagctaca accagaagtt caggggcaag    600

gccacattaa ctgtagacaa gtcatccagc acagcctaca tggacctcct cagtctgaca    660
```

-continued

```
tctgaagact ctgcagtcta tttctgtgca aggggggggtt acgacgggag gggttttgac    720

tactggggcc aagggaccac ggtcaccgtc tcctcaggtg gaggcggttc aggcggcggt    780

ggctctagcg gtggtggatc ggacatcgag ctcactcagt ctccagcaat catgtctgca    840

tctccagggg agaaggtcac catgacctgc agtgccagct caagtgtaag ttacatgcac    900

tggtaccagc agaagtcagg cacctccccc aaaagatgga tttatgacac atccaaactg    960

gcttctggag tcccaggtcg cttcagtggc agtgggtctg gaaactctta ctctctcaca   1020

atcagcagcg tggaggctga agatgatgca acttattact gccagcagtg gagtaagcac   1080

cctctcacgt acggtgctgg gacaaagttg gaaatcaaag ctagcggtgg cggaggttct   1140

ggaggtgggg gttccttaac cacagagacg ggactccaga aagaccatgc cctctgggat   1200

cacactgccc agaatctcct tcggatgggc ctggcctttc tagtcctggt ggctctagtg   1260

tggttcctgg ttgaagactg gctcagcagg aagaggacta gagagcgagc cagcagagct   1320

tccacttggg aaggcaggag aaggctgaac acacagactc tttga                   1365
```

```
<210> SEQ ID NO 9
<211> LENGTH: 454
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ile Pro Ala Val Val Leu Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln Ser Gly Gly Gly Gly Glu Gly Arg Gly Ser
                85                  90                  95

Leu Leu Thr Cys Gly Asp Val Glu Glu Asn Pro Gly Pro Arg Met Ala
            100                 105                 110

Leu Pro Val Thr Ala Leu Leu Leu Pro Leu Ala Leu Leu Leu His Ala
        115                 120                 125

Ala Arg Pro Gly Ser Gln Val Gln Leu Gln Gln Ser Gly Pro Glu Leu
    130                 135                 140

Glu Lys Pro Gly Ala Ser Val Lys Ile Ser Cys Lys Ala Ser Gly Tyr
145                 150                 155                 160

Ser Phe Thr Gly Tyr Thr Met Asn Trp Val Lys Gln Ser His Gly Lys
                165                 170                 175

Ser Leu Glu Trp Ile Gly Leu Ile Thr Pro Tyr Asn Gly Ala Ser Ser
            180                 185                 190

Tyr Asn Gln Lys Phe Arg Gly Lys Ala Thr Leu Thr Val Asp Lys Ser
        195                 200                 205

Ser Ser Thr Ala Tyr Met Asp Leu Leu Ser Leu Thr Ser Glu Asp Ser
    210                 215                 220

Ala Val Tyr Phe Cys Ala Arg Gly Gly Tyr Asp Gly Arg Gly Phe Asp
225                 230                 235                 240
```

Tyr Trp Gly Gln Gly Thr Thr Val Thr Val Ser Ser Gly Gly Gly Gly
245 250 255

Ser Gly Gly Gly Gly Ser Ser Gly Gly Gly Ser Asp Ile Glu Leu Thr
260 265 270

Gln Ser Pro Ala Ile Met Ser Ala Ser Pro Gly Glu Lys Val Thr Met
275 280 285

Thr Cys Ser Ala Ser Ser Ser Val Ser Tyr Met His Trp Tyr Gln Gln
290 295 300

Lys Ser Gly Thr Ser Pro Lys Arg Trp Ile Tyr Asp Thr Ser Lys Leu
305 310 315 320

Ala Ser Gly Val Pro Gly Arg Phe Ser Gly Ser Gly Ser Gly Asn Ser
325 330 335

Tyr Ser Leu Thr Ile Ser Ser Val Glu Ala Glu Asp Asp Ala Thr Tyr
340 345 350

Tyr Cys Gln Gln Trp Ser Lys His Pro Leu Thr Tyr Gly Ala Gly Thr
355 360 365

Lys Leu Glu Ile Lys Ala Ser Gly Gly Gly Gly Ser Gly Gly Gly Gly
370 375 380

Ser Leu Thr Thr Glu Thr Gly Leu Gln Lys Asp His Ala Leu Trp Asp
385 390 395 400

His Thr Ala Gln Asn Leu Leu Arg Met Gly Leu Ala Phe Leu Val Leu
405 410 415

Val Ala Leu Val Trp Phe Leu Val Glu Asp Trp Leu Ser Arg Lys Arg
420 425 430

Thr Arg Glu Arg Ala Ser Arg Ala Ser Thr Trp Glu Gly Arg Arg Arg
435 440 445

Leu Asn Thr Gln Thr Leu
450

<210> SEQ ID NO 10
<211> LENGTH: 1470
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10
atggggggac ttgaaccctg cagcaggttc ctgctcctgc ctctcctgct ggctgtaagt 60
ggtctccgtc ctgtccaggt ccaggcccag agcgattgca gttgctctac ggtgagcccg 120
ggcgtgctgg cagggatcgt gatgggagac ctggtgctga cagtgctcat tgccctggcc 180
gtgtacttcc tgggccggct ggtccctcgg gggcgagggg ctgcggaggc agcgacccgg 240
aaacagcgta tcactgagac cgagtcgcct tatcaggagc tccagggtca gaggtcggat 300
gtctacagcg acctcaacac acagaggccg tattacaaag tcgagggcgg cggagagggc 360
agaggaagtc ttctaacatg cggtgacgtg gaggagaatc ccggccctag gatggcctta 420
ccagtgaccg ccttgctcct gccgctggcc ttgctgctcc acgccgccag gccgggatcc 480
gacatccaga tgacacagac tacatcctcc ctgtctgcct ctctgggaga cagagtcacc 540
atcagttgca gggcaagtca ggacattagt aaatatttaa attggtatca gcagaaacca 600
gatggaactg ttaaactcct gatctaccat acatcaagat tacactcagg agtcccatca 660
aggttcagtg gcagtgggtc tggaacagat tattctctca ccattagcaa cctggagcaa 720
gaagatattg ccacttactt ttgccaacag ggtaatacgc ttccgtacac gttcggaggg 780

```
gggactaagt tggaaataac aggtggcggt ggctcgggcg gtggtgggtc gggtggcggc    840

ggatctgagg tgaaactgca ggagtcagga cctggcctgg tggcgccctc acagagcctg    900

tccgtcacat gcactgtctc aggggtctca ttacccgact atggtgtaag ctggattcgc    960

cagcctccac gaaagggtct ggagtggctg ggagtaatat ggggtagtga aaccacatac   1020

tataattcag ctctcaaatc cagactgacc atcatcaagg acaactccaa gagccaagtt   1080

ttcttaaaaa tgaacagtct gcaaactgat gacacagcca tttactactg tgccaaacat   1140

tattactacg gtggtagcta tgctatggac tactggggtc aaggaacctc agtcaccgtc   1200

tcctcagcta gcggtggcgg aggttctgga ggtgggggtt cctcacccac tgaaccaagc   1260

tccaaaaccg gtaaccccag acacctgcat gttctgattg ggacctcagt ggtcaaaatc   1320

cctttcacca tcctcctctt ctttctcctt catcgctggt gctccaacaa aaaaaatgct   1380

gctgtaatgg accaagagcc tgcagggaac agaacagtga acagcgagga ttctgatgaa   1440

caagaccatc aggaggtgtc atacgcataa                                    1470
```

```
<210> SEQ ID NO 11
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Gly Leu Glu Pro Cys Ser Arg Phe Leu Leu Leu Pro Leu Leu
1               5                   10                  15

Leu Ala Val Ser Gly Leu Arg Pro Val Gln Val Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
                85                  90                  95

Gln Arg Ser Asp Val Tyr Ser Asp Leu Asn Thr Gln Arg Pro Tyr Tyr
            100                 105                 110

Lys Val Glu Gly Gly Gly Glu Gly Arg Gly Ser Leu Leu Thr Cys Gly
        115                 120                 125

Asp Val Glu Glu Asn Pro Gly Pro Arg Met Ala Leu Pro Val Thr Ala
    130                 135                 140

Leu Leu Leu Pro Leu Ala Leu Leu Leu His Ala Ala Arg Pro Gly Ser
145                 150                 155                 160

Asp Ile Gln Met Thr Gln Thr Thr Ser Ser Leu Ser Ala Ser Leu Gly
                165                 170                 175

Asp Arg Val Thr Ile Ser Cys Arg Ala Ser Gln Asp Ile Ser Lys Tyr
            180                 185                 190

Leu Asn Trp Tyr Gln Gln Lys Pro Asp Gly Thr Val Lys Leu Leu Ile
        195                 200                 205

Tyr His Thr Ser Arg Leu His Ser Gly Val Pro Ser Arg Phe Ser Gly
    210                 215                 220

Ser Gly Ser Gly Thr Asp Tyr Ser Leu Thr Ile Ser Asn Leu Glu Gln
```

```
225                 230                 235                 240

Glu Asp Ile Ala Thr Tyr Phe Cys Gln Gln Gly Asn Thr Leu Pro Tyr
                245                 250                 255

Thr Phe Gly Gly Gly Thr Lys Leu Glu Ile Thr Gly Gly Gly Gly Ser
            260                 265                 270

Gly Gly Gly Gly Ser Gly Gly Gly Gly Ser Glu Val Lys Leu Gln Glu
        275                 280                 285

Ser Gly Pro Gly Leu Val Ala Pro Ser Gln Ser Leu Ser Val Thr Cys
    290                 295                 300

Thr Val Ser Gly Val Ser Leu Pro Asp Tyr Gly Val Ser Trp Ile Arg
305                 310                 315                 320

Gln Pro Pro Arg Lys Gly Leu Glu Trp Leu Gly Val Ile Trp Gly Ser
                325                 330                 335

Glu Thr Thr Tyr Tyr Asn Ser Ala Leu Lys Ser Arg Leu Thr Ile Ile
            340                 345                 350

Lys Asp Asn Ser Lys Ser Gln Val Phe Leu Lys Met Asn Ser Leu Gln
        355                 360                 365

Thr Asp Asp Thr Ala Ile Tyr Tyr Cys Ala Lys His Tyr Tyr Tyr Gly
    370                 375                 380

Gly Ser Tyr Ala Met Asp Tyr Trp Gly Gln Gly Thr Ser Val Thr Val
385                 390                 395                 400

Ser Ser Ala Ser Gly Gly Gly Gly Ser Gly Gly Gly Gly Ser Ser Pro
                405                 410                 415

Thr Glu Pro Ser Ser Lys Thr Gly Asn Pro Arg His Leu His Val Leu
            420                 425                 430

Ile Gly Thr Ser Val Val Lys Ile Pro Phe Thr Ile Leu Leu Phe Phe
        435                 440                 445

Leu Leu His Arg Trp Cys Ser Asn Lys Lys Asn Ala Ala Val Met Asp
    450                 455                 460

Gln Glu Pro Ala Gly Asn Arg Thr Val Asn Ser Glu Asp Ser Asp Glu
465                 470                 475                 480

Gln Asp His Gln Glu Val Ser Tyr Ala
                485
```

<210> SEQ ID NO 12
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 13
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 14
<211> LENGTH: 97
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu
```

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

```
Ala Val Ser Leu Ser Lys Met Leu Lys Lys Arg Ser Pro Leu Thr Thr
1               5                   10                  15

Gly Val Tyr Val Lys Met Pro Pro Thr Glu Pro Glu Cys Glu Lys Gln
            20                  25                  30

Phe Gln Pro Tyr Phe Ile Pro Ile Asn
        35                  40
```

<210> SEQ ID NO 16
<211> LENGTH: 242
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 16

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Ser Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 17
<211> LENGTH: 242
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 17

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80
```

-continued

```
Glu Asp Phe Ala Val Tyr Phe Cys Gln Gln Gly Asn Thr Leu Pro Tyr
            85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Gln Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser


<210> SEQ ID NO 18
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190
```

-continued

```
Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys


<210> SEQ ID NO 19
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys


<210> SEQ ID NO 20
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Ser Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245
```

```
<210> SEQ ID NO 21
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21
```

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
```

```
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Gln Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245


<210> SEQ ID NO 22
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Ser Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205
```

```
Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245
```

<210> SEQ ID NO 23
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Gln Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245
```

<210> SEQ ID NO 24
<211> LENGTH: 247
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

-continued

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Gln Glu Ser Gly Pro Gly Leu Val Lys Pro Ser Glu Thr
    130                 135                 140

Leu Ser Leu Thr Cys Thr Val Ser Gly Val Ser Leu Pro Asp Tyr Gly
145                 150                 155                 160

Val Ser Trp Ile Arg Gln Pro Pro Gly Lys Gly Leu Glu Trp Ile Gly
                165                 170                 175

Val Ile Trp Gly Ser Glu Thr Thr Tyr Tyr Asn Ser Ser Leu Lys Ser
            180                 185                 190

Arg Val Thr Ile Ser Lys Asp Asn Ser Lys Asn Gln Val Ser Leu Lys
        195                 200                 205

Leu Ser Ser Val Thr Ala Ala Asp Thr Ala Val Tyr Tyr Cys Ala Lys
    210                 215                 220

His Tyr Tyr Tyr Gly Gly Ser Tyr Ala Met Asp Tyr Trp Gly Gln Gly
225                 230                 235                 240

Thr Leu Val Thr Val Ser Ser
                245
```

<210> SEQ ID NO 25
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110
```

```
Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Glu Ile Val Met
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Asp Ile Ser Lys Tyr Leu Asn Trp Tyr
                165                 170                 175

Gln Gln Lys Pro Gly Gln Ala Pro Arg Leu Leu Ile Tyr His Thr Ser
            180                 185                 190

Arg Leu His Ser Gly Ile Pro Ala Arg Phe Ser Gly Ser Gly Ser Gly
        195                 200                 205

Thr Asp Tyr Thr Leu Thr Ile Ser Ser Leu Gln Pro Glu Asp Phe Ala
    210                 215                 220

Val Tyr Phe Cys Gln Gln Gly Asn Thr Leu Pro Tyr Thr Phe Gly Gln
225                 230                 235                 240

Gly Thr Lys Leu Glu Ile Lys
                245


<210> SEQ ID NO 26
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Asp Ile Ser Lys Tyr
            20                  25                  30

Leu Asn Trp Tyr Gln Gln Lys Pro Gly Gln Ala Pro Arg Leu Leu Ile
        35                  40                  45

Tyr His Thr Ser Arg Leu His Ser Gly Ile Pro Ala Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Val Tyr Phe Cys Gln Gln Gly Asn Thr Leu Pro Tyr
                85                  90                  95

Thr Phe Gly Gln Gly Thr Lys Leu Glu Ile Lys Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Glu Thr Leu Ser Leu Thr Cys
    130                 135                 140

Thr Val Ser Gly Val Ser Leu Pro Asp Tyr Gly Val Ser Trp Ile Arg
145                 150                 155                 160

Gln Pro Pro Gly Lys Gly Leu Glu Trp Ile Gly Val Ile Trp Gly Ser
                165                 170                 175

Glu Thr Thr Tyr Tyr Asn Ser Ser Leu Lys Ser Arg Val Thr Ile Ser
            180                 185                 190

Lys Asp Asn Ser Lys Asn Gln Val Ser Leu Lys Leu Ser Ser Val Thr
        195                 200                 205

Ala Ala Asp Thr Ala Val Tyr Tyr Cys Ala Lys His Tyr Tyr Tyr Gly
```

```
    210                 215                 220

Gly Ser Tyr Ala Met Asp Tyr Trp Gly Gln Gly Thr Leu Val Thr Val
225                 230                 235                 240

Ser Ser


<210> SEQ ID NO 27
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ser Leu Lys
    50                  55                  60

Ser Arg Val Thr Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Met Thr Gln Ser Pro Ala
    130                 135                 140

Thr Leu Ser Leu Ser Pro Gly Glu Arg Ala Thr Leu Ser Cys Arg Ala
145                 150                 155                 160

Ser Gln Asp Ile Ser Lys Tyr Leu Asn Trp Tyr Gln Gln Lys Pro Gly
                165                 170                 175

Gln Ala Pro Arg Leu Leu Ile Tyr His Thr Ser Arg Leu His Ser Gly
            180                 185                 190

Ile Pro Ala Arg Phe Ser Gly Ser Gly Ser Gly Thr Asp Tyr Thr Leu
        195                 200                 205

Thr Ile Ser Ser Leu Gln Pro Glu Asp Phe Ala Val Tyr Phe Cys Gln
    210                 215                 220

Gln Gly Asn Thr Leu Pro Tyr Thr Phe Gly Gln Gly Thr Lys Leu Glu
225                 230                 235                 240

Ile Lys


<210> SEQ ID NO 28
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Thr Thr Ser Ser Leu Ser Ala Ser Leu Gly
1               5                   10                  15
```

```
Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 29
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys Gly
            100                 105                 110

Gly Gly Gly Ser Gly Gly Gly Gly Ser Ser Gly Gly Gly Ser Gln Ile
        115                 120                 125
```

-continued

Gln Leu Val Gln Ser Gly Pro Glu Leu Lys Lys Pro Gly Glu Thr Val
    130                 135                 140

Lys Ile Ser Cys Lys Ala Ser Gly Tyr Ile Phe Thr Asn Tyr Gly Met
145                 150                 155                 160

Asn Trp Val Lys Gln Ala Pro Gly Lys Ser Phe Lys Trp Met Gly Trp
                165                 170                 175

Ile Asn Thr Tyr Thr Gly Glu Ser Thr Tyr Ser Ala Asp Phe Lys Gly
            180                 185                 190

Arg Phe Ala Phe Ser Leu Glu Thr Ser Ala Ser Thr Ala Tyr Leu His
        195                 200                 205

Ile Asn Asp Leu Lys Asn Glu Asp Thr Ala Thr Tyr Phe Cys Ala Arg
    210                 215                 220

Ser Gly Gly Tyr Asp Pro Met Asp Tyr Trp Gly Gln Gly Thr Ser Val
225                 230                 235                 240

Thr Val Ser Ser

<210> SEQ ID NO 30
<211> LENGTH: 237
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Asp
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Lys Tyr Pro Tyr
                85                  90                  95

Thr Phe Gly Gly Gly Thr Lys Leu Glu Ile Lys Gly Gly Gly Gly Ser
            100                 105                 110

Gly Gly Gly Gly Ser Ser Gly Gly Gly Ser Gln Val Gln Leu Gln Gln
        115                 120                 125

Pro Gly Ala Glu Leu Val Arg Pro Gly Ala Ser Val Lys Leu Ser Cys
    130                 135                 140

Lys Ala Ser Gly Tyr Thr Phe Thr Ser Tyr Trp Met Asn Trp Val Lys
145                 150                 155                 160

Gln Arg Pro Asp Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Tyr Cys Ala Arg Gly Asn Trp Asp
    210                 215                 220

Asp Tyr Trp Gly Gln Gly Thr Thr Leu Thr Val Ser Ser
225                 230                 235

<210> SEQ ID NO 31
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ser Glu Leu Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245
```

<210> SEQ ID NO 32
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45
```

```
Lys Leu Leu Ile Tyr Arg Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ala Glu Val Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
        195                 200                 205

Thr Ala Tyr Met Glu Leu Ser Ser Leu Arg Ser Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245


<210> SEQ ID NO 33
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ser Glu Leu Lys Lys
    130                 135                 140

Pro Gly Ala Ser Val Lys Val Ser Cys Lys Ala Ser Gly Tyr Ile Phe
145                 150                 155                 160
```

```
Thr Asn Tyr Gly Met Asn Trp Val Arg Gln Ala Pro Gly Gln Gly Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Phe Val Phe Ser Leu Asp Thr Ser Val Ser
        195                 200                 205

Thr Ala Tyr Leu Gln Ile Asn Ala Leu Lys Ala Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245


<210> SEQ ID NO 34
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Asp Asn Tyr
            20                  25                  30

Gly Asn Thr Phe Met His Trp Tyr Gln Gln Lys Pro Gly Gln Ala Pro
        35                  40                  45

Arg Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Ser
65                  70                  75                  80

Ser Leu Glu Pro Glu Asp Val Ala Val Tyr Tyr Cys Gln Gln Ser Asn
                85                  90                  95

Glu Asp Pro Pro Thr Phe Gly Gln Gly Thr Lys Leu Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Gln Ile Gln Leu Val Gln Ser Gly Ala Glu Val Lys Lys
    130                 135                 140

Pro Gly Ala Ser Val Lys Val Ser Cys Lys Ala Ser Gly Tyr Ile Phe
145                 150                 155                 160

Thr Asn Tyr Gly Met Asn Trp Val Arg Gln Ala Pro Gly Gln Arg Leu
                165                 170                 175

Glu Trp Met Gly Trp Ile Asn Thr Tyr Thr Gly Glu Ser Thr Tyr Ser
            180                 185                 190

Ala Asp Phe Lys Gly Arg Val Thr Ile Thr Leu Asp Thr Ser Ala Ser
        195                 200                 205

Thr Ala Tyr Met Glu Leu Ser Ser Leu Arg Ser Glu Asp Thr Ala Val
    210                 215                 220

Tyr Tyr Cys Ala Arg Ser Gly Gly Tyr Asp Pro Met Asp Tyr Trp Gly
225                 230                 235                 240

Gln Gly Thr Thr Val Thr Val Ser Ser
                245
```

<210> SEQ ID NO 35
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ser Ala Asp Phe
    50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Leu Thr Gln
    130                 135                 140

Ser Pro Asp Ser Leu Ala Val Ser Leu Gly Glu Arg Ala Thr Ile Asn
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
            180                 185                 190

Ala Ser Asn Leu Glu Ser Gly Val Pro Asp Arg Phe Ser Gly Ser Gly
        195                 200                 205

Ser Arg Thr Asp Phe Thr Leu Thr Ile Ser Ser Leu Gln Ala Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245
```

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

```
Gln Ile Gln Leu Val Gln Ser Gly Ser Glu Leu Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Ser Thr Tyr Ser Ala Asp Phe
```

```
    50                  55                  60

Lys Gly Arg Phe Val Phe Ser Leu Asp Thr Ser Val Ser Thr Ala Tyr
65                  70                  75                  80

Leu Gln Ile Asn Ala Leu Lys Ala Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
            180                 185                 190

Ala Ser Asn Leu Glu Ser Gly Ile Pro Ala Arg Phe Ser Gly Ser Gly
        195                 200                 205

Ser Arg Thr Asp Phe Thr Leu Thr Ile Ser Ser Leu Glu Pro Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245


<210> SEQ ID NO 37
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ser Thr Tyr Ser Ala Asp Phe
    50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Asp Ile Val Leu Thr Gln
    130                 135                 140

Ser Pro Asp Ser Leu Ala Val Ser Leu Gly Glu Arg Ala Thr Ile Asn
145                 150                 155                 160
```

```
Cys Arg Ala Ser Glu Ser Val Asp Asn Tyr Gly Asn Thr Phe Met His
                165                 170                 175

Trp Tyr Gln Gln Lys Pro Gly Gln Pro Pro Lys Leu Leu Ile Tyr Arg
            180                 185                 190

Ala Ser Asn Leu Glu Ser Gly Val Pro Asp Arg Phe Ser Gly Ser Gly
        195                 200                 205

Ser Arg Thr Asp Phe Thr Leu Thr Ile Ser Ser Leu Gln Ala Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245


<210> SEQ ID NO 38
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Gly Met Asn Trp Val Arg Gln Ala Pro Gly Gln Arg Leu Glu Trp Met
        35                  40                  45

Gly Trp Ile Asn Thr Tyr Thr Gly Glu Ser Thr Tyr Ser Ala Asp Phe
    50                  55                  60

Lys Gly Arg Val Thr Ile Thr Leu Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Gly Tyr Asp Pro Met Asp Tyr Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Glu Ser Val Asp Asn Tyr Gly Asn Thr Phe Met His
                165                 170                 175

Trp Tyr Gln Gln Lys Pro Gly Gln Ala Pro Arg Leu Leu Ile Tyr Arg
            180                 185                 190

Ala Ser Asn Leu Glu Ser Gly Ile Pro Ala Arg Phe Ser Gly Ser Gly
        195                 200                 205

Ser Arg Thr Asp Phe Thr Leu Thr Ile Ser Ser Leu Glu Pro Glu Asp
    210                 215                 220

Val Ala Val Tyr Tyr Cys Gln Gln Ser Asn Glu Asp Pro Pro Thr Phe
225                 230                 235                 240

Gly Gln Gly Thr Lys Leu Glu Ile Lys
                245


<210> SEQ ID NO 39
```

<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Asp Ser
    130                 135                 140

Leu Ala Val Ser Leu Gly Glu Arg Ala Thr Ile Asn Cys Lys Ser Ser
145                 150                 155                 160

Gln Ser Leu Leu Asp Ser Asp Gly Lys Thr Tyr Leu Asn Trp Leu Gln
                165                 170                 175

Gln Lys Pro Gly Gln Pro Pro Lys Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Thr Ile Ser Ser Leu Gln Ala Glu Asp Val Ala Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 40
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Asp Val Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asp Ser
            20                  25                  30

Asp Gly Lys Thr Tyr Leu Asn Trp Leu Gln Gln Lys Pro Gly Gln Pro
        35                  40                  45

Pro Lys Arg Leu Ile Ser Leu Val Ser Lys Leu Asp Ser Gly Val Pro
    50                  55                  60
```

```
Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245


<210> SEQ ID NO 41
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly His Val Thr Ile Ser Ala Asp Thr Ser Ile Asn Thr Val Tyr
65                  70                  75                  80

Leu Gln Trp Ser Ser Leu Lys Ala Ser Asp Thr Ala Met Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
```

```
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245


<210> SEQ ID NO 42
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Glu Ser Leu Arg Ile Ser Cys Lys Gly Ser Gly Phe Asn
145                 150                 155                 160

Ile Glu Asp Tyr Tyr Ile His Trp Val Arg Gln Met Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245


<210> SEQ ID NO 43
<211> LENGTH: 246
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
Glu Ile Gln Leu Val Gln Ser Gly Ala Glu Val Lys Lys Pro Gly Ala
1               5                   10                  15

Thr Val Lys Ile Ser Cys Lys Gly Ser Gly Phe Asn Ile Glu Asp Tyr
            20                  25                  30

Tyr Ile His Trp Val Gln Gln Ala Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60

Gln Gly Arg Val Thr Ile Thr Ala Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Phe Arg Gly Gly Val Tyr Trp Gly Gln Gly Thr Thr Val Thr Val
            100                 105                 110

Ser Ser Gly Gly Gly Gly Ser Gly Gly Gly Gly Ser Gly Gly Gly Gly
        115                 120                 125

Ser Gly Gly Gly Gly Ser Asp Val Val Met Thr Gln Ser Pro Leu Ser
    130                 135                 140

Leu Pro Val Thr Leu Gly Gln Pro Ala Ser Ile Ser Cys Lys Ser Ser
145                 150                 155                 160

Gln Ser Leu Leu Asp Ser Asp Gly Lys Thr Tyr Leu Asn Trp Leu Gln
                165                 170                 175

Gln Arg Pro Gly Gln Ser Pro Arg Arg Leu Ile Ser Leu Val Ser Lys
            180                 185                 190

Leu Asp Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Val
    210                 215                 220

Tyr Tyr Cys Trp Gln Gly Thr His Phe Pro Gly Thr Phe Gly Gly Gly
225                 230                 235                 240

Thr Lys Val Glu Ile Lys
                245
```

<210> SEQ ID NO 44
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

```
Glu Ile Gln Leu Val Gln Ser Gly Ala Glu Val Lys Lys Pro Gly Glu
1               5                   10                  15

Ser Leu Arg Ile Ser Cys Lys Gly Ser Gly Phe Asn Ile Glu Asp Tyr
            20                  25                  30

Tyr Ile His Trp Val Arg Gln Met Pro Gly Lys Gly Leu Glu Trp Met
        35                  40                  45

Gly Arg Ile Asp Pro Glu Asn Asp Glu Thr Lys Tyr Gly Pro Ile Phe
    50                  55                  60
```

-continued

Gln Gly His Val Thr Ile Ser Ala Asp Thr Ser Ile Asn Thr Val Tyr
65 70 75 80

Leu Gln Trp Ser Ser Leu Lys Ala Ser Asp Thr Ala Met Tyr Tyr Cys
85 90 95

Ala Phe Arg Gly Gly Val Tyr Trp Gly Gln Gly Thr Thr Val Thr Val
100 105 110

Ser Ser Gly Gly Gly Gly Ser Gly Gly Gly Gly Ser Gly Gly Gly Gly
115 120 125

Ser Gly Gly Gly Gly Ser Asp Val Val Met Thr Gln Ser Pro Asp Ser
130 135 140

Leu Ala Val Ser Leu Gly Glu Arg Ala Thr Ile Asn Cys Lys Ser Ser
145 150 155 160

Gln Ser Leu Leu Asp Ser Asp Gly Lys Thr Tyr Leu Asn Trp Leu Gln
165 170 175

Gln Lys Pro Gly Gln Pro Pro Lys Arg Leu Ile Ser Leu Val Ser Lys
180 185 190

Leu Asp Ser Gly Val Pro Asp Arg Phe Ser Gly Ser Gly Ser Gly Thr
195 200 205

Asp Phe Thr Leu Thr Ile Ser Ser Leu Gln Ala Glu Asp Val Ala Val
210 215 220

Tyr Tyr Cys Trp Gln Gly Thr His Phe Pro Gly Thr Phe Gly Gly Gly
225 230 235 240

Thr Lys Val Glu Ile Lys
245

<210> SEQ ID NO 45
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Asp Val Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asp Ser
20 25 30

Asp Gly Lys Thr Tyr Leu Asn Trp Leu Gln Gln Lys Pro Gly Gln Pro
35 40 45

Pro Lys Arg Leu Ile Ser Leu Val Ser Lys Leu Asp Ser Gly Val Pro
50 55 60

Asp Arg Phe Ser Gly Ser Gly Ser Gly Thr Asp Phe Thr Leu Thr Ile
65 70 75 80

Ser Ser Leu Gln Ala Glu Asp Val Ala Val Tyr Tyr Cys Trp Gln Gly
85 90 95

Thr His Phe Pro Gly Thr Phe Gly Gly Gly Thr Lys Val Glu Ile Lys
100 105 110

Gly Gly Gly Gly Ser Gly Gly Gly Gly Ser Gly Gly Gly Gly Ser Gly
115 120 125

Gly Gly Gly Ser Glu Ile Gln Leu Val Gln Ser Gly Ala Glu Val Lys
130 135 140

Lys Pro Gly Glu Ser Leu Arg Ile Ser Cys Lys Gly Ser Gly Phe Asn
145 150 155 160

Ile Glu Asp Tyr Tyr Ile His Trp Val Arg Gln Met Pro Gly Lys Gly
165 170 175

-continued

```
Leu Glu Trp Met Gly Arg Ile Asp Pro Glu Asn Asp Glu Thr Lys Tyr
            180                 185                 190

Gly Pro Ile Phe Gln Gly His Val Thr Ile Ser Ala Asp Thr Ser Ile
        195                 200                 205

Asn Thr Val Tyr Leu Gln Trp Ser Ser Leu Lys Ala Ser Asp Thr Ala
    210                 215                 220

Met Tyr Tyr Cys Ala Phe Arg Gly Gly Val Tyr Trp Gly Gln Gly Thr
225                 230                 235                 240

Thr Val Thr Val Ser Ser
                245


<210> SEQ ID NO 46
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Arg Arg Leu Ile Ser Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gly Thr Phe Gly Gly Gly Thr Lys Val Glu Ile Lys
            100                 105                 110

Gly Gly Gly Gly Ser Gly Gly Gly Gly Ser Gly Gly Gly Gly Ser Gly
        115                 120                 125

Gly Gly Gly Ser Glu Ile Gln Leu Val Gln Ser Gly Ala Glu Val Lys
    130                 135                 140

Lys Pro Gly Ala Thr Val Lys Ile Ser Cys Lys Gly Ser Gly Phe Asn
145                 150                 155                 160

Ile Glu Asp Tyr Tyr Ile His Trp Val Gln Gln Ala Pro Gly Lys Gly
                165                 170                 175

Leu Glu Trp Met Gly Arg Ile Asp Pro Glu Asn Asp Glu Thr Lys Tyr
            180                 185                 190

Gly Pro Ile Phe Gln Gly Arg Val Thr Ile Thr Ala Asp Thr Ser Thr
        195                 200                 205

Asn Thr Val Tyr Met Glu Leu Ser Ser Leu Arg Ser Glu Asp Thr Ala
    210                 215                 220

Val Tyr Tyr Cys Ala Phe Arg Gly Gly Val Tyr Trp Gly Gln Gly Thr
225                 230                 235                 240

Thr Val Thr Val Ser Ser
                245


<210> SEQ ID NO 47
<211> LENGTH: 243
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 47

Glu Ile Gln Leu Gln Gln Ser Gly Ala Glu Leu Val Lys Pro Gly Ala
1               5                   10                  15

Ser Val Lys Leu Ser Cys Thr Gly Ser Gly Phe Asn Ile Glu Asp Tyr
            20                  25                  30

Tyr Ile His Trp Val Lys Gln Arg Thr Glu Gln Gly Leu Glu Trp Ile
        35                  40                  45

Gly Arg Ile Asp Pro Glu Asn Asp Glu Thr Lys Tyr Gly Pro Ile Phe
    50                  55                  60

Gln Gly Arg Ala Thr Ile Thr Ala Asp Thr Ser Ser Asn Thr Val Tyr
65                  70                  75                  80

Leu Gln Leu Ser Ser Leu Thr Ser Glu Asp Thr Ala Val Tyr Tyr Cys
                85                  90                  95

Ala Phe Arg Gly Gly Val Tyr Trp Gly Pro Gly Thr Thr Leu Thr Val
            100                 105                 110

Ser Ser Gly Gly Gly Gly Ser Gly Gly Gly Gly Ser Gly Gly Gly Gly
        115                 120                 125

Ser His Met Asp Val Val Met Thr Gln Ser Pro Leu Thr Leu Ser Val
    130                 135                 140

Ala Ile Gly Gln Ser Ala Ser Ile Ser Cys Lys Ser Ser Gln Ser Leu
145                 150                 155                 160

Leu Asp Ser Asp Gly Lys Thr Tyr Leu Asn Trp Leu Leu Gln Arg Pro
                165                 170                 175

Gly Gln Ser Pro Lys Arg Leu Ile Ser Leu Val Ser Lys Leu Asp Ser
            180                 185                 190

Gly Val Pro Asp Arg Phe Thr Gly Ser Gly Ser Gly Thr Asp Phe Thr
        195                 200                 205

Leu Arg Ile Ser Arg Val Glu Ala Glu Asp Leu Gly Ile Tyr Tyr Cys
    210                 215                 220

Trp Gln Gly Thr His Phe Pro Gly Thr Phe Gly Gly Gly Thr Lys Leu
225                 230                 235                 240

Glu Ile Lys

<210> SEQ ID NO 48
<211> LENGTH: 239
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 48

Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
85 90 95

Ala Arg Gly Gly Tyr Asp Gly Arg Gly Phe Asp Tyr Trp Gly Gln Gly
100 105 110

Thr Thr Val Thr Val Ser Ser Gly Gly Gly Ser Gly Gly Gly Gly
115 120 125

Ser Gly Gly Gly Gly Ser Asp Ile Glu Leu Thr Gln Ser Pro Ala Ile
130 135 140

Met Ser Ala Ser Pro Gly Glu Lys Val Thr Met Thr Cys Ser Ala Ser
145 150 155 160

Ser Ser Val Ser Tyr Met His Trp Tyr Gln Gln Lys Ser Gly Thr Ser
165 170 175

Pro Lys Arg Trp Ile Tyr Asp Thr Ser Lys Leu Ala Ser Gly Val Pro
180 185 190

Gly Arg Phe Ser Gly Ser Gly Ser Gly Asn Ser Tyr Ser Leu Thr Ile
195 200 205

Ser Ser Val Glu Ala Glu Asp Asp Ala Thr Tyr Tyr Cys Gln Gln Trp
210 215 220

Ser Gly Tyr Pro Leu Thr Phe Gly Ala Gly Thr Lys Leu Glu Ile
225 230 235

<210> SEQ ID NO 49
<211> LENGTH: 230
<212> TYPE: PRT
<213> ORGANISM: Homo sapiens

<400> SEQUENCE: 49

Glu Ser Lys Tyr Gly Pro Pro Cys Pro Pro Cys Pro Ala Pro Glu Phe
1 5 10 15

Leu Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Thr Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser 210 215 220

Leu Ser Leu Gly Lys Met
225 230

<210> SEQ ID NO 50
<211> LENGTH: 282
<212> TYPE: PRT
<213> ORGANISM: Homo sapiens

<400> SEQUENCE: 50

Arg Trp Pro Glu Ser Pro Lys Ala Gln Ala Ser Ser Val Pro Thr Ala
1 5 10 15

Gln Pro Gln Ala Glu Gly Ser Leu Ala Lys Ala Thr Thr Ala Pro Ala
20 25 30

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys
165 170 175

Leu Ser Leu Asn Leu Leu Ala Ser Ser Asp Pro Pro Glu Ala Ala Ser
180 185 190

Trp Leu Leu Cys Glu Val Ser Gly Phe Ser Pro Pro Asn Ile Leu Leu
195 200 205

Met Trp Leu Glu Asp Gln Arg Glu Val Asn Thr Ser Gly Phe Ala Pro
210 215 220

Ala Arg Pro Pro Pro Gln Pro Gly Ser Thr Thr Phe Trp Ala Trp Ser
225 230 235 240

Val Leu Arg Val Pro Ala Pro Pro Ser Pro Gln Pro Ala Thr Tyr Thr
245 250 255

Cys Val Val Ser His Glu Asp Ser Arg Thr Leu Leu Asn Ala Ser Arg
260 265 270

Ser Leu Glu Val Ser Tyr Val Thr Asp His
275 280

<210> SEQ ID NO 51
<211> LENGTH: 43
<212> TYPE: PRT
<213> ORGANISM: Homo sapiens

<400> SEQUENCE: 51

Thr Thr Thr Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly

```
            20                  25                  30

Gly Ala Val His Thr Arg Gly Leu Asp Phe Ala
        35                  40


<210> SEQ ID NO 52
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (36)..(947)

<400> SEQUENCE: 52

ctggggcgcg gccgcctgtc tgcacagaca gcacc atg tcg ctc atg gtc gtc        53
                                       Met Ser Leu Met Val Val
                                       1               5

agc atg gcg tgt gtt ggg ttc ttc ttg ctg cag ggg gcc tgg cca cat      101
Ser Met Ala Cys Val Gly Phe Phe Leu Leu Gln Gly Ala Trp Pro His
            10                  15                  20

gag gga gtc cac aga aaa cct tcc ctc ctg gcc cac cca ggt ccc ctg      149
Glu Gly Val His Arg Lys Pro Ser Leu Leu Ala His Pro Gly Pro Leu
        25                  30                  35

gtg aaa tca gaa gag aca gtc atc ctg caa tgt tgg tca gat gtc agg      197
Val Lys Ser Glu Glu Thr Val Ile Leu Gln Cys Trp Ser Asp Val Arg
    40                  45                  50

ttt gag cac ttc ctt ctg cac aga gag ggg aag tat aag gac act ttg      245
Phe Glu His Phe Leu Leu His Arg Glu Gly Lys Tyr Lys Asp Thr Leu
55                  60                  65                  70

cac ctc att gga gag cac cat gat ggg gtc tcc aag gcc aac ttc tcc      293
His Leu Ile Gly Glu His His Asp Gly Val Ser Lys Ala Asn Phe Ser
                75                  80                  85

atc ggt ccc atg atg caa gac ctt gca ggg acc tac aga tgc tac ggt      341
Ile Gly Pro Met Met Gln Asp Leu Ala Gly Thr Tyr Arg Cys Tyr Gly
            90                  95                  100

tct gtt act cac tcc ccc tat cag ttg tca gct ccc agt gac cct ctg      389
Ser Val Thr His Ser Pro Tyr Gln Leu Ser Ala Pro Ser Asp Pro Leu
        105                 110                 115

gac atc gtc atc aca ggt cta tat gag aaa cct tct ctc tca gcc cag      437
Asp Ile Val Ile Thr Gly Leu Tyr Glu Lys Pro Ser Leu Ser Ala Gln
    120                 125                 130

ccg ggc ccc acg gtt ttg gca gga gag agc gtg acc ttg tcc tgc agc      485
Pro Gly Pro Thr Val Leu Ala Gly Glu Ser Val Thr Leu Ser Cys Ser
135                 140                 145                 150

tcc cgg agc tcc tat gac atg tac cat cta tcc agg gag ggg gag gcc      533
Ser Arg Ser Ser Tyr Asp Met Tyr His Leu Ser Arg Glu Gly Glu Ala
                155                 160                 165

cat gaa cgt agg ttc tct gca ggg ccc aag gtc aac gga aca ttc cag      581
His Glu Arg Arg Phe Ser Ala Gly Pro Lys Val Asn Gly Thr Phe Gln
            170                 175                 180

gcc gac ttt cct ctg ggc cct gcc acc cac gga gga acc tac aga tgc      629
Ala Asp Phe Pro Leu Gly Pro Ala Thr His Gly Gly Thr Tyr Arg Cys
        185                 190                 195

ttc ggc tct ttc cgt gac tct ccc tat gag tgg tca aac tcg agt gac      677
Phe Gly Ser Phe Arg Asp Ser Pro Tyr Glu Trp Ser Asn Ser Ser Asp
    200                 205                 210

cca ctg ctt gtt tct gtc aca gga aac cct tca aat agt tgg cct tca      725
Pro Leu Leu Val Ser Val Thr Gly Asn Pro Ser Asn Ser Trp Pro Ser
215                 220                 225                 230
```

```
ccc act gaa cca agc tcc aaa acc ggt aac ccc aga cac ctg cat gtt      773
Pro Thr Glu Pro Ser Ser Lys Thr Gly Asn Pro Arg His Leu His Val
                235                 240                 245

ctg att ggg acc tca gtg gtc aaa atc cct ttc acc atc ctc ctc ttc      821
Leu Ile Gly Thr Ser Val Val Lys Ile Pro Phe Thr Ile Leu Leu Phe
            250                 255                 260

ttt ctc ctt cat cgc tgg tgc tcc aac aaa aaa aat gct gct gta atg      869
Phe Leu Leu His Arg Trp Cys Ser Asn Lys Lys Asn Ala Ala Val Met
        265                 270                 275

gac caa gag cct gca ggg aac aga aca gtg aac agc gag gat tct gat      917
Asp Gln Glu Pro Ala Gly Asn Arg Thr Val Asn Ser Glu Asp Ser Asp
    280                 285                 290

gaa caa gac cat cag gag gtg tca tac gca taattggatc actgtgtttt        967
Glu Gln Asp His Gln Glu Val Ser Tyr Ala
295                 300

cacacagaga aaaatcactc gcccttctga gaggcccaag acacccccaa cagataccag   1027

catgtacata gaacttccaa atgctgagcc cagatccaaa gttgtcttct gtccacgagc   1087

accacagtca ggccttgagg ggatcttcta gggagacaac agccctgtct caaaaccggg   1147

ttgccagctc ccatgtacca gcagctggaa tctgaaggca tcagtcttca tcttagggca   1207

tcgctcttcc tcacaccacg aatctgaaca tgcctctctc ttgcttacaa atgtctaagg   1267

tccccactgc ctgctggaga gaaaacacac tcctttgctt agcccacaat tctccatttc   1327

acttgacccc tgcccacctc tccaacctaa ctggcttact tcctagtcta cctgaggctg   1387

caatcacact gaggaactca caattccaaa catacaagag gctgcctctt aacacagcac   1447

ttagacacgt gctgttccac ctcccttcag actatctttc agccttctgc cagcagtaaa   1507

acttataaat tttttaaata atttcaatgt agttttcccg ccttcaaata aacatgtctg   1567

ccctcatgaa a                                                         1578


<210> SEQ ID NO 53
<211> LENGTH: 304
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Met Ser Leu Met Val Val Ser Met Ala Cys Val Gly Phe Phe Leu Leu
1               5                   10                  15

Gln Gly Ala Trp Pro His Glu Gly Val His Arg Lys Pro Ser Leu Leu
            20                  25                  30

Ala His Pro Gly Pro Leu Val Lys Ser Glu Glu Thr Val Ile Leu Gln
        35                  40                  45

Cys Trp Ser Asp Val Arg Phe Glu His Phe Leu Leu His Arg Glu Gly
    50                  55                  60

Lys Tyr Lys Asp Thr Leu His Leu Ile Gly Glu His His Asp Gly Val
65                  70                  75                  80

Ser Lys Ala Asn Phe Ser Ile Gly Pro Met Met Gln Asp Leu Ala Gly
                85                  90                  95

Thr Tyr Arg Cys Tyr Gly Ser Val Thr His Ser Pro Tyr Gln Leu Ser
            100                 105                 110

Ala Pro Ser Asp Pro Leu Asp Ile Val Ile Thr Gly Leu Tyr Glu Lys
        115                 120                 125

Pro Ser Leu Ser Ala Gln Pro Gly Pro Thr Val Leu Ala Gly Glu Ser
    130                 135                 140
```

```
Val Thr Leu Ser Cys Ser Ser Arg Ser Ser Tyr Asp Met Tyr His Leu
145                 150                 155                 160

Ser Arg Glu Gly Glu Ala His Glu Arg Arg Phe Ser Ala Gly Pro Lys
                165                 170                 175

Val Asn Gly Thr Phe Gln Ala Asp Phe Pro Leu Gly Pro Ala Thr His
            180                 185                 190

Gly Gly Thr Tyr Arg Cys Phe Gly Ser Phe Arg Asp Ser Pro Tyr Glu
        195                 200                 205

Trp Ser Asn Ser Ser Asp Pro Leu Leu Val Ser Val Thr Gly Asn Pro
    210                 215                 220

Ser Asn Ser Trp Pro Ser Pro Thr Glu Pro Ser Ser Lys Thr Gly Asn
225                 230                 235                 240

Pro Arg His Leu His Val Leu Ile Gly Thr Ser Val Val Lys Ile Pro
                245                 250                 255

Phe Thr Ile Leu Leu Phe Phe Leu Leu His Arg Trp Cys Ser Asn Lys
            260                 265                 270

Lys Asn Ala Ala Val Met Asp Gln Glu Pro Ala Gly Asn Arg Thr Val
        275                 280                 285

Asn Ser Glu Asp Ser Asp Glu Gln Asp His Gln Glu Val Ser Tyr Ala
    290                 295                 300


<210> SEQ ID NO 54
<211> LENGTH: 1596
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (38)..(1060)

<400> SEQUENCE: 54

agctggggcg cggccgcctg tctgcacaga cagcacc atg tcg ctc atg gtc gtc      55
                                         Met Ser Leu Met Val Val
                                         1               5

agc atg gtg tgt gtt ggg ttc ttc ttg ctg cag ggg gcc tgg cca cat      103
Ser Met Val Cys Val Gly Phe Phe Leu Leu Gln Gly Ala Trp Pro His
            10                  15                  20

gag gga gtc cac aga aaa cct tcc ctc ctg gcc cac cca ggt ccc ctg      151
Glu Gly Val His Arg Lys Pro Ser Leu Leu Ala His Pro Gly Pro Leu
        25                  30                  35

gtg aaa tca gaa gag aca gtc atc ctg caa tgt tgg tca gat gtc agg      199
Val Lys Ser Glu Glu Thr Val Ile Leu Gln Cys Trp Ser Asp Val Arg
    40                  45                  50

ttt cag cac ttc ctt ctg cac aga gaa ggg aag ttt aag gac act ttg      247
Phe Gln His Phe Leu Leu His Arg Glu Gly Lys Phe Lys Asp Thr Leu
55                  60                  65                  70

cac ctc att gga gag cac cat gat ggg gtc tcc aag gcc aac ttc tcc      295
His Leu Ile Gly Glu His His Asp Gly Val Ser Lys Ala Asn Phe Ser
                75                  80                  85

atc ggt ccc atg atg caa gac ctt gca ggg acc tac aga tgc tac ggt      343
Ile Gly Pro Met Met Gln Asp Leu Ala Gly Thr Tyr Arg Cys Tyr Gly
            90                  95                  100

tct gtt act cac tcc ccc tat cag ttg tca gct ccc agt gac cct ctg      391
Ser Val Thr His Ser Pro Tyr Gln Leu Ser Ala Pro Ser Asp Pro Leu
        105                 110                 115

gac atc gtc atc aca ggt cta tat gag aaa cct tct ctc tca gcc cag      439
Asp Ile Val Ile Thr Gly Leu Tyr Glu Lys Pro Ser Leu Ser Ala Gln
```

-continued

```
    120                 125                 130

ccg ggc ccc acg gtt ctg gca gga gag agc gtg acc ttg tcc tgc agc      487
Pro Gly Pro Thr Val Leu Ala Gly Glu Ser Val Thr Leu Ser Cys Ser
135                 140                 145                 150

tcc cgg agc tcc tat gac atg tac cat cta tcc agg gag ggg gag gcc      535
Ser Arg Ser Ser Tyr Asp Met Tyr His Leu Ser Arg Glu Gly Glu Ala
                155                 160                 165

cat gaa cgt agg ttc tct gca ggg ccc aag gtc aac gga aca ttc cag      583
His Glu Arg Arg Phe Ser Ala Gly Pro Lys Val Asn Gly Thr Phe Gln
            170                 175                 180

gcc gac ttt cct ctg ggc cct gcc acc cac gga gga acc tac aga tgc      631
Ala Asp Phe Pro Leu Gly Pro Ala Thr His Gly Gly Thr Tyr Arg Cys
        185                 190                 195

ttc ggc tct ttc cgt gac tct cca tac gag tgg tca aac tcg agt gac      679
Phe Gly Ser Phe Arg Asp Ser Pro Tyr Glu Trp Ser Asn Ser Ser Asp
    200                 205                 210

cca ctg ctt gtt tct gtc aca gga aac cct tca aat agt tgg cct tca      727
Pro Leu Leu Val Ser Val Thr Gly Asn Pro Ser Asn Ser Trp Pro Ser
215                 220                 225                 230

ccc act gaa cca agc tcc gaa acc ggt aac ccc aga cac ctg cat gtt      775
Pro Thr Glu Pro Ser Ser Glu Thr Gly Asn Pro Arg His Leu His Val
                235                 240                 245

ctg att ggg acc tca gtg gtc atc atc ctc ttc atc ctc ctc ctc ttc      823
Leu Ile Gly Thr Ser Val Val Ile Ile Leu Phe Ile Leu Leu Leu Phe
            250                 255                 260

ttt ctc ctt cat cgc tgg tgc tgc aac aaa aaa aat gct gtt gta atg      871
Phe Leu Leu His Arg Trp Cys Cys Asn Lys Lys Asn Ala Val Val Met
        265                 270                 275

gac caa gag cct gca ggg aac aga aca gtg aac agg gag gac tct gat      919
Asp Gln Glu Pro Ala Gly Asn Arg Thr Val Asn Arg Glu Asp Ser Asp
    280                 285                 290

gaa caa gac cct cag gag gtg aca tat gca cag ttg aat cac tgc gtt      967
Glu Gln Asp Pro Gln Glu Val Thr Tyr Ala Gln Leu Asn His Cys Val
295                 300                 305                 310

ttc aca cag aga aaa atc act cgc cct tct cag agg ccc aag aca ccc     1015
Phe Thr Gln Arg Lys Ile Thr Arg Pro Ser Gln Arg Pro Lys Thr Pro
                315                 320                 325

cca aca gat atc atc gtg tac acg gaa ctt cca aat gct gag ccc         1060
Pro Thr Asp Ile Ile Val Tyr Thr Glu Leu Pro Asn Ala Glu Pro
            330                 335                 340

tgatccaaag ttgtctcctg cccatgagca ccacagtcag gccttgaggg gatcttctag   1120

ggagacaaca gccctgtctc aaaactgggt tgccagctcc aatgtaccag cagctggaat   1180

ctgaaggcgt gagtctgcat cttagggcat cgctcttcct cacaccacaa atctgaacgt   1240

gcctctccct tgcttacaaa tgtctaaggt ccccactgcc tgctggagag aaaacacact   1300

cctttgctta gcccacaatt ctccatttca cttgacccct gcccacctct ccaacctaac   1360

tggcttactt cctagtctac ttgaggctgc aatcacactg aggaactcac aattccaaac   1420

atacaagagg ctccctctta acacggcact tagacacgtg ctgttccacc ttccctcatg   1480

ctgttccacc tcccctcaga ctagctttca gccttctgtc agcagtaaaa cttatatatt   1540

ttttaaaata atttcaatgt agttttccct ccttcaaata aacatgtctg ccctca       1596
```

<210> SEQ ID NO 55
<211> LENGTH: 341
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Met Ser Leu Met Val Val Ser Met Val Cys Val Gly Phe Phe Leu Leu
1 5 10 15

Gln Gly Ala Trp Pro His Glu Gly Val His Arg Lys Pro Ser Leu Leu
20 25 30

Ala His Pro Gly Pro Leu Val Lys Ser Glu Glu Thr Val Ile Leu Gln
35 40 45

Cys Trp Ser Asp Val Arg Phe Gln His Phe Leu Leu His Arg Glu Gly
50 55 60

Lys Phe Lys Asp Thr Leu His Leu Ile Gly Glu His His Asp Gly Val
65 70 75 80

Ser Lys Ala Asn Phe Ser Ile Gly Pro Met Met Gln Asp Leu Ala Gly
85 90 95

Thr Tyr Arg Cys Tyr Gly Ser Val Thr His Ser Pro Tyr Gln Leu Ser
100 105 110

Ala Pro Ser Asp Pro Leu Asp Ile Val Ile Thr Gly Leu Tyr Glu Lys
115 120 125

Pro Ser Leu Ser Ala Gln Pro Gly Pro Thr Val Leu Ala Gly Glu Ser
130 135 140

Val Thr Leu Ser Cys Ser Ser Arg Ser Ser Tyr Asp Met Tyr His Leu
145 150 155 160

Ser Arg Glu Gly Glu Ala His Glu Arg Arg Phe Ser Ala Gly Pro Lys
165 170 175

Val Asn Gly Thr Phe Gln Ala Asp Phe Pro Leu Gly Pro Ala Thr His
180 185 190

Gly Gly Thr Tyr Arg Cys Phe Gly Ser Phe Arg Asp Ser Pro Tyr Glu
195 200 205

Trp Ser Asn Ser Ser Asp Pro Leu Leu Val Ser Val Thr Gly Asn Pro
210 215 220

Ser Asn Ser Trp Pro Ser Pro Thr Glu Pro Ser Ser Glu Thr Gly Asn
225 230 235 240

Pro Arg His Leu His Val Leu Ile Gly Thr Ser Val Val Ile Ile Leu
245 250 255

Phe Ile Leu Leu Leu Phe Phe Leu Leu His Arg Trp Cys Cys Asn Lys
260 265 270

Lys Asn Ala Val Val Met Asp Gln Glu Pro Ala Gly Asn Arg Thr Val
275 280 285

Asn Arg Glu Asp Ser Asp Glu Gln Asp Pro Gln Glu Val Thr Tyr Ala
290 295 300

Gln Leu Asn His Cys Val Phe Thr Gln Arg Lys Ile Thr Arg Pro Ser
305 310 315 320

Gln Arg Pro Lys Thr Pro Pro Thr Asp Ile Ile Val Tyr Thr Glu Leu
325 330 335

Pro Asn Ala Glu Pro
340

<210> SEQ ID NO 56
<211> LENGTH: 1153
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:

```
<221> NAME/KEY: CDS
<222> LOCATION: (39)..(950)

<400> SEQUENCE: 56

tccccactgc tcagcactag gccggcagaa tctgagcg atg tct tcc aca ctc cct      56
                                          Met Ser Ser Thr Leu Pro
                                          1               5

gcc ctg ctc tgc gtc ggg ctg tgt ctg agt cag agg atc agc gcc cag       104
Ala Leu Leu Cys Val Gly Leu Cys Leu Ser Gln Arg Ile Ser Ala Gln
            10                  15                  20

cag cag act ctc cca aaa ccg ttc atc tgg gcc gag ccc cat ttc atg       152
Gln Gln Thr Leu Pro Lys Pro Phe Ile Trp Ala Glu Pro His Phe Met
        25                  30                  35

gtt cca aag gaa aag caa gtg acc atc tgt tgc cag gga aat tat ggg       200
Val Pro Lys Glu Lys Gln Val Thr Ile Cys Cys Gln Gly Asn Tyr Gly
    40                  45                  50

gct gtt gaa tac cag ctg cac ttt gaa gga agc ctt ttt gcc gtg gac       248
Ala Val Glu Tyr Gln Leu His Phe Glu Gly Ser Leu Phe Ala Val Asp
55                  60                  65                  70

aga cca aaa ccc cct gag cgg att aac aaa gtc caa ttc tac atc ccg       296
Arg Pro Lys Pro Pro Glu Arg Ile Asn Lys Val Gln Phe Tyr Ile Pro
                75                  80                  85

gac atg aac tcc cgc atg gca ggg caa tac agc tgc atc tat cgg gtt       344
Asp Met Asn Ser Arg Met Ala Gly Gln Tyr Ser Cys Ile Tyr Arg Val
            90                  95                  100

ggg gag ctc tgg tca gag ccc agc aac ttg ctg gat ctg gtg gta aca       392
Gly Glu Leu Trp Ser Glu Pro Ser Asn Leu Leu Asp Leu Val Val Thr
        105                 110                 115

gaa atg tat gac aca ccc acc ctc tcg gtt cat cct gga ccc gaa gtg       440
Glu Met Tyr Asp Thr Pro Thr Leu Ser Val His Pro Gly Pro Glu Val
    120                 125                 130

atc tcg gga gag aag gtg acc ttc tac tgc cgt cta gac act gca aca       488
Ile Ser Gly Glu Lys Val Thr Phe Tyr Cys Arg Leu Asp Thr Ala Thr
135                 140                 145                 150

agc atg ttc tta ctg ctc aag gag gga aga tcc agc cac gta cag cgc       536
Ser Met Phe Leu Leu Leu Lys Glu Gly Arg Ser Ser His Val Gln Arg
                155                 160                 165

gga tac ggg aag gtc cag gcg gag ttc ccc ctg ggc cct gtg acc aca       584
Gly Tyr Gly Lys Val Gln Ala Glu Phe Pro Leu Gly Pro Val Thr Thr
            170                 175                 180

gcc cac aga ggg aca tac cga tgt ttt ggc tcc tat aac aac cat gcc       632
Ala His Arg Gly Thr Tyr Arg Cys Phe Gly Ser Tyr Asn Asn His Ala
        185                 190                 195

tgg tct ttc ccc agt gag cca gtg aag ctc ctg gtc aca ggc gac att       680
Trp Ser Phe Pro Ser Glu Pro Val Lys Leu Leu Val Thr Gly Asp Ile
    200                 205                 210

gag aac acc agc ctt gca cct gaa gac ccc acc ttt cct gca gac act       728
Glu Asn Thr Ser Leu Ala Pro Glu Asp Pro Thr Phe Pro Ala Asp Thr
215                 220                 225                 230

tgg ggc acc tac ctt tta acc aca gag acg gga ctc cag aaa gac cat       776
Trp Gly Thr Tyr Leu Leu Thr Thr Glu Thr Gly Leu Gln Lys Asp His
                235                 240                 245

gcc ctc tgg gat cac act gcc cag aat ctc ctt cgg atg ggc ctg gcc       824
Ala Leu Trp Asp His Thr Ala Gln Asn Leu Leu Arg Met Gly Leu Ala
            250                 255                 260

ttt cta gtc ctg gtg gct cta gtg tgg ttc ctg gtt gaa gac tgg ctc       872
Phe Leu Val Leu Val Ala Leu Val Trp Phe Leu Val Glu Asp Trp Leu
        265                 270                 275

agc agg aag agg act aga gag cga gcc agc aga gct tcc act tgg gaa       920
Ser Arg Lys Arg Thr Arg Glu Arg Ala Ser Arg Ala Ser Thr Trp Glu
```

280 285 290 ggc agg aga agg ctg aac aca cag act ctt tgaagaatga ccatgagaca 970
Gly Arg Arg Arg Leu Asn Thr Gln Thr Leu
295 300 cagtggccat gggtggatct gaaagctggt gttgagcctg ggcggcgtga gctctgtgtt 1030
ggacccacgg aggagggagt cactgcaggg aaagagggac actggcattc catttgtcag 1090
agcatcccgg acgatgcaga gggtgggaga actacatgct aaatttcttt ttttttttt 1150 ttg 1153

<210> SEQ ID NO 57
<211> LENGTH: 304
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Met Ser Ser Thr Leu Pro Ala Leu Leu Cys Val Gly Leu Cys Leu Ser
1 5 10 15

Gln Arg Ile Ser Ala Gln Gln Gln Thr Leu Pro Lys Pro Phe Ile Trp
20 25 30

Ala Glu Pro His Phe Met Val Pro Lys Glu Lys Gln Val Thr Ile Cys
35 40 45

Cys Gln Gly Asn Tyr Gly Ala Val Glu Tyr Gln Leu His Phe Glu Gly
50 55 60

Ser Leu Phe Ala Val Asp Arg Pro Lys Pro Pro Glu Arg Ile Asn Lys
65 70 75 80

Val Gln Phe Tyr Ile Pro Asp Met Asn Ser Arg Met Ala Gly Gln Tyr
85 90 95

Ser Cys Ile Tyr Arg Val Gly Glu Leu Trp Ser Glu Pro Ser Asn Leu
100 105 110

Leu Asp Leu Val Val Thr Glu Met Tyr Asp Thr Pro Thr Leu Ser Val
115 120 125

His Pro Gly Pro Glu Val Ile Ser Gly Glu Lys Val Thr Phe Tyr Cys
130 135 140

Arg Leu Asp Thr Ala Thr Ser Met Phe Leu Leu Leu Lys Glu Gly Arg
145 150 155 160

Ser Ser His Val Gln Arg Gly Tyr Gly Lys Val Gln Ala Glu Phe Pro
165 170 175

Leu Gly Pro Val Thr Thr Ala His Arg Gly Thr Tyr Arg Cys Phe Gly
180 185 190

Ser Tyr Asn Asn His Ala Trp Ser Phe Pro Ser Glu Pro Val Lys Leu
195 200 205

Leu Val Thr Gly Asp Ile Glu Asn Thr Ser Leu Ala Pro Glu Asp Pro
210 215 220

Thr Phe Pro Ala Asp Thr Trp Gly Thr Tyr Leu Leu Thr Thr Glu Thr
225 230 235 240

Gly Leu Gln Lys Asp His Ala Leu Trp Asp His Thr Ala Gln Asn Leu
245 250 255

Leu Arg Met Gly Leu Ala Phe Leu Val Leu Val Ala Leu Val Trp Phe
260 265 270

Leu Val Glu Asp Trp Leu Ser Arg Lys Arg Thr Arg Glu Arg Ala Ser
275 280 285

```
Arg Ala Ser Thr Trp Glu Gly Arg Arg Arg Leu Asn Thr Gln Thr Leu
    290                 295                 300


<210> SEQ ID NO 58
<211> LENGTH: 1053
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1050)

<400> SEQUENCE: 58

atg gcc tta cca gtg acc gcc ttg ctc ctg ccg ctg gcc ttg ctg ctc       48
Met Ala Leu Pro Val Thr Ala Leu Leu Leu Pro Leu Ala Leu Leu Leu
1               5                   10                  15

cac gcc gcc agg ccg gga tcc cag gta caa ctg cag cag tct ggg cct       96
His Ala Ala Arg Pro Gly Ser Gln Val Gln Leu Gln Gln Ser Gly Pro
            20                  25                  30

gag ctg gag aag cct ggc gct tca gtg aag ata tcc tgc aag gct tct      144
Glu Leu Glu Lys Pro Gly Ala Ser Val Lys Ile Ser Cys Lys Ala Ser
        35                  40                  45

ggt tac tca ttc act ggc tac acc atg aac tgg gtg aag cag agc cat      192
Gly Tyr Ser Phe Thr Gly Tyr Thr Met Asn Trp Val Lys Gln Ser His
    50                  55                  60

gga aag agc ctt gag tgg att gga ctt att act cct tac aat ggt gct      240
Gly Lys Ser Leu Glu Trp Ile Gly Leu Ile Thr Pro Tyr Asn Gly Ala
65                  70                  75                  80

tct agc tac aac cag aag ttc agg ggc aag gcc aca tta act gta gac      288
Ser Ser Tyr Asn Gln Lys Phe Arg Gly Lys Ala Thr Leu Thr Val Asp
                85                  90                  95

aag tca tcc agc aca gcc tac atg gac ctc ctc agt ctg aca tct gaa      336
Lys Ser Ser Ser Thr Ala Tyr Met Asp Leu Leu Ser Leu Thr Ser Glu
            100                 105                 110

gac tct gca gtc tat ttc tgt gca agg ggg ggt tac gac ggg agg ggt      384
Asp Ser Ala Val Tyr Phe Cys Ala Arg Gly Gly Tyr Asp Gly Arg Gly
        115                 120                 125

ttt gac tac tgg ggc caa ggg acc acg gtc acc gtc tcc tca ggt gga      432
Phe Asp Tyr Trp Gly Gln Gly Thr Thr Val Thr Val Ser Ser Gly Gly
    130                 135                 140

ggc ggt tca ggc ggc ggt ggc tct agc ggt ggt gga tcg gac atc gag      480
Gly Gly Ser Gly Gly Gly Gly Ser Ser Gly Gly Gly Ser Asp Ile Glu
145                 150                 155                 160

ctc act cag tct cca gca atc atg tct gca tct cca ggg gag aag gtc      528
Leu Thr Gln Ser Pro Ala Ile Met Ser Ala Ser Pro Gly Glu Lys Val
                165                 170                 175

acc atg acc tgc agt gcc agc tca agt gta agt tac atg cac tgg tac      576
Thr Met Thr Cys Ser Ala Ser Ser Ser Val Ser Tyr Met His Trp Tyr
            180                 185                 190

cag cag aag tca ggc acc tcc ccc aaa aga tgg att tat gac aca tcc      624
Gln Gln Lys Ser Gly Thr Ser Pro Lys Arg Trp Ile Tyr Asp Thr Ser
        195                 200                 205

aaa ctg gct tct gga gtc cca ggt cgc ttc agt ggc agt ggg tct gga      672
Lys Leu Ala Ser Gly Val Pro Gly Arg Phe Ser Gly Ser Gly Ser Gly
    210                 215                 220

aac tct tac tct ctc aca atc agc agc gtg gag gct gaa gat gat gca      720
Asn Ser Tyr Ser Leu Thr Ile Ser Ser Val Glu Ala Glu Asp Asp Ala
225                 230                 235                 240

act tat tac tgc cag cag tgg agt aag cac cct ctc acg tac ggt gct      768
Thr Tyr Tyr Cys Gln Gln Trp Ser Lys His Pro Leu Thr Tyr Gly Ala
```

```
                245                 250                 255

ggg aca aag ttg gaa atc aaa gct agc ggt ggc gga ggt tct gga ggt      816
Gly Thr Lys Leu Glu Ile Lys Ala Ser Gly Gly Gly Gly Ser Gly Gly
            260                 265                 270

ggg ggt tcc tca ccc act gaa cca agc tcc aaa acc ggt aac ccc aga      864
Gly Gly Ser Ser Pro Thr Glu Pro Ser Ser Lys Thr Gly Asn Pro Arg
        275                 280                 285

cac ctg cat gtt ctg att ggg acc tca gtg gtc aaa atc cct ttc acc      912
His Leu His Val Leu Ile Gly Thr Ser Val Val Lys Ile Pro Phe Thr
    290                 295                 300

atc ctc ctc ttc ttt ctc ctt cat cgc tgg tgc tcc aac aaa aaa aat      960
Ile Leu Leu Phe Phe Leu Leu His Arg Trp Cys Ser Asn Lys Lys Asn
305                 310                 315                 320

gct gct gta atg gac caa gag cct gca ggg aac aga aca gtg aac agc     1008
Ala Ala Val Met Asp Gln Glu Pro Ala Gly Asn Arg Thr Val Asn Ser
                325                 330                 335

gag gat tct gat gaa caa gac cat cag gag gtg tca tac gca taa         1053
Glu Asp Ser Asp Glu Gln Asp His Gln Glu Val Ser Tyr Ala
            340                 345                 350


<210> SEQ ID NO 59
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Glu Leu Glu Lys Pro Gly Ala Ser Val Lys Ile Ser Cys Lys Ala Ser
        35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65                  70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140

Gly Gly Ser Gly Gly Gly Gly Ser Ser Gly Gly Gly Ser Asp Ile Glu
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
    210                 215                 220
```

```
Asn Ser Tyr Ser Leu Thr Ile Ser Ser Val Glu Ala Glu Asp Asp Ala
225                 230                 235                 240

Thr Tyr Tyr Cys Gln Gln Trp Ser Lys His Pro Leu Thr Tyr Gly Ala
                245                 250                 255

Gly Thr Lys Leu Glu Ile Lys Ala Ser Gly Gly Gly Gly Ser Gly Gly
            260                 265                 270

Gly Gly Ser Ser Pro Thr Glu Pro Ser Ser Lys Thr Gly Asn Pro Arg
        275                 280                 285

His Leu His Val Leu Ile Gly Thr Ser Val Val Lys Ile Pro Phe Thr
    290                 295                 300

Ile Leu Leu Phe Phe Leu Leu His Arg Trp Cys Ser Asn Lys Lys Asn
305                 310                 315                 320

Ala Ala Val Met Asp Gln Glu Pro Ala Gly Asn Arg Thr Val Asn Ser
                325                 330                 335

Glu Asp Ser Asp Glu Gln Asp His Gln Glu Val Ser Tyr Ala
            340                 345                 350


<210> SEQ ID NO 60
<211> LENGTH: 1698
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1695)

<400> SEQUENCE: 60

atg gcc tta cca gtg acc gcc ttg ctc ctg ccg ctg gcc ttg ctg ctc       48
Met Ala Leu Pro Val Thr Ala Leu Leu Leu Pro Leu Ala Leu Leu Leu
1               5                   10                  15

cac gcc gcc agg ccg gga tcc cag gta caa ctg cag cag tct ggg cct       96
His Ala Ala Arg Pro Gly Ser Gln Val Gln Leu Gln Gln Ser Gly Pro
            20                  25                  30

gag ctg gag aag cct ggc gct tca gtg aag ata tcc tgc aag gct tct      144
Glu Leu Glu Lys Pro Gly Ala Ser Val Lys Ile Ser Cys Lys Ala Ser
        35                  40                  45

ggt tac tca ttc act ggc tac acc atg aac tgg gtg aag cag agc cat      192
Gly Tyr Ser Phe Thr Gly Tyr Thr Met Asn Trp Val Lys Gln Ser His
    50                  55                  60

gga aag agc ctt gag tgg att gga ctt att act cct tac aat ggt gct      240
Gly Lys Ser Leu Glu Trp Ile Gly Leu Ile Thr Pro Tyr Asn Gly Ala
65                  70                  75                  80

tct agc tac aac cag aag ttc agg ggc aag gcc aca tta act gta gac      288
Ser Ser Tyr Asn Gln Lys Phe Arg Gly Lys Ala Thr Leu Thr Val Asp
                85                  90                  95

aag tca tcc agc aca gcc tac atg gac ctc ctc agt ctg aca tct gaa      336
Lys Ser Ser Ser Thr Ala Tyr Met Asp Leu Leu Ser Leu Thr Ser Glu
            100                 105                 110

gac tct gca gtc tat ttc tgt gca agg ggg ggt tac gac ggg agg ggt      384
Asp Ser Ala Val Tyr Phe Cys Ala Arg Gly Gly Tyr Asp Gly Arg Gly
        115                 120                 125

ttt gac tac tgg ggc caa ggg acc acg gtc acc gtc tcc tca ggt gga      432
Phe Asp Tyr Trp Gly Gln Gly Thr Thr Val Thr Val Ser Ser Gly Gly
    130                 135                 140

ggc ggt tca ggc ggc ggt ggc tct agc ggt ggt gga tcg gac atc gag      480
Gly Gly Ser Gly Gly Gly Gly Ser Ser Gly Gly Gly Ser Asp Ile Glu
145                 150                 155                 160

ctc act cag tct cca gca atc atg tct gca tct cca ggg gag aag gtc      528
```

-continued

```
Leu Thr Gln Ser Pro Ala Ile Met Ser Ala Ser Pro Gly Glu Lys Val
                165                 170                 175

acc atg acc tgc agt gcc agc tca agt gta agt tac atg cac tgg tac      576
Thr Met Thr Cys Ser Ala Ser Ser Ser Val Ser Tyr Met His Trp Tyr
            180                 185                 190

cag cag aag tca ggc acc tcc ccc aaa aga tgg att tat gac aca tcc      624
Gln Gln Lys Ser Gly Thr Ser Pro Lys Arg Trp Ile Tyr Asp Thr Ser
        195                 200                 205

aaa ctg gct tct gga gtc cca ggt cgc ttc agt ggc agt ggg tct gga      672
Lys Leu Ala Ser Gly Val Pro Gly Arg Phe Ser Gly Ser Gly Ser Gly
    210                 215                 220

aac tct tac tct ctc aca atc agc agc gtg gag gct gaa gat gat gca      720
Asn Ser Tyr Ser Leu Thr Ile Ser Ser Val Glu Ala Glu Asp Asp Ala
225                 230                 235                 240

act tat tac tgc cag cag tgg agt aag cac cct ctc acg tac ggt gct      768
Thr Tyr Tyr Cys Gln Gln Trp Ser Lys His Pro Leu Thr Tyr Gly Ala
                245                 250                 255

ggg aca aag ttg gaa atc aaa gct agc acg cgt ggt ggc gga ggt tct      816
Gly Thr Lys Leu Glu Ile Lys Ala Ser Thr Arg Gly Gly Gly Gly Ser
            260                 265                 270

gga ggt ggg ggt tcc cag ggg gcc tgg cca cat gag gga gtc cac aga      864
Gly Gly Gly Gly Ser Gln Gly Ala Trp Pro His Glu Gly Val His Arg
        275                 280                 285

aaa cct tcc ctc ctg gcc cac cca ggt ccc ctg gtg aaa tca gaa gag      912
Lys Pro Ser Leu Leu Ala His Pro Gly Pro Leu Val Lys Ser Glu Glu
    290                 295                 300

aca gtc atc ctg caa tgt tgg tca gat gtc agg ttt gag cac ttc ctt      960
Thr Val Ile Leu Gln Cys Trp Ser Asp Val Arg Phe Glu His Phe Leu
305                 310                 315                 320

ctg cac aga gag ggg aag tat aag gac act ttg cac ctc att gga gag     1008
Leu His Arg Glu Gly Lys Tyr Lys Asp Thr Leu His Leu Ile Gly Glu
                325                 330                 335

cac cat gat ggg gtc tcc aag gcc aac ttc tcc atc ggt ccc atg atg     1056
His His Asp Gly Val Ser Lys Ala Asn Phe Ser Ile Gly Pro Met Met
            340                 345                 350

caa gac ctt gca ggg acc tac aga tgc tac ggt tct gtt act cac tcc     1104
Gln Asp Leu Ala Gly Thr Tyr Arg Cys Tyr Gly Ser Val Thr His Ser
        355                 360                 365

ccc tat cag ttg tca gct ccc agt gac cct ctg gac atc gtc atc aca     1152
Pro Tyr Gln Leu Ser Ala Pro Ser Asp Pro Leu Asp Ile Val Ile Thr
    370                 375                 380

ggt cta tat gag aaa cct tct ctc tca gcc cag ccg ggc ccc acg gtt     1200
Gly Leu Tyr Glu Lys Pro Ser Leu Ser Ala Gln Pro Gly Pro Thr Val
385                 390                 395                 400

ttg gca gga gag agc gtg acc ttg tcc tgc agc tcc cgg agc tcc tat     1248
Leu Ala Gly Glu Ser Val Thr Leu Ser Cys Ser Ser Arg Ser Ser Tyr
                405                 410                 415

gac atg tac cat cta tcc agg gag ggg gag gcc cat gaa cgt agg ttc     1296
Asp Met Tyr His Leu Ser Arg Glu Gly Glu Ala His Glu Arg Arg Phe
            420                 425                 430

tct gca ggg ccc aag gtc aac gga aca ttc cag gcc gac ttt cct ctg     1344
Ser Ala Gly Pro Lys Val Asn Gly Thr Phe Gln Ala Asp Phe Pro Leu
        435                 440                 445

ggc cct gcc acc cac gga gga acc tac aga tgc ttc ggc tct ttc cgt     1392
Gly Pro Ala Thr His Gly Gly Thr Tyr Arg Cys Phe Gly Ser Phe Arg
    450                 455                 460

gac tct ccc tat gag tgg tca aac tcg agt gac cca ctg ctt gtt tct     1440
Asp Ser Pro Tyr Glu Trp Ser Asn Ser Ser Asp Pro Leu Leu Val Ser
465                 470                 475                 480
```

-continued

```
gtc aca gga aac cct tca aat agt tgg cct tca ccc act gaa cca agc     1488
Val Thr Gly Asn Pro Ser Asn Ser Trp Pro Ser Pro Thr Glu Pro Ser
                485                 490                 495

tcc aaa acc ggt aac ccc aga cac ctg cat gtt ctg att ggg acc tca     1536
Ser Lys Thr Gly Asn Pro Arg His Leu His Val Leu Ile Gly Thr Ser
            500                 505                 510

gtg gtc aaa atc cct ttc acc atc ctc ctc ttc ttt ctc ctt cat cgc     1584
Val Val Lys Ile Pro Phe Thr Ile Leu Leu Phe Phe Leu Leu His Arg
        515                 520                 525

tgg tgc tcc aac aaa aaa aat gct gct gta atg gac caa gag cct gca     1632
Trp Cys Ser Asn Lys Lys Asn Ala Ala Val Met Asp Gln Glu Pro Ala
    530                 535                 540

ggg aac aga aca gtg aac agc gag gat tct gat gaa caa gac cat cag     1680
Gly Asn Arg Thr Val Asn Ser Glu Asp Ser Asp Glu Gln Asp His Gln
545                 550                 555                 560

gag gtg tca tac gca taa                                             1698
Glu Val Ser Tyr Ala
                565


<210> SEQ ID NO 61
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Glu Leu Glu Lys Pro Gly Ala Ser Val Lys Ile Ser Cys Lys Ala Ser
        35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65                  70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140

Gly Gly Ser Gly Gly Gly Gly Ser Ser Gly Gly Gly Ser Asp Ile Glu
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
    210                 215                 220

Asn Ser Tyr Ser Leu Thr Ile Ser Ser Val Glu Ala Glu Asp Asp Ala
225                 230                 235                 240
```

```
Thr Tyr Tyr Cys Gln Gln Trp Ser Lys His Pro Leu Thr Tyr Gly Ala
                245                 250                 255

Gly Thr Lys Leu Glu Ile Lys Ala Ser Thr Arg Gly Gly Gly Gly Ser
            260                 265                 270

Gly Gly Gly Gly Ser Gln Gly Ala Trp Pro His Glu Gly Val His Arg
        275                 280                 285

Lys Pro Ser Leu Leu Ala His Pro Gly Pro Leu Val Lys Ser Glu Glu
    290                 295                 300

Thr Val Ile Leu Gln Cys Trp Ser Asp Val Arg Phe Glu His Phe Leu
305                 310                 315                 320

Leu His Arg Glu Gly Lys Tyr Lys Asp Thr Leu His Leu Ile Gly Glu
                325                 330                 335

His His Asp Gly Val Ser Lys Ala Asn Phe Ser Ile Gly Pro Met Met
            340                 345                 350

Gln Asp Leu Ala Gly Thr Tyr Arg Cys Tyr Gly Ser Val Thr His Ser
        355                 360                 365

Pro Tyr Gln Leu Ser Ala Pro Ser Asp Pro Leu Asp Ile Val Ile Thr
    370                 375                 380

Gly Leu Tyr Glu Lys Pro Ser Leu Ser Ala Gln Pro Gly Pro Thr Val
385                 390                 395                 400

Leu Ala Gly Glu Ser Val Thr Leu Ser Cys Ser Ser Arg Ser Ser Tyr
                405                 410                 415

Asp Met Tyr His Leu Ser Arg Glu Gly Glu Ala His Glu Arg Arg Phe
            420                 425                 430

Ser Ala Gly Pro Lys Val Asn Gly Thr Phe Gln Ala Asp Phe Pro Leu
        435                 440                 445

Gly Pro Ala Thr His Gly Gly Thr Tyr Arg Cys Phe Gly Ser Phe Arg
    450                 455                 460

Asp Ser Pro Tyr Glu Trp Ser Asn Ser Ser Asp Pro Leu Leu Val Ser
465                 470                 475                 480

Val Thr Gly Asn Pro Ser Asn Ser Trp Pro Ser Pro Thr Glu Pro Ser
                485                 490                 495

Ser Lys Thr Gly Asn Pro Arg His Leu His Val Leu Ile Gly Thr Ser
            500                 505                 510

Val Val Lys Ile Pro Phe Thr Ile Leu Leu Phe Phe Leu Leu His Arg
        515                 520                 525

Trp Cys Ser Asn Lys Lys Asn Ala Ala Val Met Asp Gln Glu Pro Ala
    530                 535                 540

Gly Asn Arg Thr Val Asn Ser Glu Asp Ser Asp Glu Gln Asp His Gln
545                 550                 555                 560

Glu Val Ser Tyr Ala
                565
```

<210> SEQ ID NO 62
<211> LENGTH: 1035
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1032)

<400> SEQUENCE: 62

```
atg gcc tta cca gtg acc gcc ttg ctc ctg ccg ctg gcc ttg ctg ctc       48
```

```
Met Ala Leu Pro Val Thr Ala Leu Leu Leu Pro Leu Ala Leu Leu Leu
1               5                   10                  15

cac gcc gcc agg ccg gga tcc cag gta caa ctg cag cag tct ggg cct        96
His Ala Ala Arg Pro Gly Ser Gln Val Gln Leu Gln Gln Ser Gly Pro
            20                  25                  30

gag ctg gag aag cct ggc gct tca gtg aag ata tcc tgc aag gct tct       144
Glu Leu Glu Lys Pro Gly Ala Ser Val Lys Ile Ser Cys Lys Ala Ser
        35                  40                  45

ggt tac tca ttc act ggc tac acc atg aac tgg gtg aag cag agc cat       192
Gly Tyr Ser Phe Thr Gly Tyr Thr Met Asn Trp Val Lys Gln Ser His
    50                  55                  60

gga aag agc ctt gag tgg att gga ctt att act cct tac aat ggt gct       240
Gly Lys Ser Leu Glu Trp Ile Gly Leu Ile Thr Pro Tyr Asn Gly Ala
65                  70                  75                  80

tct agc tac aac cag aag ttc agg ggc aag gcc aca tta act gta gac       288
Ser Ser Tyr Asn Gln Lys Phe Arg Gly Lys Ala Thr Leu Thr Val Asp
                85                  90                  95

aag tca tcc agc aca gcc tac atg gac ctc ctc agt ctg aca tct gaa       336
Lys Ser Ser Ser Thr Ala Tyr Met Asp Leu Leu Ser Leu Thr Ser Glu
            100                 105                 110

gac tct gca gtc tat ttc tgt gca agg ggg ggt tac gac ggg agg ggt       384
Asp Ser Ala Val Tyr Phe Cys Ala Arg Gly Gly Tyr Asp Gly Arg Gly
        115                 120                 125

ttt gac tac tgg ggc caa ggg acc acg gtc acc gtc tcc tca ggt gga       432
Phe Asp Tyr Trp Gly Gln Gly Thr Thr Val Thr Val Ser Ser Gly Gly
    130                 135                 140

ggc ggt tca ggc ggc ggt ggc tct agc ggt ggt gga tcg gac atc gag       480
Gly Gly Ser Gly Gly Gly Gly Ser Ser Gly Gly Gly Ser Asp Ile Glu
145                 150                 155                 160

ctc act cag tct cca gca atc atg tct gca tct cca ggg gag aag gtc       528
Leu Thr Gln Ser Pro Ala Ile Met Ser Ala Ser Pro Gly Glu Lys Val
                165                 170                 175

acc atg acc tgc agt gcc agc tca agt gta agt tac atg cac tgg tac       576
Thr Met Thr Cys Ser Ala Ser Ser Ser Val Ser Tyr Met His Trp Tyr
            180                 185                 190

cag cag aag tca ggc acc tcc ccc aaa aga tgg att tat gac aca tcc       624
Gln Gln Lys Ser Gly Thr Ser Pro Lys Arg Trp Ile Tyr Asp Thr Ser
        195                 200                 205

aaa ctg gct tct gga gtc cca ggt cgc ttc agt ggc agt ggg tct gga       672
Lys Leu Ala Ser Gly Val Pro Gly Arg Phe Ser Gly Ser Gly Ser Gly
    210                 215                 220

aac tct tac tct ctc aca atc agc agc gtg gag gct gaa gat gat gca       720
Asn Ser Tyr Ser Leu Thr Ile Ser Ser Val Glu Ala Glu Asp Asp Ala
225                 230                 235                 240

act tat tac tgc cag cag tgg agt aag cac cct ctc acg tac ggt gct       768
Thr Tyr Tyr Cys Gln Gln Trp Ser Lys His Pro Leu Thr Tyr Gly Ala
                245                 250                 255

ggg aca aag ttg gaa atc aaa gct agc ggt ggc gga ggt tct gga ggt       816
Gly Thr Lys Leu Glu Ile Lys Ala Ser Gly Gly Gly Gly Ser Gly Gly
            260                 265                 270

ggg ggt tcc tta acc aca gag acg gga ctc cag aaa gac cat gcc ctc       864
Gly Gly Ser Leu Thr Thr Glu Thr Gly Leu Gln Lys Asp His Ala Leu
        275                 280                 285

tgg gat cac act gcc cag aat ctc ctt cgg atg ggc ctg gcc ttt cta       912
Trp Asp His Thr Ala Gln Asn Leu Leu Arg Met Gly Leu Ala Phe Leu
    290                 295                 300

gtc ctg gtg gct cta gtg tgg ttc ctg gtt gaa gac tgg ctc agc agg       960
Val Leu Val Ala Leu Val Trp Phe Leu Val Glu Asp Trp Leu Ser Arg
305                 310                 315                 320
```

```
aag agg act aga gag cga gcc agc aga gct tcc act tgg gaa ggc agg     1008
Lys Arg Thr Arg Glu Arg Ala Ser Arg Ala Ser Thr Trp Glu Gly Arg
            325                 330                 335

aga agg ctg aac aca cag act ctt tga                                 1035
Arg Arg Leu Asn Thr Gln Thr Leu
            340


<210> SEQ ID NO 63
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Glu Leu Glu Lys Pro Gly Ala Ser Val Lys Ile Ser Cys Lys Ala Ser
        35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65                  70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140

Gly Gly Ser Gly Gly Gly Gly Ser Ser Gly Gly Gly Ser Asp Ile Glu
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
    210                 215                 220

Asn Ser Tyr Ser Leu Thr Ile Ser Ser Val Glu Ala Glu Asp Asp Ala
225                 230                 235                 240

Thr Tyr Tyr Cys Gln Gln Trp Ser Lys His Pro Leu Thr Tyr Gly Ala
                245                 250                 255

Gly Thr Lys Leu Glu Ile Lys Ala Ser Gly Gly Gly Gly Ser Gly Gly
            260                 265                 270

Gly Gly Ser Leu Thr Thr Glu Thr Gly Leu Gln Lys Asp His Ala Leu
        275                 280                 285

Trp Asp His Thr Ala Gln Asn Leu Leu Arg Met Gly Leu Ala Phe Leu
    290                 295                 300

Val Leu Val Ala Leu Val Trp Phe Leu Val Glu Asp Trp Leu Ser Arg
305                 310                 315                 320
```

```
Lys Arg Thr Arg Glu Arg Ala Ser Arg Ala Ser Thr Trp Glu Gly Arg
                325                 330                 335

Arg Arg Leu Asn Thr Gln Thr Leu
            340


<210> SEQ ID NO 64
<211> LENGTH: 1194
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1191)

<400> SEQUENCE: 64

atg gcc tta cca gtg acc gcc ttg ctc ctg ccg ctg gcc ttg ctg ctc       48
Met Ala Leu Pro Val Thr Ala Leu Leu Leu Pro Leu Ala Leu Leu Leu
1               5                   10                  15

cac gcc gcc agg ccg gga tcc cag gta caa ctg cag cag tct ggg cct       96
His Ala Ala Arg Pro Gly Ser Gln Val Gln Leu Gln Gln Ser Gly Pro
            20                  25                  30

gag ctg gag aag cct ggc gct tca gtg aag ata tcc tgc aag gct tct      144
Glu Leu Glu Lys Pro Gly Ala Ser Val Lys Ile Ser Cys Lys Ala Ser
        35                  40                  45

ggt tac tca ttc act ggc tac acc atg aac tgg gtg aag cag agc cat      192
Gly Tyr Ser Phe Thr Gly Tyr Thr Met Asn Trp Val Lys Gln Ser His
    50                  55                  60

gga aag agc ctt gag tgg att gga ctt att act cct tac aat ggt gct      240
Gly Lys Ser Leu Glu Trp Ile Gly Leu Ile Thr Pro Tyr Asn Gly Ala
65                  70                  75                  80

tct agc tac aac cag aag ttc agg ggc aag gcc aca tta act gta gac      288
Ser Ser Tyr Asn Gln Lys Phe Arg Gly Lys Ala Thr Leu Thr Val Asp
                85                  90                  95

aag tca tcc agc aca gcc tac atg gac ctc ctc agt ctg aca tct gaa      336
Lys Ser Ser Ser Thr Ala Tyr Met Asp Leu Leu Ser Leu Thr Ser Glu
            100                 105                 110

gac tct gca gtc tat ttc tgt gca agg ggg ggt tac gac ggg agg ggt      384
Asp Ser Ala Val Tyr Phe Cys Ala Arg Gly Gly Tyr Asp Gly Arg Gly
        115                 120                 125

ttt gac tac tgg ggc caa ggg acc acg gtc acc gtc tcc tca ggt gga      432
Phe Asp Tyr Trp Gly Gln Gly Thr Thr Val Thr Val Ser Ser Gly Gly
    130                 135                 140

ggc ggt tca ggc ggc ggt ggc tct ggc ggt ggc gga tcg gac atc gag      480
Gly Gly Ser Gly Gly Gly Gly Ser Gly Gly Gly Gly Ser Asp Ile Glu
145                 150                 155                 160

ctc act cag tct cca gca atc atg tct gca tct cca ggg gag aag gtc      528
Leu Thr Gln Ser Pro Ala Ile Met Ser Ala Ser Pro Gly Glu Lys Val
                165                 170                 175

acc atg acc tgc agt gcc agc tca agt gta agt tac atg cac tgg tac      576
Thr Met Thr Cys Ser Ala Ser Ser Ser Val Ser Tyr Met His Trp Tyr
            180                 185                 190

cag cag aag tca ggc acc tcc ccc aaa aga tgg att tat gac aca tcc      624
Gln Gln Lys Ser Gly Thr Ser Pro Lys Arg Trp Ile Tyr Asp Thr Ser
        195                 200                 205

aaa ctg gct tct gga gtc cca ggt cgc ttc agt ggc agt ggg tct gga      672
Lys Leu Ala Ser Gly Val Pro Gly Arg Phe Ser Gly Ser Gly Ser Gly
    210                 215                 220

aac tct tac tct ctc aca atc agc agc gtg gag gct gaa gat gat gca      720
Asn Ser Tyr Ser Leu Thr Ile Ser Ser Val Glu Ala Glu Asp Asp Ala
225                 230                 235                 240
```

```
act tat tac tgc cag cag tgg agt ggt tac cct ctc acg ttc ggt gct      768
Thr Tyr Tyr Cys Gln Gln Trp Ser Gly Tyr Pro Leu Thr Phe Gly Ala
                245                 250                 255

ggg aca aag ttg gaa atc aaa ggt gga gac tac aag gac gac gac gac      816
Gly Thr Lys Leu Glu Ile Lys Gly Gly Asp Tyr Lys Asp Asp Asp Asp
            260                 265                 270

aag gct agc ggt ggc gga ggt tct gga ggt ggg ggt tcc tca ccc act      864
Lys Ala Ser Gly Gly Gly Gly Ser Gly Gly Gly Gly Ser Ser Pro Thr
        275                 280                 285

gaa cca agc tcc gaa acc ggt aac ccc aga cac ctg cat gtt ctg att      912
Glu Pro Ser Ser Glu Thr Gly Asn Pro Arg His Leu His Val Leu Ile
    290                 295                 300

ggg acc tca gtg gtc atc atc ctc ttc atc ctc ctc ctc ttc ttt ctc      960
Gly Thr Ser Val Val Ile Ile Leu Phe Ile Leu Leu Leu Phe Phe Leu
305                 310                 315                 320

ctt cat cgc tgg tgc tgc aac aaa aaa aat gct gtt gta atg gac caa     1008
Leu His Arg Trp Cys Cys Asn Lys Lys Asn Ala Val Val Met Asp Gln
                325                 330                 335

gag cct gca ggg aac aga aca gtg aac agg gag gac tct gat gaa caa     1056
Glu Pro Ala Gly Asn Arg Thr Val Asn Arg Glu Asp Ser Asp Glu Gln
            340                 345                 350

gac cct cag gag gtg aca tat gca cag ttg aat cac tgc gtt ttc aca     1104
Asp Pro Gln Glu Val Thr Tyr Ala Gln Leu Asn His Cys Val Phe Thr
        355                 360                 365

cag aga aaa atc act cac cct tct cag agg ccc aag aca ccc cca aca     1152
Gln Arg Lys Ile Thr His Pro Ser Gln Arg Pro Lys Thr Pro Pro Thr
    370                 375                 380

gat atc atc gtg tac acg gaa ctt cca aat gct gag ccc tga             1194
Asp Ile Ile Val Tyr Thr Glu Leu Pro Asn Ala Glu Pro
385                 390                 395
```

<210> SEQ ID NO 65
<211> LENGTH: 397
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Glu Leu Glu Lys Pro Gly Ala Ser Val Lys Ile Ser Cys Lys Ala Ser
        35                  40                  45

Gly Tyr Ser Phe Thr Gly Tyr Thr Met Asn Trp Val Lys Gln Ser His
    50                  55                  60

Gly Lys Ser Leu Glu Trp Ile Gly Leu Ile Thr Pro Tyr Asn Gly Ala
65                  70                  75                  80

Ser Ser Tyr Asn Gln Lys Phe Arg Gly Lys Ala Thr Leu Thr Val Asp
                85                  90                  95

Lys Ser Ser Ser Thr Ala Tyr Met Asp Leu Leu Ser Leu Thr Ser Glu
            100                 105                 110

Asp Ser Ala Val Tyr Phe Cys Ala Arg Gly Gly Tyr Asp Gly Arg Gly
        115                 120                 125

Phe Asp Tyr Trp Gly Gln Gly Thr Thr Val Thr Val Ser Ser Gly Gly
    130                 135                 140
```

```
Gly Gly Ser Gly Gly Gly Gly Ser Gly Gly Gly Gly Ser Asp Ile Glu
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met His Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Gly Arg Phe Ser Gly Ser Gly Ser Gly
    210                 215                 220

Asn Ser Tyr Ser Leu Thr Ile Ser Ser Val Glu Ala Glu Asp Asp Ala
225                 230                 235                 240

Thr Tyr Tyr Cys Gln Gln Trp Ser Gly Tyr Pro Leu Thr Phe Gly Ala
                245                 250                 255

Gly Thr Lys Leu Glu Ile Lys Gly Gly Asp Tyr Lys Asp Asp Asp Asp
            260                 265                 270

Lys Ala Ser Gly Gly Gly Gly Ser Gly Gly Gly Gly Ser Ser Pro Thr
        275                 280                 285

Glu Pro Ser Ser Glu Thr Gly Asn Pro Arg His Leu His Val Leu Ile
    290                 295                 300

Gly Thr Ser Val Val Ile Ile Leu Phe Ile Leu Leu Leu Phe Phe Leu
305                 310                 315                 320

Leu His Arg Trp Cys Cys Asn Lys Lys Asn Ala Val Val Met Asp Gln
                325                 330                 335

Glu Pro Ala Gly Asn Arg Thr Val Asn Arg Glu Asp Ser Asp Glu Gln
            340                 345                 350

Asp Pro Gln Glu Val Thr Tyr Ala Gln Leu Asn His Cys Val Phe Thr
        355                 360                 365

Gln Arg Lys Ile Thr His Pro Ser Gln Arg Pro Lys Thr Pro Pro Thr
    370                 375                 380

Asp Ile Ile Val Tyr Thr Glu Leu Pro Asn Ala Glu Pro
385                 390                 395


<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Gly Gly Gly Ser
1               5


<210> SEQ ID NO 67
<211> LENGTH: 5000
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(5000)
<223> OTHER INFORMATION: This sequence may encompass 50-5000
      nucleotides, wherein some positions may be absent
<220> FEATURE:
<223> OTHER INFORMATION: see specification as filed for detailed
      description of substitutions and preferred embodiments
```

<400> SEQUENCE: 67
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040
aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340

-continued aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380
aaaaaaaaaa aaaaaaaaaa aaaaaaaaaa aaaaaaaaaa aaaaaaaaaa aaaaaaaaaa 4440
aaaaaaaaaa aaaaaaaaaa aaaaaaaaaa aaaaaaaaaa aaaaaaaaaa aaaaaaaaaa 4500
aaaaaaaaaa aaaaaaaaaa aaaaaaaaaa aaaaaaaaaa aaaaaaaaaa aaaaaaaaaa 4560
aaaaaaaaaa aaaaaaaaaa aaaaaaaaaa aaaaaaaaaa aaaaaaaaaa aaaaaaaaaa 4620
aaaaaaaaaa aaaaaaaaaa aaaaaaaaaa aaaaaaaaaa aaaaaaaaaa aaaaaaaaaa 4680

```
aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 68
<211> LENGTH: 16
<212> TYPE: PRT
<213> ORGANISM: Unknown
<220> FEATURE:
<223> OTHER INFORMATION: Description of Unknown: ITAM
      motif peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (5)..(12)
<223> OTHER INFORMATION: Any amino acid
<220> FEATURE:
<221> NAME/KEY: misc_feature
<222> LOCATION: (5)..(12)
<223> OTHER INFORMATION: This region may encompass 6-8 residues,
      wherein some positions may be absent
<220> FEATURE:
<221> NAME/KEY: MOD_RES
<222> LOCATION: (14)..(15)
<223> OTHER INFORMATION: Any amino acid

<400> SEQUENCE: 68

Tyr Xaa Xaa Leu Xaa Xaa Xaa Xaa Xaa Xaa Xaa Xaa Tyr Xaa Xaa Leu
1               5                   10                  15


<210> SEQ ID NO 69
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1-10 'Gly-Gly-Gly-
      Ser' repeating units, wherein some positions may be absent

<400> SEQUENCE: 69

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70
```

Gly Gly Gly Gly Ser Gly Gly Gly Gly Ser Gly Gly Gly Gly Ser Gly
1 5 10 15

Gly Gly Gly Ser
20

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Gly Gly Gly Gly Ser Gly Gly Gly Gly Ser Gly Gly Gly Gly Ser
1 5 10 15

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Gly Gly Gly Ser
1

<210> SEQ ID NO 73
<211> LENGTH: 100
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73
tttttttttt tttttttttt tttttttttt tttttttttt tttttttttt tttttttttt 60
tttttttttt tttttttttt tttttttttt tttttttttt 100

<210> SEQ ID NO 74
<211> LENGTH: 5000
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(5000)
<223> OTHER INFORMATION: This sequence may encompass 50-5000 nucleotides, wherein some positions may be absent

<400> SEQUENCE: 74
tttttttttt tttttttttt tttttttttt tttttttttt tttttttttt tttttttttt 60
tttttttttt tttttttttt tttttttttt tttttttttt tttttttttt tttttttttt 120
tttttttttt tttttttttt tttttttttt tttttttttt tttttttttt tttttttttt 180
tttttttttt tttttttttt tttttttttt tttttttttt tttttttttt tttttttttt 240
tttttttttt tttttttttt tttttttttt tttttttttt tttttttttt tttttttttt 300
tttttttttt tttttttttt tttttttttt tttttttttt tttttttttt tttttttttt 360
tttttttttt tttttttttt tttttttttt tttttttttt tttttttttt tttttttttt 420

-continued tttttttttt tttttttttt tttttttttt tttttttttt tttttttttt tttttttttt 480
tttttttttt tttttttttt tttttttttt tttttttttt tttttttttt tttttttttt 540
tttttttttt tttttttttt tttttttttt tttttttttt tttttttttt tttttttttt 600
tttttttttt tttttttttt tttttttttt tttttttttt tttttttttt tttttttttt 660
tttttttttt tttttttttt tttttttttt tttttttttt tttttttttt tttttttttt 720
tttttttttt tttttttttt tttttttttt tttttttttt tttttttttt tttttttttt 780
tttttttttt tttttttttt tttttttttt tttttttttt tttttttttt tttttttttt 840
tttttttttt tttttttttt tttttttttt tttttttttt tttttttttt tttttttttt 900
tttttttttt tttttttttt tttttttttt tttttttttt tttttttttt tttttttttt 960
tttttttttt tttttttttt tttttttttt tttttttttt tttttttttt tttttttttt 1020
tttttttttt tttttttttt tttttttttt tttttttttt tttttttttt tttttttttt 1080
tttttttttt tttttttttt tttttttttt tttttttttt tttttttttt tttttttttt 1140
tttttttttt tttttttttt tttttttttt tttttttttt tttttttttt tttttttttt 1200
tttttttttt tttttttttt tttttttttt tttttttttt tttttttttt tttttttttt 1260
tttttttttt tttttttttt tttttttttt tttttttttt tttttttttt tttttttttt 1320
tttttttttt tttttttttt tttttttttt tttttttttt tttttttttt tttttttttt 1380
tttttttttt tttttttttt tttttttttt tttttttttt tttttttttt tttttttttt 1440
tttttttttt tttttttttt tttttttttt tttttttttt tttttttttt tttttttttt 1500
tttttttttt tttttttttt tttttttttt tttttttttt tttttttttt tttttttttt 1560
tttttttttt tttttttttt tttttttttt tttttttttt tttttttttt tttttttttt 1620
tttttttttt tttttttttt tttttttttt tttttttttt tttttttttt tttttttttt 1680
tttttttttt tttttttttt tttttttttt tttttttttt tttttttttt tttttttttt 1740
tttttttttt tttttttttt tttttttttt tttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttttt tttttttttt tttttttttt tttttttttt tttttttttt 2040
tttttttttt tttttttttt tttttttttt tttttttttt tttttttttt tttttttttt 2100
tttttttttt tttttttttt tttttttttt tttttttttt tttttttttt tttttttttt 2160
tttttttttt tttttttttt tttttttttt tttttttttt tttttttttt tttttttttt 2220
tttttttttt tttttttttt tttttttttt tttttttttt tttttttttt tttttttttt 2280
tttttttttt tttttttttt tttttttttt tttttttttt tttttttttt tttttttttt 2340
tttttttttt tttttttttt tttttttttt tttttttttt tttttttttt tttttttttt 2400
tttttttttt tttttttttt tttttttttt tttttttttt tttttttttt tttttttttt 2460
tttttttttt tttttttttt tttttttttt tttttttttt tttttttttt tttttttttt 2520
tttttttttt tttttttttt tttttttttt tttttttttt tttttttttt tttttttttt 2580
tttttttttt tttttttttt tttttttttt tttttttttt tttttttttt tttttttttt 2640
tttttttttt tttttttttt tttttttttt tttttttttt tttttttttt tttttttttt 2700
tttttttttt tttttttttt tttttttttt tttttttttt tttttttttt tttttttttt 2760
tttttttttt tttttttttt tttttttttt tttttttttt tttttttttt tttttttttt 2820

-continued tttttttttt tttttttttt tttttttttt tttttttttt tttttttttt tttttttttt 2880
tttttttttt tttttttttt tttttttttt tttttttttt tttttttttt tttttttttt 2940
tttttttttt tttttttttt tttttttttt tttttttttt tttttttttt tttttttttt 3000
tttttttttt tttttttttt tttttttttt tttttttttt tttttttttt tttttttttt 3060
tttttttttt tttttttttt tttttttttt tttttttttt tttttttttt tttttttttt 3120
tttttttttt tttttttttt tttttttttt tttttttttt tttttttttt tttttttttt 3180
tttttttttt tttttttttt tttttttttt tttttttttt tttttttttt tttttttttt 3240
tttttttttt tttttttttt tttttttttt tttttttttt tttttttttt tttttttttt 3300
tttttttttt tttttttttt tttttttttt tttttttttt tttttttttt tttttttttt 3360
tttttttttt tttttttttt tttttttttt tttttttttt tttttttttt tttttttttt 3420
tttttttttt tttttttttt tttttttttt tttttttttt tttttttttt tttttttttt 3480
tttttttttt tttttttttt tttttttttt tttttttttt tttttttttt tttttttttt 3540
tttttttttt tttttttttt tttttttttt tttttttttt tttttttttt tttttttttt 3600
tttttttttt tttttttttt tttttttttt tttttttttt tttttttttt tttttttttt 3660
tttttttttt tttttttttt tttttttttt tttttttttt tttttttttt tttttttttt 3720
tttttttttt tttttttttt tttttttttt tttttttttt tttttttttt tttttttttt 3780
tttttttttt tttttttttt tttttttttt tttttttttt tttttttttt tttttttttt 3840
tttttttttt tttttttttt tttttttttt tttttttttt tttttttttt tttttttttt 3900
tttttttttt tttttttttt tttttttttt tttttttttt tttttttttt tttttttttt 3960
tttttttttt tttttttttt tttttttttt tttttttttt tttttttttt tttttttttt 4020
tttttttttt tttttttttt tttttttttt tttttttttt tttttttttt tttttttttt 4080
tttttttttt tttttttttt tttttttttt tttttttttt tttttttttt tttttttttt 4140
tttttttttt tttttttttt tttttttttt tttttttttt tttttttttt tttttttttt 4200
tttttttttt tttttttttt tttttttttt tttttttttt tttttttttt tttttttttt 4260
tttttttttt tttttttttt tttttttttt tttttttttt tttttttttt tttttttttt 4320
tttttttttt tttttttttt tttttttttt tttttttttt tttttttttt tttttttttt 4380
tttttttttt tttttttttt tttttttttt tttttttttt tttttttttt tttttttttt 4440
tttttttttt tttttttttt tttttttttt tttttttttt tttttttttt tttttttttt 4500
tttttttttt tttttttttt tttttttttt tttttttttt tttttttttt tttttttttt 4560
tttttttttt tttttttttt tttttttttt tttttttttt tttttttttt tttttttttt 4620
tttttttttt tttttttttt tttttttttt tttttttttt tttttttttt tttttttttt 4680
tttttttttt tttttttttt tttttttttt tttttttttt tttttttttt tttttttttt 4740
tttttttttt tttttttttt tttttttttt tttttttttt tttttttttt tttttttttt 4800
tttttttttt tttttttttt tttttttttt tttttttttt tttttttttt tttttttttt 4860
tttttttttt tttttttttt tttttttttt tttttttttt tttttttttt tttttttttt 4920
tttttttttt tttttttttt tttttttttt tttttttttt tttttttttt tttttttttt 4980
tttttttttt tttttttttt 5000

<210> SEQ ID NO 75
<211> LENGTH: 5000
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(5000)
<223> OTHER INFORMATION: This sequence may encompass 100-5000 nucleotides, wherein some positions may be absent

<400> SEQUENCE: 75
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa aaaaaaaaaa aaaaaaaaaa aaaaaaaaaa 180
aaaaaaaaaa aaaaaaaaaa aaaaaaaaaa aaaaaaaaaa aaaaaaaaaa aaaaaaaaaa 240
aaaaaaaaaa aaaaaaaaaa aaaaaaaaaa aaaaaaaaaa aaaaaaaaaa aaaaaaaaaa 300
aaaaaaaaaa aaaaaaaaaa aaaaaaaaaa aaaaaaaaaa aaaaaaaaaa aaaaaaaaaa 360
aaaaaaaaaa aaaaaaaaaa aaaaaaaaaa aaaaaaaaaa aaaaaaaaaa aaaaaaaaaa 420
aaaaaaaaaa aaaaaaaaaa aaaaaaaaaa aaaaaaaaaa aaaaaaaaaa aaaaaaaaaa 480
aaaaaaaaaa aaaaaaaaaa aaaaaaaaaa aaaaaaaaaa aaaaaaaaaa aaaaaaaaaa 540
aaaaaaaaaa aaaaaaaaaa aaaaaaaaaa aaaaaaaaaa aaaaaaaaaa aaaaaaaaaa 600
aaaaaaaaaa aaaaaaaaaa aaaaaaaaaa aaaaaaaaaa aaaaaaaaaa aaaaaaaaaa 660
aaaaaaaaaa aaaaaaaaaa aaaaaaaaaa aaaaaaaaaa aaaaaaaaaa aaaaaaaaaa 720
aaaaaaaaaa aaaaaaaaaa aaaaaaaaaa aaaaaaaaaa aaaaaaaaaa aaaaaaaaaa 780
aaaaaaaaaa aaaaaaaaaa aaaaaaaaaa aaaaaaaaaa aaaaaaaaaa aaaaaaaaaa 840
aaaaaaaaaa aaaaaaaaaa aaaaaaaaaa aaaaaaaaaa aaaaaaaaaa aaaaaaaaaa 900
aaaaaaaaaa aaaaaaaaaa aaaaaaaaaa aaaaaaaaaa aaaaaaaaaa aaaaaaaaaa 960
aaaaaaaaaa aaaaaaaaaa aaaaaaaaaa aaaaaaaaaa aaaaaaaaaa aaaaaaaaaa 1020
aaaaaaaaaa aaaaaaaaaa aaaaaaaaaa aaaaaaaaaa aaaaaaaaaa aaaaaaaaaa 1080
aaaaaaaaaa aaaaaaaaaa aaaaaaaaaa aaaaaaaaaa aaaaaaaaaa aaaaaaaaaa 1140
aaaaaaaaaa aaaaaaaaaa aaaaaaaaaa aaaaaaaaaa aaaaaaaaaa aaaaaaaaaa 1200
aaaaaaaaaa aaaaaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaaaa aaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaaa aaaaaaaaaa aaaaaaaaaa aaaaaaaaaa aaaaaaaaaa aaaaaaaaaa 1560
aaaaaaaaaa aaaaaaaaaa aaaaaaaaaa aaaaaaaaaa aaaaaaaaaa aaaaaaaaaa 1620
aaaaaaaaaa aaaaaaaaaa aaaaaaaaaa aaaaaaaaaa aaaaaaaaaa aaaaaaaaaa 1680
aaaaaaaaaa aaaaaaaaaa aaaaaaaaaa aaaaaaaaaa aaaaaaaaaa aaaaaaaaaa 1740
aaaaaaaaaa aaaaaaaaaa aaaaaaaaaa aaaaaaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaaaaaaa 1920
aaaaaaaaaa aaaaaaaaaa aaaaaaaaaa aaaaaaaaaa aaaaaaaaaa aaaaaaaaaa 1980
aaaaaaaaaa aaaaaaaaaa aaaaaaaaaa aaaaaaaaaa aaaaaaaaaa aaaaaaaaaa 2040

-continued aaaaaaaaaa aaaaaaaaaa aaaaaaaaaa aaaaaaaaaa aaaaaaaaaa aaaaaaaaaa 2100
aaaaaaaaaa aaaaaaaaaa aaaaaaaaaa aaaaaaaaaa aaaaaaaaaa aaaaaaaaaa 2160
aaaaaaaaaa aaaaaaaaaa aaaaaaaaaa aaaaaaaaaa aaaaaaaaaa aaaaaaaaaa 2220
aaaaaaaaaa aaaaaaaaaa aaaaaaaaaa aaaaaaaaaa aaaaaaaaaa aaaaaaaaaa 2280
aaaaaaaaaa aaaaaaaaaa aaaaaaaaaa aaaaaaaaaa aaaaaaaaaa aaaaaaaaaa 2340
aaaaaaaaaa aaaaaaaaaa aaaaaaaaaa aaaaaaaaaa aaaaaaaaaa aaaaaaaaaa 2400
aaaaaaaaaa aaaaaaaaaa aaaaaaaaaa aaaaaaaaaa aaaaaaaaaa aaaaaaaaaa 2460
aaaaaaaaaa aaaaaaaaaa aaaaaaaaaa aaaaaaaaaa aaaaaaaaaa aaaaaaaaaa 2520
aaaaaaaaaa aaaaaaaaaa aaaaaaaaaa aaaaaaaaaa aaaaaaaaaa aaaaaaaaaa 2580
aaaaaaaaaa aaaaaaaaaa aaaaaaaaaa aaaaaaaaaa aaaaaaaaaa aaaaaaaaaa 2640
aaaaaaaaaa aaaaaaaaaa aaaaaaaaaa aaaaaaaaaa aaaaaaaaaa aaaaaaaaaa 2700
aaaaaaaaaa aaaaaaaaaa aaaaaaaaaa aaaaaaaaaa aaaaaaaaaa aaaaaaaaaa 2760
aaaaaaaaaa aaaaaaaaaa aaaaaaaaaa aaaaaaaaaa aaaaaaaaaa aaaaaaaaaa 2820
aaaaaaaaaa aaaaaaaaaa aaaaaaaaaa aaaaaaaaaa aaaaaaaaaa aaaaaaaaaa 2880
aaaaaaaaaa aaaaaaaaaa aaaaaaaaaa aaaaaaaaaa aaaaaaaaaa aaaaaaaaaa 2940
aaaaaaaaaa aaaaaaaaaa aaaaaaaaaa aaaaaaaaaa aaaaaaaaaa aaaaaaaaaa 3000
aaaaaaaaaa aaaaaaaaaa aaaaaaaaaa aaaaaaaaaa aaaaaaaaaa aaaaaaaaaa 3060
aaaaaaaaaa aaaaaaaaaa aaaaaaaaaa aaaaaaaaaa aaaaaaaaaa aaaaaaaaaa 3120
aaaaaaaaaa aaaaaaaaaa aaaaaaaaaa aaaaaaaaaa aaaaaaaaaa aaaaaaaaaa 3180
aaaaaaaaaa aaaaaaaaaa aaaaaaaaaa aaaaaaaaaa aaaaaaaaaa aaaaaaaaaa 3240
aaaaaaaaaa aaaaaaaaaa aaaaaaaaaa aaaaaaaaaa aaaaaaaaaa aaaaaaaaaa 3300
aaaaaaaaaa aaaaaaaaaa aaaaaaaaaa aaaaaaaaaa aaaaaaaaaa aaaaaaaaaa 3360
aaaaaaaaaa aaaaaaaaaa aaaaaaaaaa aaaaaaaaaa aaaaaaaaaa aaaaaaaaaa 3420
aaaaaaaaaa aaaaaaaaaa aaaaaaaaaa aaaaaaaaaa aaaaaaaaaa aaaaaaaaaa 3480
aaaaaaaaaa aaaaaaaaaa aaaaaaaaaa aaaaaaaaaa aaaaaaaaaa aaaaaaaaaa 3540
aaaaaaaaaa aaaaaaaaaa aaaaaaaaaa aaaaaaaaaa aaaaaaaaaa aaaaaaaaaa 3600
aaaaaaaaaa aaaaaaaaaa aaaaaaaaaa aaaaaaaaaa aaaaaaaaaa aaaaaaaaaa 3660
aaaaaaaaaa aaaaaaaaaa aaaaaaaaaa aaaaaaaaaa aaaaaaaaaa aaaaaaaaaa 3720
aaaaaaaaaa aaaaaaaaaa aaaaaaaaaa aaaaaaaaaa aaaaaaaaaa aaaaaaaaaa 3780
aaaaaaaaaa aaaaaaaaaa aaaaaaaaaa aaaaaaaaaa aaaaaaaaaa aaaaaaaaaa 3840
aaaaaaaaaa aaaaaaaaaa aaaaaaaaaa aaaaaaaaaa aaaaaaaaaa aaaaaaaaaa 3900
aaaaaaaaaa aaaaaaaaaa aaaaaaaaaa aaaaaaaaaa aaaaaaaaaa aaaaaaaaaa 3960
aaaaaaaaaa aaaaaaaaaa aaaaaaaaaa aaaaaaaaaa aaaaaaaaaa aaaaaaaaaa 4020
aaaaaaaaaa aaaaaaaaaa aaaaaaaaaa aaaaaaaaaa aaaaaaaaaa aaaaaaaaaa 4080
aaaaaaaaaa aaaaaaaaaa aaaaaaaaaa aaaaaaaaaa aaaaaaaaaa aaaaaaaaaa 4140
aaaaaaaaaa aaaaaaaaaa aaaaaaaaaa aaaaaaaaaa aaaaaaaaaa aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaaaa 4320
aaaaaaaaaa aaaaaaaaaa aaaaaaaaaa aaaaaaaaaa aaaaaaaaaa aaaaaaaaaa 4380

-continued

```
aaaaaaaaaa aaaaaaaaaa aaaaaaaaaa aaaaaaaaaa aaaaaaaaaa aaaaaaaaaa   4440

aaaaaaaaaa aaaaaaaaaa aaaaaaaaaa aaaaaaaaaa aaaaaaaaaa aaaaaaaaaa   4500

aaaaaaaaaa aaaaaaaaaa aaaaaaaaaa aaaaaaaaaa aaaaaaaaaa aaaaaaaaaa   4560

aaaaaaaaaa aaaaaaaaaa aaaaaaaaaa aaaaaaaaaa aaaaaaaaaa aaaaaaaaaa   4620

aaaaaaaaaa aaaaaaaaaa aaaaaaaaaa aaaaaaaaaa aaaaaaaaaa aaaaaaaaaa   4680

aaaaaaaaaa aaaaaaaaaa aaaaaaaaaa aaaaaaaaaa aaaaaaaaaa aaaaaaaaaa   4740

aaaaaaaaaa aaaaaaaaaa aaaaaaaaaa aaaaaaaaaa aaaaaaaaaa aaaaaaaaaa   4800

aaaaaaaaaa aaaaaaaaaa aaaaaaaaaa aaaaaaaaaa aaaaaaaaaa aaaaaaaaaa   4860

aaaaaaaaaa aaaaaaaaaa aaaaaaaaaa aaaaaaaaaa aaaaaaaaaa aaaaaaaaaa   4920

aaaaaaaaaa aaaaaaaaaa aaaaaaaaaa aaaaaaaaaa aaaaaaaaaa aaaaaaaaaa   4980

aaaaaaaaaa aaaaaaaaaa                                               5000


<210> SEQ ID NO 76
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa                          100


<210> SEQ ID NO 77
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(400)
<223> OTHER INFORMATION: This sequence may encompass 300-400
      nucleotides, wherein some positions may be absent

<400> SEQUENCE: 77

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa aaaaaaaaaa aaaaaaaaaa aaaaaaaaaa    180

aaaaaaaaaa aaaaaaaaaa aaaaaaaaaa aaaaaaaaaa aaaaaaaaaa aaaaaaaaaa    240

aaaaaaaaaa aaaaaaaaaa aaaaaaaaaa aaaaaaaaaa aaaaaaaaaa aaaaaaaaaa    300

aaaaaaaaaa aaaaaaaaaa aaaaaaaaaa aaaaaaaaaa aaaaaaaaaa aaaaaaaaaa    360

aaaaaaaaaa aaaaaaaaaa aaaaaaaaaa aaaaaaaaaa                          400
```

UNITED STATES PATENT AND TRADEMARK OFFICE
CERTIFICATE OF CORRECTION

| | |
|---|---|
| PATENT NO. | : 9,745,368 B2 |
| APPLICATION NO. | : 14/214824 |
| DATED | : August 29, 2017 |
| INVENTOR(S) | : Michael C. Milone et al. |

It is certified that error appears in the above-identified patent and that said Letters Patent is hereby corrected as shown below:

In the Specification

At Column 1, Line number 11, delete "This invention was made with government support under PN2 EY016586 awarded by the National Institutes of Health (NIH)." and insert --This invention was made with government support under EY016586 awarded by the National Institutes of Health (NIH).--

Signed and Sealed this
Twenty-fourth Day of May, 2022

Katherine Kelly Vidal
*Director of the United States Patent and Trademark Office*